United States Patent
Ichinohe et al.

(10) Patent No.: US 11,773,152 B2
(45) Date of Patent: *Oct. 3, 2023

(54) TECHNIQUE FOR CREATING ANTIGEN-SPECIFIC REGULATORY T CELLS (TREG) IN WHICH EFFECTOR T CELL (TEFF) ANTIGEN RECEPTORS ARE USED

(71) Applicants: Hiroshima University, Higashi-Hiroshima (JP); Repertoire Genesis Incorporation, Ibaraki (JP)

(72) Inventors: Tatsuo Ichinohe, Hiroshima (JP); Takashi Yamamoto, Higashi-Hiroshima (JP); Tetsushi Sakuma, Higashi-Hiroshima (JP); Yasuko Honjo, Hiroshima (JP); Takakazu Kawase, Hiroshima (JP); Takahiko Miyama, Hiroshima (JP); Ryuji Suzuki, Ibaraki (JP)

(73) Assignees: Hiroshima University, Higashi-Hiroshima (JP); Reperptoire Genesis Incorpration, Ibaraki (JP)

( * ) Notice: Subject to any disclaimer, the term of this patent is extended or adjusted under 35 U.S.C. 154(b) by 323 days.

This patent is subject to a terminal disclaimer.

(21) Appl. No.: 16/755,125

(22) PCT Filed: Oct. 9, 2018

(86) PCT No.: PCT/JP2018/037591
§ 371 (c)(1),
(2) Date: Apr. 9, 2020

(87) PCT Pub. No.: WO2019/073965
PCT Pub. Date: Apr. 18, 2019

(65) Prior Publication Data
US 2022/0064253 A1 Mar. 3, 2022

(30) Foreign Application Priority Data
Oct. 10, 2017 (JP) ................ 2017-197013

(51) Int. Cl.
*C07K 14/725* (2006.01)
*A61P 37/06* (2006.01)
*A61K 35/17* (2015.01)
*C12N 15/90* (2006.01)
*C12Q 1/6869* (2018.01)

(52) U.S. Cl.
CPC .......... *C07K 14/7051* (2013.01); *A61K 35/17* (2013.01); *A61P 37/06* (2018.01); *C12N 15/907* (2013.01); *C12Q 1/6869* (2013.01)

(58) Field of Classification Search
CPC .. C07K 14/7051; A61K 35/17; C12N 15/907; C12Q 1/6869; A61P 37/06
See application file for complete search history.

(56) References Cited

U.S. PATENT DOCUMENTS

2016/0186151 A1 6/2016 Yamamoto et al.
2016/0289760 A1 10/2016 Suzuki et al.

FOREIGN PATENT DOCUMENTS

| EP | 3091074 A1 | 11/2016 |
|---|---|---|
| JP | 2014/039523 A1 | 3/2014 |
| JP | 2014/153470 A2 | 9/2014 |
| JP | 2014/191527 A1 | 12/2014 |
| JP | 2015/075939 A1 | 5/2015 |
| JP | 2015-528298 A | 9/2015 |
| JP | 5931022 B2 | 5/2016 |
| JP | 2016-515822 A | 6/2016 |
| JP | 2016-520320 A | 7/2016 |
| WO | 2006/026002 A2 | 3/2006 |
| WO | 2011/139371 A1 | 11/2011 |
| WO | 2016/069282 A1 | 5/2016 |
| WO | 2017/044672 A1 | 3/2017 |
| WO | 2017/070429 A1 | 4/2017 |

OTHER PUBLICATIONS

Restriction Requirement dated Jun. 29, 2022, for U.S. Appl. No. 16/755,074, 10 pages.
Adair et al., "Human Tregs Made Antigen Specific by Gene Modification: the Power to Treat Autoimmunity and Antidrug Antibodies with Precision," *Front Immunol* 8:1117, 10 pages.
Honjo et al., "T-cell receptor gene editing by transcription activator-like effector nuclease (TALEN) as a novel tool for adoptive T-cell immunotherapy," *Journal of Germfree Life and Gnotobiology* 47(1), 5 pages, 2017.
Hull et al., "Generation of human islet-specific regulatory T cells by TCR gene transfer," *Journal of Autoimmunity* 79:63-73, 2017.
Mastaglio et al., "NY-ESO-1 TCR single edited stem and central memory T cells to treat multiple myeloma without graft-versus-host disease," *Blood* 130(5):606-618, 2017.
Miyama et al., "OS2-11B-2 TALEN-mediated T-cell receptor gene editing as a novel tool for adoptive T-cell immunotherapy," *Proceedings of the Fiftieth Annual Meeting of the Japanese Association of Germfree Life and Gnotobiology*, Tokyo, Japan, Jun. 7-10, 2017, 3 pages.
Sakuma et al., "Repeating pattern of non-RVD variations in DNA-binding modules enhances TALEN activity," *Scientific Reports* 3:3379, 2013, 8 pages.

(Continued)

*Primary Examiner* — Ruixiang Li
(74) *Attorney, Agent, or Firm* — Seed IP Law Group LLP

(57) ABSTRACT

The present disclosure provides a technique for producing regulatory T cells specific to a desired antigen. Regulatory T cells specific to an antigen are produced by a method that includes: a step for identifying a T cell receptor (TCR) clone present in an effector T cell population specific to an antigen in an effector T cell donor; and a step for introducing all or part of the nucleic acid sequence of the TCRα gene and all or part of the nucleic acid sequence of the TCRβ gene included in the clone into a regulatory T cell, said step comprising introducing the TCRα and the TCRβ so as to be expressed in pairs.

21 Claims, 30 Drawing Sheets

Specification includes a Sequence Listing.

(56) References Cited

OTHER PUBLICATIONS

Sakuma et al., "Engineering Customized TALENs Using the Platinum Gate TALEN Kit," *TALENs: Methods and Protocols, Methods in Molecular Biology* 1338, 11 pages, 2016.

Wright et al., "Adoptive therapy with redirected primary regulatory T cells results in antigen-specific suppression of arthritis," *PNAS* 106(45):19078-19083, 2009.

Genovese et al., "Abstract 209, TCR Gene Editing in a Single Step of T Cell Activation to Redirect T Cell Specificity and Prevent GvHD," *Abstracts of the ASGCT 18th Annual Meeting, Molecular Therapy* 23(1):s82-s83, May 2015.

Provasi et al., "Editing T cell specificity towards leukemia by zinc finger nucleases and lentiviral gene transfer," *Nature Medicine* 18(5), doi:10.1038/nm.2700, 11 pages, 2012.

Studer et al., "Residue mutations and their impact on protein structure and function: detecting beneficial and pathogenic changes," *Biochem. J.* 449:581-594 (2013).

Continuation of FIG.6
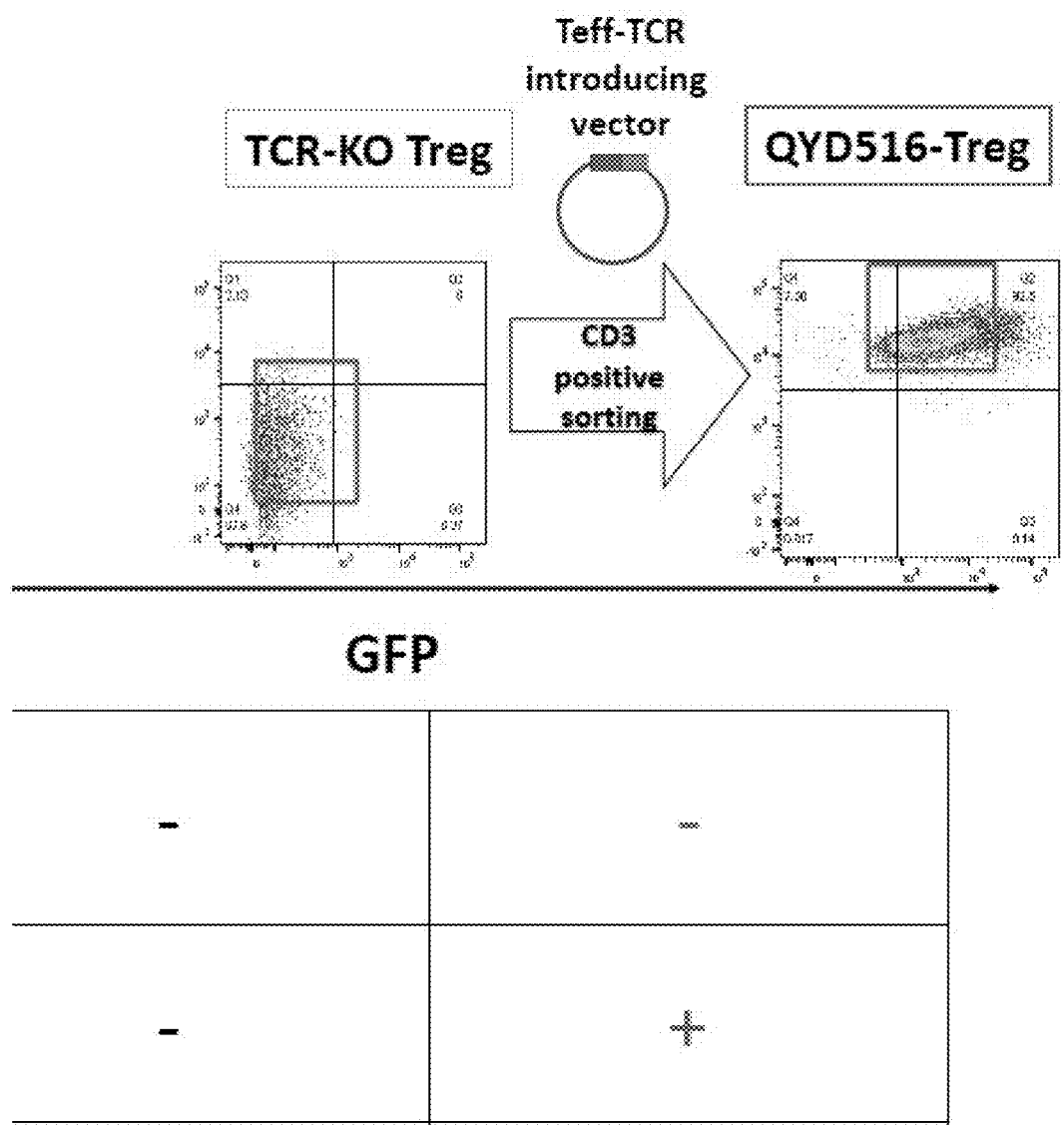

Separation of peripheral blood T cells

Continuation of FIG.7
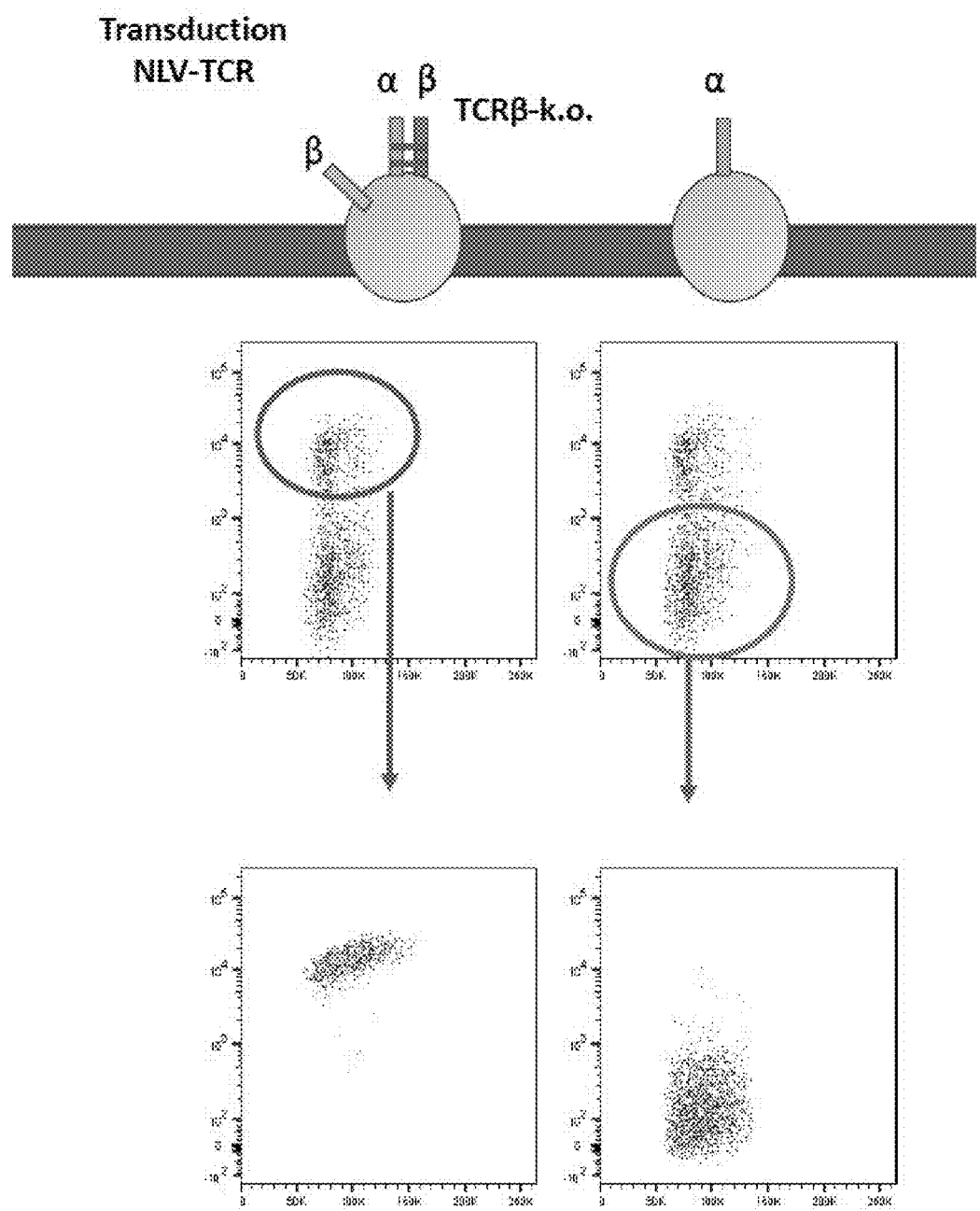

Continuation of FIG.7
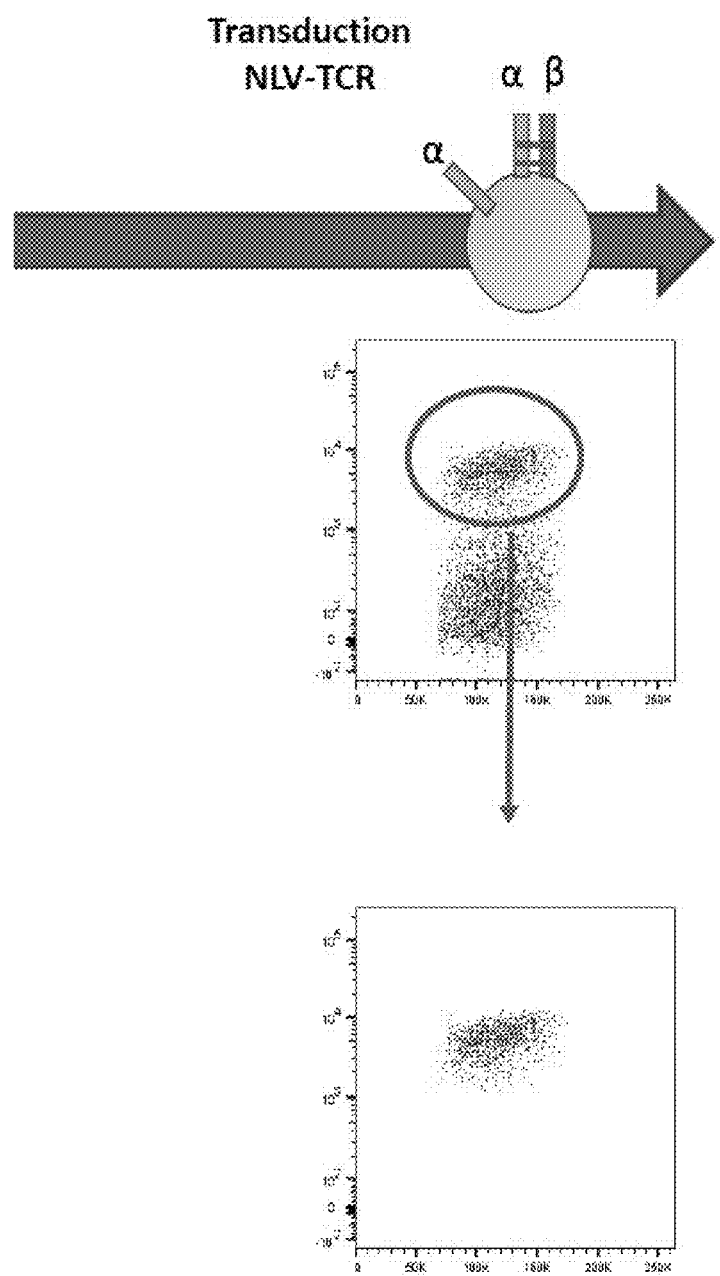

Continuation of FIG.10
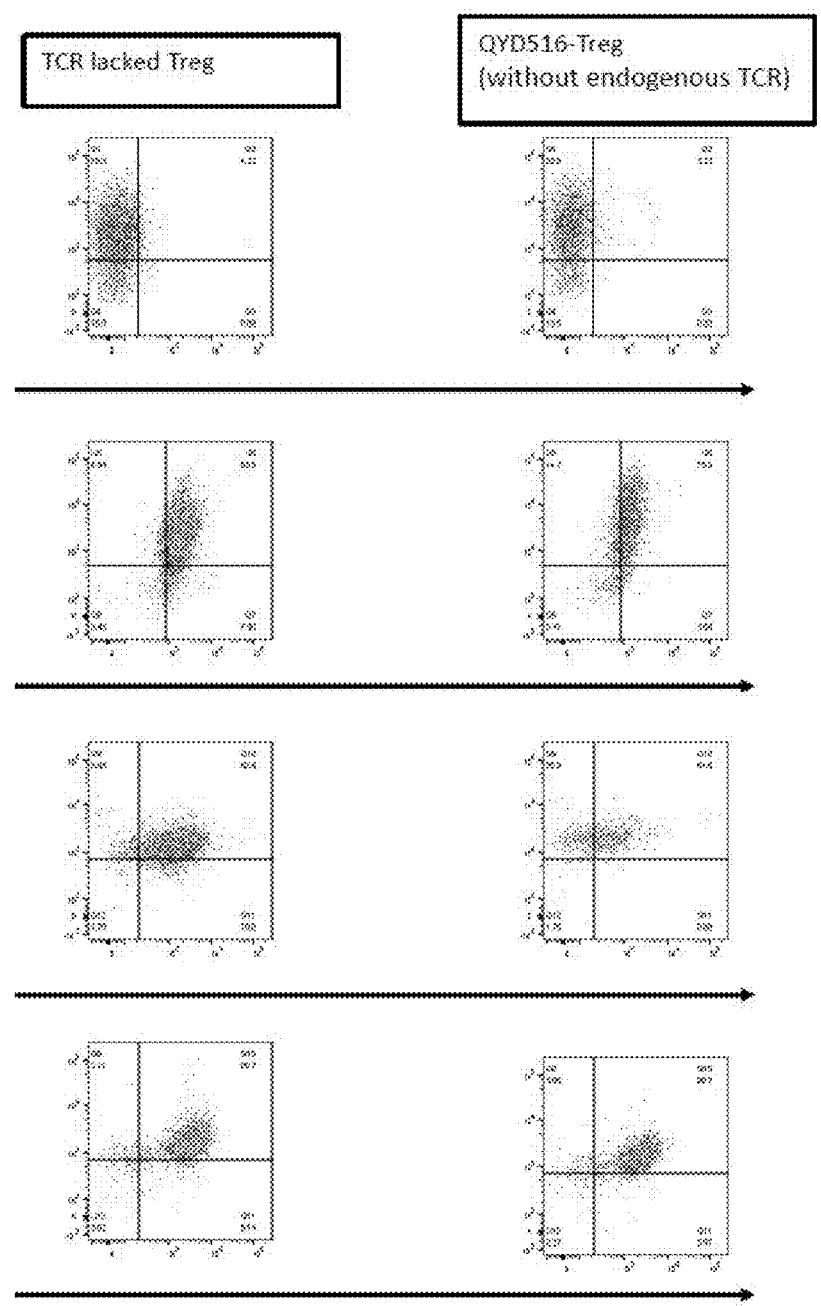

Day0

Poly-Treg
QYD stim-

Poly-Treg
QYD stim+

QYD516-Treg
QYD stim-

QYD516-Treg
QYD stim+

Celltrace Violet

Continuation of FIG.13
Day3            Day5
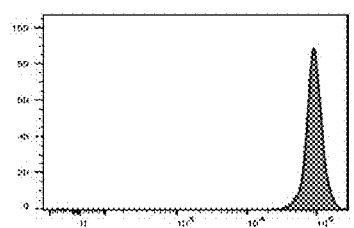
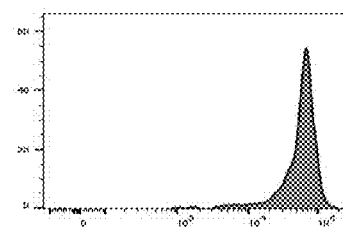
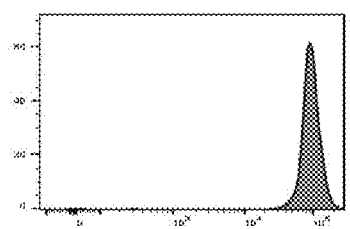
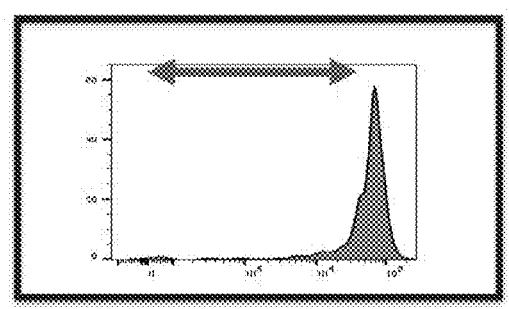
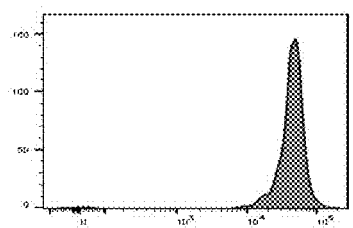
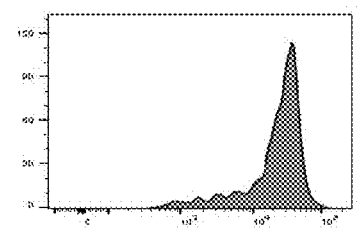
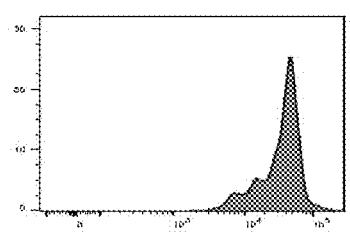
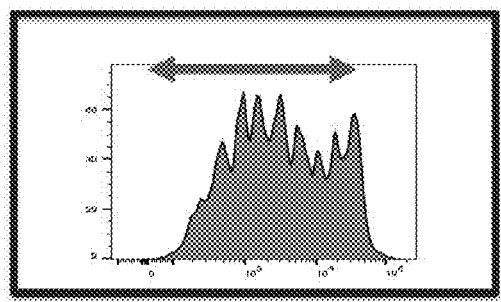

Continuation of FIG.14
1 : 2   1 : 1
29 %   20.7 %
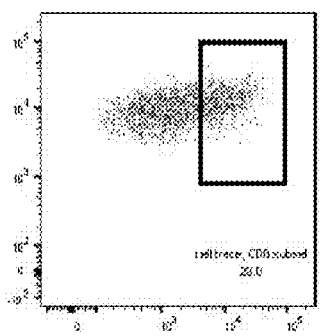 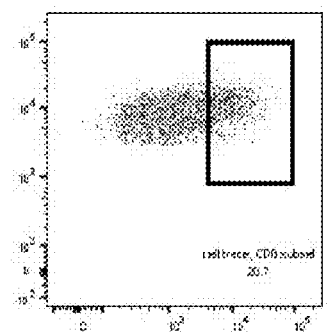
44.5 %   36.2 %
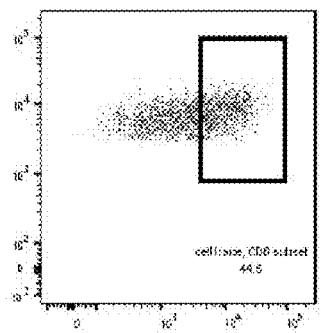 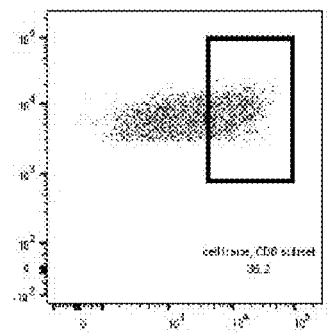

Continuation of FIG.14
1 : 0.5    1 : 0.125
13.4 %    11.5 %
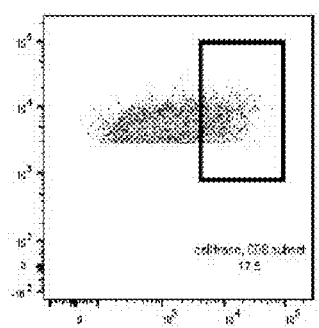 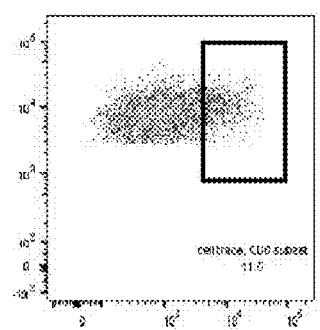
27.4 %    19.1 %
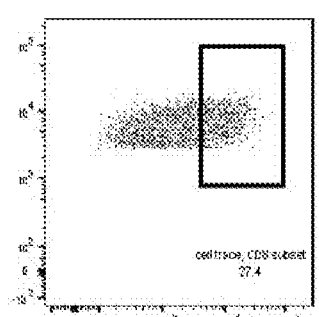 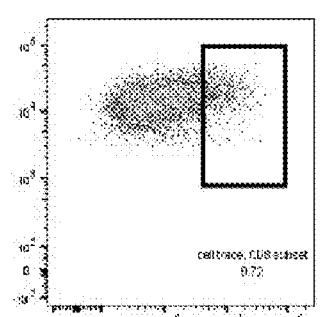

Voytas TALEN

LTPDQVVAIASHDGGKQALETVQRLLPVLCQDHG

Platinum TALEN

LTPDQVVAIASHDGGKQALETVQRLLPVLCQDHG
LTPEQVVAIASHDGGKQALETVQRLLPVLCQAHG
LTPDQVVAIASHDGGKQALETVQRLLPVLCQAHG
LTPAQVVAIASHDGGKQALETVQRLLPVLCQDHG

Zhang TALEN (EA type SuperTALEN)

LTPEQVVAIASHDGGKQALETVQRLLPVLCQAHG

Repeat-variable diresidue (RVD)

SEQUENCE LISTING

```
<160> NUMBER OF SEQ ID NOS: 118

<210> SEQ ID NO 1
<211> LENGTH: 34
<212> TYPE: PRT
<213> ORGANISM: artificial sequence
<220> FEATURE:
<223> OTHER INFORMATION: Exemplary amino acid sequence of TALE DNA
      binding module

<400> SEQUENCE: 1

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30
```

His Gly

<210> SEQ ID NO 2
<211> LENGTH: 9
<212> TYPE: PRT
<213> ORGANISM: artificial sequence
<220> FEATURE:
<223> OTHER INFORMATION: HLA-A*02-restricted CMV pp65 peptide

<400> SEQUENCE: 2

Asn Leu Val Pro Met Val Ala Thr Val
1               5

<210> SEQ ID NO 3
<211> LENGTH: 9
<212> TYPE: PRT
<213> ORGANISM: artificial sequence
<220> FEATURE:
<223> OTHER INFORMATION: HLA-A2-HIV

<400> SEQUENCE: 3

Lys Leu Thr Pro Leu Cys Val Thr Leu
1               5

<210> SEQ ID NO 4
<211> LENGTH: 35
<212> TYPE: DNA
<213> ORGANISM: artificial sequence
<220> FEATURE:
<223> OTHER INFORMATION: BSL-18E primer
<220> FEATURE:
<221> NAME/KEY: misc_feature
<222> LOCATION: (35)..(35)
<223> OTHER INFORMATION: n is a, c, g, t or u

<400> SEQUENCE: 4
aaagcggccg catgcttttt tttttttttt tttvn                              35

<210> SEQ ID NO 5
<211> LENGTH: 20
<212> TYPE: DNA
<213> ORGANISM: artificial sequence
<220> FEATURE:
<223> OTHER INFORMATION: P20EA primer

<400> SEQUENCE: 5
taatacgact ccgaattccc                                               20

<210> SEQ ID NO 6
<211> LENGTH: 10
<212> TYPE: DNA
<213> ORGANISM: artificial sequence
<220> FEATURE:
<223> OTHER INFORMATION: P10EA primer

<400> SEQUENCE: 6
gggaattcgg                                                          10

<210> SEQ ID NO 7
<211> LENGTH: 23
<212> TYPE: DNA
<213> ORGANISM: artificial sequence
<220> FEATURE:
<223> OTHER INFORMATION: CA1 primer

<400> SEQUENCE: 7
tgttgaaggc gtttgcacat gca                                           23

```
<210> SEQ ID NO 8
<211> LENGTH: 23
<212> TYPE: DNA
<213> ORGANISM: artificial sequence
<220> FEATURE:
<223> OTHER INFORMATION: CA2 primer

<400> SEQUENCE: 8
gtgcatagac ctcatgtcta gca                                          23

<210> SEQ ID NO 9
<211> LENGTH: 23
<212> TYPE: DNA
<213> ORGANISM: artificial sequence
<220> FEATURE:
<223> OTHER INFORMATION: CB1 primer

<400> SEQUENCE: 9
gaactggact tgacagcgga act                                          23

<210> SEQ ID NO 10
<211> LENGTH: 23
<212> TYPE: DNA
<213> ORGANISM: artificial sequence
<220> FEATURE:
<223> OTHER INFORMATION: CB2 primer

<400> SEQUENCE: 10
aggcagtatc tggagtcatt gag                                          23

<210> SEQ ID NO 11
<211> LENGTH: 63
<212> TYPE: DNA
<213> ORGANISM: artificial sequence
<220> FEATURE:
<223> OTHER INFORMATION: HuVbF primer
<220> FEATURE:
<221> NAME/KEY: misc_feature
<222> LOCATION: 31...40
<223> OTHER INFORMATION: n = a, t, c, or g
<220> FEATURE:
<221> NAME/KEY: misc_feature
<222> LOCATION: (31)..(40)
<223> OTHER INFORMATION: MID tag sequence

<400> SEQUENCE: 11
ccatctcatc cctgcgtgtc tccgactcag nnnnnnnnnn ataggcagac agacttgtca  60
ctg                                                                63

<210> SEQ ID NO 12
<211> LENGTH: 63
<212> TYPE: DNA
<213> ORGANISM: artificial sequence
<220> FEATURE:
<223> OTHER INFORMATION: HuVbF primer
<220> FEATURE:
<221> NAME/KEY: misc_feature
<222> LOCATION: 31...40
<223> OTHER INFORMATION: n = a, t, c, or g
<220> FEATURE:
<221> NAME/KEY: misc_feature
<222> LOCATION: (31)..(40)
<223> OTHER INFORMATION: MID tag sequence

<400> SEQUENCE: 12
ccatctcatc cctgcgtgtc tccgactcag nnnnnnnnnn acaccagtgt ggccttttgg  60
``` gtg                                                                                          63

<210> SEQ ID NO 13
<211> LENGTH: 46
<212> TYPE: DNA
<213> ORGANISM: artificial sequence
<220> FEATURE:
<223> OTHER INFORMATION: B-P20EA primer

<400> SEQUENCE: 13
cctatcccct gtgtgccttg gcagtctaat acgactccga attccc            46

<210> SEQ ID NO 14
<211> LENGTH: 10
<212> TYPE: DNA
<213> ORGANISM: artificial sequence
<220> FEATURE:
<223> OTHER INFORMATION: MID1

<400> SEQUENCE: 14
acgagtgcgt                                                                                   10

<210> SEQ ID NO 15
<211> LENGTH: 10
<212> TYPE: DNA
<213> ORGANISM: artificial sequence
<220> FEATURE:
<223> OTHER INFORMATION: MID2

<400> SEQUENCE: 15
acgctcgaca                                                                                   10

<210> SEQ ID NO 16
<211> LENGTH: 10
<212> TYPE: DNA
<213> ORGANISM: artificial sequence
<220> FEATURE:
<223> OTHER INFORMATION: MID3

<400> SEQUENCE: 16
agacgcactc                                                                                   10

<210> SEQ ID NO 17
<211> LENGTH: 10
<212> TYPE: DNA
<213> ORGANISM: artificial sequence
<220> FEATURE:
<223> OTHER INFORMATION: MID4

<400> SEQUENCE: 17
agcactgtag                                                                                   10

<210> SEQ ID NO 18
<211> LENGTH: 10
<212> TYPE: DNA
<213> ORGANISM: artificial sequence
<220> FEATURE:
<223> OTHER INFORMATION: MID5

<400> SEQUENCE: 18
atcagacacg                                                                                   10

<210> SEQ ID NO 19
<211> LENGTH: 10
<212> TYPE: DNA
<213> ORGANISM: artificial sequence

```
<220> FEATURE:
<223> OTHER INFORMATION: MID6

<400> SEQUENCE: 19
atatcgcgag                                                                10

<210> SEQ ID NO 20
<211> LENGTH: 10
<212> TYPE: DNA
<213> ORGANISM: artificial sequence
<220> FEATURE:
<223> OTHER INFORMATION: MID7

<400> SEQUENCE: 20
cgtgtctcta                                                                10

<210> SEQ ID NO 21
<211> LENGTH: 10
<212> TYPE: DNA
<213> ORGANISM: artificial sequence
<220> FEATURE:
<223> OTHER INFORMATION: MID8

<400> SEQUENCE: 21
ctcgcgtgtc                                                                10

<210> SEQ ID NO 22
<211> LENGTH: 10
<212> TYPE: DNA
<213> ORGANISM: artificial sequence
<220> FEATURE:
<223> OTHER INFORMATION: MID10

<400> SEQUENCE: 22
tctctatgcg                                                                10

<210> SEQ ID NO 23
<211> LENGTH: 10
<212> TYPE: DNA
<213> ORGANISM: artificial sequence
<220> FEATURE:
<223> OTHER INFORMATION: MID11

<400> SEQUENCE: 23
tgatacgtct                                                                10

<210> SEQ ID NO 24

<400> SEQUENCE: 24

000

<210> SEQ ID NO 25
<211> LENGTH: 10
<212> TYPE: DNA
<213> ORGANISM: artificial sequence
<220> FEATURE:
<223> OTHER INFORMATION: MID16

<400> SEQUENCE: 25
tcacgtacta                                                                10

<210> SEQ ID NO 26
<211> LENGTH: 10
<212> TYPE: DNA
<213> ORGANISM: artificial sequence
```

```
<220> FEATURE:
<223> OTHER INFORMATION: MID17

<400> SEQUENCE: 26
cgtctagtac                                                                10

<210> SEQ ID NO 27
<211> LENGTH: 10
<212> TYPE: DNA
<213> ORGANISM: artificial sequence
<220> FEATURE:
<223> OTHER INFORMATION: MID18

<400> SEQUENCE: 27
tctacgtagc                                                                10

<210> SEQ ID NO 28
<211> LENGTH: 10
<212> TYPE: DNA
<213> ORGANISM: artificial sequence
<220> FEATURE:
<223> OTHER INFORMATION: MID19

<400> SEQUENCE: 28
tgtactactc                                                                10

<210> SEQ ID NO 29
<211> LENGTH: 10
<212> TYPE: DNA
<213> ORGANISM: artificial sequence
<220> FEATURE:
<223> OTHER INFORMATION: MID20

<400> SEQUENCE: 29
acgactacag                                                                10

<210> SEQ ID NO 30
<211> LENGTH: 10
<212> TYPE: DNA
<213> ORGANISM: artificial sequence
<220> FEATURE:
<223> OTHER INFORMATION: MID21

<400> SEQUENCE: 30
cgtagactag                                                                10

<210> SEQ ID NO 31
<211> LENGTH: 10
<212> TYPE: DNA
<213> ORGANISM: artificial sequence
<220> FEATURE:
<223> OTHER INFORMATION: MID22

<400> SEQUENCE: 31
tacgagtatg                                                                10

<210> SEQ ID NO 32
<211> LENGTH: 10
<212> TYPE: DNA
<213> ORGANISM: artificial sequence
<220> FEATURE:
<223> OTHER INFORMATION: MID23

<400> SEQUENCE: 32
tactctcgtg                                                                10
```

```
<210> SEQ ID NO 33
<211> LENGTH: 10
<212> TYPE: DNA
<213> ORGANISM: artificial sequence
<220> FEATURE:
<223> OTHER INFORMATION: MID24

<400> SEQUENCE: 33
tagagacgag                                                                 10

<210> SEQ ID NO 34
<211> LENGTH: 26
<212> TYPE: DNA
<213> ORGANISM: artificial sequence
<220> FEATURE:
<223> OTHER INFORMATION: A adaptor sequence

<400> SEQUENCE: 34
ccatctcatc cctgcgtgtc tccgac                                               26

<210> SEQ ID NO 35
<211> LENGTH: 55
<212> TYPE: DNA
<213> ORGANISM: artificial sequence
<220> FEATURE:
<223> OTHER INFORMATION: P22EA-ST1-R primer

<400> SEQUENCE: 35
gtctcgtggg ctcggagatg tgtataagag acagctaata cgactccgaa ttccc              55

<210> SEQ ID NO 36
<211> LENGTH: 33
<212> TYPE: DNA
<213> ORGANISM: artificial sequence
<220> FEATURE:
<223> OTHER INFORMATION: Tag-1 primer

<400> SEQUENCE: 36
gtctcgtggg ctcggagatg tgtataagag aca                                       33

<210> SEQ ID NO 37
<211> LENGTH: 33
<212> TYPE: DNA
<213> ORGANISM: artificial sequence
<220> FEATURE:
<223> OTHER INFORMATION: Tag-2 primer

<400> SEQUENCE: 37
tcgtcggcag cgtcagatgt gtataagaga cag                                       33

<210> SEQ ID NO 38
<211> LENGTH: 51
<212> TYPE: DNA
<213> ORGANISM: artificial sequence
<220> FEATURE:
<223> OTHER INFORMATION: CA-ST1-R

<400> SEQUENCE: 38
tcgtcggcag cgtcagatgt gtataagaga caggagggtc agggttctgg a                   51

<210> SEQ ID NO 39
<211> LENGTH: 52
<212> TYPE: DNA
<213> ORGANISM: artificial sequence
<220> FEATURE:
<223> OTHER INFORMATION: CB-ST1-R
```

-continued

<400> SEQUENCE: 39
tcgtcggcag cgtcagatgt gtataagaga caggctcaaa cacagcgacc tc            52

<210> SEQ ID NO 40
<211> LENGTH: 29
<212> TYPE: DNA
<213> ORGANISM: artificial sequence
<220> FEATURE:
<223> OTHER INFORMATION: TSO oligo

<400> SEQUENCE: 40
gtcgcacggt ccatcgcagc agtcacagg                                      29

<210> SEQ ID NO 41
<211> LENGTH: 24
<212> TYPE: DNA
<213> ORGANISM: artificial sequence
<220> FEATURE:
<223> OTHER INFORMATION: TSO PCR primer

<400> SEQUENCE: 41
gtcgcacggt ccatcgcagc agtc                                           24

<210> SEQ ID NO 42
<211> LENGTH: 23
<212> TYPE: DNA
<213> ORGANISM: artificial sequence
<220> FEATURE:
<223> OTHER INFORMATION: SMART PCR primer

<400> SEQUENCE: 42
aagcagtggt atcaacgcag agt                                            23

<210> SEQ ID NO 43
<211> LENGTH: 59
<212> TYPE: DNA
<213> ORGANISM: artificial sequence
<220> FEATURE:
<223> OTHER INFORMATION: TSO_TAG primer

<400> SEQUENCE: 43
gtctcgtggg ctcggagatg tgtataagag acagcgtcgc acggtccatc gcagcagtc     59

<210> SEQ ID NO 44
<211> LENGTH: 56
<212> TYPE: DNA
<213> ORGANISM: artificial sequence
<220> FEATURE:
<223> OTHER INFORMATION: SMART_TAG primer

<400> SEQUENCE: 44
tcgtcggcag cgtcagatgt gtataagaga cagaagcagt ggtatcaacg cagagt        56

<210> SEQ ID NO 45
<211> LENGTH: 23
<212> TYPE: DNA
<213> ORGANISM: artificial sequence
<220> FEATURE:
<223> OTHER INFORMATION: SMART sequence in oligo bead

<400> SEQUENCE: 45
aagcagtggt atcaacgcag agt                                            23

<210> SEQ ID NO 46

<211> LENGTH: 8363
<212> TYPE: DNA
<213> ORGANISM: artificial sequence
<220> FEATURE:
<223> OTHER INFORMATION: TALEN-TCR-alpha2_L19 plasmid full length

<400> SEQUENCE: 46

| | |
|---|---|
| agccatctgt tgtttgcccc tcccccgtgc cttccttgac cctggaaggt gccactccca | 60 |
| ctgtcctttc ctaataaaat gaggaaattg catcacaaca ctcaaccctc tctcggtcta | 120 |
| ttcttttgat ttataaggga ttttgccgat ttcggcctat tggttaaaaa atgagctgat | 180 |
| ttaacaaaaa tttaacgcga attaattctg tggaatgtgt gtcagttagg gtgtggaaag | 240 |
| tccccaggct ccccagcagg cagaagtatg caaagcatgc atctcaatta gtcagcaacc | 300 |
| aggtgtggaa agtccccagg ctccccagca ggcagaagta tgcaaagcat gcatctcaat | 360 |
| tagtcagcaa ccatagtccc gcccctaact ccgcccatcc cgcccctaac tccgcccagt | 420 |
| tccgcccatt ctccgcccca tggctgacta atttttttta tttatgcaga ggccgaggcc | 480 |
| gcctctgcct ctgagctatt ccagaagtag tgaggaggct tttttggagg cctaggcttt | 540 |
| tgcaaaaagc tcccgggagc ttgtatatcc attttcggat ctgatcagca cgtgatgaaa | 600 |
| aagcctgaac tcaccgcgac gtctgtcgag aagtttctga tcgaaaagtt cgacagcgtt | 660 |
| tccgacctga tgcagctctc ggagggcgaa gaatctcgtg cttttcagct tcgatgtagga | 720 |
| gggcgtggat atgtcctgcg ggtaaatagc tgcgccgatg gtttctacaa agatcgttat | 780 |
| gtttatcggc actttgcatc ggccgcgctc ccgattccgg aagtgcttga cattgggaa | 840 |
| tcagcgaga gcctgaccta ttgcatctcc cgccgtgcac agggtgtcac gttgcaagac | 900 |
| ctgcctgaaa ccgaactgcc cgctgttctg cagccggtcg cggaggccat ggatgcgatc | 960 |
| gctgcggccg atcttagcca cgagcgggt tcggcccat tcggaccgca aggaatcggt | 1020 |
| caatacacta catggcgtga tttcatatgc gcgattgctg atccccatgt gtatcactgg | 1080 |
| caaactgtga tggacgacac cgtcagtgcg tccgtcgcgc aggctctcga tgagctgatg | 1140 |
| ctttgggccg aggactgccc cgaagtccgg cacctcgtgc acgcggattt cggctccaac | 1200 |
| aatgtcctga cggacaatgg ccgcataaca gcggtcattg actggagcga ggcgatgttc | 1260 |
| ggggattccc aatacgaggt cgccaacatc ttcttctgga ggccgtggtt ggcttgtatg | 1320 |
| gagcagcaga cgcgctactt cgagcggagg catccggagc ttgcaggatc gccgcggctc | 1380 |
| cgggcgtata tgctccgcat tggtcttgac caactctatc agagcttggt tgacggcaat | 1440 |
| ttcgatgatg cagcttgggc gcagggtcga tgcgacgcaa tcgtccgatc cggagccggg | 1500 |
| actgtcgggc gtacacaaat cgcccgcaga agcgcggccg tctggaccga tggctgtgta | 1560 |
| gaagtactcg ccgatagtgg aaaccgacgc cccagcactc gtccgagggc aaaggaatag | 1620 |
| cacgtgctac gagatttcga ttccaccgcc gccttctatg aaaggttggg cttcggaatc | 1680 |
| gttttccggg acgccggctg atgatcctc cagcgcgggg atctcatgct ggagttcttc | 1740 |
| gcccacccca acttgtttat tgcagcttat aatggttaca aataaagcaa tagcatcaca | 1800 |
| aatttcacaa ataaagcatt tttttcactg cattctagtt gtggtttgtc caaactcatc | 1860 |
| aatgtatctt atcatgtctg tataccgtcg acctctagct agagcttggc gtaatcatgg | 1920 |
| tcattaccaa tgcttaatca gtgaggcacc tatctcagcg atctgtctat ttcgttcatc | 1980 |
| catagttgcc tgactccccg tcgtgtagat aactacgata cgggagggct taccatctgg | 2040 |
| ccccagcgct gcgatgatac cgcgagaacc acgctcaccg gctccggatt tatcagcaat | 2100 |
| aaaccagcca gccggaaggg ccgagcgcag aagtggtcct gcaactttat ccgcctccat | 2160 |

```
ccagtctatt aattgttgcc gggaagctag agtaagtagt tcgccagtta atagtttgcg    2220
caacgttgtt gccatcgcta caggcatcgt ggtgtcacgc tcgtcgtttg gtatggcttc    2280
attcagctcc ggttcccaac gatcaaggcg agttacatga tcccccatgt tgtgcaaaaa    2340
agcggttagc tccttcggtc ctccgatcgt tgtcagaagt aagttggccg cagtgttatc    2400
actcatggtt atggcagcac tgcataattc tcttactgtc atgccatccg taagatgctt    2460
ttctgtgact ggtgagtact caaccaagtc attctgagaa tagtgtatgc ggcgaccgag    2520
ttgctcttgc ccggcgtcaa tacgggataa taccgcgcca catagcagaa ctttaaaagt    2580
gctcatcatt ggaaaacgtt cttcggggcg aaaactctca aggatcttac cgctgttgag    2640
atccagttcg atgtaaccca ctcgtgcacc caactgatct tcagcatctt tactttcac    2700 cagcgtttct gggtgagcaa aaacaggaag gcaaaatgcc gcaaaaaagg aataagggc    2760 gacacggaaa tgttgaatac tcatattctt ccttttcaa tattattgaa gcatttatca    2820
gggttattgt ctcatgagcg gatacatatt tgaatgtatt tagaaaaata aacaaatagg    2880
ggtcagtgtt acaaccaatt aaccaattct gaacattatc gcgagcccat ttatacctga    2940
atatggctca taacacccct tgctcatgac caaaatccct taacgtgagt tacgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactcttttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggcctttta    3660 cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggcctttttg cgtttctaca aactcttct    3900 gtgttgtaaa acgacggcca gtcttaagct cgggccccct gggcggttct gataacgagt    3960
aatcgttaat ccgcaaataa cgtaaaaacc cgcttcggcg gtttttta tggggggagt    4020 ttagggaaag agcatttgtc agaatattta agggcgcctg tcactttgct tgatatatga    4080
gaattattta accttataaa tgagaaaaaa gcaacgcact ttaaataaga tacgttgctt    4140
tttcgattga tgaacaccta aattaaact attcatctat tatttatgat ttttgtata    4200 tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata caattacga gcttcatgca cagtggcgtt gacattgatt attgactagt    4440
tattaatagt aatcaattac ggggtcatta gttcatagcc catatatgga gttccgcgtt    4500
```

| | |
|---|---|
| acataactta cggtaaatgg cccgcctggc tgaccgccca acgaccccg cccattgacg | 4560 |
| tcaataatga cgtatgttcc catagtaacg ccaataggga cttttccattg acgtcaatgg | 4620 |
| gtggagtatt tacggtaaac tgcccacttg gcagtacatc aagtgtatca tatgccaagt | 4680 |
| acgcccccta ttgacgtcaa tgacggtaaa tggcccgcct ggcattatgc ccagtacatg | 4740 |
| accttatggg actttcctac ttggcagtac atctacgtat tagtcatcgc tattaccatg | 4800 |
| gtgatgcggt tttggcagta catcaatggg cgtggatagc ggtttgactc acggggattt | 4860 |
| ccaagtctcc accccattga cgtcaatggg agtttgtttt ggcaccaaaa tcaacgggac | 4920 |
| tttccaaaat gtcgtaacaa ctccgcccca ttgacgcaaa tgggcggtag gcgtgtacgg | 4980 |
| tgggaggtct atataagcag agctctctgg ctaactagag aacccactgc ttactggctt | 5040 |
| atcgaaatta atacgactca ctatagggaa gcttcttgtt cttttttgcag aagctcagaa | 5100 |
| taaacgctca actttggcct cgaggccacc atggcttcct cccctccaaa gaaaagaga | 5160 |
| aaggttgcgg ccgctgacta caaggatgac gacgataaaa gttggaagga cgcaagtggt | 5220 |
| tggtctagaa tgcatgcggc cccgacgg cgtgctgcgc aaccctccga cgcttcgccg | 5280 |
| gccgcgcagg tggatctacg cacgctcggc tacagtcagc agcagcaaga gaagatcaaa | 5340 |
| ccgaaggtgc gttcgacagt ggcgcagcac cacgaggcac tggtgggcca tgggtttaca | 5400 |
| cacgcgcaca tcgttgcgct cagccaacac ccggcagcgt tagggaccgt cgctgtcacg | 5460 |
| tatcagcaca taatcacggc gttgccagag gcgacacacg aagacatcgt tggcgtcggc | 5520 |
| aaacagtggt ccggcgcacg cgccctggag gccttgctca cggatgcggg ggagttgaga | 5580 |
| ggtccgccgt tacagttgga cacaggccaa cttgtgaaga ttgcaaaacg tggcggcgtg | 5640 |
| accgcaatgg aggcagtgca tgcatcgcgc aatgcgctca cgggagcacc cctcaacctg | 5700 |
| accccagacc aagttgtcgc gattgcaagc aacaacggag gcaaacaagc cttagaaaca | 5760 |
| gtccagagat tgttgccggt gctgtgccaa gaccacggcc tgaccccga acaggttgtc | 5820 |
| gctattgcta gtaacggcgg aggcaaacag gcgctggaaa cagttcagcg cctcttgccg | 5880 |
| gtcttgtgtc aggcccacgg cctgaccccg gaccaggtgg ttgcaatcgc gtcacacgat | 5940 |
| gggggaaagc aggccctaga aaccgttcag cgactcctgc ccgtcctgtg ccaggcccac | 6000 |
| ggcctgaccc ccgcccaggt tgtcgctatt gctagtaacg gcggaggcaa acaggcgctg | 6060 |
| gaaacagttc agcgcctctt gccggtcttg tgtcaggacc acggcctgac cccagaccaa | 6120 |
| gttgtcgcga ttgcaagcaa caacggaggc aaacaagcct tagaaacagt ccagagattg | 6180 |
| ttgccggtgt tgtgccaaga ccacggcctg accccgaaac aggtggttgc aatcgcgtca | 6240 |
| cacgatgggg gaaagcaggc cctagaaacc gttcagcgac tcctgcccgt cctgtgccag | 6300 |
| gcccacggcc tgaccccgga ccaggtggtt gcaatcgcgt cacacgatgg gggaaagcag | 6360 |
| gccctagaaa ccgttcagcg actcctgccc gtcctgtgcc aggcccacgg cctgaccccc | 6420 |
| gcccaggttg tcgctattgc tagtaacggc ggaggcaaac aggcgctgga aacagttcag | 6480 |
| cgcctcttgc cggtcttgtg tcaggaccac ggcctgaccc cagaccaggt tgtggccatc | 6540 |
| gccagcaaca taggtggcaa gcaggccctc gaaaccgtcc agagactgtt accggttctc | 6600 |
| tgccaggacc acgcctgac ccccgaacag gttgtcgcta ttgctagtaa cggcggaggc | 6660 |
| aaacaggcgc tggaaacagt tcagcgcctc ttgccggtct tgtgtcaggc ccacggcctg | 6720 |
| accccgacc aggttgtcgc tattgctagt aacggcggag gcaaacaggc gctggaaaca | 6780 |
| gttcagcgct cttgccggt cttgtgtcag gcccacggcc tgaccccggc ccaggtggtt | 6840 |
| gcaatcgcgt cacacgatgg gggaaagcag gccctagaaa ccgttcagcg actcctgccc | 6900 |

```
gtcctgtgcc aggaccacgg cctgacccca gaccaggttg tggccatcgc cagcaacata    6960
ggtggcaagc aggccctcga aaccgtccag agactgttac cggttctctg ccaggaccac    7020
ggcctgaccc cggaacaggt ggttgcaatc gcgtcacacg atgggggaaa gcaggcccta    7080
gaaaccgttc agcgactcct gcccgtcctg tgccaggccc acggcctgac cccggaccag    7140
gtggttgcaa tcgcgtcaca cgatggggga agcaggccc tagaaaccgt tcagcgactc     7200
ctgcccgtcc tgtgccaggc ccacggcctg accccagccc aagttgtcgc gattgcaagc    7260
aacaacggag gcaaacaagc cttagaaaca gtccagagat tgttgccggt gctgtgccaa    7320
gaccacggcc tgaccccaga ccaggttgtg gccatcgcca gcaacatagg tggcaagcag    7380
gccctcgaaa ccgtccagag actgttaccg gttctctgcc aggaccacgg cctgaccccc    7440
gaacaggttg tcgctattgc tagtaacggc ggaggcaaac aggcgctgga aacagttcag    7500
cgcctcttgc cggtcttgtg tcaggcccac ggcctgacgc ctgagcaggt agtggctatt    7560
gcatccaacg gagggggcag acccgcactg gagtcaatcg tggcccagct ttcgaggccg    7620
gaccccgcgc tggccgcact cactaatgat catcttgtag cgctggcctg cctcggcgga    7680
cgtcctgcca tggatgcagt gaaaaaggga ttgccgcacg cgccggaatt gatcagatcc    7740
cagctagtga atctgaatt ggaagagaag aaatctgaac ttagacataa attgaaatat     7800
gtgccacatg aatatattga attgattgaa atcgcaagaa attcaactca ggatagaatc    7860
cttgaaatga aggtgatgga gttctttatg aaggtttatg gttatcgtgg taaacatttg    7920
ggtggatcaa ggaaaccaga cggagcaatt tatactgtcg gatctcctat tgattacggt    7980
gtgatcgttg atactaaggc atattcagga ggttataatc ttccaattgg tcaagcagat    8040
gaaatgcaaa gatatgtcga agagaatcaa acaagaaaca agcatatcaa ccctaatgaa    8100
tggtggaaag tctatccatc ttcagtaaca gaatttaagt tcttgtttgt gagtggtcat    8160
ttcaaaggaa actacaaagc tcagcttaca agattgaatc atatcactaa ttgtaatgga    8220
gctgttctta gtgtagaaga cttttgatt ggtggagaaa tgattaaagc tggtacattg     8280
acacttgagg aagtgagaag gaaatttaat aacggtgaga taaactttta aaaaatcagc    8340
ctcgactgtg ccttctagtt gcc                                            8363
```

<210> SEQ ID NO 47
<211> LENGTH: 8363
<212> TYPE: DNA
<213> ORGANISM: artificial sequence
<220> FEATURE:
<223> OTHER INFORMATION: TALEN-TCR-alpha2_R19 plasmid full length

<400> SEQUENCE: 47

```
agccatctgt tgtttgcccc tcccccgtgc cttccttgac cctggaaggt gccactccca      60
ctgtcctttc ctaataaaat gaggaaattg catcacaaca ctcaaccta tctcggtcta     120 ttcttttgat ttataaggga ttttgccgat ttcggcctat tggttaaaaa atgagctgat     180
ttaacaaaaa tttaacgcga attaattctg tggaatgtgt gtcagttagg gtgtggaaag     240
tccccaggct ccccagcagg cagaagtatg caaagcatgc atctcaatta gtcagcaacc     300
aggtgtggaa agtccccagg ctccccagca ggcagaagta tgcaaagcat gcatctcaat     360
tagtcagcaa ccatagtccc gcccctaact ccgcccatcc cgccctaac tccgcccagt      420 tccgcccatt ctccgcccca tggctgacta attttttta tttatgcaga ggccgaggcc      480
gcctctgcct ctgagctatt ccagaagtag tgaggaggct ttttggagg cctaggcttt      540
```

-continued

```
tgcaaaaagc tcccgggagc ttgtatatcc attttcggat ctgatcagca cgtgatgaaa      600
aagcctgaac tcaccgcgac gtctgtcgag aagtttctga tcgaaaagtt cgacagcgtt      660
tccgacctga tgcagctctc ggagggcgaa gaatctcgtg ctttcagctt cgatgtagga      720
gggcgtggat atgtcctgcg ggtaaatagc tgcgccgatg gtttctacaa agatcgttat      780
gtttatcggc actttgcatc ggccgcgctc ccgattccgg aagtgcttga cattggggaa      840
ttcagcgaga gcctgaccta ttgcatctcc cgccgtgcac agggtgtcac gttgcaagac      900
ctgcctgaaa ccgaactgcc cgctgttctg cagccggtcg cggaggccat ggatgcgatc      960
gctgcggccg atcttagcca gacgagcggg ttcggcccat tcggaccgca aggaatcggt     1020
caatacacta catggcgtga tttcatatgc gcgattgctg atccccatgt gtatcactgg     1080
caaactgtga tggacgacac cgtcagtgcg tccgtcgcgc aggctctcga tgagctgatg     1140 cttttgggccg aggactgccc cgaagtccgg cacctcgtgc acgcggattt cggctccaac     1200
aatgtcctga cggacaatgg ccgcataaca gcggtcattg actggagcga ggcgatgttc     1260
ggggattccc aatacgaggt cgccaacatc ttcttctgga ggccgtggtt ggcttgtatg     1320
gagcagcaga cgcgctactt cgagcggagg catccggagc ttgcaggatc gccgcggctc     1380
cgggcgtata tgctccgcat tggtcttgac caactctatc agagcttggt tgacggcaat     1440
ttcgatgatg cagcttgggc gcagggtcga tgcgacgcaa tcgtccgatc cggagccggg     1500
actgtcgggc gtacacaaat cgcccgcaga agcgcggccg tctggaccga tggctgtgta     1560
gaagtactcg ccgatagtgg aaaccgacgc cccagcactc gtccgagggc aaaggaatag     1620
cacgtgctac gagatttcga ttccaccgcc gccttctatg aaaggttggg cttcggaatc     1680
gttttccggg acgccggctg gatgatcctc cagcgcgggg atctcatgct ggagttcttc     1740
gcccacccca acttgtttat tgcagcttat aatggttaca aataaagcaa tagcatcaca     1800
aatttcacaa ataaagcatt tttttcactg cattctagtt gtggtttgtc caaactcatc     1860
aatgtatctt atcatgtctg tataccgtcg acctctagct agagcttggc gtaatcatgg     1920
tcattaccaa tgcttaatca gtgaggcacc tatctcagcg atctgtctat tcgttcatc      1980 catagttgcc tgactccccg tcgtgtagat aactacgata cgggagggct taccatctgg     2040
ccccagcgct gcgatgatac cgcgagaacc acgctcaccg gctccggatt tatcagcaat     2100
aaaccagcca gccggaaggg ccgagcgcag aagtggtcct gcaactttat ccgcctccat     2160
ccagtctatt aattgttgcc gggaagctag agtaagtagt tcgccagtta atagtttgcg     2220
caacgttgtt gccatcgcta caggcatcgt ggtgtcacgc tcgtcgtttg gtatggcttc     2280
attcagctcc ggttcccaac gatcaaggcg agttacatga tcccccatgt tgtgcaaaaa     2340
agcggttagc tccttcggtc ctccgatcgt tgtcagaagt aagttggccg cagtgttatc     2400
actcatggtt atggcagcac tgcataattc tcttactgtc atgccatccg taagatgctt     2460
ttctgtgact ggtgagtact caaccaagtc attctgagaa tagtgtatgc ggcgaccgag     2520
ttgctcttgc ccggcgtcaa tacgggataa taccgcgcca catagcagaa ctttaaaagt     2580
gctcatcatt ggaaaacgtt cttcggggcg aaaactctca aggatcttac cgctgttgag     2640
atccagttcg atgtaaccca ctcgtgcacc caactgatct tcagcatctt ttactttcac     2700
cagcgtttct gggtgagcaa aaacaggaag gcaaaatgcc gcaaaaaagg gaataagggc     2760
gacacggaaa tgttgaatac tcatattctt ccttttttcaa tattattgaa gcatttatca     2820
gggttattgt ctcatgagcg gatacatatt tgaatgtatt tagaaaaata aacaaatagg     2880
ggtcagtgtt acaaccaatt aaccaattct gaacattatc gcgagcccat ttatacctga     2940
```

```
atatggctca taacacccct tgctcatgac caaaatccct taacgtgagt tacgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactctttt ccgaaggtaa ctggcttcag cagagcgcag    3180
ataccaaata ctgttcttct agtgtagccg tagttagccc caccacttcaa gaactctgta    3240 gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcagggg gcggagccta tggaaaaacg ccagcaacgc ggccttttta    3660
cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggccttttg cgtttctaca aactcttttct    3900 gtgttgtaaa acgacggcca gtcttaagct cgggcccct gggcggttct gataacgagt    3960
aatcgttaat ccgcaaataa cgtaaaaacc cgcttcggcg gtttttttta tgggggagt    4020 ttagggaaag agcatttgtc agaatattta agggcgcctg tcactttgct tgatatatga    4080
gaattattta accttataaa tgagaaaaaa gcaacgcact ttaaataaga tacgttgctt    4140
tttcgattga tgaacaccta taattaaact attcatctat tatttatgat tttttgtata    4200
tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
tattaatagt aatcaattac ggggtcatta gttcatagcc catatatgga gttccgcgtt    4500
acataactta cggtaaatgg cccgcctggc tgaccgccca acgaccccg cccattgacg    4560 tcaataatga cgtatgttcc catagtaacg ccaatagga cttccattg acgtcaatgg    4620 gtggagtatt tacggtaaac tgcccacttg gcagtacatc aagtgtatca tatgccaagt    4680 acgccccta ttgacgtcaa tgacggtaaa tggcccgcct ggcattatgc ccagtacatg    4740
accttatggg actttcctac ttggcagtac atctacgtat tagtcatcgc tattaccatg    4800
gtgatgcggt tttggcagta catcaatggg cgtggatagc ggtttgactc acggggattt    4860
ccaagtctcc accccattga cgtcaatggg agtttgtttt ggcaccaaaa tcaacgggac    4920
tttccaaaat gtcgtaacaa ctccgcccca ttgacgcaaa tgggcggtag cgtgtacgg    4980 tgggaggtct atataagcag agctctctgg ctaactagag aacccactgc ttactggctt    5040
atcgaaatta atacgactca ctatagggaa gcttcttgtt cttttttgcag aagctcagaa    5100 taaacgctca actttggcct cgaggccacc atggcttcct cccctccaaa gaaaagaga    5160 aaggttgcgg ccgctgacta caaggatgac gacgataaaa gttggaagga cgcaagtggt    5220
tggtctagaa tgcatgcggc cccgcgacgg cgtgctgcgc aaccctccga cgcttcgccg    5280
```

```
gccgcgcagg tggatctacg cacgctcggc tacagtcagc agcagcaaga gaagatcaaa    5340
ccgaaggtgc gttcgacagt ggcgcagcac cacgaggcac tggtgggcca tgggtttaca    5400
cacgcgcaca tcgttgcgct cagccaacac ccggcagcgt tagggaccgt cgctgtcacg    5460
tatcagcaca taatcacggc gttgccgagg gcgacacacg aagacatcgt tggcgtcggc    5520
aaacagtggt ccggcgcacg cgccctggag gccttgctca cggatgcggg ggagttgaga    5580
ggtccgccgt tacagttgga cacaggccaa cttgtgaaga ttgcaaaacg tggcggcgtg    5640
accgcaatgg aggcagtgca tgcatcgcgc aatgcgctca cgggagcacc cctcaacctg    5700
accccggacc aggtggttgc aatcgcgtca cacgatgggg gaaagcaggc cctagaaacc    5760
gttcagcgac tcctgcccgt cctgtgccag gaccacggcc tgaccccgga acaggtggtt    5820
gcaatcgcgt cacacgatgg gggaaagcag gccctagaaa ccgttcagcg actcctgccc    5880
gtcctgtgcc aggcccacgg cctgaccccc gaccaggttg tcgctattgc tagtaacggc    5940
ggaggcaaac aggcgctgga aacagttcag cgcctcttgc cggtcttgtg tcaggcccac    6000
ggcctgaccc ccgcccaggt tgtcgctatt gctagtaacg gcggaggcaa acaggcgctg    6060
gaaacagttc agcgcctctt gccggtcttg tgtcaggacc acggcctgac cccagaccag    6120
gttgtggcca tcgccagcaa cataggtggc aagcaggccc tcgaaaccgt ccagagactg    6180
ttaccggttc tctgccagga ccacggcctg accccggaac aggtggttgc aatcgcgtca    6240
cacgatgggg gaaagcaggc cctagaaacc gttcagcgac tcctgcccgt cctgtgccag    6300
gcccacggcc tgaccccga ccaggttgtc gctattgcta gtaacggcgg aggcaaacag    6360
gcgctggaaa cagttcagcg cctcttgccg gtcttgtgtc aggcccacgg cctgaccccc    6420
gcccaggttg tcgctattgc tagtaacggc ggaggcaaac aggcgctgga aacagttcag    6480
cgcctcttgc cggtcttgtg tcaggaccac ggcctgaccc cgaccaggt tgtcgctatt    6540 gctagtaacg gcggaggcaa acaggcgctg gaaacagttc agcgcctctt gccggtcttg    6600
tgtcaggacc acgcctgac cccagaacaa gttgtcgcga ttgcaagcaa caacggaggc    6660
aaacaagcct tagaaacagt ccagagattg ttgccggtgc tgtgccaagc ccacggcctg    6720 accccgacc aggttgtcgc tattgctagt aacggcggag gcaaacaggc gctggaaaca    6780
gttcagcgcc tcttgccggt cttgtgtcag gcccacggcc tgaccccagc caagttgtc    6840 gcgattgcaa gcaacaacgg aggcaaacaa gccttagaaa cagtccagag attgttgccg    6900
gtgctgtgcc aagaccacgg cctgacccca gaccaggttg tggccatcgc cagcaacata    6960
ggtggcaagc aggccctcga aaccgtccag agactgttac cggttctctg ccaggaccac    7020
ggcctgaccc cggaacaggt ggttgcaatc gcgtcacacg atgggggaaa gcaggcccta    7080
gaaaccgttc agcgactcct gcccgtcctg tgccaggccc acggcctgac cccagaccag    7140
gttgtggcca tcgccagcaa cataggtggc aagcaggccc tcgaaaccgt ccagagactg    7200
ttaccggttc tctgccaggc ccacggcctg accccggccc aggtggttgc aatcgcgtca    7260
cacgatgggg gaaagcaggc cctagaaacc gttcagcgac tcctgcccgt cctgtgccag    7320
gaccacggcc tgaccccaga ccaggttgtg gccatcgcca gcaacatagg tggcaagcag    7380
gccctcgaaa ccgtccagag actgttaccg gttctctgcc aggaccacgg cctgacccc    7440 gaacaggttg tcgctattgc tagtaacggc ggaggcaaac aggcgctgga aacagttcag    7500
cgcctcttgc cggtcttgtg tcaggcccac ggcctgacgc ctgagcaggt agtggctatt    7560
gcatccaacg gaggggcag acccgcactg gagtcaatcg tggcccagct ttcgaggccg    7620
gaccccgcgc tggccgcact cactaatgat catcttgtag cgctggcctg cctcggcgga    7680
```

-continued

```
cgtcctgcca tggatgcagt gaaaaaggga ttgccgcacg cgccggaatt gatcagatcc      7740
cagctagtga atctgaatt ggaagagaag aaatctgaac ttagacataa attgaaatat      7800
gtgccacatg aatatattga attgattgaa atcgcaagaa attcaactca ggatagaatc      7860
cttgaaatga aggtgatgga gttctttatg aaggtttatg gttatcgtgg taaacatttg      7920
ggtggatcaa ggaaaccaga cggagcaatt tatactgtcg gatctcctat tgattacggt      7980
gtgatcgttg atactaaggc atattcagga ggttataatc ttccaattgg tcaagcagat      8040
gaaatgcaaa gatatgtcga agagaatcaa acaagaaaca agcatatcaa ccctaatgaa      8100
tggtggaaag tctatccatc ttcagtaaca gaatttaagt tcttgtttgt gagtggtcat      8160
ttcaaaggaa actacaaagc tcagcttaca agattgaatc atatcactaa ttgtaatgga      8220
gctgttctta gtgtagaaga cttttgatt ggtggagaaa tgattaaagc tggtacattg      8280
acacttgagg aagtgagaag gaaatttaat aacggtgaga taaacttta aaaaatcagc      8340 ctcgactgtg ccttctagtt gcc                                             8363

<210> SEQ ID NO 48
<211> LENGTH: 8363
<212> TYPE: DNA
<213> ORGANISM: artificial sequence
<220> FEATURE:
<223> OTHER INFORMATION: TALEN-TCR-beta1_L19 plasmid full length

<400> SEQUENCE: 48
agccatctgt tgtttgcccc tcccccgtgc cttccttgac cctggaaggt gccactccca        60
ctgtcctttc ctaataaaat gaggaaattg catcacaaca ctcaaccta tctcggtcta       120 ttcttttgat ttataaggga ttttgccgat ttcggcctat tggttaaaaa atgagctgat       180
ttaacaaaaa tttaacgcga attaattctg tggaatgtgt gtcagttagg gtgtggaaag       240
tccccaggct ccccagcagg cagaagtatg caaagcatgc atctcaatta gtcagcaacc       300
aggtgtggaa agtccccagg ctccccagca ggcagaagta tgcaaagcat gcatctcaat       360
tagtcagcaa ccatagtccc gcccctaact ccgcccatcc cgcccctaac tccgcccagt       420
tccgcccatt ctccgcccca tggctgacta attttttta tttatgcaga ggccgaggcc       480
gcctctgcct ctgagctatt ccagaagtag tgaggaggct ttttggagg cctaggcttt       540 tgcaaaaagc tcccgggagc ttgtatatcc attttcggat ctgatcagca cgtgatgaaa       600
aagcctgaac tcaccgcgac gtctgtcgag aagtttctga tcgaaaagtt cgacagcgtt       660
tccgacctga tgcagctctc ggagggcgaa gaatctcgtg ctttcagctt cgatgtagga       720
gggcgtggat atgtcctgcg ggtaaatagc tgcgccgatg gtttctacaa agatcgttat       780
gtttatcggc actttgcatc ggccgcgctc ccgattccgg aagtgcttga cattgggaa       840 ttcagcgaga gcctgaccta ttgcatctcc cgccgtgcac agggtgtcac gttgcaagac       900
ctgcctgaaa ccgaactgcc cgctgttctg cagccggtcg cggaggccat ggatgcgatc       960
gctgcggccg atcttagcca cgagcgggg ttcggcccat tcggaccgca aggaatcggt      1020
caatacacta catggcgtga tttcatatgc gcgattgctg atccccatgt gtatcactgg      1080
caaactgtga tggacgacac cgtcagtgcg tccgtcgcgc aggctctcga tgagctgatg      1140
ctttgggccg aggactgccc cgaagtccgg cacctcgtgc acgcggattt cggctccaac      1200
aatgtcctga cggacaatgg ccgcataaca gcggtcattg actggagcga ggcgatgttc      1260
ggggattccc aatacgaggt cgccaacatc ttcttctgga ggccgtggtt ggcttgtatg      1320
```

```
gagcagcaga cgcgctactt cgagcggagg catccggagc ttgcaggatc gccgcggctc    1380
cgggcgtata tgctccgcat tggtcttgac caactctatc agagcttggt tgacggcaat    1440
ttcgatgatg cagcttgggc gcagggtcga tgcgacgcaa tcgtccgatc cggagccggg    1500
actgtcgggc gtacacaaat cgcccgcaga agcgcggccg tctggaccga tggctgtgta    1560
gaagtactcg ccgatagtgg aaaccgacgc cccagcactc gtccgagggc aaaggaatag    1620
cacgtgctac gagatttcga ttccaccgcc gccttctatg aaaggttggg cttcggaatc    1680
gttttccggg acgccggctg gatgatcctc cagcgcgggg atctcatgct ggagttcttc    1740
gcccacccca acttgtttat tgcagcttat aatggttaca aataaagcaa tagcatcaca    1800
aatttcacaa ataaagcatt tttttcactg cattctagtt gtggtttgtc caaactcatc    1860
aatgtatctt atcatgtctg tataccgtcg acctctagct agagcttggc gtaatcatgg    1920
tcattaccaa tgcttaatca gtgaggcacc tatctcagcg atctgtctat ttcgttcatc    1980
catagttgcc tgactcccng tcgtgtagat aactacgata cgggagggct taccatctgg    2040
ccccagcgct gcgatgatac cgcgagaacc acgctcaccg gctccggatt tatcagcaat    2100
aaaccagcca gccggaaggg ccgagcgcag aagtggtcct gcaactttat ccgcctccat    2160
ccagtctatt aattgttgcc gggaagctag agtaagtagt tcgccagtta atagtttgcg    2220
caacgttgtt gccatcgcta caggcatcgt ggtgtcacgc tcgtcgtttg gtatggcttc    2280
attcagctcc ggttcccaac gatcaaggcg agttacatga tcccccatgt tgtgcaaaaa    2340
agcggttagc tccttcggtc ctccgatcgt tgtcagaagt aagttggccg cagtgttatc    2400
actcatggtt atggcagcac tgcataattc tcttactgtc atgccatccg taagatgctt    2460
ttctgtgact ggtgagtact caaccaagtc attctgagaa tagtgtatgc ggcgaccgag    2520
ttgctcttgc ccggcgtcaa tacgggataa taccgcgcca catagcagaa ctttaaaagt    2580
gctcatcatt ggaaaacgtt cttcgggggcg aaaactctca aggatcttac cgctgttgag    2640
atccagttcg atgtaaccca ctcgtgcacc caactgatct tcagcatctt ttactttcac    2700
cagcgtttct gggtgagcaa aaacaggaag gcaaaatgcc gcaaaaaagg gaataagggc    2760
gacacggaaa tgttgaatac tcatattctt cctttttcaa tattattgaa gcatttatca    2820
gggttattgt ctcatgagcg gatacatatt tgaatgtatt tagaaaaata aacaaatagg    2880
ggtcagtgtt acaaccaatt aaccaattct gaacattatc gcgagcccat ttatacctga    2940
atatggctca taacacccct tgctcatgac caaaatccct taacgtgagt acgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggttttgt    3120
ttgccggatc aagagctacc aactcttttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct ccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg gccttttgct cacatgttct ttcctgcgtt atcccctgat    3720
```

```
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggccttttg cgtttctaca aactctttct     3900
gtgttgtaaa acgacggcca gtcttaagct cgggcccct gggcggttct gataacgagt     3960
aatcgttaat ccgcaaataa cgtaaaaacc cgcttcggcg gtttttta tgggggagt       4020 ttagggaaag agcatttgtc agaatattta agggcgcctg tcactttgct tgatatatga    4080
gaattattta accttataaa tgagaaaaaa gcaacgcact ttaaataaga tacgttgctt    4140
tttcgattga tgaacaccta taattaaact attcatctat tatttatgat tttttgtata   4200
tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
tattaatagt aatcaattac ggggtcatta gttcatagcc catatatgga gttccgcgtt    4500
acataactta cggtaaatgg cccgcctggc tgaccgccca acgaccccg cccattgacg     4560 tcaataatga cgtatgttcc catagtaacg ccaataggga ctttccattg acgtcaatgg    4620
gtggagtatt tacggtaaac tgcccacttg gcagtacatc aagtgtatca tatgccaagt    4680
acgcccccta ttgacgtcaa tgacggtaaa tggcccgcct ggcattatgc ccagtacatg    4740
acctatgggg actttcctac ttggcagtac atctacgtat tagtcatcgc tattaccatg    4800
gtgatgcggt tttggcagta catcaatggg cgtggatagc ggtttgactc acggggattt    4860
ccaagtctcc accccattga cgtcaatggg agtttgtttt ggcaccaaaa tcaacgggac    4920
tttccaaaat gtcgtaacaa ctccgcccca ttgacgcaaa tgggcggtag gcgtgtacgg    4980
tgggaggtct atataagcag agctctctgg ctaactagag aacccactgc ttactggctt    5040
atcgaaatta atacgactca ctatagggaa gcttcttgtt cttttgcag aagctcagaa     5100 taaacgctca actttggcct cgaggccacc atggcttcct cccctccaaa gaaaagaga     5160 aaggttgcgg ccgctgacta caaggatgac gacgataaaa gttggaagga cgcaagtggt    5220
tggtctagaa tgcatgcggc cccgcgacgg cgtgctgcgc aaccctccga cgcttcgccg    5280
gccgcgcagg tggatctacg cacgctcggc tacagtcagc agcagcaaga gaagatcaaa    5340
ccgaaggtgc gttcgacagt ggcgcagcac cacgaggcac tggtgggcca tgggtttaca    5400
cacgcgcaca tcgttgcgct cagccaacac ccggcagcgt tagggaccgt cgctgtcacg    5460
tatcagcaca taatcacggc gttgccagag gcgacacacg aagacatcgt tggcgtcggc    5520
aaacagtggt ccgcgcacg cgccctggag gccttgctca cggatgcggg ggagttgaga    5580
ggtccgccgt tacagttgga cacaggccaa cttgtgaaga ttgcaaaacg tggcggcgtg    5640
accgcaatgg aggcagtgca tgcatcgcgc aatgcgctca cggagcacac cctcaacctg    5700
accccagacc aagttgtcgc gattgcaagc aacaacggag gcaaacaagc cttagaaaca    5760
gtccagagat tgttgccggt gctgtgccaa gaccacggcc tgaccccga acaggttgtc      5820 gctattgcta gtaacggcgg aggcaaacag gcgctgaaa cagttcagcg cctcttgccg     5880
gtcttgtgtc aggcccacgg cctgaccccc gaccaggttg tcgctattgc tagtaacggc    5940
ggaggcaaac aggcgctgga aacagttcag cgcctcttgc cggtcttgtg tcaggcccac    6000
ggcctgaccc cggcccaggt ggttgcaatc gcgtcacacg atgggggaaa gcaggcccta    6060
```

```
gaaaccgttc agcgactcct gcccgtcctg tgccaggacc acggcctgac cccggaccag      6120
gtggttgcaa tcgcgtcaca cgatggggga aagcaggccc tagaaaccgt tcagcgactc      6180
ctgcccgtcc tgtgccagga ccacggcctg accccggaac aggtggttgc aatcgcgtca      6240
cacgatgggg gaaagcaggc cctagaaacc gttcagcgac tcctgcccgt cctgtgccag      6300
gcccacggcc tgaccccaga ccaggttgtg ccatcgcca gcaacatagg tggcaagcag       6360
gccctcgaaa ccgtccagag actgttaccg gttctctgcc aggccacgg cctgaccccg       6420
gcccaggtgg ttgcaatcgc gtcacacgat ggggaaagc aggccctaga aaccgttcag       6480
cgactcctgc ccgtcctgtg ccaggaccac ggcctgaccc cggaccaggt ggttgcaatc      6540
gcgtcacacg atgggggaaa gcaggcccta gaaaccgttc agcgactcct gcccgtcctg      6600
tgccaggacc acggcctgac cccggaacag gtggttgcaa tcgcgtcaca cgatggggga      6660
aagcaggccc tagaaaccgt tcagcgactc ctgcccgtcc tgtgccaggc ccacggcctg      6720
accccagacc aagttgtcgc gattgcaagc aacaacggag gcaaacaagc cttagaaaca      6780
gtccagagat tgttgcctgt gctgtgccaa gcccacggcc tgaccccagc ccaggttgtg      6840
gccatcgcca gcaacatagg tggcaagcag gccctcgaaa ccgtccagag actgttaccg      6900
gttctctgcc aggaccacgg cctgaccccga gaccaagttg tcgcgattgc aagcaacaac     6960
ggaggcaaac aagccttaga aacagtccag agattgttgc cggtgctgtg ccaagaccac      7020
ggcctgaccc cagaacaagt tgtcgcgatt gcaagcaaca acggaggcaa acaagccttag    7080
gaaacagtcc agagattgtt ccggtgctg tgccaagccc acggcctgac ccccgaccag      7140
gttgtcgcta ttgctagtaa cggcggaggc aaacaggcgc tggaaacagt tcagcgcctc     7200
ttgccggtct tgtgtcaggc ccacggcctg accccggccc aggtggttgc aatcgcgtca     7260
cacgatgggg gaaagcaggc cctagaaacc gttcagcgac tcctgcccgt cctgtgccag      7320
gaccacggcc tgaccccaga ccaagttgtc gcgattgcaa gcaacaacgg aggcaaacaa     7380
gccttagaaa cagtccagag attgttgccg gtgctgtgcc aagaccacgg cctgaccccg      7440
gaacaggtgg ttgcaatcgc gtcacacgat ggggaaagc aggccctaga aaccgttcag      7500
cgactcctgc ccgtcctgtg ccaggcccac ggcctgacgc ctgagcaggt agtggctatt     7560
gcatccaacg gaggggggcag acccgcactg gagtcaatcg tggcccagct ttcgaggccg    7620
gaccccgcgc tggccgcact cactaatgat catcttgtag cgctggcctg cctcggcgga     7680
cgtcctgcca tggatgcagt gaaaaaggga ttgccgcacg cgccggaatt gatcagatcc     7740
cagctagtga atctgaatt ggaagagaag aaatctgaac ttagacataa attgaaatat     7800
gtgccacatg aatatattga attgattgaa atcgcaagaa attcaactca ggatagaatc     7860
cttgaaatga aggtgatgga gttctttatg aaggtttatg gttatcgtgg taaacatttg     7920
ggtggatcaa ggaaaccaga cggagcaatt tatactgtcg gatctcctat tgattacggt     7980
gtgatcgttg atactaaggc atattcagga ggttataatc ttccaattgg tcaagcagat     8040
gaaatgcaaa gatatgtcga agagaatcaa acaagaaaca agcatatcaa ccctaatgaa     8100
tggtggaaag tctatccatc ttcagtaaca gaatttaagt tcttgttgt gagtggtcat      8160
ttcaaaggaa actacaaagc tcagcttaca agattgaatc atatcactaa ttgtaatgga     8220
gctgttctta gtgtagaaga gcttttgatt ggtggagaaa tgattaaagc tggtacattg     8280
acacttgagg aagtgagaag gaaatttaat aacggtgaga taaacttta aaaaatcagc     8340
ctcgactgtg ccttctagtt gcc                                             8363
```

<210> SEQ ID NO 49
<211> LENGTH: 8363
<212> TYPE: DNA
<213> ORGANISM: artificial sequence
<220> FEATURE:
<223> OTHER INFORMATION: TALEN-TCR-beta1_R19 plasmid full length

<400> SEQUENCE: 49

| | | | | | |
|---|---|---|---|---|---|
| agccatctgt | tgtttgcccc | tcccccgtgc | cttccttgac | cctggaaggt | gccactccca | 60 |
| ctgtcctttc | ctaataaaat | gaggaaattg | catcacaaca | ctcaaccctd | tctcggtcta | 120 |
| ttcttttgat | ttataaggga | ttttgccgat | ttcggcctat | tggttaaaaa | atgagctgat | 180 |
| ttaacaaaaa | tttaacgcga | attaattctg | tggaatgtgt | gtcagttagg | gtgtggaaag | 240 |
| tccccaggct | ccccagcagg | cagaagtatg | caaagcatgc | atctcaatta | gtcagcaacc | 300 |
| aggtgtggaa | agtccccagg | ctccccagca | ggcagaagta | tgcaaagcat | gcatctcaat | 360 |
| tagtcagcaa | ccatagtccc | gcccctaact | ccgcccatcc | cgcccctaac | tccgcccagt | 420 |
| tccgcccatt | ctccgcccca | tggctgacta | atttttttta | tttatgcaga | ggccgaggcc | 480 |
| gcctctgcct | ctgagctatt | ccagaagtag | tgaggaggct | tttttggagg | cctaggcttt | 540 |
| tgcaaaaagc | tcccgggagc | ttgtatatcc | attttcggat | ctgatcagca | cgtgatgaaa | 600 |
| aagcctgaac | tcaccgcgac | gtctgtcgag | aagtttctga | tcgaaaagtt | cgacagcgtt | 660 |
| tccgacctga | tgcagctctc | ggagggcgaa | gaatctcgtg | ctttcagctt | cgatgtagga | 720 |
| gggcgtggat | atgtcctgcg | ggtaaatagc | tgcgccgatg | gtttctacaa | agatcgttat | 780 |
| gtttatcggc | actttgcatc | ggccgcgctc | ccgattccgg | aagtgcttga | cattggggaa | 840 |
| ttcagcgaga | gcctgaccta | ttgcatctcc | cgccgtgcac | agggtgtcac | gttgcaagac | 900 |
| ctgcctgaaa | ccgaactgcc | cgctgttctg | cagccggtcg | cggaggccat | ggatgcgatc | 960 |
| gctgcggccg | atcttagcca | gacgagcggg | ttcggcccat | tcggaccgca | aggaatcggt | 1020 |
| caatacacta | catggcgtga | tttcatatgc | gcgattgctg | atccccatgt | gtatcactgg | 1080 |
| caaactgtga | tggacgacac | cgtcagtgcg | tccgtcgcgc | aggctctcga | tgagctgatg | 1140 |
| ctttgggccg | aggactgccc | cgaagtccgg | cacctcgtgc | acgcggattt | cggctccaac | 1200 |
| aatgtcctga | cggacaatgg | ccgcataaca | gcggtcattg | actggagcga | ggcgatgttc | 1260 |
| ggggattccc | aatacgaggt | cgccaacatc | ttcttctgga | ggccgtggtt | ggcttgtatg | 1320 |
| gagcagcaga | cgcgctactt | cgagcggagg | catccggagc | ttgcaggatc | gccgcggctc | 1380 |
| cgggcgtata | tgctccgcat | tggtcttgac | caactctatc | agagcttggt | tgacggcaat | 1440 |
| ttcgatgatg | cagcttgggc | gcagggtcga | tgcgacgcaa | tcgtccgatc | cggagccggg | 1500 |
| actgtcgggc | gtacacaaat | cgcccgcaga | agcgcggccg | tctggaccga | tggctgtgta | 1560 |
| gaagtactcg | ccgatagtgg | aaaccgacgc | cccagcactc | gtccgagggc | aaaggaatag | 1620 |
| cacgtgctac | gagatttcga | ttccaccgcc | gccttctatg | aaaggttggg | cttcggaatc | 1680 |
| gttttccggg | acgccggctg | gatgatcctc | cagcgcgggg | atctcatgct | ggagttcttc | 1740 |
| gcccacccca | acttgtttat | tgcagcttat | aatggttaca | aataaagcaa | tagcatcaca | 1800 |
| aatttcacaa | ataaagcatt | ttttcactg | cattctagtt | gtggtttgtc | caaactcatc | 1860 |
| aatgtatctt | atcatgtctg | tataccgtcg | acctctagct | agagcttggc | gtaatcatgg | 1920 |
| tcattaccaa | tgcttaatca | gtgaggcacc | tatctcagcg | atctgtctat | ttcgttcatc | 1980 |
| catagttgcc | tgactccccg | tcgtgtagat | aactacgata | cgggagggct | taccatctgg | 2040 |
| ccccagcgct | gcgatgatac | cgcgagaacc | acgctcaccg | gctccggatt | tatcagcaat | 2100 |

```
aaaccagcca gccggaaggg ccgagcgcag aagtggtcct gcaactttat ccgcctccat    2160
ccagtctatt aattgttgcc gggaagctag agtaagtagt tcgccagtta atagtttgcg    2220
caacgttgtt gccatcgcta caggcatcgt ggtgtcacgc tcgtcgtttg gtatggcttc    2280
attcagctcc ggttcccaac gatcaaggcg agttacatga tccccatgt tgtgcaaaaa    2340 agcggttagc tccttcggtc ctccgatcgt tgtcagaagt aagttggccg cagtgttatc    2400
actcatggtt atggcagcac tgcataattc tcttactgtc atgccatccg taagatgctt    2460
ttctgtgact ggtgagtact caaccaagtc attctgagaa tagtgtatgc ggcgaccgag    2520
ttgctcttgc ccggcgtcaa tacgggataa taccgcgcca catagcagaa ctttaaaagt    2580
gctcatcatt ggaaaacgtt cttcggggcg aaaactctca aggatcttac cgctgttgag    2640
atccagttcg atgtaaccca ctcgtgcacc caactgatct tcagcatctt ttactttcac    2700
cagcgtttct gggtgagcaa aaacaggaag gcaaaatgcc gcaaaaaagg gaataagggc    2760
gacacggaaa tgttgaatac tcatattctt cctttttcaa tattattgaa gcatttatca    2820
gggttattgt ctcatgagcg gatacatatt tgaatgtatt tagaaaaata aacaaatagg    2880
ggtcagtgtt acaaccaatt aaccaattct gaacattatc gcgagcccat ttatacctga    2940
atatggctca taacacccct tgctcatgac caaaatccct taacgtgagt tacgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactcttttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggcctttttg cgtttctaca aactctttct    3900
gtgttgtaaa acgacggcca gtcttaagct cgggcccct gggcggttct gataacgagt    3960
aatcgttaat ccgcaaataa cgtaaaaacc cgcttcggcg gtttttttta tggggggagt    4020
ttagggaaag agcatttgtc agaatattta agggcgcctg tcactttgct tgatatatga    4080
gaattattta accttataaa tgagaaaaaa gcaacgcact ttaaataaga tacgttgctt    4140
tttcgattga tgaacaccta taattaaact attcatctat tatttatgat ttttgtata    4200 tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
tattaatagt aatcaattac ggggtcatta gttcatagcc catatatgga gttccgcgtt    4500
```

```
acataactta cggtaaatgg cccgcctggc tgaccgccca acgaccccg cccattgacg    4560 tcaataatga cgtatgttcc catagtaacg ccaatagggga ctttccattg acgtcaatgg   4620
gtggagtatt tacggtaaac tgcccacttg gcagtacatc aagtgtatca tatgccaagt   4680 acgccccta ttgacgtcaa tgacggtaaa tggcccgcct ggcattatgc ccagtacatg    4740
accttatggg actttcctac ttggcagtac atctacgtat tagtcatcgc tattaccatg   4800
gtgatgcggt tttggcagta catcaatggg cgtggatagc ggtttgactc acggggattt   4860
ccaagtctcc accccattga cgtcaatggg agtttgtttt ggcaccaaaa tcaacgggac   4920
tttccaaaat gtcgtaacaa ctccgcccca ttgacgcaaa tgggcggtag gcgtgtacgg   4980
tgggaggtct atataagcag agctctctgg ctaactagag aacccactgc ttactggctt   5040
atcgaaatta atacgactca ctataggaa gcttcttgtt cttttttgcag aagctcagaa    5100 taaacgctca actttggcct cgaggccacc atggcttcct cccctccaaa gaaaaagaga    5160
aaggttgcgg ccgctgacta caaggatgac gacgataaaa gttggaagga cgcaagtggt   5220
tggtctagaa tgcatgcggc cccgcgacgg cgtgctgcgc aaccctccga cgcttcgccg   5280
gccgcgcagg tggatctacg cacgctcggc tacagtcagc agcagcaaga gaagatcaaa   5340
ccgaaggtgc gttcgacagt ggcgcagcac cacgaggcac tggtgggcca tgggtttaca   5400
cacgcgcaca tcgttgcgct cagccaacac ccggcagcgt tagggaccgt cgctgtcacg   5460
tatcagcaca taatcacggc gttgccagag gcgacacacg aagacatcgt tggcgtcggc   5520
aaacagtggt ccggcgcacg cgccctggag gccttgctca cggatgcggg ggagttgaga   5580
ggtccgccgt tacagttgga cacaggccaa cttgtgaaga ttgcaaaacg tggcggcgtg   5640
accgcaatgg aggcagtgca tgcatcgcgc aatgcgctca cgggagcacc cctcaacctg   5700
accccagacc aagttgtcgc gattgcaagc aacaacggag gcaaacaagc cttagaaaca   5760
gtccagagat tgttgccggt gctgtgccaa gaccacggcc tgaccccga acaggttgtc    5820 gctattgcta gtaacggcgg aggcaaacag gcgctggaaa cagttcagcg cctcttgccg   5880
gtcttgtgtc aggcccacgg cctgaccca gaccaagttg tcgcgattgc aagcaacaac    5940
ggaggcaaac aagccttaga aacagtccag agattgttgc ctgtgctgtg ccaagcccac   6000
ggcctgaccc cagcccaagt tgtcgcgatt gcaagcaaca acggaggcaa acaagcctta   6060
gaaacagtcc agagattgtt gccggtgctg tgccaagacc acggcctgac cccagaccaa   6120
gttgtcgcga ttgcaagcaa caacggaggc aaacaagcct tagaaacagt ccagagattg   6180
ttgccggtgc tgtgccaaga ccacggcctg accccagaac aggttgtggc catcgccagc   6240
aacataggtg gcaagcaggc cctcgaaacc gtccagagac tgttaccggt tctctgccag   6300
gcccacggct gaccccaga ccaagttgtc gcgattgcaa gcaacaacgg aggcaaacaa    6360
gccttagaaa cagtccagag attgttgcct gtgctgtgcc aagcccacgg cctgacccca   6420
gcccaggttg tggccatcgc cagcaacata ggtggcaagc aggccctcga accgtccag    6480 agactgttac cggttctctg ccaggaccac ggcctgaccc ccgaccaggt tgtcgctatt   6540
gctagtaacg gcggaggcaa acaggcgctg aaacagttc agcgcctctt gccggtcttg    6600
tgtcaggacc acgcctgac cccggaacag gtggttgcaa tcgcgtcaca cgatggggga    6660
aagcaggccc tagaaaccgt tcagcgactc ctgcccgtcc tgtgccaggc ccacggcctg   6720 accccgacc aggttgtcgc tattgctagt aacggcggag gcaaacaggc gctgaaaaca    6780
gttcagcgcc tcttgccggt cttgtgtcag gcccacggcc tgaccccggc ccaggtggtt   6840
```

| | |
|---|---|
| gcaatcgcgt cacacgatgg gggaaagcag gccctagaaa ccgttcagcg actcctgccc | 6900 |
| gtcctgtgcc aggaccacgg cctgaccccc gaccaggttg tcgctattgc tagtaacggc | 6960 |
| ggaggcaaac aggcgctgga aacagttcag cgcctcttgc cggtcttgtg tcaggaccac | 7020 |
| ggcctgaccc cagaacaagt tgtcgcgatt gcaagcaaca acggaggcaa acaagcctta | 7080 |
| gaaacagtcc agagattgtt gccggtgctg tgccaagccc acggcctgac cccggaccag | 7140 |
| gtggttgcaa tcgcgtcaca cgatggggga agcaggccc tagaaaccgt tcagcgactc | 7200 |
| ctgcccgtcc tgtgccaggc ccacggcctg accccgccc aggttgtcgc tattgctagt | 7260 |
| aacggcggag gcaaacaggc gctggaaaca gttcagcgcc tcttgccggt cttgtgtcag | 7320 |
| gaccacggcc tgaccccga ccaggttgtc gctattgcta gtaacggcgg aggcaaacag | 7380 |
| gcgctggaaa cagttcagcg cctcttgccg tcttgtgtc aggaccacgg cctgaccccg | 7440 |
| gaacaggtgg ttgcaatcgc gtcacacgat gggggaaagc aggccctaga aaccgttcag | 7500 |
| cgactcctgc ccgtcctgtg ccaggccac ggcctgacgc ctgagcaggt agtggctatt | 7560 |
| gcatccaacg gaggggcag acccgcactg gagtcaatcg tggcccagct ttcgaggccg | 7620 |
| gaccccgcgc tggccgcact cactaatgat catcttgtag cgctggcctg cctcggcgga | 7680 |
| cgtcctgcca tggatgcagt gaaaaaggga ttgccgcacg cgccggaatt gatcagatcc | 7740 |
| cagctagtga atctgaatt ggaagagaag aaatctgaac ttagacataa attgaaatat | 7800 |
| gtgccacatg aatatattga attgattgaa atcgcaagaa attcaactca ggatagaatc | 7860 |
| cttgaaatga aggtgatgga gttctttatg aaggtttatg ttatcgtgg taaacatttg | 7920 |
| ggtggatcaa ggaaaccaga cggagcaatt tatactgtcg gatctcctat tgattacggt | 7980 |
| gtgatcgttg atactaaggc atattcagga ggttataatc ttccaattgg tcaagcagat | 8040 |
| gaaatgcaaa gatatgtcga agagaatcaa acaagaaaca agcatatcaa ccctaatgaa | 8100 |
| tggtggaaag tctatccatc ttcagtaaca gaatttaagt tcttgtttgt gagtggtcat | 8160 |
| ttcaaaggaa actacaaagc tcagcttaca agattgaatc atatcactaa ttgtaatgga | 8220 |
| gctgttctta gtgtagaaga gcttttgatt ggtggagaaa tgattaaagc tggtacattg | 8280 |
| acacttgagg aagtgagaag gaaatttaat aacggtgaga taaactttta aaaaatcagc | 8340 |
| ctcgactgtg ccttctagtt gcc | 8363 |

<210> SEQ ID NO 50
<211> LENGTH: 8363
<212> TYPE: DNA
<213> ORGANISM: artificial sequence
<220> FEATURE:
<223> OTHER INFORMATION: TALEN-TCR-beta3_L19 plasmid full length

<400> SEQUENCE: 50

| | |
|---|---|
| agccatctgt tgtttgcccc tccccgtgc cttccttgac cctggaaggt gccactccca | 60 |
| ctgtcctttc ctaataaaat gaggaaattg catcacaaca ctcaaccta tctcggtcta | 120 |
| ttcttttgat ttataaggga ttttgccgat ttcggcctat tggttaaaaa atgagctgat | 180 |
| ttaacaaaaa tttaacgcga attaattctg tggaatgtgt gtcagttagg gtgtggaaag | 240 |
| tccccaggct ccccagcagg cagaagtatg caaagcatgc atctcaatta gtcagcaacc | 300 |
| aggtgtggaa agtccccagg ctccccagca ggcagaagta tgcaaagcat gcatctcaat | 360 |
| tagtcagcaa ccatagtccc gcccctaact ccgcccatcc cgcccctaac tccgcccagt | 420 |
| tccgcccatt ctccgcccca tggctgacta attttttta tttatgcaga ggccgaggcc | 480 |
| gcctctgcct ctgagctatt ccagaagtag tgaggaggct ttttggagg cctaggcttt | 540 |

```
tgcaaaaagc tcccgggagc ttgtatatcc attttcggat ctgatcagca cgtgatgaaa    600
aagcctgaac tcaccgcgac gtctgtcgag aagtttctga tcgaaaagtt cgacagcgtt    660
tccgacctga tgcagctctc ggagggcgaa gaatctcgtg ctttcagctt cgatgtagga    720
gggcgtggat atgtcctgcg ggtaaatagc tgcgccgatg gtttctacaa agatcgttat    780
gtttatcggc actttgcatc ggccgcgctc ccgattccgg aagtgcttga cattggggaa    840
ttcagcgaga gcctgaccta ttgcatctcc cgccgtgcac agggtgtcac gttgcaagac    900
ctgcctgaaa ccgaactgcc cgctgttctg cagccggtcg cggaggccat ggatgcgatc    960
gctgcggccg atcttagcca gacgagcggg ttcggcccat tcggaccgca aggaatcggt   1020
caatacacta catggcgtga tttcatatgc gcgattgctg atccccatgt gtatcactgg   1080
caaactgtga tggacgacac cgtcagtgcg tccgtcgcgc aggctctcga tgagctgatg   1140
ctttgggccg aggactgccc cgaagtccgg cacctcgtgc acgcggattt cggctccaac   1200
aatgtcctga cggacaatgg ccgcataaca gcggtcattg actggagcga ggcgatgttc   1260
ggggattccc aatacgaggt cgccaacatc ttcttctgga ggccgtggtt ggcttgtatg   1320
gagcagcaga cgcgctactt cgagcggagg catccggagc ttgcaggatc gccgcggctc   1380
cgggcgtata tgctccgcat tggtcttgac caactctatc agagcttggt tgacggcaat   1440
ttcgatgatg cagcttgggc gcagggtcga tgcgacgcaa tcgtccgatc cggagccggg   1500
actgtcgggc gtacacaaat cgcccgcaga agcgcggccg tctggaccga tggctgtgta   1560
gaagtactcg ccgatagtgg aaaccgacgc cccagcactc gtccgagggc aaaggaatag   1620
cacgtgctac gagatttcga ttccaccgcc gccttctatg aaaggttggg cttcggaatc   1680
gttttccggg acgccggctg gatgatcctc cagcgcgggg atctcatgct ggagttcttc   1740
gcccacccca acttgtttat tgcagcttat aatggttaca aataaagcaa tagcatcaca   1800
aatttcacaa ataaagcatt tttttcactg cattctagtt gtggtttgtc caaactcatc   1860
aatgtatctt atcatgtctg tataccgtcg acctctagct agagcttggc gtaatcatgg   1920
tcattaccaa tgcttaatca gtgaggcacc tatctcagcg atctgtctat ttcgttcatc   1980
catagttgcc tgactccccg tcgtgtagat aactacgata cgggagggct taccatctgg   2040
ccccagcgct gcgatgatac cgcgagaacc acgctcaccg gctccggatt tatcagcaat   2100
aaaccagcca gccggaaggg ccgagcgcag aagtggtcct gcaactttat ccgcctccat   2160
ccagtctatt aattgttgcc gggaagctag agtaagtagt tcgccagtta atagtttgcg   2220
caacgttgtt gccatcgcta caggcatcgt ggtgtcacgc tcgtcgtttg gtatggcttc   2280
attcagctcc ggttcccaac gatcaaggcg agttacatga tcccccatgt tgtgcaaaaa   2340
agcggttagc tccttcggtc ctccgatcgt tgtcagaagt aagttggccg cagtgttatc   2400
actcatggtt atggcagcac tgcataattc tcttactgtc atgccatccg taagatgctt   2460
ttctgtgact ggtgagtact caaccaagtc attctgagaa tagtgtatgc ggcgaccgag   2520
ttgctcttgc ccggcgtcaa tacgggataa taccgcgcca catagcagaa ctttaaaagt   2580
gctcatcatt ggaaaacgtt cttcggggcg aaaactctca aggatcttac cgctgttgag   2640
atccagttcg atgtaaccca ctcgtgcacc caactgatct tcagcatctt ttactttcac   2700
cagcgtttct gggtgagcaa aaacaggaag gcaaaatgcc gcaaaaaagg gaataagggc   2760
gacacggaaa tgttgaatac tcatattctt cctttttcaa tattattgaa gcatttatca   2820
gggttattgt ctcatgagcg gatacatatt tgaatgtatt tagaaaaata aacaaatagg   2880
```

```
ggtcagtgtt acaaccaatt aaccaattct gaacattatc gcgagcccat ttatacctga    2940
atatggctca taacacccct tgctcatgac caaaatccct taacgtgagt tacgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactctttt ccgaaggtaa ctggcttcag cagagcgcag    3180
ataccaaata ctgttcttct agtgtagccg tagttagccc caccttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggcctttttg cgtttctaca aactcttct    3900
gtgttgtaaa acgacggcca gtcttaagct cgggcccct gggcggttct gataacgagt    3960
aatcgttaat ccgcaaataa cgtaaaaacc cgcttcggcg gtttttta tggggggagt    4020
ttagggaaag agcatttgtc agaatattta agggcgcctg tcactttgct tgatatatga    4080
gaattattta accttataaa tgagaaaaa gcaacgcact ttaaataaga tacgttgctt    4140
tttcgattga tgaacaccta taattaaact attcatctat tatttatgat tttttgtata    4200
tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
tattaatagt aatcaattac ggggtcatta gttcatagcc catatatgga gttccgcgtt    4500
acataactta cggtaaatgg cccgcctggc tgaccgccca acgacccccg cccattgacg    4560
tcaataatga cgtatgttcc catagtaacg ccaatagga cttccattg acgtcaatgg    4620
gtggagtatt tacggtaaac tgcccacttg gcagtacatc aagtgtatca tatgccaagt    4680
acgccccta ttgacgtcaa tgacggtaaa tggcccgcct ggcattatgc ccagtacatg    4740
accttatggg actttcctac ttggcagtac atctacgtat tagtcatcgc tattaccatg    4800
gtgatgcggt tttggcagta catcaatggg cgtggatagc ggtttgactc acggggattt    4860
ccaagtctcc accccattga cgtcaatggg agtttgtttt ggcaccaaaa tcaacgggac    4920
tttccaaaat gtcgtaacaa ctccgcccca ttgacgcaaa tgggcggtag cgtgtacgg    4980
tgggaggtct atataagcag agctctctgg ctaactagag aacccactgc ttactggctt    5040
atcgaaatta atacgactca ctatagggaa gcttcttgtt cttttgcag aagctcagaa    5100
taaacgctca actttggcct cgaggccacc atggcttcct cccctccaaa gaaaagaga    5160
aaggttgcgg ccgctgacta caaggatgac gacgataaaa gttggaagga cgcaagtggt    5220
tggtctagaa tgcatgcggc cccgcgacgg cgtgctgcgc aaccctccga cgcttcgccg    5280
```

```
gccgcgcagg tggatctacg cacgctcggc tacagtcagc agcagcaaga gaagatcaaa   5340
ccgaaggtgc gttcgacagt ggcgcagcac cacgaggcac tggtgggcca tgggtttaca   5400
cacgcgcaca tcgttgcgct cagccaacac ccggcagcgt tagggaccgt cgctgtcacg   5460
tatcagcaca taatcacggc gttgccgagg gcgacacacg aagacatcgt tggcgtcggc   5520
aaacagtggt ccggcgcacg cgccctggag gccttgctca cggatgcggg ggagttgaga   5580
ggtccgccgt tacagttgga cacaggccaa cttgtgaaga ttgcaaaacg tggcggcgtg   5640
accgcaatgg aggcagtgca tgcatcgcgc aatgcgctca cgggagcacc cctcaacctg   5700
accccagacc aagttgtcgc gattgcaagc aacaacggag gcaaacaagc cttagaaaca   5760
gtccagagat tgttgccggt gctgtgccaa gaccacggcc tgaccccga acaggttgtc   5820
gctattgcta gtaacggcgg aggcaaacag gcgctggaaa cagttcagcg cctcttgccg   5880
gtcttgtgtc aggcccacgg cctgacccca gaccaagttg tcgcgattgc aagcaacaac   5940
ggaggcaaac aagccttaga aacagtccag agattgttgc ctgtgctgtg ccaagcccac   6000
ggcctgaccc cggcccaggt ggttgcaatc gcgtcacacg atgggggaaa gcaggcccta   6060
gaaaccgttc agcgactcct gcccgtcctg tgccaggacc acggcctgac cccgaccag   6120
gtggttgcaa tcgcgtcaca cgatggggga agcaggccc tagaaaccgt tcagcgactc   6180
ctgcccgtcc tgtgccagga ccacggcctg accccgaac aggttgtcgc tattgctagt   6240
aacggcggag gcaaacaggc gctggaaaca gttcagcgcc tcttgccggt cttgtgtcag   6300
gcccacggcc tgaccccaga ccaagttgtc gcgattgcaa gcaacaacgg aggcaaacaa   6360
gccttagaaa cagtccagag attgttgcct gtgctgtgcc aagcccacgg cctgacccca   6420
gcccaagttg tcgcgattgc aagcaacaac ggaggcaaac aagccttaga aacagtccag   6480
agattgttgc cggtgctgtg ccagaccac ggcctgaccc cggaccaggt ggttgcaatc   6540
gcgtcacacg atgggggaaa gcaggcccta gaaaccgttc agcgactcct gcccgtcctg   6600
tgccaggacc acggcctgac cccggaacag gtggttgcaa tcgcgtcaca cgatggggga   6660
aagcaggccc tagaaaccgt tcagcgactc ctgcccgtcc tgtgccaggc ccacggcctg   6720
accccagacc aggttgtggc catcgccagc aacataggtg gcaagcaggc cctcgaaacc   6780
gtccagagac tgttaccggt tctctgccca gcccacggcc tgaccccggc ccaggtggtt   6840
gcaatcgcgt cacacgatgg gggaaagcag gccctagaaa ccgttcagcg actcctgccc   6900
gtcctgtgcc aggaccacgg cctgacccca gaccaggttg tggccatcgc cagcaacata   6960
ggtggcaagc aggccctcga aaccgtccag agactgttac cggttctctg ccaggaccac   7020
ggcctgaccc cagaacaagt tgtcgcgatt gcaagcaaca acggaggcaa acaagcctta   7080
gaaacagtcc agagattgtt gccggtgctg tgccaagccc acggcctgac cccagaccaa   7140
gttgtcgcga ttgcaagcaa caacggaggc aaacaagcct tagaaacagt ccagagattg   7200
ttgcctgtgt gtgccaagc ccacggcctg accccgccc aggtggttgc aatcgcgtca   7260
cacgatgggg aaagcaggc cctagaaacc gttcagcgac tcctgcccgt cctgtgccag   7320
gaccacggcc tgaccccga ccaggttgtc gctattgcta gtaacggcgg aggcaaacag   7380
gcgctggaaa cagttcagcg cctcttgccg gtcttgtgtc aggaccacgg cctgacccc   7440
gaacaggttg tcgctattgc tagtaacggc ggaggcaaac aggcgctgga aacagttcag   7500
cgcctcttgc cggtcttgtg tcaggcccac ggcctgacgc ctgagcaggt agtggctatt   7560
gcatcccacg acggggcag accgcactg gagtcaatcg tggcccagct ttcgaggccg   7620
```

```
gaccccgcgc tggccgcact cactaatgat catcttgtag cgctggcctg cctcggcgga    7680
cgtcctgcca tggatgcagt gaaaaaggga ttgccgcacg cgccggaatt gatcagatcc    7740
cagctagtga atctgaatt  ggaagagaag aaatctgaac ttagacataa attgaaatat    7800
gtgccacatg aatatattga attgattgaa atcgcaagaa attcaactca ggatagaatc    7860
cttgaaatga aggtgatgga gttctttatg aaggtttatg gttatcgtgg taaacatttg    7920
ggtggatcaa ggaaaccaga cggagcaatt tatactgtcg gatctcctat tgattacggt    7980
gtgatcgttg atactaaggc atattcagga ggttataatc ttccaattgg tcaagcagat    8040
gaaatgcaaa gatatgtcga agagaatcaa acaagaaaca agcatatcaa ccctaatgaa    8100
tggtggaaag tctatccatc ttcagtaaca gaatttaagt tcttgtttgt gagtggtcat    8160
ttcaaaggaa actacaaagc tcagcttaca agattgaatc atatcactaa ttgtaatgga    8220
gctgttctta gtgtagaaga gcttttgatt ggtggagaaa tgattaaagc tggtacattg    8280
acacttgagg aagtgagaag gaaatttaat aacggtgaga taaacttta  aaaaatcagc    8340 ctcgactgtg ccttctagtt gcc                                           8363
```

<210> SEQ ID NO 51
<211> LENGTH: 8363
<212> TYPE: DNA
<213> ORGANISM: artificial sequence
<220> FEATURE:
<223> OTHER INFORMATION: TALEN-TCR-beta3_R19 plasmid full length

<400> SEQUENCE: 51

```
agccatctgt tgtttgcccc tcccccgtgc cttccttgac cctggaaggt gccactccca      60
ctgtcctttc ctaataaaat gaggaaattg catcacaaca ctcaaccctc tctcggtcta     120
ttcttttgat ttataaggga ttttgccgat ttcggcctat tggttaaaaa atgagctgat     180
ttaacaaaaa tttaacgcga attaattctg tggaatgtgt gtcagttagg gtgtggaaag     240
tccccaggct ccccagcagg cagaagtatg caaagcatgc atctcaatta gtcagcaacc     300
aggtgtggaa agtccccagg ctccccagca ggcagaagta tgcaaagcat gcatctcaat     360
tagtcagcaa ccatagtccc gcccctaact ccgcccatcc cgcccctaac tccgcccagt     420
tccgcccatt ctccgcccca tggctgacta attttttta tttatgcaga ggccgaggcc     480
gcctctgcct ctgagctatt ccagaagtag tgaggaggct tttttggagg cctaggcttt     540
tgcaaaaagc tcccgggagc ttgtatatcc attttcggat ctgatcagca cgtgatgaaa     600
aagcctgaac tcaccgcgac gtctgtcgag aagtttctga tcgaaaagtt cgacagcgtt     660
tccgacctga tgcagctctc ggagggcgaa gaatctcgtg ctttcagctt cgatgtagga     720
gggcgtggat atgtcctgcg ggtaaatagc tgcgccgatg gtttctacaa agatcgttat     780
gtttatcggc actttgcatc ggccgcgctc ccgattccgg aagtgcttga cattgggaa      840 ttcagcgaga gcctgaccta ttgcatctcc cgccgtgcac agggtgtcac gttgcaagac     900
ctgcctgaaa ccgaactgcc cgctgttctg cagccggtcg cggaggccat ggatgcgatc     960
gctgcggccg atcttagcca gacgagcggg ttcggcccat tcggaccgca aggaatcggt    1020
caatacacta catggcgtga tttcatatgc gcgattgctg atccccatgt gtatcactgg    1080
caaactgtga tggacgacac cgtcagtgcg tccgtcgcgc aggctctcga tgagctgatg    1140
ctttgggccg aggactgccc cgaagtccgg cacctcgtgc acgcggattt cggctccaac    1200
aatgtcctga cggacaatgg ccgcataaca gcggtcattg actggagcga ggcgatgttc    1260
ggggattccc aatacgaggt cgccaacatc ttcttctgga ggccgtggtt ggcttgtatg    1320
```

```
gagcagcaga cgcgctactt cgagcggagg catccggagc ttgcaggatc gccgcggctc    1380
cgggcgtata tgctccgcat tggtcttgac caactctatc agagcttggt tgacggcaat    1440
ttcgatgatg cagcttgggc gcagggtcga tgcgacgcaa tcgtccgatc cggagccggg    1500
actgtcgggc gtacacaaat cgcccgcaga agcgcggccg tctggaccga tggctgtgta    1560
gaagtactcg ccgatagtgg aaaccgacgc cccagcactc gtccgagggc aaaggaatag    1620
cacgtgctac gagatttcga ttccaccgcc gccttctatg aaaggttggg cttcggaatc    1680
gttttccggg acgccggctg gatgatcctc cagcgcgggg atctcatgct ggagttcttc    1740
gcccacccca acttgtttat tgcagcttat aatggttaca aataaagcaa tagcatcaca    1800
aatttcacaa ataaagcatt tttttcactg cattctagtt gtggtttgtc caaactcatc    1860
aatgtatctt atcatgtctg tataccgtcg acctctagct agagcttggc gtaatcatgg    1920
tcattaccaa tgcttaatca gtgaggcacc tatctcagcg atctgtctat ttcgttcatc    1980
catagttgcc tgactcccg tcgtgtagat aactacgata cgggagggct taccatctgg    2040
ccccagcgct gcgatgatac cgcgagaacc acgctcaccg gctccggatt tatcagcaat    2100
aaaccagcca gccggaaggg ccgagcgcag aagtggtcct gcaactttat ccgcctccat    2160
ccagtctatt aattgttgcc gggaagctag agtaagtagt tcgccagtta atagtttgcg    2220
caacgttgtt gccatcgcta caggcatcgt ggtgtcacgc tcgtcgtttg gtatggcttc    2280
attcagctcc ggttcccaac gatcaaggcg agttacatga tcccccatgt tgtgcaaaaa    2340
agcggttagc tccttcggtc ctccgatcgt tgtcagaagt aagttggccg cagtgttatc    2400
actcatggtt atggcagcac tgcataattc tcttactgtc atgccatccg taagatgctt    2460
ttctgtgact ggtgagtact caaccaagtc attctgagaa tagtgtatgc ggcgaccgag    2520
ttgctcttgc ccggcgtcaa tacgggataa taccgcgcca catagcagaa ctttaaaagt    2580
gctcatcatt ggaaaacgtt cttcggggcg aaaactctca aggatcttac cgctgttgag    2640
atccagttcg atgtaaccca ctcgtgcacc caactgatct tcagcatctt ttactttcac    2700 cagcgttct gggtgagcaa aaacaggaag gcaaaatgcc gcaaaaaagg gaataagggc    2760
gacacggaaa tgttgaatac tcatattctt ccttttcaa tattattgaa gcatttatca    2820
gggttattgt ctcatgagcg gatacatatt tgaatgtatt tagaaaaata aacaaatagg    2880
ggtcagtgtt acaaccaatt aaccaattct gaacattatc gcgagcccat ttatacctga    2940
atatggctca taacacccct tgctcatgac caaaatccct taacgtgagt acgcgcgcg    3000 tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactcttttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccagggga    3540 aacgcctggt atctttatag tcctgtcggg tttcgccacc tctgacttga gcgtcgattt    3600
ttgtgatgct cgtcaggggg gcggagccta tggaaaaacg ccagcaacgc ggcctttta    3660
```

```
cggttcctgg cctttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggccttttg cgtttctaca aactctttct     3900
gtgttgtaaa acgacggcca gtcttaagct cgggcccct gggcggttct gataacgagt     3960
aatcgttaat ccgcaaataa cgtaaaaacc cgcttcggcg gtttttttta tgggggagt     4020
ttagggaaag agcatttgtc agaatattta agggcgcctg tcactttgct tgatatatga    4080
gaattattta accttataaa tgagaaaaaa gcaacgcact ttaaataaga tacgttgctt    4140
tttcgattga tgaacaccta taattaaact attcatctat tatttatgat tttttgtata    4200
tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
tattaatagt aatcaattac ggggtcatta gttcatagcc catatatgga gttccgcgtt    4500
acataactta cggtaaatgg cccgcctggc tgaccgccca acgaccccg cccattgacg     4560
tcaataatga cgtatgttcc catagtaacg ccaataggga ctttccattg acgtcaatgg    4620
gtggagtatt tacggtaaac tgcccacttg gcagtacatc aagtgtatca tatgccaagt    4680
acgcccccta ttgacgtcaa tgacggtaaa tggcccgcct ggcattatgc ccagtacatg    4740
accttatggg actttcctac ttggcagtac atctacgtat tagtcatcgc tattaccatg    4800
gtgatgcggt tttggcagta catcaatggg cgtggatagc ggtttgactc acggggattt    4860
ccaagtctcc accccattga cgtcaatggg agtttgtttt ggcaccaaaa tcaacgggac    4920
tttccaaaat gtcgtaacaa ctccgcccca ttgacgcaaa tgggcggtag gcgtgtacgg    4980
tgggaggtct atataagcag agctctctgg ctaactagag aacccactgc ttactggctt    5040
atcgaaatta atacgactca ctatagggaa gcttcttgtt cttttgcag aagctcagaa     5100
taaacgctca actttggcct cgaggccacc atggcttcct cccctccaaa gaaaaagaga    5160
aaggttgcgg ccgctgacta caaggatgac gacgataaaa gttggaagga cgcaagtggt    5220
tggtctagaa tgcatgcggc cccgcgacgg cgtgctgcgc aaccctccga cgcttcgccg    5280
gccgcgcagg tggatctacg cacgctcggc tacagtcagc agcagcaaga gaagatcaaa    5340
ccgaaggtgc gttcgacagt ggcgcagcac cacgaggcac tggtgggcca tgggtttaca    5400
cacgcgcaca tcgttgcgct cagccaacac ccggcagcgt tagggaccgt cgctgtcacg    5460
tatcagcaca taatcacggc gttgccgagg cgacacacg aagacatcgt tggcgtcggc      5520
aaacagtggt ccggcgcacg cgccctggag gccttgctca cggatgcggg ggagttgaga    5580
ggtccgccgt tacagttgga cacaggccaa cttgtgaaga ttgcaaaacg tggcggcgtg    5640
accgcaatgg aggcagtgca tgcatcgcgc aatgcgctca cggagcacc cctcaacctg     5700
accccggacc aggtggttgc aatcgcgtca cacgatgggg gaaagcaggc cctagaaacc    5760
gttcagcgac tcctgcccgt cctgtgccag gaccacggcc tgaccccaga acaggttgtg    5820
gccatcgcca gcaacatagg tggcaagcag gccctcgaaa ccgtccagag actgttaccg    5880
gttctctgcc aggcccacgg cctgaccccg gaccaggtgg ttgcaatcgc gtcacacgat    5940
gggggaaagc aggccctaga aaccgttcag cgactcctgc ccgtcctgtg ccaggcccac    6000
ggcctgaccc cggcccaggt ggttgcaatc gcgtcacacg atgggggaaa gcaggcccta    6060
```

```
gaaaccgttc agcgactcct gcccgtcctg tgccaggacc acggcctgac cccggaccag    6120
gtggttgcaa tcgcgtcaca cgatggggga aagcaggccc tagaaaccgt tcagcgactc    6180
ctgcccgtcc tgtgccagga ccacggcctg accccagaac aggttgtggc catcgccagc    6240
aacataggtg gcaagcaggc cctcgaaacc gtccagagac tgttaccggt tctctgccag    6300
gcccacggcc tgaccccgga ccaggtggtt gcaatcgcgt cacacgatgg gggaaagcag    6360
gccctagaaa ccgttcagcg actcctgccc gtcctgtgcc aggcccacgg cctgaccccg    6420
gcccaggtgg ttgcaatcgc gtcacacgat ggggaaagc aggccctaga aaccgttcag    6480
cgactcctgc ccgtcctgtg ccaggaccac ggcctgaccc cagaccaggt tgtggccatc    6540
gccagcaaca taggtggcaa gcaggccctc gaaaccgtcc agagactgtt accggttctc    6600
tgccaggacc acggcctgac cccagaacaa gttgtcgcga ttgcaagcaa caacggaggc    6660
aaacaagcct tagaaacagt ccagagattg ttgccggtgc tgtgccaagc ccacggcctg    6720
accccggacc aggtggttgc aatcgcgtca cacgatgggg aaagcaggc cctagaaacc    6780 gttcagcgac tcctgcccgt cctgtgccag gcccacggcc tgaccccgc caggttgtc    6840 gctattgcta gtaacggcgg aggcaaacag gcgctggaaa cagttcagcg cctcttgccg    6900
gtcttgtgtc aggaccacgg cctgaccccg gaccaggtgg ttgcaatcgc gtcacacgat    6960
gggggaaagc aggccctaga aaccgttcag cgactcctgc ccgtcctgtg ccaggaccac    7020
ggcctgaccc cagaacaggt tgtggccatc gccagcaaca taggtggcaa gcaggccctc    7080
gaaaccgtcc agagactgtt accggttctc tgccaggccc acggcctgac cccagaccaa    7140
gttgtcgcga ttgcaagcaa caacggaggc aaacaagcct tagaaacagt ccagagattg    7200
ttgcctgtgc tgtgccaagc ccacggcctg accccggccc aggtggttgc aatcgcgtca    7260
cacgatgggg aaagcaggc cctagaaacc gttcagcgac tcctgcccgt cctgtgccag    7320
gaccacggcc tgaccccgga ccaggttgtc gctattgcta gtaacggcgg aggcaaacag    7380
gcgctggaaa cagttcagcg cctcttgccg gtcttgtgtc aggaccacgg cctgaccccg    7440
gaacaggtgg ttgcaatcgc gtcacacgat ggggaaagc aggccctaga aaccgttcag    7500
cgactcctgc ccgtcctgtg ccaggcccac ggcctgacgc tgagcaggt agtggctatt    7560 gcatcccacg acgggggcag acccgcactg gagtcaatcg tggcccagct ttcgaggccg    7620
gaccccgcgc tggccgcact cactaatgat catcttgtag cgctggcctg cctcggcgga    7680
cgtcctgcca tggatgcagt gaaaagggga ttgccgcacg cgccggaatt gatcagatcc    7740
cagctagtga atctgaatt ggaagagaag aaatctgaac ttagacataa attgaaatat    7800
gtgccacatg aatatattga attgattgaa atcgcaagaa attcaactca ggatagaatc    7860
cttgaaatga aggtgatgga gttctttatg aaggtttatg gttatcgtgg taaacatttg    7920
ggtggatcaa ggaaaccaga cggagcaatt tatactgtcg gatctcctat tgattacggt    7980
gtgatcgttg atactaaggc atattcagga ggttataatc ttccaattgg tcaagcagat    8040
gaaatgcaaa gatatgtcga agagaatcaa acaagaaaca agcatatcaa ccctaatgaa    8100
tggtggaaag tctatccatc ttcagtaaca gaatttaagt tcttgtttgt gagtggtcat    8160
ttcaaaggaa actacaaagc tcagcttaca agattgaatc atatcactaa ttgtaatgga    8220
gctgttctta gtgtagaaga gcttttgatt ggtggagaaa tgattaaagc tggtacattg    8280
acacttgagg aagtgagaag gaaatttaat aacggtgaga taaacttta aaaaatcagc    8340 ctcgactgtg ccttctagtt gcc                                            8363
```

<210> SEQ ID NO 52
<211> LENGTH: 3201
<212> TYPE: DNA
<213> ORGANISM: artificial sequence
<220> FEATURE:
<223> OTHER INFORMATION: TALEN-TCR-alpha2_L19 TALEN coding sequence
<220> FEATURE:
<221> NAME/KEY: CDS
<222> LOCATION: (1)..(3201)

<400> SEQUENCE: 52

```
atg gct tcc tcc cct cca aag aaa aag aga aag gtt gcg gcc gct gac        48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct        96
Tyr Lys Asp Asp Asp Asp Lys Ser Trp Lys Asp Ala Ser Gly Trp Ser
                20                  25                  30 aga atg cat gcg gcc ccg cga cgg cgt gct gcg caa ccc tcc gac gct       144
Arg Met His Ala Ala Pro Arg Arg Arg Ala Ala Gln Pro Ser Asp Ala
            35                  40                  45 tcg ccg gcc gcg cag gtg gat cta cgc acg ctc ggc tac agt cag cag       192
Ser Pro Ala Ala Gln Val Asp Leu Arg Thr Leu Gly Tyr Ser Gln Gln
        50                  55                  60 cag caa gag aag atc aaa ccg aag gtg cgt tcg aca gtg gcg cag cac       240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg       288
His Glu Ala Leu Val Gly His Gly Phe Thr His Ala His Ile Val Ala
                85                  90                  95 ctc agc caa cac ccg gca gcg tta ggg acc gtc gct gtc acg tat cag       336
Leu Ser Gln His Pro Ala Ala Leu Gly Thr Val Ala Val Thr Tyr Gln
            100                 105                 110 cac ata atc acg gcg ttg cca gag gca aca cac gaa gac atc gtt ggc       384
His Ile Ile Thr Ala Leu Pro Glu Ala Thr His Glu Asp Ile Val Gly
        115                 120                 125 gtc ggc aaa cag tgg tcc ggc gca cgc gcc ctg gag gcc ttg ctc acg       432
Val Gly Lys Gln Trp Ser Gly Ala Arg Ala Leu Glu Ala Leu Leu Thr
    130                 135                 140 gat gcg ggg gag ttg aga ggt ccg ccg tta cag ttg gac aca ggc caa       480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg       528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc cca       576
His Ala Ser Arg Asn Ala Leu Thr Gly Ala Pro Leu Asn Leu Thr Pro
            180                 185                 190 gac caa gtt gtc gcg att gca agc aac aac gga ggc aaa caa gcc tta       624
Asp Gln Val Val Ala Ile Ala Ser Asn Asn Gly Gly Lys Gln Ala Leu
        195                 200                 205 gaa aca gtc cag aga ttg ttg ccg gtg ctg tgc caa gac cac ggc ctg       672
Glu Thr Val Gln Arg Leu Leu Pro Val Leu Cys Gln Asp His Gly Leu
    210                 215                 220 acc ccc gaa cag gtt gtc gct att gct agt aac ggc gga ggc aaa cag       720
Thr Pro Glu Gln Val Val Ala Ile Ala Ser Asn Gly Gly Gly Lys Gln
225                 230                 235                 240 gcg ctg gaa aca gtt cag cgc ctc ttg ccg gtc ttg tgt cag gcc cac       768
Ala Leu Glu Thr Val Gln Arg Leu Leu Pro Val Leu Cys Gln Ala His
                245                 250                 255 ggc ctg acc ccg gac cag gtg gtt gca atc gcg tca cac gat ggg gga       816
Gly Leu Thr Pro Asp Gln Val Val Ala Ile Ala Ser His Asp Gly Gly
```

-continued

```
                260                 265                 270
aag cag gcc cta gaa acc gtt cag cga ctc ctg ccc gtc ctg tgc cag    864
Lys Gln Ala Leu Glu Thr Val Gln Arg Leu Leu Pro Val Leu Cys Gln
        275                 280                 285 gcc cac ggc ctg acc ccc gcc cag gtt gtc gct att gct agt aac ggc    912
Ala His Gly Leu Thr Pro Ala Gln Val Val Ala Ile Ala Ser Asn Gly
    290                 295                 300 gga ggc aaa cag gcg ctg gaa aca gtt cag cgc ctc ttg ccg gtc ttg    960
Gly Gly Lys Gln Ala Leu Glu Thr Val Gln Arg Leu Leu Pro Val Leu
305                 310                 315                 320 tgt cag gac cac ggc ctg acc cca gac caa gtt gtc gcg att gca agc    1008
Cys Gln Asp His Gly Leu Thr Pro Asp Gln Val Val Ala Ile Ala Ser
                325                 330                 335 aac aac gga ggc aaa caa gcc tta gaa aca gtc cag aga ttg ttg ccg    1056
Asn Asn Gly Gly Lys Gln Ala Leu Glu Thr Val Gln Arg Leu Leu Pro
            340                 345                 350 gtg ctg tgc caa gac cac ggc ctg acc ccg gaa cag gtg gtt gca atc    1104
Val Leu Cys Gln Asp His Gly Leu Thr Pro Glu Gln Val Val Ala Ile
        355                 360                 365 gcg tca cac gat ggg gga aag cag gcc cta gaa acc gtt cag cga ctc    1152
Ala Ser His Asp Gly Gly Lys Gln Ala Leu Glu Thr Val Gln Arg Leu
    370                 375                 380 ctg ccc gtc ctg tgc cag gcc cac ggc ctg acc ccg gac cag gtg gtt    1200
Leu Pro Val Leu Cys Gln Ala His Gly Leu Thr Pro Asp Gln Val Val
385                 390                 395                 400 gca atc gcg tca cac gat ggg gga aag cag gcc cta gaa acc gtt cag    1248
Ala Ile Ala Ser His Asp Gly Gly Lys Gln Ala Leu Glu Thr Val Gln
                405                 410                 415 cga ctc ctg ccc gtc ctg tgc cag gcc cac ggc ctg acc ccc gcc cag    1296
Arg Leu Leu Pro Val Leu Cys Gln Ala His Gly Leu Thr Pro Ala Gln
            420                 425                 430 gtt gtc gct att gct agt aac ggc gga ggc aaa cag gcg ctg gaa aca    1344
Val Val Ala Ile Ala Ser Asn Gly Gly Gly Lys Gln Ala Leu Glu Thr
        435                 440                 445 gtt cag cgc ctc ttg ccg gtc ttg tgt cag gac cac ggc ctg acc cca    1392
Val Gln Arg Leu Leu Pro Val Leu Cys Gln Asp His Gly Leu Thr Pro
    450                 455                 460 gac cag gtt gtg gcc atc gcc agc aac ata ggt ggc aag cag gcc ctc    1440
Asp Gln Val Val Ala Ile Ala Ser Asn Ile Gly Gly Lys Gln Ala Leu
465                 470                 475                 480 gaa acc gtc cag aga ctg tta ccg gtt ctc tgc cag gac cac ggc ctg    1488
Glu Thr Val Gln Arg Leu Leu Pro Val Leu Cys Gln Asp His Gly Leu
                485                 490                 495 acc ccc gaa cag gtt gtc gct att gct agt aac ggc gga ggc aaa cag    1536
Thr Pro Glu Gln Val Val Ala Ile Ala Ser Asn Gly Gly Gly Lys Gln
            500                 505                 510 gcg ctg gaa aca gtt cag cgc ctc ttg ccg gtc ttg tgt cag gcc cac    1584
Ala Leu Glu Thr Val Gln Arg Leu Leu Pro Val Leu Cys Gln Ala His
        515                 520                 525 ggc ctg acc ccc gac cag gtt gtc gct att gct agt aac ggc gga ggc    1632
Gly Leu Thr Pro Asp Gln Val Val Ala Ile Ala Ser Asn Gly Gly Gly
    530                 535                 540 aaa cag gcg ctg gaa aca gtt cag cgc ctc ttg ccg gtc ttg tgt cag    1680
Lys Gln Ala Leu Glu Thr Val Gln Arg Leu Leu Pro Val Leu Cys Gln
545                 550                 555                 560 gcc cac ggc ctg acc ccg gcc cag gtg gtt gca atc gcg tca cac gat    1728
Ala His Gly Leu Thr Pro Ala Gln Val Val Ala Ile Ala Ser His Asp
                565                 570                 575 ggg gga aag cag gcc cta gaa acc gtt cag cga ctc ctg ccc gtc ctg    1776
```

|  |  |  |  |  |  |  |  |  |  |  |  |  |  |  |  |  |
|---|---|---|---|---|---|---|---|---|---|---|---|---|---|---|---|---|
| | Gly | Gly | Lys | Gln | Ala | Leu | Glu | Thr | Val | Gln | Arg | Leu | Leu | Pro | Val | Leu |
| | | | | 580 | | | | 585 | | | | | 590 | | | |

| tgc | cag | gac | cac | ggc | ctg | acc | cca | gac | cag | gtt | gtg | gcc | atc | gcc | agc | 1824 |
|---|---|---|---|---|---|---|---|---|---|---|---|---|---|---|---|---|
| Cys | Gln | Asp | His | Gly | Leu | Thr | Pro | Asp | Gln | Val | Val | Ala | Ile | Ala | Ser | |
| | | 595 | | | | 600 | | | | | 605 | | | | | |

| aac | ata | ggt | ggc | aag | cag | gcc | ctc | gaa | acc | gtc | cag | aga | ctg | tta | ccg | 1872 |
|---|---|---|---|---|---|---|---|---|---|---|---|---|---|---|---|---|
| Asn | Ile | Gly | Gly | Lys | Gln | Ala | Leu | Glu | Thr | Val | Gln | Arg | Leu | Leu | Pro | |
| 610 | | | | | 615 | | | | | 620 | | | | | | |

| gtt | ctc | tgc | cag | gac | cac | ggc | ctg | acc | ccg | gaa | cag | gtg | gtt | gca | atc | 1920 |
|---|---|---|---|---|---|---|---|---|---|---|---|---|---|---|---|---|
| Val | Leu | Cys | Gln | Asp | His | Gly | Leu | Thr | Pro | Glu | Gln | Val | Val | Ala | Ile | |
| 625 | | | | | 630 | | | | | 635 | | | | | 640 | |

| gcg | tca | cac | gat | ggg | gga | aag | cag | gcc | cta | gaa | acc | gtt | cag | cga | ctc | 1968 |
|---|---|---|---|---|---|---|---|---|---|---|---|---|---|---|---|---|
| Ala | Ser | His | Asp | Gly | Gly | Lys | Gln | Ala | Leu | Glu | Thr | Val | Gln | Arg | Leu | |
| | | | | 645 | | | | | 650 | | | | | 655 | | |

| ctg | ccc | gtc | ctg | tgc | cag | gcc | cac | ggc | ctg | acc | ccg | gac | cag | gtg | gtt | 2016 |
|---|---|---|---|---|---|---|---|---|---|---|---|---|---|---|---|---|
| Leu | Pro | Val | Leu | Cys | Gln | Ala | His | Gly | Leu | Thr | Pro | Asp | Gln | Val | Val | |
| | | | 660 | | | | | 665 | | | | | 670 | | | |

| gca | atc | gcg | tca | cac | gat | ggg | gga | aag | cag | gcc | cta | gaa | acc | gtt | cag | 2064 |
|---|---|---|---|---|---|---|---|---|---|---|---|---|---|---|---|---|
| Ala | Ile | Ala | Ser | His | Asp | Gly | Gly | Lys | Gln | Ala | Leu | Glu | Thr | Val | Gln | |
| | | | 675 | | | | | 680 | | | | | 685 | | | |

| cga | ctc | ctg | ccc | gtc | ctg | tgc | cag | gcc | cac | ggc | ctg | acc | cca | gcc | caa | 2112 |
|---|---|---|---|---|---|---|---|---|---|---|---|---|---|---|---|---|
| Arg | Leu | Leu | Pro | Val | Leu | Cys | Gln | Ala | His | Gly | Leu | Thr | Pro | Ala | Gln | |
| 690 | | | | | 695 | | | | | 700 | | | | | | |

| gtt | gtc | gcg | att | gca | agc | aac | aac | gga | ggc | aaa | caa | gcc | tta | gaa | aca | 2160 |
|---|---|---|---|---|---|---|---|---|---|---|---|---|---|---|---|---|
| Val | Val | Ala | Ile | Ala | Ser | Asn | Asn | Gly | Gly | Lys | Gln | Ala | Leu | Glu | Thr | |
| 705 | | | | | 710 | | | | | 715 | | | | | 720 | |

| gtc | cag | aga | ttg | ttg | ccg | gtg | ctg | tgc | caa | gac | cac | ggc | ctg | acc | cca | 2208 |
|---|---|---|---|---|---|---|---|---|---|---|---|---|---|---|---|---|
| Val | Gln | Arg | Leu | Leu | Pro | Val | Leu | Cys | Gln | Asp | His | Gly | Leu | Thr | Pro | |
| | | | | 725 | | | | | 730 | | | | | 735 | | |

| gac | cag | gtt | gtg | gcc | atc | gcc | agc | aac | ata | ggt | ggc | aag | cag | gcc | ctc | 2256 |
|---|---|---|---|---|---|---|---|---|---|---|---|---|---|---|---|---|
| Asp | Gln | Val | Val | Ala | Ile | Ala | Ser | Asn | Ile | Gly | Gly | Lys | Gln | Ala | Leu | |
| | | | 740 | | | | | 745 | | | | | 750 | | | |

| gaa | acc | gtc | cag | aga | ctg | tta | ccg | gtt | ctc | tgc | cag | gac | cac | ggc | ctg | 2304 |
|---|---|---|---|---|---|---|---|---|---|---|---|---|---|---|---|---|
| Glu | Thr | Val | Gln | Arg | Leu | Leu | Pro | Val | Leu | Cys | Gln | Asp | His | Gly | Leu | |
| | | | 755 | | | | | 760 | | | | | 765 | | | |

| acc | ccc | gaa | cag | gtt | gtc | gct | att | gct | agt | aac | ggc | gga | ggc | aaa | cag | 2352 |
|---|---|---|---|---|---|---|---|---|---|---|---|---|---|---|---|---|
| Thr | Pro | Glu | Gln | Val | Val | Ala | Ile | Ala | Ser | Asn | Gly | Gly | Gly | Lys | Gln | |
| 770 | | | | | 775 | | | | | 780 | | | | | | |

| gcg | ctg | gaa | aca | gtt | cag | cgc | ctc | ttg | ccg | gtc | ttg | tgt | cag | gcc | cac | 2400 |
|---|---|---|---|---|---|---|---|---|---|---|---|---|---|---|---|---|
| Ala | Leu | Glu | Thr | Val | Gln | Arg | Leu | Leu | Pro | Val | Leu | Cys | Gln | Ala | His | |
| 785 | | | | | 790 | | | | | 795 | | | | | 800 | |

| ggc | ctg | acg | cct | gag | cag | gta | gtg | gct | att | gca | tcc | aac | gga | ggg | ggc | 2448 |
|---|---|---|---|---|---|---|---|---|---|---|---|---|---|---|---|---|
| Gly | Leu | Thr | Pro | Glu | Gln | Val | Val | Ala | Ile | Ala | Ser | Asn | Gly | Gly | Gly | |
| | | | | 805 | | | | | 810 | | | | | 815 | | |

| aga | ccc | gca | ctg | gag | tca | atc | gtg | gcc | cag | ctt | tcg | agg | ccg | gac | ccc | 2496 |
|---|---|---|---|---|---|---|---|---|---|---|---|---|---|---|---|---|
| Arg | Pro | Ala | Leu | Glu | Ser | Ile | Val | Ala | Gln | Leu | Ser | Arg | Pro | Asp | Pro | |
| | | | 820 | | | | | 825 | | | | | 830 | | | |

| gcg | ctg | gcc | gca | ctc | act | aat | gat | cat | ctt | gta | gcg | ctg | gcc | tgc | ctc | 2544 |
|---|---|---|---|---|---|---|---|---|---|---|---|---|---|---|---|---|
| Ala | Leu | Ala | Ala | Leu | Thr | Asn | Asp | His | Leu | Val | Ala | Leu | Ala | Cys | Leu | |
| | | | 835 | | | | | 840 | | | | | 845 | | | |

| ggc | gga | cgt | cct | gcc | atg | gat | gca | gtg | aaa | aag | gga | ttg | ccg | cac | gcg | 2592 |
|---|---|---|---|---|---|---|---|---|---|---|---|---|---|---|---|---|
| Gly | Gly | Arg | Pro | Ala | Met | Asp | Ala | Val | Lys | Lys | Gly | Leu | Pro | His | Ala | |
| 850 | | | | | 855 | | | | | 860 | | | | | | |

| ccg | gaa | ttg | atc | aga | tcc | cag | cta | gtg | aaa | tct | gaa | ttg | gaa | gag | aag | 2640 |
|---|---|---|---|---|---|---|---|---|---|---|---|---|---|---|---|---|
| Pro | Glu | Leu | Ile | Arg | Ser | Gln | Leu | Val | Lys | Ser | Glu | Leu | Glu | Glu | Lys | |
| 865 | | | | | 870 | | | | | 875 | | | | | 880 | |

| aaa | tct | gaa | ctt | aga | cat | aaa | ttg | aaa | tat | gtg | cca | cat | gaa | tat | att | 2688 |
|---|---|---|---|---|---|---|---|---|---|---|---|---|---|---|---|---|
| Lys | Ser | Glu | Leu | Arg | His | Lys | Leu | Lys | Tyr | Val | Pro | His | Glu | Tyr | Ile | |
| | | | | 885 | | | | | 890 | | | | | 895 | | |

-continued

| | | |
|---|---|---|
| gaa ttg att gaa atc gca aga aat tca act cag gat aga atc ctt gaa<br>Glu Leu Ile Glu Ile Ala Arg Asn Ser Thr Gln Asp Arg Ile Leu Glu<br>900                      905                  910 | | 2736 |
| atg aag gtg atg gag ttc ttt atg aag gtt tat ggt tat cgt ggt aaa<br>Met Lys Val Met Glu Phe Phe Met Lys Val Tyr Gly Tyr Arg Gly Lys<br>915                      920                  925 | | 2784 |
| cat ttg ggt gga tca agg aaa cca gac gga gca att tat act gtc gga<br>His Leu Gly Gly Ser Arg Lys Pro Asp Gly Ala Ile Tyr Thr Val Gly<br>930                      935                  940 | | 2832 |
| tct cct att gat tac ggt gtg atc gtt gat act aag gca tat tca gga<br>Ser Pro Ile Asp Tyr Gly Val Ile Val Asp Thr Lys Ala Tyr Ser Gly<br>945                      950                  955                  960 | | 2880 |
| ggt tat aat ctt cca att ggt caa gca gat gaa atg caa aga tat gtc<br>Gly Tyr Asn Leu Pro Ile Gly Gln Ala Asp Glu Met Gln Arg Tyr Val<br>965                      970                  975 | | 2928 |
| gaa gag aat caa aca aga aac aag cat atc aac cct aat gaa tgg tgg<br>Glu Glu Asn Gln Thr Arg Asn Lys His Ile Asn Pro Asn Glu Trp Trp<br>980                      985                  990 | | 2976 |
| aaa gtc tat cca tct tca gta aca gaa ttt aag ttc ttg ttt gtg agt<br>Lys Val Tyr Pro Ser Ser Val Thr Glu Phe Lys Phe Leu Phe Val Ser<br>995                      1000                1005 | | 3024 |
| ggt cat ttc aaa gga aac tac aaa gct cag ctt aca aga ttg aat<br>Gly His Phe Lys Gly Asn Tyr Lys Ala Gln Leu Thr Arg Leu Asn<br>1010                    1015                1020 | | 3069 |
| cat atc act aat tgt aat gga gct gtt ctt agt gta gaa gag ctt<br>His Ile Thr Asn Cys Asn Gly Ala Val Leu Ser Val Glu Glu Leu<br>1025                    1030                1035 | | 3114 |
| ttg att ggt gga gaa atg att aaa gct ggt aca ttg aca ctt gag<br>Leu Ile Gly Gly Glu Met Ile Lys Ala Gly Thr Leu Thr Leu Glu<br>1040                    1045                1050 | | 3159 |
| gaa gtg aga agg aaa ttt aat aac ggt gag ata aac ttt taa<br>Glu Val Arg Arg Lys Phe Asn Asn Gly Glu Ile Asn Phe<br>1055                    1060                1065 | | 3201 |

<210> SEQ ID NO 53
<211> LENGTH: 1066
<212> TYPE: PRT
<213> ORGANISM: artificial sequence
<220> FEATURE:
<223> OTHER INFORMATION: Synthetic Construct

<400> SEQUENCE: 53

Met Ala Ser Ser Pro Lys Lys Lys Arg Lys Val Ala Ala Ala Asp
1               5                   10                  15

Tyr Lys Asp Asp Asp Asp Lys Ser Trp Lys Asp Ala Ser Gly Trp Ser
                20                  25                  30

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
        50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
        115                 120                 125

Val Gly Lys Gln Trp Ser Gly Ala Arg Ala Leu Glu Ala Leu Leu Thr

```
            130                 135                 140
Asp Ala Gly Glu Leu Arg Gly Pro Pro Leu Gln Leu Asp Thr Gly Gln
145                 150                 155                 160

Leu Val Lys Ile Ala Lys Arg Gly Val Thr Ala Met Glu Ala Val
                165                 170                 175

His Ala Ser Arg Asn Ala Leu Thr Gly Ala Pro Leu Asn Leu Thr Pro
                180                 185                 190

Asp Gln Val Val Ala Ile Ala Ser Asn Asn Gly Gly Lys Gln Ala Leu
                195                 200                 205

Glu Thr Val Gln Arg Leu Leu Pro Val Leu Cys Gln Asp His Gly Leu
            210                 215                 220

Thr Pro Glu Gln Val Val Ala Ile Ala Ser Asn Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser His Asp Gly Gly
                260                 265                 270

Lys Gln Ala Leu Glu Thr Val Gln Arg Leu Leu Pro Val Leu Cys Gln
            275                 280                 285

Ala His Gly Leu Thr Pro Ala Gln Val Val Ala Ile Ala Ser Asn Gly
        290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

Asn Asn Gly Gly Lys Gln Ala Leu Glu Thr Val Gln Arg Leu Leu Pro
                340                 345                 350

Val Leu Cys Gln Asp His Gly Leu Thr Pro Glu Gln Val Val Ala Ile
            355                 360                 365

Ala Ser His Asp Gly Gly Lys Gln Ala Leu Glu Thr Val Gln Arg Leu
        370                 375                 380

Leu Pro Val Leu Cys Gln Ala His Gly Leu Thr Pro Asp Gln Val Val
385                 390                 395                 400

Ala Ile Ala Ser His Asp Gly Gly Lys Gln Ala Leu Glu Thr Val Gln
                405                 410                 415

Arg Leu Leu Pro Val Leu Cys Gln Ala His Gly Leu Thr Pro Ala Gln
                420                 425                 430

Val Val Ala Ile Ala Ser Asn Gly Gly Gly Lys Gln Ala Leu Glu Thr
            435                 440                 445

Val Gln Arg Leu Leu Pro Val Leu Cys Gln Asp His Gly Leu Thr Pro
        450                 455                 460

Asp Gln Val Val Ala Ile Ala Ser Asn Ile Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser Asn Gly Gly Lys Gln
                500                 505                 510

Ala Leu Glu Thr Val Gln Arg Leu Leu Pro Val Leu Cys Gln Ala His
            515                 520                 525

Gly Leu Thr Pro Asp Gln Val Val Ala Ile Ala Ser Asn Gly Gly Gly
        530                 535                 540

Lys Gln Ala Leu Glu Thr Val Gln Arg Leu Leu Pro Val Leu Cys Gln
545                 550                 555                 560
```

-continued

```
Ala His Gly Leu Thr Pro Ala Gln Val Val Ala Ile Ala Ser His Asp
            565                 570                 575
Gly Gly Lys Gln Ala Leu Glu Thr Val Gln Arg Leu Leu Pro Val Leu
            580                 585                 590
Cys Gln Asp His Gly Leu Thr Pro Asp Gln Val Val Ala Ile Ala Ser
            595                 600                 605
Asn Ile Gly Gly Lys Gln Ala Leu Glu Thr Val Gln Arg Leu Leu Pro
610                 615                 620
Val Leu Cys Gln Asp His Gly Leu Thr Pro Glu Gln Val Val Ala Ile
625                 630                 635                 640
Ala Ser His Asp Gly Gly Lys Gln Ala Leu Glu Thr Val Gln Arg Leu
            645                 650                 655
Leu Pro Val Leu Cys Gln Ala His Gly Leu Thr Pro Asp Gln Val Val
            660                 665                 670
Ala Ile Ala Ser His Asp Gly Gly Lys Gln Ala Leu Glu Thr Val Gln
            675                 680                 685
Arg Leu Leu Pro Val Leu Cys Gln Ala His Gly Leu Thr Pro Ala Gln
            690                 695                 700
Val Val Ala Ile Ala Ser Asn Asn Gly Gly Lys Gln Ala Leu Glu Thr
705                 710                 715                 720
Val Gln Arg Leu Leu Pro Val Leu Cys Gln Asp His Gly Leu Thr Pro
            725                 730                 735
Asp Gln Val Val Ala Ile Ala Ser Asn Ile Gly Gly Lys Gln Ala Leu
            740                 745                 750
Glu Thr Val Gln Arg Leu Leu Pro Val Leu Cys Gln Asp His Gly Leu
            755                 760                 765
Thr Pro Glu Gln Val Val Ala Ile Ala Ser Asn Gly Gly Gly Lys Gln
            770                 775                 780
Ala Leu Glu Thr Val Gln Arg Leu Leu Pro Val Leu Cys Gln Ala His
785                 790                 795                 800
Gly Leu Thr Pro Glu Gln Val Val Ala Ile Ala Ser Asn Gly Gly Gly
            805                 810                 815
Arg Pro Ala Leu Glu Ser Ile Val Ala Gln Leu Ser Arg Pro Asp Pro
            820                 825                 830
Ala Leu Ala Ala Leu Thr Asn Asp His Leu Val Ala Leu Ala Cys Leu
            835                 840                 845
Gly Gly Arg Pro Ala Met Asp Ala Val Lys Lys Gly Leu Pro His Ala
850                 855                 860
Pro Glu Leu Ile Arg Ser Gln Leu Val Lys Ser Glu Leu Glu Glu Lys
865                 870                 875                 880
Lys Ser Glu Leu Arg His Lys Leu Lys Tyr Val Pro His Glu Tyr Ile
            885                 890                 895
Glu Leu Ile Glu Ile Ala Arg Asn Ser Thr Gln Asp Arg Ile Leu Glu
            900                 905                 910
Met Lys Val Met Glu Phe Phe Met Lys Val Tyr Gly Tyr Arg Gly Lys
            915                 920                 925
His Leu Gly Gly Ser Arg Lys Pro Asp Gly Ala Ile Tyr Thr Val Gly
            930                 935                 940
Ser Pro Ile Asp Tyr Gly Val Ile Val Asp Thr Lys Ala Tyr Ser Gly
945                 950                 955                 960
Gly Tyr Asn Leu Pro Ile Gly Gln Ala Asp Glu Met Gln Arg Tyr Val
            965                 970                 975
```

```
Glu Glu Asn Gln Thr Arg Asn Lys His Ile Asn Pro Asn Glu Trp Trp
            980                 985                 990

Lys Val Tyr Pro Ser Ser Val Thr Glu Phe Lys Phe Leu Phe Val Ser
        995                1000                1005

Gly His Phe Lys Gly Asn Tyr Lys Ala Gln Leu Thr Arg Leu Asn
       1010                1015                1020

His Ile Thr Asn Cys Asn Gly Ala Val Leu Ser Val Glu Glu Leu
   1025                1030                1035

Leu Ile Gly Gly Glu Met Ile Lys Ala Gly Thr Leu Thr Leu Glu
   1040                1045                1050

Glu Val Arg Arg Lys Phe Asn Asn Gly Glu Ile Asn Phe
   1055                1060                1065

<210> SEQ ID NO 54
<211> LENGTH: 3201
<212> TYPE: DNA
<213> ORGANISM: artificial sequence
<220> FEATURE:
<223> OTHER INFORMATION: TALEN-TCR-alpha2_R19 TALEN coding sequence
<220> FEATURE:
<221> NAME/KEY: CDS
<222> LOCATION: (1)..(3201)

<400> SEQUENCE: 54
```

| | | | | | | | | | | | | | | | | |
|---|---|---|---|---|---|---|---|---|---|---|---|---|---|---|---|---|
| atg | gct | tcc | tcc | cct | cca | aag | aaa | aag | aga | aag | gtt | gcg | gcc | gct | gac | 48 |
| Met | Ala | Ser | Ser | Pro | Pro | Lys | Lys | Lys | Arg | Lys | Val | Ala | Ala | Ala | Asp | |
| 1 | | | | 5 | | | | | 10 | | | | | 15 | | |
| tac | aag | gat | gac | gac | gat | aaa | agt | tgg | aag | gac | gca | agt | ggt | tgg | tct | 96 |
| Tyr | Lys | Asp | Asp | Asp | Asp | Lys | Ser | Trp | Lys | Asp | Ala | Ser | Gly | Trp | Ser | |
| | | 20 | | | | | 25 | | | | | 30 | | | | |
| aga | atg | cat | gcg | gcc | ccg | cga | cgg | cgt | gct | gcg | caa | ccc | tcc | gac | gct | 144 |
| Arg | Met | His | Ala | Ala | Pro | Arg | Arg | Arg | Ala | Ala | Gln | Pro | Ser | Asp | Ala | |
| | 35 | | | | | 40 | | | | | 45 | | | | | |
| tcg | ccg | gcc | gcg | cag | gtg | gat | cta | cgc | acg | ctc | ggc | tac | agt | cag | cag | 192 |
| Ser | Pro | Ala | Ala | Gln | Val | Asp | Leu | Arg | Thr | Leu | Gly | Tyr | Ser | Gln | Gln | |
| 50 | | | | | 55 | | | | | 60 | | | | | | |
| cag | caa | gag | aag | atc | aaa | ccg | aag | gtg | cgt | tcg | aca | gtg | gcg | cag | cac | 240 |
| Gln | Gln | Glu | Lys | Ile | Lys | Pro | Lys | Val | Arg | Ser | Thr | Val | Ala | Gln | His | |
| 65 | | | | | 70 | | | | | 75 | | | | | 80 | |
| cac | gag | gca | ctg | gtg | ggc | cat | ggg | ttt | aca | cac | gcg | cac | atc | gtt | gcg | 288 |
| His | Glu | Ala | Leu | Val | Gly | His | Gly | Phe | Thr | His | Ala | His | Ile | Val | Ala | |
| | | | | 85 | | | | | 90 | | | | | 95 | | |
| ctc | agc | caa | cac | ccg | gca | gcg | tta | ggg | acc | gtc | gct | gtc | acg | tat | cag | 336 |
| Leu | Ser | Gln | His | Pro | Ala | Ala | Leu | Gly | Thr | Val | Ala | Val | Thr | Tyr | Gln | |
| | | | 100 | | | | | 105 | | | | | 110 | | | |
| cac | ata | atc | acg | gcg | ttg | cca | gag | gcg | aca | cac | gaa | gac | atc | gtt | ggc | 384 |
| His | Ile | Ile | Thr | Ala | Leu | Pro | Glu | Ala | Thr | His | Glu | Asp | Ile | Val | Gly | |
| | | 115 | | | | | 120 | | | | | 125 | | | | |
| gtc | ggc | aaa | cag | tgg | tcc | ggc | gca | cgc | gcc | ctg | gag | gcc | ttg | ctc | acg | 432 |
| Val | Gly | Lys | Gln | Trp | Ser | Gly | Ala | Arg | Ala | Leu | Glu | Ala | Leu | Leu | Thr | |
| 130 | | | | | 135 | | | | | 140 | | | | | | |
| gat | gcg | ggg | gag | ttg | aga | ggt | ccg | ccg | tta | cag | ttg | gac | aca | ggc | caa | 480 |
| Asp | Ala | Gly | Glu | Leu | Arg | Gly | Pro | Pro | Leu | Gln | Leu | Asp | Thr | Gly | Gln | |
| 145 | | | | | 150 | | | | | 155 | | | | | 160 | |
| ctt | gtg | aag | att | gca | aaa | cgt | ggc | ggc | gtg | acc | gca | atg | gag | gca | gtg | 528 |
| Leu | Val | Lys | Ile | Ala | Lys | Arg | Gly | Gly | Val | Thr | Ala | Met | Glu | Ala | Val | |
| | | | 165 | | | | | 170 | | | | | 175 | | | |
| cat | gca | tcg | cgc | aat | gcg | ctc | acg | gga | gca | ccc | ctc | aac | ctg | acc | ccg | 576 |
| His | Ala | Ser | Arg | Asn | Ala | Leu | Thr | Gly | Ala | Pro | Leu | Asn | Leu | Thr | Pro | |
| | | | 180 | | | | | 185 | | | | | 190 | | | |

| | |
|---|---|
| gac cag gtg gtt gca atc gcg tca cac gat ggg gga aag cag gcc cta<br>Asp Gln Val Val Ala Ile Ala Ser His Asp Gly Gly Lys Gln Ala Leu<br>195　　　　　　　　200　　　　　　　　205 | 624 |
| gaa acc gtt cag cga ctc ctg ccc gtc ctg tgc cag gac cac ggc ctg<br>Glu Thr Val Gln Arg Leu Leu Pro Val Leu Cys Gln Asp His Gly Leu<br>210　　　　　　　　215　　　　　　　　220 | 672 |
| acc ccg gaa cag gtg gtt gca atc gcg tca cac gat ggg gga aag cag<br>Thr Pro Glu Gln Val Val Ala Ile Ala Ser His Asp Gly Gly Lys Gln<br>225　　　　　　　230　　　　　　　　235　　　　　　　　240 | 720 |
| gcc cta gaa acc gtt cag cga ctc ctg ccc gtc ctg tgc cag gcc cac<br>Ala Leu Glu Thr Val Gln Arg Leu Leu Pro Val Leu Cys Gln Ala His<br>　　　　　　245　　　　　　　　250　　　　　　　　255 | 768 |
| ggc ctg acc ccc gac cag gtt gtc gct att gct agt aac ggc gga ggc<br>Gly Leu Thr Pro Asp Gln Val Val Ala Ile Ala Ser Asn Gly Gly Gly<br>　　　　260　　　　　　　　265　　　　　　　　270 | 816 |
| aaa cag gcg ctg gaa aca gtt cag cgc ctc ttg ccg gtc ttg tgt cag<br>Lys Gln Ala Leu Glu Thr Val Gln Arg Leu Leu Pro Val Leu Cys Gln<br>　　　275　　　　　　　　280　　　　　　　　285 | 864 |
| gcc cac ggc ctg acc ccc gcc cag gtt gtc gct att gct agt aac ggc<br>Ala His Gly Leu Thr Pro Ala Gln Val Val Ala Ile Ala Ser Asn Gly<br>290　　　　　　　　295　　　　　　　　300 | 912 |
| gga ggc aaa cag gcg ctg gaa aca gtt cag cgc ctc ttg ccg gtc ttg<br>Gly Gly Lys Gln Ala Leu Glu Thr Val Gln Arg Leu Leu Pro Val Leu<br>305　　　　　　　　310　　　　　　　　315　　　　　　　　320 | 960 |
| tgt cag gac cac ggc ctg acc cca gac cag gtt gtg gcc atc gcc agc<br>Cys Gln Asp His Gly Leu Thr Pro Asp Gln Val Val Ala Ile Ala Ser<br>　　　　　　325　　　　　　　　330　　　　　　　　335 | 1008 |
| aac ata ggt ggc aag cag gcc ctc gaa acc gtc cag aga ctg tta ccg<br>Asn Ile Gly Gly Lys Gln Ala Leu Glu Thr Val Gln Arg Leu Leu Pro<br>　　　　340　　　　　　　　345　　　　　　　　350 | 1056 |
| gtt ctc tgc cag gac cac ggc ctg acc ccg gaa cag gtg gtt gca atc<br>Val Leu Cys Gln Asp His Gly Leu Thr Pro Glu Gln Val Val Ala Ile<br>　　　355　　　　　　　　360　　　　　　　　365 | 1104 |
| gcg tca cac gat ggg gga aag cag gcc cta gaa acc gtt cag cga ctc<br>Ala Ser His Asp Gly Gly Lys Gln Ala Leu Glu Thr Val Gln Arg Leu<br>370　　　　　　　　375　　　　　　　　380 | 1152 |
| ctg ccc gtc ctg tgc cag gcc cac ggc ctg acc ccc gac cag gtt gtc<br>Leu Pro Val Leu Cys Gln Ala His Gly Leu Thr Pro Asp Gln Val Val<br>385　　　　　　　　390　　　　　　　　395　　　　　　　　400 | 1200 |
| gct att gct agt aac ggc gga ggc aaa cag gcg ctg gaa aca gtt cag<br>Ala Ile Ala Ser Asn Gly Gly Gly Lys Gln Ala Leu Glu Thr Val Gln<br>　　　　　　405　　　　　　　　410　　　　　　　　415 | 1248 |
| cgc ctc ttg ccg gtc ttg tgt cag gcc cac ggc ctg acc ccc gcc cag<br>Arg Leu Leu Pro Val Leu Cys Gln Ala His Gly Leu Thr Pro Ala Gln<br>　　　　420　　　　　　　　425　　　　　　　　430 | 1296 |
| gtt gtc gct att gct agt aac ggc gga ggc aaa cag gcg ctg gaa aca<br>Val Val Ala Ile Ala Ser Asn Gly Gly Gly Lys Gln Ala Leu Glu Thr<br>　　　435　　　　　　　　440　　　　　　　　445 | 1344 |
| gtt cag cgc ctc ttg ccg gtc ttg tgt cag gac cac ggc ctg acc ccc<br>Val Gln Arg Leu Leu Pro Val Leu Cys Gln Asp His Gly Leu Thr Pro<br>450　　　　　　　　455　　　　　　　　460 | 1392 |
| gac cag gtt gtc gct att gct agt aac ggc gga ggc aaa cag gcg ctg<br>Asp Gln Val Val Ala Ile Ala Ser Asn Gly Gly Gly Lys Gln Ala Leu<br>465　　　　　　　　470　　　　　　　　475　　　　　　　　480 | 1440 |
| gaa aca gtt cag cgc ctc ttg ccg gtc ttg tgt cag gac cac ggc ctg<br>Glu Thr Val Gln Arg Leu Leu Pro Val Leu Cys Gln Asp His Gly Leu<br>　　　　　　485　　　　　　　　490　　　　　　　　495 | 1488 |
| acc cca gaa caa gtt gtc gcg att gca agc aac aac gga ggc aaa caa<br>Thr Pro Glu Gln Val Val Ala Ile Ala Ser Asn Asn Gly Gly Lys Gln<br>　　　　500　　　　　　　　505　　　　　　　　510 | 1536 |

```
gcc tta gaa aca gtc cag aga ttg ttg ccg gtg ctg tgc caa gcc cac    1584
Ala Leu Glu Thr Val Gln Arg Leu Leu Pro Val Leu Cys Gln Ala His
        515                 520                 525 ggc ctg acc ccc gac cag gtt gtc gct att gct agt aac ggc gga ggc    1632
Gly Leu Thr Pro Asp Gln Val Val Ala Ile Ala Ser Asn Gly Gly Gly
    530                 535                 540 aaa cag gcg ctg gaa aca gtt cag cgc ctc ttg ccg gtc ttg tgt cag    1680
Lys Gln Ala Leu Glu Thr Val Gln Arg Leu Leu Pro Val Leu Cys Gln
545                 550                 555                 560 gcc cac ggc ctg acc cca gcc caa gtt gtc gcg att gca agc aac aac    1728
Ala His Gly Leu Thr Pro Ala Gln Val Val Ala Ile Ala Ser Asn Asn
                565                 570                 575 gga ggc aaa caa gcc tta gaa aca gtc cag aga ttg ttg ccg gtg ctg    1776
Gly Gly Lys Gln Ala Leu Glu Thr Val Gln Arg Leu Leu Pro Val Leu
            580                 585                 590 tgc caa gac cac ggc ctg acc cca gac cag gtt gtg gcc atc gcc agc    1824
Cys Gln Asp His Gly Leu Thr Pro Asp Gln Val Val Ala Ile Ala Ser
        595                 600                 605 aac ata ggt ggc aag cag gcc ctc gaa acc gtc cag aga ctg tta ccg    1872
Asn Ile Gly Gly Lys Gln Ala Leu Glu Thr Val Gln Arg Leu Leu Pro
    610                 615                 620 gtt ctc tgc cag gac cac ggc ctg acc ccg gaa cag gtg gtt gca atc    1920
Val Leu Cys Gln Asp His Gly Leu Thr Pro Glu Gln Val Val Ala Ile
625                 630                 635                 640 gcg tca cac gat ggg gga aag cag gcc cta gaa acc gtt cag cga ctc    1968
Ala Ser His Asp Gly Gly Lys Gln Ala Leu Glu Thr Val Gln Arg Leu
                645                 650                 655 ctg ccc gtc ctg tgc cag gcc cac ggc ctg acc cca gac cag gtt gtg    2016
Leu Pro Val Leu Cys Gln Ala His Gly Leu Thr Pro Asp Gln Val Val
            660                 665                 670 gcc atc gcc agc aac ata ggt ggc aag cag gcc ctc gaa acc gtc cag    2064
Ala Ile Ala Ser Asn Ile Gly Gly Lys Gln Ala Leu Glu Thr Val Gln
        675                 680                 685 aga ctg tta ccg gtt ctc tgc cag gcc cac ggc ctg acc ccg gcc cag    2112
Arg Leu Leu Pro Val Leu Cys Gln Ala His Gly Leu Thr Pro Ala Gln
    690                 695                 700 gtg gtt gca atc gcg tca cac gat ggg gga aag cag gcc cta gaa acc    2160
Val Val Ala Ile Ala Ser His Asp Gly Gly Lys Gln Ala Leu Glu Thr
705                 710                 715                 720 gtt cag cga ctc ctg ccc gtc ctg tgc cag gac cac ggc ctg acc cca    2208
Val Gln Arg Leu Leu Pro Val Leu Cys Gln Asp His Gly Leu Thr Pro
                725                 730                 735 gac cag gtt gtg gcc atc gcc agc aac ata ggt ggc aag cag gcc ctc    2256
Asp Gln Val Val Ala Ile Ala Ser Asn Ile Gly Gly Lys Gln Ala Leu
            740                 745                 750 gaa acc gtc cag aga ctg tta ccg gtt ctc tgc cag gac cac ggc ctg    2304
Glu Thr Val Gln Arg Leu Leu Pro Val Leu Cys Gln Asp His Gly Leu
        755                 760                 765 acc ccc gaa cag gtt gtc gct att gct agt aac ggc gga ggc aaa cag    2352
Thr Pro Glu Gln Val Val Ala Ile Ala Ser Asn Gly Gly Gly Lys Gln
    770                 775                 780 gcg ctg gaa aca gtt cag cgc ctc ttg ccg gtc ttg tgt cag gcc cac    2400
Ala Leu Glu Thr Val Gln Arg Leu Leu Pro Val Leu Cys Gln Ala His
785                 790                 795                 800 ggc ctg acg cct gag cag gta gtg gct att gca tcc aac gga ggg ggc    2448
Gly Leu Thr Pro Glu Gln Val Val Ala Ile Ala Ser Asn Gly Gly Gly
                805                 810                 815 aga ccc gca ctg gag tca atc gtg gcc cag ctt tcg agg ccg gac ccc    2496
Arg Pro Ala Leu Glu Ser Ile Val Ala Gln Leu Ser Arg Pro Asp Pro
```

```
gcg ctg gcc gca ctc act aat gat cat ctt gta gcg ctg gcc tgc ctc    2544
Ala Leu Ala Ala Leu Thr Asn Asp His Leu Val Ala Leu Ala Cys Leu
        835                 840                 845 ggc gga cgt cct gcc atg gat gca gtg aaa aag gga ttg ccg cac gcg    2592
Gly Gly Arg Pro Ala Met Asp Ala Val Lys Lys Gly Leu Pro His Ala
850                 855                 860 ccg gaa ttg atc aga tcc cag cta gtg aaa tct gaa ttg gaa gag aag    2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att    2688
Lys Ser Glu Leu Arg His Lys Leu Lys Tyr Val Pro His Glu Tyr Ile
                885                 890                 895 gaa ttg att gaa atc gca aga aat tca act cag gat aga atc ctt gaa    2736
Glu Leu Ile Glu Ile Ala Arg Asn Ser Thr Gln Asp Arg Ile Leu Glu
            900                 905                 910 atg aag gtg atg gag ttc ttt atg aag gtt tat ggt tat cgt ggt aaa    2784
Met Lys Val Met Glu Phe Phe Met Lys Val Tyr Gly Tyr Arg Gly Lys
        915                 920                 925 cat ttg ggt gga tca agg aaa cca gac gga gca att tat act gtc gga    2832
His Leu Gly Gly Ser Arg Lys Pro Asp Gly Ala Ile Tyr Thr Val Gly
930                 935                 940 tct cct att gat tac ggt gtg atc gtt gat act aag gca tat tca gga    2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc    2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg    2976
Glu Glu Asn Gln Thr Arg Asn Lys His Ile Asn Pro Asn Glu Trp Trp
            980                 985                 990 aaa gtc tat cca tct tca gta aca gaa ttt aag ttc ttg ttt gtg agt    3024
Lys Val Tyr Pro Ser Ser Val Thr Glu Phe Lys Phe Leu Phe Val Ser
        995                 1000                1005 ggt cat ttc aaa gga aac tac aaa gct cag ctt aca aga ttg aat        3069
Gly His Phe Lys Gly Asn Tyr Lys Ala Gln Leu Thr Arg Leu Asn
    1010                1015                1020 cat atc act aat tgt aat gga gct gtt ctt agt gta gaa gag ctt        3114
His Ile Thr Asn Cys Asn Gly Ala Val Leu Ser Val Glu Glu Leu
    1025                1030                1035 ttg att ggt gga gaa atg att aaa gct ggt aca ttg aca ctt gag        3159
Leu Ile Gly Gly Glu Met Ile Lys Ala Gly Thr Leu Thr Leu Glu
    1040                1045                1050 gaa gtg aga agg aaa ttt aat aac ggt gag ata aac ttt taa            3201
Glu Val Arg Arg Lys Phe Asn Asn Gly Glu Ile Asn Phe
    1055                1060                1065
```

<210> SEQ ID NO 55
<211> LENGTH: 1066
<212> TYPE: PRT
<213> ORGANISM: artificial sequence
<220> FEATURE:
<223> OTHER INFORMATION: Synthetic Construct

<400> SEQUENCE: 55

```
Met Ala Ser Ser Pro Pro Lys Lys Lys Arg Lys Val Ala Ala Asp
1               5                   10                  15

Tyr Lys Asp Asp Asp Asp Lys Ser Trp Lys Asp Ala Ser Gly Trp Ser
                20                  25                  30

Arg Met His Ala Ala Pro Arg Arg Arg Ala Ala Gln Pro Ser Asp Ala
```

-continued

```
                35                  40                  45
Ser Pro Ala Ala Gln Val Asp Leu Arg Thr Leu Gly Tyr Ser Gln Gln
 50                  55                  60
Gln Gln Glu Lys Ile Lys Pro Lys Val Arg Ser Thr Val Ala Gln His
 65                  70                  75                  80
His Glu Ala Leu Val Gly His Gly Phe Thr His Ala His Ile Val Ala
                     85                  90                  95
Leu Ser Gln His Pro Ala Ala Leu Gly Thr Val Ala Val Thr Tyr Gln
                 100                 105                 110
His Ile Ile Thr Ala Leu Pro Glu Ala Thr His Glu Asp Ile Val Gly
                 115                 120                 125
Val Gly Lys Gln Trp Ser Gly Ala Arg Ala Leu Glu Ala Leu Leu Thr
                 130                 135                 140
Asp Ala Gly Glu Leu Arg Gly Pro Leu Gln Leu Asp Thr Gly Gln
145                 150                 155                 160
Leu Val Lys Ile Ala Lys Arg Gly Gly Val Thr Ala Met Glu Ala Val
                 165                 170                 175
His Ala Ser Arg Asn Ala Leu Thr Gly Ala Pro Leu Asn Leu Thr Pro
                 180                 185                 190
Asp Gln Val Val Ala Ile Ala Ser His Asp Gly Gly Lys Gln Ala Leu
                 195                 200                 205
Glu Thr Val Gln Arg Leu Leu Pro Val Leu Cys Gln Asp His Gly Leu
                 210                 215                 220
Thr Pro Glu Gln Val Val Ala Ile Ala Ser His Asp Gly Gly Lys Gln
225                 230                 235                 240
Ala Leu Glu Thr Val Gln Arg Leu Leu Pro Val Leu Cys Gln Ala His
                 245                 250                 255
Gly Leu Thr Pro Asp Gln Val Val Ala Ile Ala Ser Asn Gly Gly
                 260                 265                 270
Lys Gln Ala Leu Glu Thr Val Gln Arg Leu Leu Pro Val Leu Cys Gln
                 275                 280                 285
Ala His Gly Leu Thr Pro Ala Gln Val Val Ala Ile Ala Ser Asn Gly
                 290                 295                 300
Gly Gly Lys Gln Ala Leu Glu Thr Val Gln Arg Leu Leu Pro Val Leu
305                 310                 315                 320
Cys Gln Asp His Gly Leu Thr Pro Asp Gln Val Val Ala Ile Ala Ser
                 325                 330                 335
Asn Ile Gly Gly Lys Gln Ala Leu Glu Thr Val Gln Arg Leu Leu Pro
                 340                 345                 350
Val Leu Cys Gln Asp His Gly Leu Thr Pro Glu Gln Val Val Ala Ile
                 355                 360                 365
Ala Ser His Asp Gly Gly Lys Gln Ala Leu Glu Thr Val Gln Arg Leu
                 370                 375                 380
Leu Pro Val Leu Cys Gln Ala His Gly Leu Thr Pro Asp Gln Val Val
385                 390                 395                 400
Ala Ile Ala Ser Asn Gly Gly Lys Gln Ala Leu Glu Thr Val Gln
                 405                 410                 415
Arg Leu Leu Pro Val Leu Cys Gln Ala His Gly Leu Thr Pro Ala Gln
                 420                 425                 430
Val Val Ala Ile Ala Ser Asn Gly Gly Gly Lys Gln Ala Leu Glu Thr
                 435                 440                 445
Val Gln Arg Leu Leu Pro Val Leu Cys Gln Asp His Gly Leu Thr Pro
                 450                 455                 460
```

-continued

```
Asp Gln Val Val Ala Ile Ala Ser Asn Gly Gly Lys Gln Ala Leu
465                 470                 475                 480

Glu Thr Val Gln Arg Leu Leu Pro Val Leu Cys Gln Asp His Gly Leu
        485                 490                 495

Thr Pro Glu Gln Val Val Ala Ile Ala Ser Asn Asn Gly Gly Lys Gln
            500                 505                 510

Ala Leu Glu Thr Val Gln Arg Leu Leu Pro Val Leu Cys Gln Ala His
        515                 520                 525

Gly Leu Thr Pro Asp Gln Val Val Ala Ile Ala Ser Asn Gly Gly Gly
        530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Asn
                565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
            595                 600                 605

Asn Ile Gly Gly Lys Gln Ala Leu Glu Thr Val Gln Arg Leu Leu Pro
610                 615                 620

Val Leu Cys Gln Asp His Gly Leu Thr Pro Glu Gln Val Val Ala Ile
625                 630                 635                 640

Ala Ser His Asp Gly Gly Lys Gln Ala Leu Glu Thr Val Gln Arg Leu
                645                 650                 655

Leu Pro Val Leu Cys Gln Ala His Gly Leu Thr Pro Asp Gln Val Val
            660                 665                 670

Ala Ile Ala Ser Asn Ile Gly Gly Lys Gln Ala Leu Glu Thr Val Gln
            675                 680                 685

Arg Leu Leu Pro Val Leu Cys Gln Ala His Gly Leu Thr Pro Ala Gln
        690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
            725                 730                 735

Asp Gln Val Val Ala Ile Ala Ser Asn Ile Gly Gly Lys Gln Ala Leu
            740                 745                 750

Glu Thr Val Gln Arg Leu Leu Pro Val Leu Cys Gln Asp His Gly Leu
        755                 760                 765

Thr Pro Glu Gln Val Val Ala Ile Ala Ser Asn Gly Gly Gly Lys Gln
        770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser Asn Gly Gly Gly
                805                 810                 815

Arg Pro Ala Leu Glu Ser Ile Val Ala Gln Leu Ser Arg Pro Asp Pro
            820                 825                 830

Ala Leu Ala Ala Leu Thr Asn Asp His Leu Val Ala Leu Ala Cys Leu
            835                 840                 845

Gly Gly Arg Pro Ala Met Asp Ala Val Lys Lys Gly Leu Pro His Ala
        850                 855                 860

Pro Glu Leu Ile Arg Ser Gln Leu Val Lys Ser Glu Leu Glu Glu Lys
865                 870                 875                 880
```

```
Lys Ser Glu Leu Arg His Lys Leu Lys Tyr Val Pro His Glu Tyr Ile
            885                 890                 895
Glu Leu Ile Glu Ile Ala Arg Asn Ser Thr Gln Asp Arg Ile Leu Glu
        900                 905                 910
Met Lys Val Met Glu Phe Phe Met Lys Val Tyr Gly Tyr Arg Gly Lys
        915                 920                 925
His Leu Gly Gly Ser Arg Lys Pro Asp Gly Ala Ile Tyr Thr Val Gly
        930                 935                 940
Ser Pro Ile Asp Tyr Gly Val Ile Val Asp Thr Lys Ala Tyr Ser Gly
945                 950                 955                 960
Gly Tyr Asn Leu Pro Ile Gly Gln Ala Asp Glu Met Gln Arg Tyr Val
                965                 970                 975
Glu Glu Asn Gln Thr Arg Asn Lys His Ile Asn Pro Asn Glu Trp Trp
            980                 985                 990
Lys Val Tyr Pro Ser Ser Val Thr Glu Phe Lys Phe Leu Phe Val Ser
        995                 1000                1005
Gly His Phe Lys Gly Asn Tyr Lys Ala Gln Leu Thr Arg Leu Asn
        1010                1015                1020
His Ile Thr Asn Cys Asn Gly Ala Val Leu Ser Val Glu Glu Leu
        1025                1030                1035
Leu Ile Gly Gly Glu Met Ile Lys Ala Gly Thr Leu Thr Leu Glu
        1040                1045                1050
Glu Val Arg Arg Lys Phe Asn Asn Gly Glu Ile Asn Phe
        1055                1060                1065

<210> SEQ ID NO 56
<211> LENGTH: 3201
<212> TYPE: DNA
<213> ORGANISM: artificial sequence
<220> FEATURE:
<223> OTHER INFORMATION: TALEN-TCR-beta1_L19 TALEN coding sequence
<220> FEATURE:
<221> NAME/KEY: CDS
<222> LOCATION: (1)..(3201)

<400> SEQUENCE: 56 atg gct tcc tcc cct cca aag aaa aag aga aag gtt gcg gcc gct gac       48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct       96
Tyr Lys Asp Asp Asp Asp Lys Ser Trp Lys Asp Ala Ser Gly Trp Ser
            20                  25                  30 aga atg cat gcg gcc ccg cga cgg cgt gct gcg caa ccc tcc gac gct      144
Arg Met His Ala Ala Pro Arg Arg Arg Ala Ala Gln Pro Ser Asp Ala
        35                  40                  45 tcg ccg gcc gcg cag gtg gat cta cgc acg ctc ggc tac agt cag cag      192
Ser Pro Ala Ala Gln Val Asp Leu Arg Thr Leu Gly Tyr Ser Gln Gln
    50                  55                  60 cag caa gag aag atc aaa ccg aag gtg cgt tcg aca gtg gcg cag cac      240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg      288
His Glu Ala Leu Val Gly His Gly Phe Thr His Ala His Ile Val Ala
                85                  90                  95 ctc agc caa cac ccg gca gcg tta ggg acc gtc gct gtc acg tat cag      336
Leu Ser Gln His Pro Ala Ala Leu Gly Thr Val Ala Val Thr Tyr Gln
            100                 105                 110 cac ata atc acg gcg ttg cca gag gcg aca cac gaa gac atc gtt ggc      384
His Ile Ile Thr Ala Leu Pro Glu Ala Thr His Glu Asp Ile Val Gly
        115                 120                 125
```

```
                115                 120                 125
gtc ggc aaa cag tgg tcc ggc gca cgc gcc ctg gag gcc ttg ctc acg      432
Val Gly Lys Gln Trp Ser Gly Ala Arg Ala Leu Glu Ala Leu Leu Thr
    130                 135                 140 gat gcg ggg gag ttg aga ggt ccg ccg tta cag ttg gac aca ggc caa      480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg      528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc cca      576
His Ala Ser Arg Asn Ala Leu Thr Gly Ala Pro Leu Asn Leu Thr Pro
            180                 185                 190 gac caa gtt gtc gcg att gca agc aac aac gga ggc aaa caa gcc tta      624
Asp Gln Val Val Ala Ile Ala Ser Asn Asn Gly Gly Lys Gln Ala Leu
        195                 200                 205 gaa aca gtc cag aga ttg ttg ccg gtg ctg tgc caa gac cac ggc ctg      672
Glu Thr Val Gln Arg Leu Leu Pro Val Leu Cys Gln Asp His Gly Leu
    210                 215                 220 acc ccc gaa cag gtt gtc gct att gct agt aac ggc gga ggc aaa cag      720
Thr Pro Glu Gln Val Val Ala Ile Ala Ser Asn Gly Gly Gly Lys Gln
225                 230                 235                 240 gcg ctg gaa aca gtt cag cgc ctc ttg ccg gtc ttg tgt cag gcc cac      768
Ala Leu Glu Thr Val Gln Arg Leu Leu Pro Val Leu Cys Gln Ala His
                245                 250                 255 ggc ctg acc ccc gac cag gtt gtc gct att gct agt aac ggc gga ggc      816
Gly Leu Thr Pro Asp Gln Val Val Ala Ile Ala Ser Asn Gly Gly Gly
            260                 265                 270 aaa cag gcg ctg gaa aca gtt cag cgc ctc ttg ccg gtc ttg tgt cag      864
Lys Gln Ala Leu Glu Thr Val Gln Arg Leu Leu Pro Val Leu Cys Gln
        275                 280                 285 gcc cac ggc ctg acc ccg gcc cag gtg gtt gca atc gcg tca cac gat      912
Ala His Gly Leu Thr Pro Ala Gln Val Val Ala Ile Ala Ser His Asp
    290                 295                 300 ggg gga aag cag gcc cta gaa acc gtt cag cga ctc ctg ccc gtc ctg      960
Gly Gly Lys Gln Ala Leu Glu Thr Val Gln Arg Leu Leu Pro Val Leu
305                 310                 315                 320 tgc cag gac cac ggc ctg acc ccg gac cag gtg gtt gca atc gcg tca      1008
Cys Gln Asp His Gly Leu Thr Pro Asp Gln Val Val Ala Ile Ala Ser
                325                 330                 335 cac gat ggg gga aag cag gcc cta gaa acc gtt cag cga ctc ctg ccc      1056
His Asp Gly Gly Lys Gln Ala Leu Glu Thr Val Gln Arg Leu Leu Pro
            340                 345                 350 gtc ctg tgc cag gac cac ggc ctg acc ccg gaa cag gtg gtt gca atc      1104
Val Leu Cys Gln Asp His Gly Leu Thr Pro Glu Gln Val Val Ala Ile
        355                 360                 365 gcg tca cac gat ggg gga aag cag gcc cta gaa acc gtt cag cga ctc      1152
Ala Ser His Asp Gly Gly Lys Gln Ala Leu Glu Thr Val Gln Arg Leu
    370                 375                 380 ctg ccc gtc ctg tgc cag gcc cac ggc ctg acc cca gac cag gtt gtg      1200
Leu Pro Val Leu Cys Gln Ala His Gly Leu Thr Pro Asp Gln Val Val
385                 390                 395                 400 gcc atc gcc agc aac ata ggt ggc aag cag gcc ctc gaa acc gtc cag      1248
Ala Ile Ala Ser Asn Ile Gly Gly Lys Gln Ala Leu Glu Thr Val Gln
                405                 410                 415 aga ctg tta ccg gtt ctc tgc cag gcc cac ggc ctg acc ccg gcc cag      1296
Arg Leu Leu Pro Val Leu Cys Gln Ala His Gly Leu Thr Pro Ala Gln
            420                 425                 430 gtg gtt gca atc gcg tca cac gat ggg gga aag cag gcc cta gaa acc      1344
```

```
                Val Val Ala Ile Ala Ser His Asp Gly Gly Lys Gln Ala Leu Glu Thr
                            435                 440                 445 gtt cag cga ctc ctg ccc gtc ctg tgc cag gac cac ggc ctg acc ccg                1392
Val Gln Arg Leu Leu Pro Val Leu Cys Gln Asp His Gly Leu Thr Pro
        450                 455                 460 gac cag gtg gtt gca atc gcg tca cac gat ggg gga aag cag gcc cta                1440
Asp Gln Val Val Ala Ile Ala Ser His Asp Gly Gly Lys Gln Ala Leu
465                 470                 475                 480 gaa acc gtt cag cga ctc ctg ccc gtc ctg tgc cag gac cac ggc ctg                1488
Glu Thr Val Gln Arg Leu Leu Pro Val Leu Cys Gln Asp His Gly Leu
                485                 490                 495 acc ccg gaa cag gtg gtt gca atc gcg tca cac gat ggg gga aag cag                1536
Thr Pro Glu Gln Val Val Ala Ile Ala Ser His Asp Gly Gly Lys Gln
            500                 505                 510 gcc cta gaa acc gtt cag cga ctc ctg ccc gtc ctg tgc cag gcc cac                1584
Ala Leu Glu Thr Val Gln Arg Leu Leu Pro Val Leu Cys Gln Ala His
        515                 520                 525 ggc ctg acc cca gac caa gtt gtc gcg att gca agc aac aac gga ggc                1632
Gly Leu Thr Pro Asp Gln Val Val Ala Ile Ala Ser Asn Asn Gly Gly
    530                 535                 540 aaa caa gcc tta gaa aca gtc cag aga ttg ttg cct gtg ctg tgc caa                1680
Lys Gln Ala Leu Glu Thr Val Gln Arg Leu Leu Pro Val Leu Cys Gln
545                 550                 555                 560 gcc cac ggc ctg acc cca gcc cag gtt gtg gcc atc gcc agc aac ata                1728
Ala His Gly Leu Thr Pro Ala Gln Val Val Ala Ile Ala Ser Asn Ile
                565                 570                 575 ggt ggc aag cag gcc ctc gaa acc gtc cag aga ctg tta ccg gtt ctc                1776
Gly Gly Lys Gln Ala Leu Glu Thr Val Gln Arg Leu Leu Pro Val Leu
            580                 585                 590 tgc cag gac cac ggc ctg acc cca gac caa gtt gtc gcg att gca agc                1824
Cys Gln Asp His Gly Leu Thr Pro Asp Gln Val Val Ala Ile Ala Ser
        595                 600                 605 aac aac gga ggc aaa caa gcc tta gaa aca gtc cag aga ttg ttg ccg                1872
Asn Asn Gly Gly Lys Gln Ala Leu Glu Thr Val Gln Arg Leu Leu Pro
    610                 615                 620 gtg ctg tgc caa gac cac ggc ctg acc cca gaa caa gtt gtc gcg att                1920
Val Leu Cys Gln Asp His Gly Leu Thr Pro Glu Gln Val Val Ala Ile
625                 630                 635                 640 gca agc aac aac gga ggc aaa caa gcc tta gaa aca gtc cag aga ttg                1968
Ala Ser Asn Asn Gly Gly Lys Gln Ala Leu Glu Thr Val Gln Arg Leu
                645                 650                 655 ttg ccg gtg ctg tgc caa gcc cac ggc ctg acc ccc gac cag gtt gtc                2016
Leu Pro Val Leu Cys Gln Ala His Gly Leu Thr Pro Asp Gln Val Val
            660                 665                 670 gct att gct agt aac ggc gga ggc aaa cag gcg ctg gaa aca gtt cag                2064
Ala Ile Ala Ser Asn Gly Gly Gly Lys Gln Ala Leu Glu Thr Val Gln
        675                 680                 685 cgc ctc ttg ccg gtc ttg tgt cag gcc cac ggc ctg acc ccg gcc cag                2112
Arg Leu Leu Pro Val Leu Cys Gln Ala His Gly Leu Thr Pro Ala Gln
    690                 695                 700 gtg gtt gca atc gcg tca cac gat ggg gga aag cag gcc cta gaa acc                2160
Val Val Ala Ile Ala Ser His Asp Gly Gly Lys Gln Ala Leu Glu Thr
705                 710                 715                 720 gtt cag cga ctc ctg ccc gtc ctg tgc cag gac cac ggc ctg acc cca                2208
Val Gln Arg Leu Leu Pro Val Leu Cys Gln Asp His Gly Leu Thr Pro
                725                 730                 735 gac caa gtt gtc gcg att gca agc aac aac gga ggc aaa caa gcc tta                2256
Asp Gln Val Val Ala Ile Ala Ser Asn Asn Gly Gly Lys Gln Ala Leu
            740                 745                 750
```

```
gaa aca gtc cag aga ttg ttg ccg gtg ctg tgc caa gac cac ggc ctg       2304
Glu Thr Val Gln Arg Leu Leu Pro Val Leu Cys Gln Asp His Gly Leu
        755                 760                 765 acc ccg gaa cag gtg gtt gca atc gcg tca cac gat ggg gga aag cag       2352
Thr Pro Glu Gln Val Val Ala Ile Ala Ser His Asp Gly Gly Lys Gln
    770                 775                 780 gcc cta gaa acc gtt cag cga ctc ctg ccc gtc ctg tgc cag gcc cac       2400
Ala Leu Glu Thr Val Gln Arg Leu Leu Pro Val Leu Cys Gln Ala His
785                 790                 795                 800 ggc ctg acg cct gag cag gta gtg gct att gca tcc aac gga ggg ggc       2448
Gly Leu Thr Pro Glu Gln Val Val Ala Ile Ala Ser Asn Gly Gly Gly
            805                 810                 815 aga ccc gca ctg gag tca atc gtg gcc cag ctt tcg agg ccg gac ccc       2496
Arg Pro Ala Leu Glu Ser Ile Val Ala Gln Leu Ser Arg Pro Asp Pro
        820                 825                 830 gcg ctg gcc gca ctc act aat gat cat ctt gta gcg ctg gcc tgc ctc       2544
Ala Leu Ala Ala Leu Thr Asn Asp His Leu Val Ala Leu Ala Cys Leu
    835                 840                 845 ggc gga cgt cct gcc atg gat gca gtg aaa aag gga ttg ccg cac gcg       2592
Gly Gly Arg Pro Ala Met Asp Ala Val Lys Lys Gly Leu Pro His Ala
850                 855                 860 ccg gaa ttg atc aga tcc cag cta gtg aaa tct gaa ttg gaa gag aag       2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att       2688
Lys Ser Glu Leu Arg His Lys Leu Lys Tyr Val Pro His Glu Tyr Ile
            885                 890                 895 gaa ttg att gaa atc gca aga aat tca act cag gat aga atc ctt gaa       2736
Glu Leu Ile Glu Ile Ala Arg Asn Ser Thr Gln Asp Arg Ile Leu Glu
        900                 905                 910 atg aag gtg atg gag ttc ttt atg aag gtt tat ggt tat cgt ggt aaa       2784
Met Lys Val Met Glu Phe Phe Met Lys Val Tyr Gly Tyr Arg Gly Lys
    915                 920                 925 cat ttg ggt gga tca agg aaa cca gac gga gca att tat act gtc gga       2832
His Leu Gly Gly Ser Arg Lys Pro Asp Gly Ala Ile Tyr Thr Val Gly
930                 935                 940 tct cct att gat tac ggt gtg atc gtt gat act aag gca tat tca gga       2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc       2928
Gly Tyr Asn Leu Pro Ile Gly Gln Ala Asp Glu Met Gln Arg Tyr Val
            965                 970                 975 gaa gag aat caa aca aga aac aag cat atc aac cct aat gaa tgg tgg       2976
Glu Glu Asn Gln Thr Arg Asn Lys His Ile Asn Pro Asn Glu Trp Trp
        980                 985                 990 aaa gtc tat cca tct tca gta aca  gaa ttt aag ttc ttg  ttt gtg agt     3024
Lys Val Tyr Pro Ser Ser Val Thr  Glu Phe Lys Phe Leu  Phe Val Ser
    995                 1000                1005 ggt cat ttc aaa gga aac tac  aaa gct cag ctt aca  aga ttg aat         3069
Gly His Phe Lys Gly Asn Tyr  Lys Ala Gln Leu Thr  Arg Leu Asn
    1010                1015                1020 cat atc act aat tgt aat gga  gct gtt ctt agt gta  gaa gag ctt         3114
His Ile Thr Asn Cys Asn Gly  Ala Val Leu Ser Val  Glu Glu Leu
    1025                1030                1035 ttg att ggt gga gaa atg att  aaa gct ggt aca ttg  aca ctt gag         3159
Leu Ile Gly Gly Glu Met Ile  Lys Ala Gly Thr Leu  Thr Leu Glu
    1040                1045                1050 gaa gtg aga agg aaa ttt aat  aac ggt gag ata aac  ttt taa             3201
Glu Val Arg Arg Lys Phe Asn  Asn Gly Glu Ile Asn  Phe
    1055                1060                1065
```

```
<210> SEQ ID NO 57
<211> LENGTH: 1066
<212> TYPE: PRT
<213> ORGANISM: artificial sequence
<220> FEATURE:
<223> OTHER INFORMATION: Synthetic Construct

<400> SEQUENCE: 57

Met Ala Ser Ser Pro Lys Lys Arg Lys Val Ala Ala Asp
1               5                   10                  15

Tyr Lys Asp Asp Asp Lys Ser Trp Lys Asp Ala Ser Gly Trp Ser
                20                  25                  30

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
    50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
                100                 105                 110

His Ile Ile Thr Ala Leu Pro Glu Ala Thr His Glu Asp Ile Val Gly
                115                 120                 125

Val Gly Lys Gln Trp Ser Gly Ala Arg Ala Leu Glu Ala Leu Leu Thr
        130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
                180                 185                 190

Asp Gln Val Val Ala Ile Ala Ser Asn Asn Gly Gly Lys Gln Ala Leu
                195                 200                 205

Glu Thr Val Gln Arg Leu Leu Pro Val Leu Cys Gln Asp His Gly Leu
    210                 215                 220

Thr Pro Glu Gln Val Val Ala Ile Ala Ser Asn Gly Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser Asn Gly Gly Gly
                260                 265                 270

Lys Gln Ala Leu Glu Thr Val Gln Arg Leu Leu Pro Val Leu Cys Gln
        275                 280                 285

Ala His Gly Leu Thr Pro Ala Gln Val Val Ala Ile Ala Ser His Asp
        290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

His Asp Gly Gly Lys Gln Ala Leu Glu Thr Val Gln Arg Leu Leu Pro
                340                 345                 350

Val Leu Cys Gln Asp His Gly Leu Thr Pro Glu Gln Val Val Ala Ile
        355                 360                 365
```

```
Ala Ser His Asp Gly Gly Lys Gln Ala Leu Glu Thr Val Gln Arg Leu
    370                 375                 380

Leu Pro Val Leu Cys Gln Ala His Gly Leu Thr Pro Asp Gln Val Val
385                 390                 395                 400

Ala Ile Ala Ser Asn Ile Gly Gly Lys Gln Ala Leu Glu Thr Val Gln
            405                 410                 415

Arg Leu Leu Pro Val Leu Cys Gln Ala His Gly Leu Thr Pro Ala Gln
            420                 425                 430

Val Val Ala Ile Ala Ser His Asp Gly Gly Lys Gln Ala Leu Glu Thr
            435                 440                 445

Val Gln Arg Leu Leu Pro Val Leu Cys Gln Asp His Gly Leu Thr Pro
    450                 455                 460

Asp Gln Val Val Ala Ile Ala Ser His Asp Gly Gly Lys Gln Ala Leu
465                 470                 475                 480

Glu Thr Val Gln Arg Leu Leu Pro Val Leu Cys Gln Asp His Gly Leu
            485                 490                 495

Thr Pro Glu Gln Val Val Ala Ile Ala Ser His Asp Gly Gly Lys Gln
            500                 505                 510

Ala Leu Glu Thr Val Gln Arg Leu Leu Pro Val Leu Cys Gln Ala His
        515                 520                 525

Gly Leu Thr Pro Asp Gln Val Val Ala Ile Ala Ser Asn Asn Gly Gly
    530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Ile
            565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
            595                 600                 605

Asn Asn Gly Gly Lys Gln Ala Leu Glu Thr Val Gln Arg Leu Leu Pro
    610                 615                 620

Val Leu Cys Gln Asp His Gly Leu Thr Pro Glu Gln Val Val Ala Ile
625                 630                 635                 640

Ala Ser Asn Asn Gly Gly Lys Gln Ala Leu Glu Thr Val Gln Arg Leu
            645                 650                 655

Leu Pro Val Leu Cys Gln Ala His Gly Leu Thr Pro Asp Gln Val Val
            660                 665                 670

Ala Ile Ala Ser Asn Gly Gly Lys Gln Ala Leu Glu Thr Val Gln
        675                 680                 685

Arg Leu Leu Pro Val Leu Cys Gln Ala His Gly Leu Thr Pro Ala Gln
    690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
            725                 730                 735

Asp Gln Val Val Ala Ile Ala Ser Asn Asn Gly Gly Lys Gln Ala Leu
            740                 745                 750

Glu Thr Val Gln Arg Leu Leu Pro Val Leu Cys Gln Asp His Gly Leu
        755                 760                 765

Thr Pro Glu Gln Val Val Ala Ile Ala Ser His Asp Gly Gly Lys Gln
    770                 775                 780
```

```
Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser Asn Gly Gly Gly
            805                 810                 815

Arg Pro Ala Leu Glu Ser Ile Val Ala Gln Leu Ser Arg Pro Asp Pro
        820                 825                 830

Ala Leu Ala Ala Leu Thr Asn Asp His Leu Val Ala Leu Ala Cys Leu
        835                 840                 845

Gly Gly Arg Pro Ala Met Asp Ala Val Lys Lys Gly Leu Pro His Ala
850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
                885                 890                 895

Glu Leu Ile Glu Ile Ala Arg Asn Ser Thr Gln Asp Arg Ile Leu Glu
                900                 905                 910

Met Lys Val Met Glu Phe Phe Met Lys Val Tyr Gly Tyr Arg Gly Lys
                915                 920                 925

His Leu Gly Gly Ser Arg Lys Pro Asp Gly Ala Ile Tyr Thr Val Gly
            930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
                965                 970                 975

Glu Glu Asn Gln Thr Arg Asn Lys His Ile Asn Pro Asn Glu Trp Trp
            980                 985                 990

Lys Val Tyr Pro Ser Ser Val Thr Glu Phe Lys Phe Leu Phe Val Ser
                995                 1000                1005

Gly His  Phe Lys Gly Asn Tyr  Lys Ala Gln Leu Thr  Arg Leu Asn
   1010              1015               1020

His Ile  Thr Asn Cys Asn Gly  Ala Val Leu Ser Val  Glu Glu Leu
   1025              1030               1035

Leu Ile  Gly Gly Glu Met Ile  Lys Ala Gly Thr Leu  Thr Leu Glu
   1040              1045               1050

Glu Val  Arg Arg Lys Phe Asn  Asn Gly Glu Ile Asn  Phe
   1055              1060               1065

<210> SEQ ID NO 58
<211> LENGTH: 3201
<212> TYPE: DNA
<213> ORGANISM: artificial sequence
<220> FEATURE:
<223> OTHER INFORMATION: TALEN-TCR-beta1_R19 TALEN coding sequence
<220> FEATURE:
<221> NAME/KEY: CDS
<222> LOCATION: (1)..(3201)

<400> SEQUENCE: 58 atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
            20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
        35                  40                  45
```

-continued

```
tcg ccg gcc gcg cag gtg gat cta cgc acg ctc ggc tac agt cag cag    192
Ser Pro Ala Ala Gln Val Asp Leu Arg Thr Leu Gly Tyr Ser Gln Gln
 50              55                  60 cag caa gag aag atc aaa ccg aag gtg cgt tcg aca gtg gcg cag cac    240
Gln Gln Glu Lys Ile Lys Pro Lys Val Arg Ser Thr Val Ala Gln His
 65              70                  75                  80 cac gag gca ctg gtg ggc cat ggg ttt aca cac gcg cac atc gtt gcg    288
His Glu Ala Leu Val Gly His Gly Phe Thr His Ala His Ile Val Ala
                 85                  90                  95 ctc agc caa cac ccg gca gcg tta ggg acc gtc gct gtc acg tat cag    336
Leu Ser Gln His Pro Ala Ala Leu Gly Thr Val Ala Val Thr Tyr Gln
            100                 105                 110 cac ata atc acg gcg ttg cca gag gcg aca cac gaa gac atc gtt ggc    384
His Ile Ile Thr Ala Leu Pro Glu Ala Thr His Glu Asp Ile Val Gly
        115                 120                 125 gtc ggc aaa cag tgg tcc ggc gca cgc gcc ctg gag gcc ttg ctc acg    432
Val Gly Lys Gln Trp Ser Gly Ala Arg Ala Leu Glu Ala Leu Leu Thr
130                 135                 140 gat gcg ggg gag ttg aga ggt ccg ccg tta cag ttg gac aca ggc caa    480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg    528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc cca    576
His Ala Ser Arg Asn Ala Leu Thr Gly Ala Pro Leu Asn Leu Thr Pro
            180                 185                 190 gac caa gtt gtc gcg att gca agc aac aac gga ggc aaa caa gcc tta    624
Asp Gln Val Val Ala Ile Ala Ser Asn Asn Gly Gly Lys Gln Ala Leu
        195                 200                 205 gaa aca gtc cag aga ttg ttg ccg gtg ctg tgc caa gac cac ggc ctg    672
Glu Thr Val Gln Arg Leu Leu Pro Val Leu Cys Gln Asp His Gly Leu
210                 215                 220 acc ccc gaa cag gtt gtc gct att gct agt aac ggc gga ggc aaa cag    720
Thr Pro Glu Gln Val Val Ala Ile Ala Ser Asn Gly Gly Gly Lys Gln
225                 230                 235                 240 gcg ctg gaa aca gtt cag cgc ctc ttg ccg gtc ttg tgt cag gcc cac    768
Ala Leu Glu Thr Val Gln Arg Leu Leu Pro Val Leu Cys Gln Ala His
                245                 250                 255 ggc ctg acc cca gac caa gtt gtc gcg att gca agc aac aac gga ggc    816
Gly Leu Thr Pro Asp Gln Val Val Ala Ile Ala Ser Asn Asn Gly Gly
            260                 265                 270 aaa caa gcc tta gaa aca gtc cag aga ttg ttg cct gtg ctg tgc caa    864
Lys Gln Ala Leu Glu Thr Val Gln Arg Leu Leu Pro Val Leu Cys Gln
        275                 280                 285 gcc cac ggc ctg acc cca gcc caa gtt gtc gcg att gca agc aac aac    912
Ala His Gly Leu Thr Pro Ala Gln Val Val Ala Ile Ala Ser Asn Asn
290                 295                 300 gga ggc aaa caa gcc tta gaa aca gtc cag aga ttg ttg ccg gtg ctg    960
Gly Gly Lys Gln Ala Leu Glu Thr Val Gln Arg Leu Leu Pro Val Leu
305                 310                 315                 320 tgc caa gac cac ggc ctg acc cca gac caa gtt gtc gcg att gca agc   1008
Cys Gln Asp His Gly Leu Thr Pro Asp Gln Val Val Ala Ile Ala Ser
                325                 330                 335 aac aac gga ggc aaa caa gcc tta gaa aca gtc cag aga ttg ttg ccg   1056
Asn Asn Gly Gly Lys Gln Ala Leu Glu Thr Val Gln Arg Leu Leu Pro
            340                 345                 350 gtg ctg tgc caa gac cac ggc ctg acc cca gaa cag gtt gtg gcc atc   1104
Val Leu Cys Gln Asp His Gly Leu Thr Pro Glu Gln Val Val Ala Ile
        355                 360                 365
```

| | | |
|---|---|---|
| gcc agc aac ata ggt ggc aag cag gcc ctc gaa acc gtc cag aga ctg<br>Ala Ser Asn Ile Gly Gly Lys Gln Ala Leu Glu Thr Val Gln Arg Leu<br>370                           375                     380 | | 1152 |
| tta ccg gtt ctc tgc cag gcc cac ggc ctg acc cca gac caa gtt gtc<br>Leu Pro Val Leu Cys Gln Ala His Gly Leu Thr Pro Asp Gln Val Val<br>385                      390                       395                 400 | | 1200 |
| gcg att gca agc aac aac gga ggc aaa caa gcc tta gaa aca gtc cag<br>Ala Ile Ala Ser Asn Asn Gly Gly Lys Gln Ala Leu Glu Thr Val Gln<br>                       405                     410                     415 | | 1248 |
| aga ttg ttg cct gtg ctg tgc caa gcc cac ggc ctg acc cca gcc cag<br>Arg Leu Leu Pro Val Leu Cys Gln Ala His Gly Leu Thr Pro Ala Gln<br>                   420                     425                     430 | | 1296 |
| gtt gtg gcc atc gcc agc aac ata ggt ggc aag cag gcc ctc gaa acc<br>Val Val Ala Ile Ala Ser Asn Ile Gly Gly Lys Gln Ala Leu Glu Thr<br>              435                     440                     445 | | 1344 |
| gtc cag aga ctg tta ccg gtt ctc tgc cag gac cac ggc ctg acc ccc<br>Val Gln Arg Leu Leu Pro Val Leu Cys Gln Asp His Gly Leu Thr Pro<br>450                           455                       460 | | 1392 |
| gac cag gtt gtc gct att gct agt aac ggc gga ggc aaa cag gcg ctg<br>Asp Gln Val Val Ala Ile Ala Ser Asn Gly Gly Gly Lys Gln Ala Leu<br>465                      470                     475                     480 | | 1440 |
| gaa aca gtt cag cgc ctc ttg ccg gtc ttg tgt cag gac cac ggc ctg<br>Glu Thr Val Gln Arg Leu Leu Pro Val Leu Cys Gln Asp His Gly Leu<br>                   485                     490                     495 | | 1488 |
| acc ccg gaa cag gtg gtt gca atc gcg tca cac gat ggg gga aag cag<br>Thr Pro Glu Gln Val Val Ala Ile Ala Ser His Asp Gly Gly Lys Gln<br>                   500                     505                     510 | | 1536 |
| gcc cta gaa acc gtt cag cga ctc ctg ccc gtc ctg tgc cag gcc cac<br>Ala Leu Glu Thr Val Gln Arg Leu Leu Pro Val Leu Cys Gln Ala His<br>              515                     520                     525 | | 1584 |
| ggc ctg acc ccc gac cag gtt gtc gct att gct agt aac ggc gga ggc<br>Gly Leu Thr Pro Asp Gln Val Val Ala Ile Ala Ser Asn Gly Gly Gly<br>         530                     535                     540 | | 1632 |
| aaa cag gcg ctg gaa aca gtt cag cgc ctc ttg ccg gtc ttg tgt cag<br>Lys Gln Ala Leu Glu Thr Val Gln Arg Leu Leu Pro Val Leu Cys Gln<br>545                           550                     555                 560 | | 1680 |
| gcc cac ggc ctg acc ccg gcc cag gtg gtt gca atc gcg tca cac gat<br>Ala His Gly Leu Thr Pro Ala Gln Val Val Ala Ile Ala Ser His Asp<br>                   565                     570                     575 | | 1728 |
| ggg gga aag cag gcc cta gaa acc gtt cag cga ctc ctg ccc gtc ctg<br>Gly Gly Lys Gln Ala Leu Glu Thr Val Gln Arg Leu Leu Pro Val Leu<br>                  580                     585                   590 | | 1776 |
| tgc cag gac cac ggc ctg acc ccc gac cag gtt gtc gct att gct agt<br>Cys Gln Asp His Gly Leu Thr Pro Asp Gln Val Val Ala Ile Ala Ser<br>              595                     600                     605 | | 1824 |
| aac ggc gga ggc aaa cag gcg ctg gaa aca gtt cag cgc ctc ttg ccg<br>Asn Gly Gly Gly Lys Gln Ala Leu Glu Thr Val Gln Arg Leu Leu Pro<br>610                           615                     620 | | 1872 |
| gtc ttg tgt cag gac cac ggc ctg acc cca gaa caa gtt gtc gcg att<br>Val Leu Cys Gln Asp His Gly Leu Thr Pro Glu Gln Val Val Ala Ile<br>625                         630                     635                 640 | | 1920 |
| gca agc aac aac gga ggc aaa caa gcc tta gaa aca gtc cag aga ttg<br>Ala Ser Asn Asn Gly Gly Lys Gln Ala Leu Glu Thr Val Gln Arg Leu<br>                   645                     650                     655 | | 1968 |
| ttg ccg gtg ctg tgc caa gcc cac ggc ctg acc ccg gac cag gtg gtt<br>Leu Pro Val Leu Cys Gln Ala His Gly Leu Thr Pro Asp Gln Val Val<br>                   660                     665                     670 | | 2016 |
| gca atc gcg tca cac gat ggg gga aag cag gcc cta gaa acc gtt cag<br>Ala Ile Ala Ser His Asp Gly Gly Lys Gln Ala Leu Glu Thr Val Gln | | 2064 |

-continued

```
            675                 680                 685
cga ctc ctg ccc gtc ctg tgc cag gcc cac ggc ctg acc ccc gcc cag        2112
Arg Leu Leu Pro Val Leu Cys Gln Ala His Gly Leu Thr Pro Ala Gln
    690                 695                 700 gtt gtc gct att gct agt aac ggc gga ggc aaa cag gcg ctg gaa aca        2160
Val Val Ala Ile Ala Ser Asn Gly Gly Gly Lys Gln Ala Leu Glu Thr
705                 710                 715                 720 gtt cag cgc ctc ttg ccg gtc ttg tgt cag gac cac ggc ctg acc ccc        2208
Val Gln Arg Leu Leu Pro Val Leu Cys Gln Asp His Gly Leu Thr Pro
                725                 730                 735 gac cag gtt gtc gct att gct agt aac ggc gga ggc aaa cag gcg ctg        2256
Asp Gln Val Val Ala Ile Ala Ser Asn Gly Gly Gly Lys Gln Ala Leu
            740                 745                 750 gaa aca gtt cag cgc ctc ttg ccg gtc ttg tgt cag gac cac ggc ctg        2304
Glu Thr Val Gln Arg Leu Leu Pro Val Leu Cys Gln Asp His Gly Leu
        755                 760                 765 acc ccg gaa cag gtg gtt gca atc gcg tca cac gat ggg gga aag cag        2352
Thr Pro Glu Gln Val Val Ala Ile Ala Ser His Asp Gly Gly Lys Gln
    770                 775                 780 gcc cta gaa acc gtt cag cga ctc ctg ccc gtc ctg tgc cag gcc cac        2400
Ala Leu Glu Thr Val Gln Arg Leu Leu Pro Val Leu Cys Gln Ala His
785                 790                 795                 800 ggc ctg acg cct gag cag gta gtg gct att gca tcc aac gga ggg ggc        2448
Gly Leu Thr Pro Glu Gln Val Val Ala Ile Ala Ser Asn Gly Gly Gly
                805                 810                 815 aga ccc gca ctg gag tca atc gtg gcc cag ctt tcg agg ccg gac ccc        2496
Arg Pro Ala Leu Glu Ser Ile Val Ala Gln Leu Ser Arg Pro Asp Pro
            820                 825                 830 gcg ctg gcc gca ctc act aat gat cat ctt gta gcg ctg gcc tgc ctc        2544
Ala Leu Ala Ala Leu Thr Asn Asp His Leu Val Ala Leu Ala Cys Leu
        835                 840                 845 ggc gga cgt cct gcc atg gat gca gtg aaa aag gga ttg ccg cac gcg        2592
Gly Gly Arg Pro Ala Met Asp Ala Val Lys Lys Gly Leu Pro His Ala
    850                 855                 860 ccg gaa ttg atc aga tcc cag cta gtg aaa tct gaa ttg gaa gag aag        2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att        2688
Lys Ser Glu Leu Arg His Lys Leu Lys Tyr Val Pro His Glu Tyr Ile
                885                 890                 895 gaa ttg att gaa atc gca aga aat tca act cag gat aga atc ctt gaa        2736
Glu Leu Ile Glu Ile Ala Arg Asn Ser Thr Gln Asp Arg Ile Leu Glu
            900                 905                 910 atg aag gtg atg gag ttc ttt atg aag gtt tat ggt tat cgt ggt aaa        2784
Met Lys Val Met Glu Phe Phe Met Lys Val Tyr Gly Tyr Arg Gly Lys
        915                 920                 925 cat ttg ggt gga tca agg aaa cca gac gga gca att tat act gtc gga        2832
His Leu Gly Gly Ser Arg Lys Pro Asp Gly Ala Ile Tyr Thr Val Gly
    930                 935                 940 tct cct att gat tac ggt gtg atc gtt gat act aag gca tat tca gga        2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc        2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg        2976
Glu Glu Asn Gln Thr Arg Asn Lys His Ile Asn Pro Asn Glu Trp Trp
            980                 985                 990 aaa gtc tat cca tct tca gta aca  gaa ttt aag ttc ttg  ttt gtg agt     3024
```

```
Lys Val Tyr Pro Ser Ser Val Thr Glu Phe Lys Phe Leu Phe Val Ser
            995                 1000                1005 ggt cat ttc aaa gga aac tac aaa gct cag ctt aca aga ttg aat          3069
Gly His Phe Lys Gly Asn Tyr Lys Ala Gln Leu Thr Arg Leu Asn
    1010                1015                1020 cat atc act aat tgt aat gga gct gtt ctt agt gta gaa gag ctt          3114
His Ile Thr Asn Cys Asn Gly Ala Val Leu Ser Val Glu Glu Leu
    1025                1030                1035 ttg att ggt gga gaa atg att aaa gct ggt aca ttg aca ctt gag          3159
Leu Ile Gly Gly Glu Met Ile Lys Ala Gly Thr Leu Thr Leu Glu
    1040                1045                1050 gaa gtg aga agg aaa ttt aat aac ggt gag ata aac ttt taa              3201
Glu Val Arg Arg Lys Phe Asn Asn Gly Glu Ile Asn Phe
    1055                1060                1065

<210> SEQ ID NO 59
<211> LENGTH: 1066
<212> TYPE: PRT
<213> ORGANISM: artificial sequence
<220> FEATURE:
<223> OTHER INFORMATION: Synthetic Construct

<400> SEQUENCE: 59

Met Ala Ser Ser Pro Lys Lys Lys Arg Lys Val Ala Ala Asp
1               5                   10                  15

Tyr Lys Asp Asp Asp Asp Lys Ser Trp Lys Ala Ser Gly Trp Ser
            20                  25                  30

Arg Met His Ala Ala Pro Arg Arg Ala Ala Gln Pro Ser Asp Ala
        35                  40                  45

Ser Pro Ala Ala Gln Val Asp Leu Arg Thr Leu Gly Tyr Ser Gln Gln
50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
        115                 120                 125

Val Gly Lys Gln Trp Ser Gly Ala Arg Ala Leu Glu Ala Leu Leu Thr
    130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
            180                 185                 190

Asp Gln Val Val Ala Ile Ala Ser Asn Asn Gly Gly Lys Gln Ala Leu
        195                 200                 205

Glu Thr Val Gln Arg Leu Leu Pro Val Leu Cys Gln Asp His Gly Leu
    210                 215                 220

Thr Pro Glu Gln Val Val Ala Ile Ala Ser Asn Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser Asn Asn Gly Gly
            260                 265                 270
```

```
Lys Gln Ala Leu Glu Thr Val Gln Arg Leu Leu Pro Val Leu Cys Gln
            275                 280                 285

Ala His Gly Leu Thr Pro Ala Gln Val Val Ala Ile Ala Ser Asn Asn
        290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

Asn Asn Gly Gly Lys Gln Ala Leu Glu Thr Val Gln Arg Leu Leu Pro
            340                 345                 350

Val Leu Cys Gln Asp His Gly Leu Thr Pro Glu Gln Val Val Ala Ile
        355                 360                 365

Ala Ser Asn Ile Gly Gly Lys Gln Ala Leu Glu Thr Val Gln Arg Leu
    370                 375                 380

Leu Pro Val Leu Cys Gln Ala His Gly Leu Thr Pro Asp Gln Val Val
385                 390                 395                 400

Ala Ile Ala Ser Asn Asn Gly Gly Lys Gln Ala Leu Glu Thr Val Gln
                405                 410                 415

Arg Leu Leu Pro Val Leu Cys Gln Ala His Gly Leu Thr Pro Ala Gln
            420                 425                 430

Val Val Ala Ile Ala Ser Asn Ile Gly Gly Lys Gln Ala Leu Glu Thr
        435                 440                 445

Val Gln Arg Leu Leu Pro Val Leu Cys Gln Asp His Gly Leu Thr Pro
    450                 455                 460

Asp Gln Val Val Ala Ile Ala Ser Asn Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser His Asp Gly Gly Lys Gln
            500                 505                 510

Ala Leu Glu Thr Val Gln Arg Leu Leu Pro Val Leu Cys Gln Ala His
        515                 520                 525

Gly Leu Thr Pro Asp Gln Val Val Ala Ile Ala Ser Asn Gly Gly Gly
    530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser His Asp
                565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
        595                 600                 605

Asn Gly Gly Gly Lys Gln Ala Leu Glu Thr Val Gln Arg Leu Leu Pro
    610                 615                 620

Val Leu Cys Gln Asp His Gly Leu Thr Pro Glu Gln Val Val Ala Ile
625                 630                 635                 640

Ala Ser Asn Asn Gly Gly Lys Gln Ala Leu Glu Thr Val Gln Arg Leu
                645                 650                 655

Leu Pro Val Leu Cys Gln Ala His Gly Leu Thr Pro Asp Gln Val Val
            660                 665                 670

Ala Ile Ala Ser His Asp Gly Gly Lys Gln Ala Leu Glu Thr Val Gln
        675                 680                 685
```

```
Arg Leu Leu Pro Val Leu Cys Gln Ala His Gly Leu Thr Pro Ala Gln
    690             695                 700

Val Val Ala Ile Ala Ser Asn Gly Gly Gly Lys Gln Ala Leu Glu Thr
705                 710                 715                 720

Val Gln Arg Leu Leu Pro Val Leu Cys Gln Asp His Gly Leu Thr Pro
            725                 730                 735

Asp Gln Val Val Ala Ile Ala Ser Asn Gly Gly Gly Lys Gln Ala Leu
        740                 745                 750

Glu Thr Val Gln Arg Leu Leu Pro Val Leu Cys Gln Asp His Gly Leu
            755                 760                 765

Thr Pro Glu Gln Val Val Ala Ile Ala Ser His Asp Gly Gly Lys Gln
770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser Asn Gly Gly Gly
            805                 810                 815

Arg Pro Ala Leu Glu Ser Ile Val Ala Gln Leu Ser Arg Pro Asp Pro
        820                 825                 830

Ala Leu Ala Ala Leu Thr Asn Asp His Leu Val Ala Leu Ala Cys Leu
            835                 840                 845

Gly Gly Arg Pro Ala Met Asp Ala Val Lys Lys Gly Leu Pro His Ala
850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
            885                 890                 895

Glu Leu Ile Glu Ile Ala Arg Asn Ser Thr Gln Asp Arg Ile Leu Glu
        900                 905                 910

Met Lys Val Met Glu Phe Phe Met Lys Val Tyr Gly Tyr Arg Gly Lys
            915                 920                 925

His Leu Gly Gly Ser Arg Lys Pro Asp Gly Ala Ile Tyr Thr Val Gly
930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
            965                 970                 975

Glu Glu Asn Gln Thr Arg Asn Lys His Ile Asn Pro Asn Glu Trp Trp
        980                 985                 990

Lys Val Tyr Pro Ser Ser Val Thr Glu Phe Lys Phe Leu Phe Val Ser
            995                 1000                1005

Gly His Phe Lys Gly Asn Tyr Lys Ala Gln Leu Thr Arg Leu Asn
    1010            1015                1020

His Ile Thr Asn Cys Asn Gly Ala Val Leu Ser Val Glu Glu Leu
    1025            1030                1035

Leu Ile Gly Gly Glu Met Ile Lys Ala Gly Thr Leu Thr Leu Glu
    1040            1045                1050

Glu Val Arg Arg Lys Phe Asn Asn Gly Glu Ile Asn Phe
    1055            1060                1065

<210> SEQ ID NO 60
<211> LENGTH: 3201
<212> TYPE: DNA
<213> ORGANISM: artificial sequence
<220> FEATURE:
<223> OTHER INFORMATION: TALEN-TCR-beta3_L19 TALEN coding sequence
```

<220> FEATURE:
<221> NAME/KEY: CDS
<222> LOCATION: (1)..(3201)

<400> SEQUENCE: 60

| | | | | | | | | | | | | | | | | |
|---|---|---|---|---|---|---|---|---|---|---|---|---|---|---|---|---|
| atg | gct | tcc | tcc | cct | cca | aag | aaa | aag | aga | aag | gtt | gcg | gcc | gct | gac | 48 |
| Met | Ala | Ser | Ser | Pro | Pro | Lys | Lys | Lys | Arg | Lys | Val | Ala | Ala | Ala | Asp | |
| 1 | | | | 5 | | | | | 10 | | | | | 15 | | |
| tac | aag | gat | gac | gac | gat | aaa | agt | tgg | aag | gac | gca | agt | ggt | tgg | tct | 96 |
| Tyr | Lys | Asp | Asp | Asp | Asp | Lys | Ser | Trp | Lys | Asp | Ala | Ser | Gly | Trp | Ser | |
| | | | 20 | | | | | 25 | | | | | 30 | | | |
| aga | atg | cat | gcg | gcc | ccg | cga | cgg | cgt | gct | gcg | caa | ccc | tcc | gac | gct | 144 |
| Arg | Met | His | Ala | Ala | Pro | Arg | Arg | Arg | Ala | Ala | Gln | Pro | Ser | Asp | Ala | |
| | | 35 | | | | | 40 | | | | | 45 | | | | |
| tcg | ccg | gcc | gcg | cag | gtg | gat | cta | cgc | acg | ctc | ggc | tac | agt | cag | cag | 192 |
| Ser | Pro | Ala | Ala | Gln | Val | Asp | Leu | Arg | Thr | Leu | Gly | Tyr | Ser | Gln | Gln | |
| 50 | | | | | 55 | | | | | 60 | | | | | | |
| cag | caa | gag | aag | atc | aaa | ccg | aag | gtg | cgt | tcg | aca | gtg | gcg | cag | cac | 240 |
| Gln | Gln | Glu | Lys | Ile | Lys | Pro | Lys | Val | Arg | Ser | Thr | Val | Ala | Gln | His | |
| 65 | | | | 70 | | | | | 75 | | | | | 80 | | |
| cac | gag | gca | ctg | gtg | ggc | cat | ggg | ttt | aca | cac | gcg | cac | atc | gtt | gcg | 288 |
| His | Glu | Ala | Leu | Val | Gly | His | Gly | Phe | Thr | His | Ala | His | Ile | Val | Ala | |
| | | | | 85 | | | | | 90 | | | | | 95 | | |
| ctc | agc | caa | cac | ccg | gca | gcg | tta | ggg | acc | gtc | gct | gtc | acg | tat | cag | 336 |
| Leu | Ser | Gln | His | Pro | Ala | Ala | Leu | Gly | Thr | Val | Ala | Val | Thr | Tyr | Gln | |
| | | | 100 | | | | | 105 | | | | | 110 | | | |
| cac | ata | atc | acg | gcg | ttg | cca | gag | gcg | aca | cac | gaa | gac | atc | gtt | ggc | 384 |
| His | Ile | Ile | Thr | Ala | Leu | Pro | Glu | Ala | Thr | His | Glu | Asp | Ile | Val | Gly | |
| | | 115 | | | | | 120 | | | | | 125 | | | | |
| gtc | ggc | aaa | cag | tgg | tcc | ggc | gca | cgc | gcc | ctg | gag | gcc | ttg | ctc | acg | 432 |
| Val | Gly | Lys | Gln | Trp | Ser | Gly | Ala | Arg | Ala | Leu | Glu | Ala | Leu | Leu | Thr | |
| | 130 | | | | | 135 | | | | | 140 | | | | | |
| gat | gcg | ggg | gag | ttg | aga | ggt | ccg | ccg | tta | cag | ttg | gac | aca | ggc | caa | 480 |
| Asp | Ala | Gly | Glu | Leu | Arg | Gly | Pro | Pro | Leu | Gln | Leu | Asp | Thr | Gly | Gln | |
| 145 | | | | | 150 | | | | | 155 | | | | | 160 | |
| ctt | gtg | aag | att | gca | aaa | cgt | ggc | ggc | gtg | acc | gca | atg | gag | gca | gtg | 528 |
| Leu | Val | Lys | Ile | Ala | Lys | Arg | Gly | Gly | Val | Thr | Ala | Met | Glu | Ala | Val | |
| | | | | 165 | | | | | 170 | | | | | 175 | | |
| cat | gca | tcg | cgc | aat | gcg | ctc | acg | gga | gca | ccc | ctc | aac | ctg | acc | cca | 576 |
| His | Ala | Ser | Arg | Asn | Ala | Leu | Thr | Gly | Ala | Pro | Leu | Asn | Leu | Thr | Pro | |
| | | | 180 | | | | | 185 | | | | | 190 | | | |
| gac | caa | gtt | gtc | gcg | att | gca | agc | aac | aac | gga | ggc | aaa | caa | gcc | tta | 624 |
| Asp | Gln | Val | Val | Ala | Ile | Ala | Ser | Asn | Asn | Gly | Gly | Lys | Gln | Ala | Leu | |
| | | 195 | | | | | 200 | | | | | 205 | | | | |
| gaa | aca | gtc | cag | aga | ttg | ttg | ccg | gtg | ctg | tgc | caa | gac | cac | ggc | ctg | 672 |
| Glu | Thr | Val | Gln | Arg | Leu | Leu | Pro | Val | Leu | Cys | Gln | Asp | His | Gly | Leu | |
| | 210 | | | | | 215 | | | | | 220 | | | | | |
| acc | ccc | gaa | cag | gtt | gtc | gct | att | gct | agt | aac | ggc | gga | ggc | aaa | cag | 720 |
| Thr | Pro | Glu | Gln | Val | Val | Ala | Ile | Ala | Ser | Asn | Gly | Gly | Gly | Lys | Gln | |
| 225 | | | | | 230 | | | | | 235 | | | | | 240 | |
| gcg | ctg | gaa | aca | gtt | cag | cgc | ctc | ttg | ccg | gtc | ttg | tgt | cag | gcc | cac | 768 |
| Ala | Leu | Glu | Thr | Val | Gln | Arg | Leu | Leu | Pro | Val | Leu | Cys | Gln | Ala | His | |
| | | | | 245 | | | | | 250 | | | | | 255 | | |
| ggc | ctg | acc | cca | gac | caa | gtt | gtc | gcg | att | gca | agc | aac | aac | gga | ggc | 816 |
| Gly | Leu | Thr | Pro | Asp | Gln | Val | Val | Ala | Ile | Ala | Ser | Asn | Asn | Gly | Gly | |
| | | | 260 | | | | | 265 | | | | | 270 | | | |
| aaa | caa | gcc | tta | gaa | aca | gtc | cag | aga | ttg | ttg | cct | gtg | ctg | tgc | caa | 864 |
| Lys | Gln | Ala | Leu | Glu | Thr | Val | Gln | Arg | Leu | Leu | Pro | Val | Leu | Cys | Gln | |
| | | 275 | | | | | 280 | | | | | 285 | | | | |
| gcc | cac | ggc | ctg | acc | ccg | gcc | cag | gtg | gtt | gca | atc | gcg | tca | cac | gat | 912 |

```
                Ala His Gly Leu Thr Pro Ala Gln Val Val Ala Ile Ala Ser His Asp
                    290                 295                 300 gga aag cag gcc cta gaa acc gtt cag cga ctc ctg ccc gtc ctg          960
Gly Gly Lys Gln Ala Leu Glu Thr Val Gln Arg Leu Leu Pro Val Leu
305                 310                 315                 320 tgc cag gac cac ggc ctg acc ccg gac cag gtg gtt gca atc gcg tca     1008
Cys Gln Asp His Gly Leu Thr Pro Asp Gln Val Val Ala Ile Ala Ser
                    325                 330                 335 cac gat ggg gga aag cag gcc cta gaa acc gtt cag cga ctc ctg ccc     1056
His Asp Gly Gly Lys Gln Ala Leu Glu Thr Val Gln Arg Leu Leu Pro
                340                 345                 350 gtc ctg tgc cag gac cac ggc ctg acc ccc gaa cag gtt gtc gct att     1104
Val Leu Cys Gln Asp His Gly Leu Thr Pro Glu Gln Val Val Ala Ile
            355                 360                 365 gct agt aac ggc gga ggc aaa cag gcg ctg gaa aca gtt cag cgc ctc     1152
Ala Ser Asn Gly Gly Gly Lys Gln Ala Leu Glu Thr Val Gln Arg Leu
        370                 375                 380 ttg ccg gtc ttg tgt cag gcc cac ggc ctg acc cca gac caa gtt gtc     1200
Leu Pro Val Leu Cys Gln Ala His Gly Leu Thr Pro Asp Gln Val Val
385                 390                 395                 400 gcg att gca agc aac aac gga ggc aaa caa gcc tta gaa aca gtc cag     1248
Ala Ile Ala Ser Asn Asn Gly Gly Lys Gln Ala Leu Glu Thr Val Gln
                    405                 410                 415 aga ttg ttg cct gtg ctg tgc aag gcc cac ggc ctg acc cca gcc caa     1296
Arg Leu Leu Pro Val Leu Cys Gln Ala His Gly Leu Thr Pro Ala Gln
                    420                 425                 430 gtt gtc gcg att gca agc aac aac gga ggc aaa caa gcc tta gaa aca     1344
Val Val Ala Ile Ala Ser Asn Asn Gly Gly Lys Gln Ala Leu Glu Thr
                435                 440                 445 gtc cag aga ttg ttg ccg gtg ctg tgc caa gac cac ggc ctg acc ccg     1392
Val Gln Arg Leu Leu Pro Val Leu Cys Gln Asp His Gly Leu Thr Pro
            450                 455                 460 gac cag gtg gtt gca atc gcg tca cac gat ggg gga aag cag gcc cta     1440
Asp Gln Val Val Ala Ile Ala Ser His Asp Gly Gly Lys Gln Ala Leu
465                 470                 475                 480 gaa acc gtt cag cga ctc ctg ccc gtc ctg tgc cag gac cac ggc ctg     1488
Glu Thr Val Gln Arg Leu Leu Pro Val Leu Cys Gln Asp His Gly Leu
                    485                 490                 495 acc ccg gaa cag gtg gtt gca atc gcg tca cac gat ggg gga aag cag     1536
Thr Pro Glu Gln Val Val Ala Ile Ala Ser His Asp Gly Gly Lys Gln
                500                 505                 510 gcc cta gaa acc gtt cag cga ctc ctg ccc gtc ctg tgc cag gcc cac     1584
Ala Leu Glu Thr Val Gln Arg Leu Leu Pro Val Leu Cys Gln Ala His
            515                 520                 525 ggc ctg acc cca gac cag gtt gtg gcc atc gcc agc aac ata ggt ggc     1632
Gly Leu Thr Pro Asp Gln Val Val Ala Ile Ala Ser Asn Ile Gly Gly
        530                 535                 540 aag cag gcc ctc gaa acc gtc cag aga ctg tta ccg gtt ctc tgc cag     1680
Lys Gln Ala Leu Glu Thr Val Gln Arg Leu Leu Pro Val Leu Cys Gln
545                 550                 555                 560 gcc cac ggc ctg acc ccg gcc cag gtg gtt gca atc gcg tca cac gat     1728
Ala His Gly Leu Thr Pro Ala Gln Val Val Ala Ile Ala Ser His Asp
                    565                 570                 575 ggg gga aag cag gcc cta gaa acc gtt cag cga ctc ctg ccc gtc ctg     1776
Gly Gly Lys Gln Ala Leu Glu Thr Val Gln Arg Leu Leu Pro Val Leu
                580                 585                 590 tgc cag gac cac ggc ctg acc cca gac cag gtt gtg gcc atc gcc agc     1824
Cys Gln Asp His Gly Leu Thr Pro Asp Gln Val Val Ala Ile Ala Ser
            595                 600                 605
```

-continued

| | |
|---|---|
| aac ata ggt ggc aag cag gcc ctc gaa acc gtc cag aga ctg tta ccg<br>Asn Ile Gly Gly Lys Gln Ala Leu Glu Thr Val Gln Arg Leu Leu Pro<br>610                       615                       620 | 1872 |
| gtt ctc tgc cag gac cac ggc ctg acc cca gaa caa gtt gtc gcg att<br>Val Leu Cys Gln Asp His Gly Leu Thr Pro Glu Gln Val Val Ala Ile<br>625                       630                       635               640 | 1920 |
| gca agc aac aac gga ggc aaa caa gcc tta gaa aca gtc cag aga ttg<br>Ala Ser Asn Asn Gly Gly Lys Gln Ala Leu Glu Thr Val Gln Arg Leu<br>                       645                       650                       655 | 1968 |
| ttg ccg gtg ctg tgc caa gcc cac ggc ctg acc cca gac caa gtt gtc<br>Leu Pro Val Leu Cys Gln Ala His Gly Leu Thr Pro Asp Gln Val Val<br>   660                       665                       670 | 2016 |
| gcg att gca agc aac aac gga ggc aaa caa gcc tta gaa aca gtc cag<br>Ala Ile Ala Ser Asn Asn Gly Gly Lys Gln Ala Leu Glu Thr Val Gln<br>             675                       680                       685 | 2064 |
| aga ttg ttg cct gtg ctg tgc caa gcc cac ggc ctg acc ccg gcc cag<br>Arg Leu Leu Pro Val Leu Cys Gln Ala His Gly Leu Thr Pro Ala Gln<br>690                       695                       700 | 2112 |
| gtg gtt gca atc gcg tca cac gat ggg gga aag cag gcc cta gaa acc<br>Val Val Ala Ile Ala Ser His Asp Gly Gly Lys Gln Ala Leu Glu Thr<br>705                       710                       715               720 | 2160 |
| gtt cag cga ctc ctg ccc gtc ctg tgc cag gac cac ggc ctg acc ccc<br>Val Gln Arg Leu Leu Pro Val Leu Cys Gln Asp His Gly Leu Thr Pro<br>             725                       730                       735 | 2208 |
| gac cag gtt gtc gct att gct agt aac ggc gga ggc aaa cag gcg ctg<br>Asp Gln Val Val Ala Ile Ala Ser Asn Gly Gly Gly Lys Gln Ala Leu<br>                 740                       745                       750 | 2256 |
| gaa aca gtt cag cgc ctc ttg ccg gtc ttg tgt cag gac cac ggc ctg<br>Glu Thr Val Gln Arg Leu Leu Pro Val Leu Cys Gln Asp His Gly Leu<br>                       755                       760                       765 | 2304 |
| acc ccc gaa cag gtt gtc gct att gct agt aac ggc gga ggc aaa cag<br>Thr Pro Glu Gln Val Val Ala Ile Ala Ser Asn Gly Gly Gly Lys Gln<br>770                       775                       780 | 2352 |
| gcg ctg gaa aca gtt cag cgc ctc ttg ccg gtc ttg tgt cag gcc cac<br>Ala Leu Glu Thr Val Gln Arg Leu Leu Pro Val Leu Cys Gln Ala His<br>785                       790                       795               800 | 2400 |
| ggc ctg acg cct gag cag gta gtg gct att gca tcc cac gac ggg ggc<br>Gly Leu Thr Pro Glu Gln Val Val Ala Ile Ala Ser His Asp Gly Gly<br>                 805                       810                       815 | 2448 |
| aga ccc gca ctg gag tca atc gtg gcc cag ctt tcg agg ccg gac ccc<br>Arg Pro Ala Leu Glu Ser Ile Val Ala Gln Leu Ser Arg Pro Asp Pro<br>             820                       825                       830 | 2496 |
| gcg ctg gcc gca ctc act aat gat cat ctt gta gcg ctg gcc tgc ctc<br>Ala Leu Ala Ala Leu Thr Asn Asp His Leu Val Ala Leu Ala Cys Leu<br>835                       840                       845 | 2544 |
| ggc gga cgt cct gcc atg gat gca gtg aaa aag gga ttg ccg cac gcg<br>Gly Gly Arg Pro Ala Met Asp Ala Val Lys Lys Gly Leu Pro His Ala<br>850                       855                       860 | 2592 |
| ccg gaa ttg atc aga tcc cag cta gtg aaa tct gaa ttg gaa gag aag<br>Pro Glu Leu Ile Arg Ser Gln Leu Val Lys Ser Glu Leu Glu Glu Lys<br>865                       870                       875               880 | 2640 |
| aaa tct gaa ctt aga cat aaa ttg aaa tat gtg cca cat gaa tat att<br>Lys Ser Glu Leu Arg His Lys Leu Lys Tyr Val Pro His Glu Tyr Ile<br>                 885                       890                       895 | 2688 |
| gaa ttg att gaa atc gca aga aat tca act cag gat aga atc ctt gaa<br>Glu Leu Ile Glu Ile Ala Arg Asn Ser Thr Gln Asp Arg Ile Leu Glu<br>             900                       905                       910 | 2736 |
| atg aag gtg atg gag ttc ttt atg aag gtt tat ggt tat cgt ggt aaa<br>Met Lys Val Met Glu Phe Phe Met Lys Val Tyr Gly Tyr Arg Gly Lys<br>                 915                       920                       925 | 2784 |

```
cat ttg ggt gga tca agg aaa cca gac gga gca att tat act gtc gga    2832
His Leu Gly Gly Ser Arg Lys Pro Asp Gly Ala Ile Tyr Thr Val Gly
        930                 935                 940 tct cct att gat tac ggt gtg atc gtt gat act aag gca tat tca gga    2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc    2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg    2976
Glu Glu Asn Gln Thr Arg Asn Lys His Ile Asn Pro Asn Glu Trp Trp
            980                 985                 990 aaa gtc tat cca tct tca gta aca gaa ttt aag ttc ttg ttt gtg agt    3024
Lys Val Tyr Pro Ser Ser Val Thr Glu Phe Lys Phe Leu Phe Val Ser
        995                1000                1005 ggt cat ttc aaa gga aac tac aaa gct cag ctt aca aga ttg aat         3069
Gly His Phe Lys Gly Asn Tyr Lys Ala Gln Leu Thr Arg Leu Asn
   1010                1015                1020 cat atc act aat tgt aat gga gct gtt ctt agt gta gaa gag ctt        3114
His Ile Thr Asn Cys Asn Gly Ala Val Leu Ser Val Glu Glu Leu
   1025                1030                1035 ttg att ggt gga gaa atg att aaa gct ggt aca ttg aca ctt gag        3159
Leu Ile Gly Gly Glu Met Ile Lys Ala Gly Thr Leu Thr Leu Glu
   1040                1045                1050 gaa gtg aga agg aaa ttt aat aac ggt gag ata aac ttt taa            3201
Glu Val Arg Arg Lys Phe Asn Asn Gly Glu Ile Asn Phe
   1055                1060                1065

<210> SEQ ID NO 61
<211> LENGTH: 1066
<212> TYPE: PRT
<213> ORGANISM: artificial sequence
<220> FEATURE:
<223> OTHER INFORMATION: Synthetic Construct

<400> SEQUENCE: 61

Met Ala Ser Ser Pro Lys Lys Arg Lys Val Ala Ala Asp
1               5                   10                  15

Tyr Lys Asp Asp Asp Lys Ser Trp Lys Asp Ala Ser Gly Trp Ser
                20                  25                  30

Arg Met His Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
                100                 105                 110

His Ile Ile Thr Ala Leu Pro Glu Ala Thr His Glu Asp Ile Val Gly
        115                 120                 125

Val Gly Lys Gln Trp Ser Gly Ala Arg Ala Leu Glu Ala Leu Leu Thr
    130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175
```

```
His Ala Ser Arg Asn Ala Leu Thr Gly Ala Pro Leu Asn Leu Thr Pro
                180                 185                 190

Asp Gln Val Val Ala Ile Ala Ser Asn Asn Gly Gly Lys Gln Ala Leu
                195                 200                 205

Glu Thr Val Gln Arg Leu Leu Pro Val Leu Cys Gln Asp His Gly Leu
                210                 215                 220

Thr Pro Glu Gln Val Val Ala Ile Ala Ser Asn Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser Asn Asn Gly Gly
                260                 265                 270

Lys Gln Ala Leu Glu Thr Val Gln Arg Leu Leu Pro Val Leu Cys Gln
                275                 280                 285

Ala His Gly Leu Thr Pro Ala Gln Val Val Ala Ile Ala Ser His Asp
                290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

His Asp Gly Gly Lys Gln Ala Leu Glu Thr Val Gln Arg Leu Leu Pro
                340                 345                 350

Val Leu Cys Gln Asp His Gly Leu Thr Pro Glu Gln Val Val Ala Ile
                355                 360                 365

Ala Ser Asn Gly Gly Lys Gln Ala Leu Glu Thr Val Gln Arg Leu
                370                 375                 380

Leu Pro Val Leu Cys Gln Ala His Gly Leu Thr Pro Asp Gln Val Val
385                 390                 395                 400

Ala Ile Ala Ser Asn Asn Gly Gly Lys Gln Ala Leu Glu Thr Val Gln
                405                 410                 415

Arg Leu Leu Pro Val Leu Cys Gln Ala His Gly Leu Thr Pro Ala Gln
                420                 425                 430

Val Val Ala Ile Ala Ser Asn Asn Gly Gly Lys Gln Ala Leu Glu Thr
                435                 440                 445

Val Gln Arg Leu Leu Pro Val Leu Cys Gln Asp His Gly Leu Thr Pro
                450                 455                 460

Asp Gln Val Val Ala Ile Ala Ser His Asp Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser His Asp Gly Gly Lys Gln
                500                 505                 510

Ala Leu Glu Thr Val Gln Arg Leu Leu Pro Val Leu Cys Gln Ala His
                515                 520                 525

Gly Leu Thr Pro Asp Gln Val Val Ala Ile Ala Ser Asn Ile Gly Gly
                530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser His Asp
                565                 570                 575

Gly Gly Lys Gln Ala Leu Glu Thr Val Gln Arg Leu Leu Pro Val Leu
                580                 585                 590
```

```
Cys Gln Asp His Gly Leu Thr Pro Asp Gln Val Val Ala Ile Ala Ser
        595                 600                 605

Asn Ile Gly Gly Lys Gln Ala Leu Glu Thr Val Gln Arg Leu Leu Pro
    610                 615                 620

Val Leu Cys Gln Asp His Gly Leu Thr Pro Glu Gln Val Val Ala Ile
625                 630                 635                 640

Ala Ser Asn Asn Gly Gly Lys Gln Ala Leu Glu Thr Val Gln Arg Leu
            645                 650                 655

Leu Pro Val Leu Cys Gln Ala His Gly Leu Thr Pro Asp Gln Val Val
            660                 665                 670

Ala Ile Ala Ser Asn Asn Gly Gly Lys Gln Ala Leu Glu Thr Val Gln
        675                 680                 685

Arg Leu Leu Pro Val Leu Cys Gln Ala His Gly Leu Thr Pro Ala Gln
    690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
            725                 730                 735

Asp Gln Val Val Ala Ile Ala Ser Asn Gly Gly Gly Lys Gln Ala Leu
                740                 745                 750

Glu Thr Val Gln Arg Leu Leu Pro Val Leu Cys Gln Asp His Gly Leu
        755                 760                 765

Thr Pro Glu Gln Val Val Ala Ile Ala Ser Asn Gly Gly Gly Lys Gln
    770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser His Asp Gly Gly
            805                 810                 815

Arg Pro Ala Leu Glu Ser Ile Val Ala Gln Leu Ser Arg Pro Asp Pro
                820                 825                 830

Ala Leu Ala Ala Leu Thr Asn Asp His Leu Val Ala Leu Ala Cys Leu
        835                 840                 845

Gly Gly Arg Pro Ala Met Asp Ala Val Lys Lys Gly Leu Pro His Ala
    850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
            885                 890                 895

Glu Leu Ile Glu Ile Ala Arg Asn Ser Thr Gln Asp Arg Ile Leu Glu
                900                 905                 910

Met Lys Val Met Glu Phe Phe Met Lys Val Tyr Gly Tyr Arg Gly Lys
        915                 920                 925

His Leu Gly Gly Ser Arg Lys Pro Asp Gly Ala Ile Tyr Thr Val Gly
    930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
            965                 970                 975

Glu Glu Asn Gln Thr Arg Asn Lys His Ile Asn Pro Asn Glu Trp Trp
                980                 985                 990

Lys Val Tyr Pro Ser Ser Val Thr  Glu Phe Lys Phe Leu  Phe Val Ser
        995                 1000                1005

Gly His  Phe Lys Gly Asn Tyr  Lys Ala Gln Leu Thr  Arg Leu Asn
```

```
                    1010                1015                1020

His Ile Thr Asn Cys Asn Gly Ala Val Leu Ser Val Glu Glu Leu
        1025                1030                1035

Leu Ile Gly Gly Glu Met Ile Lys Ala Gly Thr Leu Thr Leu Glu
        1040                1045                1050

Glu Val Arg Arg Lys Phe Asn Asn Gly Glu Ile Asn Phe
        1055                1060                1065

<210> SEQ ID NO 62
<211> LENGTH: 3201
<212> TYPE: DNA
<213> ORGANISM: artificial sequence
<220> FEATURE:
<223> OTHER INFORMATION: TALEN-TCR-beta3_R19 TALEN coding sequence
<220> FEATURE:
<221> NAME/KEY: CDS
<222> LOCATION: (1)..(3201)

<400> SEQUENCE: 62 atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
            20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
        35                  40                  45 tcg ccg gcc gcg cag gtg gat cta cgc acg ctc ggc tac agt cag cag     192
Ser Pro Ala Ala Gln Val Asp Leu Arg Thr Leu Gly Tyr Ser Gln Gln
    50                  55                  60 cag caa gag aag atc aaa ccg aag gtg cgt tcg aca gtg gcg cag cac     240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg     288
His Glu Ala Leu Val Gly His Gly Phe Thr His Ala His Ile Val Ala
                85                  90                  95 ctc agc caa cac ccg gca gcg tta ggg acc gtc gct gtc acg tat cag     336
Leu Ser Gln His Pro Ala Ala Leu Gly Thr Val Ala Val Thr Tyr Gln
            100                 105                 110 cac ata atc acg gcg ttg cca gag gcg aca cac gaa gac atc gtt ggc     384
His Ile Ile Thr Ala Leu Pro Glu Ala Thr His Glu Asp Ile Val Gly
        115                 120                 125 gtc ggc aaa cag tgg tcc ggc gca cgc gcc ctg gag gcc ttg ctc acg     432
Val Gly Lys Gln Trp Ser Gly Ala Arg Ala Leu Glu Ala Leu Leu Thr
    130                 135                 140 gat gcg ggg gag ttg aga ggt ccg ccg tta cag ttg gac aca ggc caa     480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg     528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc ccg     576
His Ala Ser Arg Asn Ala Leu Thr Gly Ala Pro Leu Asn Leu Thr Pro
            180                 185                 190 gac cag gtg gtt gca atc gcg tca cac gat ggg gga aag cag gcc cta     624
Asp Gln Val Val Ala Ile Ala Ser His Asp Gly Gly Lys Gln Ala Leu
        195                 200                 205 gaa acc gtt cag cga ctc ctg ccc gtc ctg tgc cag gac cac ggc ctg     672
Glu Thr Val Gln Arg Leu Leu Pro Val Leu Cys Gln Asp His Gly Leu
    210                 215                 220
```

-continued

| | |
|---|---|
| acc cca gaa cag gtt gtg gcc atc gcc agc aac ata ggt ggc aag cag<br>Thr Pro Glu Gln Val Val Ala Ile Ala Ser Asn Ile Gly Gly Lys Gln<br>225               230               235               240 | 720 |
| gcc ctc gaa acc gtc cag aga ctg tta ccg gtt ctc tgc cag gcc cac<br>Ala Leu Glu Thr Val Gln Arg Leu Leu Pro Val Leu Cys Gln Ala His<br>               245               250               255 | 768 |
| ggc ctg acc ccg gac cag gtg gtt gca atc gcg tca cac gat ggg gga<br>Gly Leu Thr Pro Asp Gln Val Val Ala Ile Ala Ser His Asp Gly Gly<br>          260               265               270 | 816 |
| aag cag gcc cta gaa acc gtt cag cga ctc ctg ccc gtc ctg tgc cag<br>Lys Gln Ala Leu Glu Thr Val Gln Arg Leu Leu Pro Val Leu Cys Gln<br>275               280               285 | 864 |
| gcc cac ggc ctg acc ccg gcg cag gtg gtt gca atc gcg tca cac gat<br>Ala His Gly Leu Thr Pro Ala Gln Val Val Ala Ile Ala Ser His Asp<br>    290               295               300 | 912 |
| ggg gga aag cag gcc cta gaa acc gtt cag cga ctc ctg ccc gtc ctg<br>Gly Gly Lys Gln Ala Leu Glu Thr Val Gln Arg Leu Leu Pro Val Leu<br>305               310               315               320 | 960 |
| tgc cag gac cac ggc ctg acc ccg gac cag gtg gtt gca atc gcg tca<br>Cys Gln Asp His Gly Leu Thr Pro Asp Gln Val Val Ala Ile Ala Ser<br>               325               330               335 | 1008 |
| cac gat ggg gga aag cag gcc cta gaa acc gtt cag cga ctc ctg ccc<br>His Asp Gly Gly Lys Gln Ala Leu Glu Thr Val Gln Arg Leu Leu Pro<br>          340               345               350 | 1056 |
| gtc ctg tgc cag gac cac ggc ctg acc cca gaa cag gtt gtg gcc atc<br>Val Leu Cys Gln Asp His Gly Leu Thr Pro Glu Gln Val Val Ala Ile<br>        355               360               365 | 1104 |
| gcc agc aac ata ggt ggc aag cag gcc ctc gaa acc gtc cag aga ctg<br>Ala Ser Asn Ile Gly Gly Lys Gln Ala Leu Glu Thr Val Gln Arg Leu<br>370               375               380 | 1152 |
| tta ccg gtt ctc tgc cag gcc cac ggc ctg acc ccg gac cag gtg gtt<br>Leu Pro Val Leu Cys Gln Ala His Gly Leu Thr Pro Asp Gln Val Val<br>385               390               395               400 | 1200 |
| gca atc gcg tca cac gat ggg gga aag cag gcc cta gaa acc gtt cag<br>Ala Ile Ala Ser His Asp Gly Gly Lys Gln Ala Leu Glu Thr Val Gln<br>               405               410               415 | 1248 |
| cga ctc ctg ccc gtc ctg tgc cag gcc cac ggc ctg acc ccg gcc cag<br>Arg Leu Leu Pro Val Leu Cys Gln Ala His Gly Leu Thr Pro Ala Gln<br>          420               425               430 | 1296 |
| gtg gtt gca atc gcg tca cac gat ggg gga aag cag gcc cta gaa acc<br>Val Val Ala Ile Ala Ser His Asp Gly Gly Lys Gln Ala Leu Glu Thr<br>        435               440               445 | 1344 |
| gtt cag cga ctc ctg ccc gtc ctg tgc cag gac cac ggc ctg acc cca<br>Val Gln Arg Leu Leu Pro Val Leu Cys Gln Asp His Gly Leu Thr Pro<br>450               455               460 | 1392 |
| gac cag gtt gtg gcc atc gcc agc aac ata ggt ggc aag cag gcc ctc<br>Asp Gln Val Val Ala Ile Ala Ser Asn Ile Gly Gly Lys Gln Ala Leu<br>465               470               475               480 | 1440 |
| gaa acc gtc cag aga ctg tta ccg gtt ctc tgc cag gac cac ggc ctg<br>Glu Thr Val Gln Arg Leu Leu Pro Val Leu Cys Gln Asp His Gly Leu<br>               485               490               495 | 1488 |
| acc cca gaa caa gtt gtc gcg att gca agc aac aac gga ggc aaa caa<br>Thr Pro Glu Gln Val Val Ala Ile Ala Ser Asn Asn Gly Gly Lys Gln<br>          500               505               510 | 1536 |
| gcc tta gaa aca gtc cag aga ttg ttg ccg gtg ctg tgc caa gcc cac<br>Ala Leu Glu Thr Val Gln Arg Leu Leu Pro Val Leu Cys Gln Ala His<br>        515               520               525 | 1584 |
| ggc ctg acc ccg gac cag gtg gtt gca atc gcg tca cac gat ggg gga<br>Gly Leu Thr Pro Asp Gln Val Val Ala Ile Ala Ser His Asp Gly Gly | 1632 |

-continued

|  |  |
|---|---|
| 530 535 540 | |
| aag cag gcc cta gaa acc gtt cag cga ctc ctg ccc gtc ctg tgc cag<br>Lys Gln Ala Leu Glu Thr Val Gln Arg Leu Leu Pro Val Leu Cys Gln<br>545 550 555 560 | 1680 |
| gcc cac ggc ctg acc ccc gcc cag gtt gtc gct att gct agt aac ggc<br>Ala His Gly Leu Thr Pro Ala Gln Val Val Ala Ile Ala Ser Asn Gly<br>565 570 575 | 1728 |
| gga ggc aaa cag gcg ctg gaa aca gtt cag cgc ctc ttg ccg gtc ttg<br>Gly Gly Lys Gln Ala Leu Glu Thr Val Gln Arg Leu Leu Pro Val Leu<br>580 585 590 | 1776 |
| tgt cag gac cac ggc ctg acc ccg gac cag gtg gtt gca atc gcg tca<br>Cys Gln Asp His Gly Leu Thr Pro Asp Gln Val Val Ala Ile Ala Ser<br>595 600 605 | 1824 |
| cac gat ggg gga aag cag gcc cta gaa acc gtt cag cga ctc ctg ccc<br>His Asp Gly Gly Lys Gln Ala Leu Glu Thr Val Gln Arg Leu Leu Pro<br>610 615 620 | 1872 |
| gtc ctg tgc cag gac cac ggc ctg acc cca gaa cag gtt gtg gcc atc<br>Val Leu Cys Gln Asp His Gly Leu Thr Pro Glu Gln Val Val Ala Ile<br>625 630 635 640 | 1920 |
| gcc agc aac ata ggt ggc aag cag gcc ctc gaa acc gtc cag aga ctg<br>Ala Ser Asn Ile Gly Gly Lys Gln Ala Leu Glu Thr Val Gln Arg Leu<br>645 650 655 | 1968 |
| tta ccg gtt ctc tgc cag gcc cac ggc ctg acc cca gac caa gtt gtc<br>Leu Pro Val Leu Cys Gln Ala His Gly Leu Thr Pro Asp Gln Val Val<br>660 665 670 | 2016 |
| gcg att gca agc aac aac gga ggc aaa caa gcc tta gaa aca gtc cag<br>Ala Ile Ala Ser Asn Asn Gly Gly Lys Gln Ala Leu Glu Thr Val Gln<br>675 680 685 | 2064 |
| aga ttg ttg cct gtg ctg tgc caa gcc cac ggc ctg acc ccg gcc cag<br>Arg Leu Leu Pro Val Leu Cys Gln Ala His Gly Leu Thr Pro Ala Gln<br>690 695 700 | 2112 |
| gtg gtt gca atc gcg tca cac gat ggg gga aag cag gcc cta gaa acc<br>Val Val Ala Ile Ala Ser His Asp Gly Gly Lys Gln Ala Leu Glu Thr<br>705 710 715 720 | 2160 |
| gtt cag cga ctc ctg ccc gtc ctg tgc cag gac cac ggc ctg acc ccc<br>Val Gln Arg Leu Leu Pro Val Leu Cys Gln Asp His Gly Leu Thr Pro<br>725 730 735 | 2208 |
| gac cag gtt gtc gct att gct agt aac ggc gga ggc aaa cag gcg ctg<br>Asp Gln Val Val Ala Ile Ala Ser Asn Gly Gly Gly Lys Gln Ala Leu<br>740 745 750 | 2256 |
| gaa aca gtt cag cgc ctc ttg ccg gtc ttg tgt cag gac cac ggc ctg<br>Glu Thr Val Gln Arg Leu Leu Pro Val Leu Cys Gln Asp His Gly Leu<br>755 760 765 | 2304 |
| acc ccg gaa cag gtg gtt gca atc gcg tca cac gat ggg gga aag cag<br>Thr Pro Glu Gln Val Val Ala Ile Ala Ser His Asp Gly Gly Lys Gln<br>770 775 780 | 2352 |
| gcc cta gaa acc gtt cag cga ctc ctg ccc gtc ctg tgc cag gcc cac<br>Ala Leu Glu Thr Val Gln Arg Leu Leu Pro Val Leu Cys Gln Ala His<br>785 790 795 800 | 2400 |
| ggc ctg acg cct gag cag gta gtg gct att gca tcc cac gac ggg ggc<br>Gly Leu Thr Pro Glu Gln Val Val Ala Ile Ala Ser His Asp Gly Gly<br>805 810 815 | 2448 |
| aga ccc gca ctg gag tca atc gtg gcc cag ctt tcg agg ccg gac ccc<br>Arg Pro Ala Leu Glu Ser Ile Val Ala Gln Leu Ser Arg Pro Asp Pro<br>820 825 830 | 2496 |
| gcg ctg gcc gca ctc act aat gat cat ctt gta gcg ctg gcc tgc ctc<br>Ala Leu Ala Ala Leu Thr Asn Asp His Leu Val Ala Leu Ala Cys Leu<br>835 840 845 | 2544 |
| ggc gga cgt cct gcc atg gat gca gtg aaa aag gga ttg ccg cac gcg<br> | 2592 |

```
Gly Gly Arg Pro Ala Met Asp Ala Val Lys Lys Gly Leu Pro His Ala
    850                 855                 860 ccg gaa ttg atc aga tcc cag cta gtg aaa tct gaa ttg gaa gag aag      2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att      2688
Lys Ser Glu Leu Arg His Lys Leu Lys Tyr Val Pro His Glu Tyr Ile
                    885                 890                 895 gaa ttg att gaa atc gca aga aat tca act cag gat aga atc ctt gaa      2736
Glu Leu Ile Glu Ile Ala Arg Asn Ser Thr Gln Asp Arg Ile Leu Glu
                900                 905                 910 atg aag gtg atg gag ttc ttt atg aag gtt tat ggt tat cgt ggt aaa      2784
Met Lys Val Met Glu Phe Phe Met Lys Val Tyr Gly Tyr Arg Gly Lys
            915                 920                 925 cat ttg ggt gga tca agg aaa cca gac gga gca att tat act gtc gga      2832
His Leu Gly Gly Ser Arg Lys Pro Asp Gly Ala Ile Tyr Thr Val Gly
        930                 935                 940 tct cct att gat tac ggt gtg atc gtt gat act aag gca tat tca gga      2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc      2928
Gly Tyr Asn Leu Pro Ile Gly Gln Ala Asp Glu Met Gln Arg Tyr Val
                    965                 970                 975 gaa gag aat caa aca aga aac aag cat atc aac cct aat gaa tgg tgg      2976
Glu Glu Asn Gln Thr Arg Asn Lys His Ile Asn Pro Asn Glu Trp Trp
                980                 985                 990 aaa gtc tat cca tct tca gta aca  gaa ttt aag ttc ttg  ttt gtg agt    3024
Lys Val Tyr Pro Ser Ser Val Thr Glu Phe Lys Phe Leu  Phe Val Ser
            995                 1000                1005 ggt cat  ttc aaa gga aac tac  aaa gct cag ctt aca  aga ttg aat       3069
Gly His Phe Lys Gly Asn Tyr Lys Ala Gln Leu Thr Arg Leu Asn
        1010                1015                1020 cat atc  act aat tgt aat gga  gct gtt ctt agt gta  gaa gag ctt       3114
His Ile Thr Asn Cys Asn Gly Ala Val Leu Ser Val  Glu Glu Leu
    1025                1030                1035 ttg att  ggt gga gaa atg att  aaa gct ggt aca ttg  aca ctt gag       3159
Leu Ile Gly Gly Glu Met Ile Lys Ala Gly Thr Leu Thr Leu Glu
1040                1045                1050 gaa gtg aga agg aaa ttt aat  aac ggt gag ata aac  ttt taa            3201
Glu Val Arg Arg Lys Phe Asn Asn Gly Glu Ile Asn Phe
1055                1060                1065

<210> SEQ ID NO 63
<211> LENGTH: 1066
<212> TYPE: PRT
<213> ORGANISM: artificial sequence
<220> FEATURE:
<223> OTHER INFORMATION: Synthetic Construct

<400> SEQUENCE: 63

Met Ala Ser Ser Pro Pro Lys Lys Lys Arg Lys Val Ala Ala Ala Asp
1               5                   10                  15

Tyr Lys Asp Asp Asp Asp Lys Ser Trp Lys Asp Ala Ser Gly Trp Ser
                20                  25                  30

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
    50                  55                  60

Gln Gln Glu Lys Ile Lys Pro Lys Val Arg Ser Thr Val Ala Gln His
65                  70                  75                  80
```

```
His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
                100                 105                 110

His Ile Ile Thr Ala Leu Pro Glu Ala Thr His Glu Asp Ile Val Gly
                115                 120                 125

Val Gly Lys Gln Trp Ser Gly Ala Arg Ala Leu Glu Ala Leu Leu Thr
        130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
                180                 185                 190

Asp Gln Val Val Ala Ile Ala Ser His Asp Gly Gly Lys Gln Ala Leu
                195                 200                 205

Glu Thr Val Gln Arg Leu Leu Pro Val Leu Cys Gln Asp His Gly Leu
        210                 215                 220

Thr Pro Glu Gln Val Val Ala Ile Ala Ser Asn Ile Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser His Asp Gly Gly
                260                 265                 270

Lys Gln Ala Leu Glu Thr Val Gln Arg Leu Leu Pro Val Leu Cys Gln
        275                 280                 285

Ala His Gly Leu Thr Pro Ala Gln Val Val Ala Ile Ala Ser His Asp
290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

His Asp Gly Gly Lys Gln Ala Leu Glu Thr Val Gln Arg Leu Leu Pro
                340                 345                 350

Val Leu Cys Gln Asp His Gly Leu Thr Pro Glu Gln Val Val Ala Ile
        355                 360                 365

Ala Ser Asn Ile Gly Gly Lys Gln Ala Leu Glu Thr Val Gln Arg Leu
370                 375                 380

Leu Pro Val Leu Cys Gln Ala His Gly Leu Thr Pro Asp Gln Val Val
385                 390                 395                 400

Ala Ile Ala Ser His Asp Gly Gly Lys Gln Ala Leu Glu Thr Val Gln
                405                 410                 415

Arg Leu Leu Pro Val Leu Cys Gln Ala His Gly Leu Thr Pro Ala Gln
                420                 425                 430

Val Val Ala Ile Ala Ser His Asp Gly Gly Lys Gln Ala Leu Glu Thr
        435                 440                 445

Val Gln Arg Leu Leu Pro Val Leu Cys Gln Asp His Gly Leu Thr Pro
450                 455                 460

Asp Gln Val Val Ala Ile Ala Ser Asn Ile Gly Gly Lys Gln Ala Leu
465                 470                 475                 480

Glu Thr Val Gln Arg Leu Leu Pro Val Leu Cys Gln Asp His Gly Leu
                485                 490                 495
```

```
Thr Pro Glu Gln Val Val Ala Ile Ala Ser Asn Asn Gly Gly Lys Gln
            500                 505                 510

Ala Leu Glu Thr Val Gln Arg Leu Leu Pro Val Leu Cys Gln Ala His
            515                 520                 525

Gly Leu Thr Pro Asp Gln Val Val Ala Ile Ala Ser His Asp Gly Gly
            530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Gly
            565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
            595                 600                 605

His Asp Gly Gly Lys Gln Ala Leu Glu Thr Val Gln Arg Leu Leu Pro
            610                 615                 620

Val Leu Cys Gln Asp His Gly Leu Thr Pro Glu Gln Val Val Ala Ile
625                 630                 635                 640

Ala Ser Asn Ile Gly Gly Lys Gln Ala Leu Glu Thr Val Gln Arg Leu
            645                 650                 655

Leu Pro Val Leu Cys Gln Ala His Gly Leu Thr Pro Asp Gln Val Val
            660                 665                 670

Ala Ile Ala Ser Asn Asn Gly Gly Lys Gln Ala Leu Glu Thr Val Gln
            675                 680                 685

Arg Leu Leu Pro Val Leu Cys Gln Ala His Gly Leu Thr Pro Ala Gln
            690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
            725                 730                 735

Asp Gln Val Val Ala Ile Ala Ser Asn Gly Gly Gly Lys Gln Ala Leu
            740                 745                 750

Glu Thr Val Gln Arg Leu Leu Pro Val Leu Cys Gln Asp His Gly Leu
            755                 760                 765

Thr Pro Glu Gln Val Val Ala Ile Ala Ser His Asp Gly Gly Lys Gln
770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser His Asp Gly Gly
            805                 810                 815

Arg Pro Ala Leu Glu Ser Ile Val Ala Gln Leu Ser Arg Pro Asp Pro
            820                 825                 830

Ala Leu Ala Ala Leu Thr Asn Asp His Leu Val Ala Leu Ala Cys Leu
            835                 840                 845

Gly Gly Arg Pro Ala Met Asp Ala Val Lys Lys Gly Leu Pro His Ala
            850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
            885                 890                 895

Glu Leu Ile Glu Ile Ala Arg Asn Ser Thr Gln Asp Arg Ile Leu Glu
            900                 905                 910

Met Lys Val Met Glu Phe Phe Met Lys Val Tyr Gly Tyr Arg Gly Lys
```

```
            915                 920                 925
His Leu Gly Gly Ser Arg Lys Pro Asp Gly Ala Ile Tyr Thr Val Gly
    930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
                965                 970                 975

Glu Glu Asn Gln Thr Arg Asn Lys His Ile Asn Pro Asn Glu Trp Trp
            980                 985                 990

Lys Val Tyr Pro Ser Ser Val Thr Glu Phe Lys Phe Leu Phe Val Ser
            995                1000                1005

Gly His Phe Lys Gly Asn Tyr Lys Ala Gln Leu Thr Arg Leu Asn
       1010                1015                1020

His Ile Thr Asn Cys Asn Gly Ala Val Leu Ser Val Glu Glu Leu
       1025                1030                1035

Leu Ile Gly Gly Glu Met Ile Lys Ala Gly Thr Leu Thr Leu Glu
       1040                1045                1050

Glu Val Arg Arg Lys Phe Asn Asn Gly Glu Ile Asn Phe
       1055                1060                1065

<210> SEQ ID NO 64
<211> LENGTH: 26
<212> TYPE: DNA
<213> ORGANISM: artificial sequence
<220> FEATURE:
<223> OTHER INFORMATION: TCR-alpha2-f primer

<400> SEQUENCE: 64
ctctgcatga ctcactagca ctctat                                  26

<210> SEQ ID NO 65
<211> LENGTH: 26
<212> TYPE: DNA
<213> ORGANISM: artificial sequence
<220> FEATURE:
<223> OTHER INFORMATION: TCR-alpha2-r primer

<400> SEQUENCE: 65
gactgactta gtgagctggg aaagat                                  26

<210> SEQ ID NO 66
<211> LENGTH: 25
<212> TYPE: DNA
<213> ORGANISM: artificial sequence
<220> FEATURE:
<223> OTHER INFORMATION: TCR-beta1-c1-f primer

<400> SEQUENCE: 66
ctaatatgtg tcactacccc acgag                                   25

<210> SEQ ID NO 67
<211> LENGTH: 26
<212> TYPE: DNA
<213> ORGANISM: artificial sequence
<220> FEATURE:
<223> OTHER INFORMATION: TCR-beta1-c1-r primer

<400> SEQUENCE: 67
gagagttaca caggccacat agaaag                                  26

<210> SEQ ID NO 68
```

```
<211> LENGTH: 25
<212> TYPE: DNA
<213> ORGANISM: artificial sequence
<220> FEATURE:
<223> OTHER INFORMATION: TCR-beta1-c2-f primer

<400> SEQUENCE: 68
gaggagacat cacctggaat gttag                                    25

<210> SEQ ID NO 69
<211> LENGTH: 26
<212> TYPE: DNA
<213> ORGANISM: artificial sequence
<220> FEATURE:
<223> OTHER INFORMATION: TCR-beta1-c2-r primer

<400> SEQUENCE: 69
gatatattag gctgtgctct ggctct                                   26

<210> SEQ ID NO 70
<211> LENGTH: 20
<212> TYPE: DNA
<213> ORGANISM: artificial sequence
<220> FEATURE:
<223> OTHER INFORMATION: Forward primer for Va cloning

<400> SEQUENCE: 70
tggaggagaa ccctggacct                                          20

<210> SEQ ID NO 71
<211> LENGTH: 21
<212> TYPE: DNA
<213> ORGANISM: artificial sequence
<220> FEATURE:
<223> OTHER INFORMATION: Reverse primer for Va cloning

<400> SEQUENCE: 71
ggtgaatagg cagacagact t                                        21

<210> SEQ ID NO 72
<211> LENGTH: 20
<212> TYPE: DNA
<213> ORGANISM: artificial sequence
<220> FEATURE:
<223> OTHER INFORMATION: Forward primer for Ca cloning

<400> SEQUENCE: 72
gagactctaa atccagtgac                                          20

<210> SEQ ID NO 73
<211> LENGTH: 35
<212> TYPE: DNA
<213> ORGANISM: artificial sequence
<220> FEATURE:
<223> OTHER INFORMATION: Reverse primer for Ca cloning

<400> SEQUENCE: 73
gggggcggaa tttacgtagc ggccgctcag ctgct                         35

<210> SEQ ID NO 74
<211> LENGTH: 43
<212> TYPE: DNA
<213> ORGANISM: artificial sequence
<220> FEATURE:
<223> OTHER INFORMATION: Forward primer for Vb cloning

<400> SEQUENCE: 74
```

```
tgccggatct agctagttaa ttaaggatcc gaattcctgc agg                              43
```

<210> SEQ ID NO 75
<211> LENGTH: 20
<212> TYPE: DNA
<213> ORGANISM: artificial sequence
<220> FEATURE:
<223> OTHER INFORMATION: Reverse primer for Vb cloning

<400> SEQUENCE: 75

```
ttcacccacc agctcagctc                                                       20
```

<210> SEQ ID NO 76
<211> LENGTH: 20
<212> TYPE: DNA
<213> ORGANISM: artificial sequence
<220> FEATURE:
<223> OTHER INFORMATION: Forward primer for Cb cloning

<400> SEQUENCE: 76

```
ttcacccacc agctcagctc                                                       20
```

<210> SEQ ID NO 77
<211> LENGTH: 20
<212> TYPE: DNA
<213> ORGANISM: artificial sequence
<220> FEATURE:
<223> OTHER INFORMATION: Reverse primer for Cb cloning

<400> SEQUENCE: 77

```
aggtccaggg ttctcctcca                                                       20
```

<210> SEQ ID NO 78
<211> LENGTH: 141
<212> TYPE: PRT
<213> ORGANISM: artificial sequence
<220> FEATURE:
<223> OTHER INFORMATION: TCRalpha constant region for introduction
<220> FEATURE:
<221> NAME/KEY: misc_feature
<222> LOCATION: (1)..(1)
<223> OTHER INFORMATION: Xaa can be any naturally occurring amino acid

<400> SEQUENCE: 78

Xaa Ile Gln Asn Pro Asp Pro Ala Val Tyr Gln Leu Arg Asp Ser Lys
 1               5                  10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

```
<210> SEQ ID NO 79
<211> LENGTH: 177
<212> TYPE: PRT
<213> ORGANISM: artificial sequence
<220> FEATURE:
<223> OTHER INFORMATION: TCRbeta constant region for introduction

<400> SEQUENCE: 79
```

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

```
<210> SEQ ID NO 80
<211> LENGTH: 9
<212> TYPE: PRT
<213> ORGANISM: artificial sequence
<220> FEATURE:
<223> OTHER INFORMATION: QYD peptide

<400> SEQUENCE: 80
```

Gln Tyr Asp Pro Val Ala Ala Leu Phe
1               5

```
<210> SEQ ID NO 81
<211> LENGTH: 13
<212> TYPE: PRT
<213> ORGANISM: Homo sapiens

<400> SEQUENCE: 81
```

Cys Ala Glu Thr Pro Thr Asn Asp Tyr Lys Leu Ser Phe
1               5                   10

```
<210> SEQ ID NO 82
<211> LENGTH: 8
<212> TYPE: PRT
<213> ORGANISM: Homo sapiens

<400> SEQUENCE: 82
```

Ser Ser Gly Asn Gln Phe Tyr Phe

```
1               5
```

<210> SEQ ID NO 83
<211> LENGTH: 11
<212> TYPE: PRT
<213> ORGANISM: Homo sapiens

<400> SEQUENCE: 83

```
Cys Ala Asp Tyr Tyr Gly Gln Asn Phe Val Phe
1               5                   10
```

<210> SEQ ID NO 84
<211> LENGTH: 16
<212> TYPE: PRT
<213> ORGANISM: Homo sapiens

<400> SEQUENCE: 84

```
Cys Ala Ser Ser Ser Glu Thr Glu Leu Leu Tyr Tyr Gly Tyr Thr Phe
1               5                   10                  15
```

<210> SEQ ID NO 85
<211> LENGTH: 15
<212> TYPE: PRT
<213> ORGANISM: Homo sapiens

<400> SEQUENCE: 85

```
Cys Ala Ser Ser Gln Gln Thr Gly Thr Ile Gly Gly Tyr Thr Phe
1               5                   10                  15
```

<210> SEQ ID NO 86
<211> LENGTH: 13
<212> TYPE: PRT
<213> ORGANISM: Homo sapiens

<400> SEQUENCE: 86

```
Cys Ala Ser Ser Phe Gln Gly Phe Thr Glu Ala Phe Phe
1               5                   10
```

<210> SEQ ID NO 87
<211> LENGTH: 11
<212> TYPE: PRT
<213> ORGANISM: Homo sapiens

<400> SEQUENCE: 87

```
Cys Ala Ser Pro Thr Gly Asn Gln Phe Tyr Phe
1               5                   10
```

<210> SEQ ID NO 88
<211> LENGTH: 13
<212> TYPE: PRT
<213> ORGANISM: Homo sapiens

<400> SEQUENCE: 88

```
Cys Ala Glu Ile Pro Ser Asn Asp Tyr Lys Leu Ser Phe
1               5                   10
```

<210> SEQ ID NO 89
<211> LENGTH: 11
<212> TYPE: PRT
<213> ORGANISM: Homo sapiens

<400> SEQUENCE: 89

```
Cys Ala Ser Gly Ser Gln Gly Asn Leu Ile Phe
1               5                   10
```

-continued

<210> SEQ ID NO 90
<211> LENGTH: 14
<212> TYPE: PRT
<213> ORGANISM: Homo sapiens

<400> SEQUENCE: 90

Cys Ala Gly Leu Thr Thr Asp Ser Trp Gly Lys Phe Gln Phe
1               5                   10

<210> SEQ ID NO 91
<211> LENGTH: 12
<212> TYPE: PRT
<213> ORGANISM: Homo sapiens

<400> SEQUENCE: 91

Cys Ala Thr Tyr Leu Thr Gly Asn Gln Phe Tyr Phe
1               5                   10

<210> SEQ ID NO 92
<211> LENGTH: 11
<212> TYPE: PRT
<213> ORGANISM: Homo sapiens

<400> SEQUENCE: 92

Cys Ala Val Cys Asn Phe Asn Lys Phe Tyr Phe
1               5                   10

<210> SEQ ID NO 93
<211> LENGTH: 16
<212> TYPE: PRT
<213> ORGANISM: Homo sapiens

<400> SEQUENCE: 93

Cys Ala Ser Ser Phe Thr Leu Gly Thr Gly Val Glu Gln Tyr Phe
1               5                   10                  15

<210> SEQ ID NO 94
<211> LENGTH: 13
<212> TYPE: PRT
<213> ORGANISM: Homo sapiens

<400> SEQUENCE: 94

Cys Ser Ala Arg Gly Gln Asp Ile Tyr Glu Gln Tyr Phe
1               5                   10

<210> SEQ ID NO 95
<211> LENGTH: 14
<212> TYPE: PRT
<213> ORGANISM: Homo sapiens

<400> SEQUENCE: 95

Cys Ala Ser Gly Leu Thr Gly Phe Met Asp Glu Gln Tyr Phe
1               5                   10

<210> SEQ ID NO 96
<211> LENGTH: 16
<212> TYPE: PRT
<213> ORGANISM: Homo sapiens

<400> SEQUENCE: 96

Cys Ala Ser Ser Val Asp Val Ala Gly Gly Tyr Asn Glu Gln Phe Phe
1               5                   10                  15

<210> SEQ ID NO 97

```
<211> LENGTH: 13
<212> TYPE: PRT
<213> ORGANISM: Homo sapiens

<400> SEQUENCE: 97

Cys Ala Ser Ser Gln Ala Leu Pro Tyr Glu Gln Tyr Phe
1               5                   10

<210> SEQ ID NO 98
<211> LENGTH: 16
<212> TYPE: PRT
<213> ORGANISM: Homo sapiens

<400> SEQUENCE: 98

Cys Ala Ser Ser Ile Thr Leu Gly Thr Gly Gly Val Glu Gln Tyr Phe
1               5                   10                  15

<210> SEQ ID NO 99
<211> LENGTH: 34
<212> TYPE: PRT
<213> ORGANISM: artificial sequence
<220> FEATURE:
<223> OTHER INFORMATION: Exemplary amino acid sequence of Platinum TALEN
      DNA binding module

<400> SEQUENCE: 99

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 100
<211> LENGTH: 34
<212> TYPE: PRT
<213> ORGANISM: artificial sequence
<220> FEATURE:
<223> OTHER INFORMATION: Exemplary amino acid sequence of Platinum TALEN
      DNA binding module

<400> SEQUENCE: 100

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 101
<211> LENGTH: 34
<212> TYPE: PRT
<213> ORGANISM: artificial sequence
<220> FEATURE:
<223> OTHER INFORMATION: Exemplary amino acid sequence of Platinum TALEN
      DNA binding module

<400> SEQUENCE: 101

Leu Thr Pro Ala Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 102
```

```
<211> LENGTH: 34
<212> TYPE: PRT
<213> ORGANISM: artificial sequence
<220> FEATURE:
<223> OTHER INFORMATION: Exemplary amino acid sequence of Zhang TALEN
      DNA binding module

<400> SEQUENCE: 102

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 103
<211> LENGTH: 60
<212> TYPE: DNA
<213> ORGANISM: artificial sequence
<220> FEATURE:
<223> OTHER INFORMATION: nucleotide sequence in Figs 20-21

<400> SEQUENCE: 103
gtctgtctgc ctattcaccg attttgattc tcaaacaaat gtgtcacaaa gtaaggattc     60

<210> SEQ ID NO 104
<211> LENGTH: 60
<212> TYPE: DNA
<213> ORGANISM: artificial sequence
<220> FEATURE:
<223> OTHER INFORMATION: nucleotide sequence in Figs 20-21

<400> SEQUENCE: 104
cagacagacg gataagtggc taaaactaag agtttgttta cacagtgttt cattcctaag     60

<210> SEQ ID NO 105
<211> LENGTH: 60
<212> TYPE: DNA
<213> ORGANISM: artificial sequence
<220> FEATURE:
<223> OTHER INFORMATION: nucleotide sequence in Figs 20-21

<400> SEQUENCE: 105
gtctgtctgc ctattcaccg attgaagatt ttgattcaat gtgtcacaaa gtaaggattc     60

<210> SEQ ID NO 106
<211> LENGTH: 60
<212> TYPE: DNA
<213> ORGANISM: artificial sequence
<220> FEATURE:
<223> OTHER INFORMATION: nucleotide sequence in Figs 20-21

<400> SEQUENCE: 106
cagacagacg gataagtggc taacttctaa aactaagtta cacagtgttt cattcctaag     60

<210> SEQ ID NO 107
<211> LENGTH: 60
<212> TYPE: DNA
<213> ORGANISM: artificial sequence
<220> FEATURE:
<223> OTHER INFORMATION: nucleotide sequence in Figs 20-21

<400> SEQUENCE: 107
gtctgtctgc ctattcaccg attcaaacaa atgtgttaat gtgtcacaaa gtaaggattc     60

<210> SEQ ID NO 108
```

-continued

```
<211> LENGTH: 60
<212> TYPE: DNA
<213> ORGANISM: artificial sequence
<220> FEATURE:
<223> OTHER INFORMATION: nucleotide sequence in Figs 20-21

<400> SEQUENCE: 108
cagacagacg gataagtggc taagtttgtt tacacaatta cacagtgttt cattcctaag      60

<210> SEQ ID NO 109
<211> LENGTH: 53
<212> TYPE: DNA
<213> ORGANISM: artificial sequence
<220> FEATURE:
<223> OTHER INFORMATION: nucleotide sequence in Figs 20-21

<400> SEQUENCE: 109
gtctgtctgc ctattcaccg attttgattc aatgtgtcac aaagtaagga ttc             53

<210> SEQ ID NO 110
<211> LENGTH: 53
<212> TYPE: DNA
<213> ORGANISM: artificial sequence
<220> FEATURE:
<223> OTHER INFORMATION: nucleotide sequence in Figs 20-21

<400> SEQUENCE: 110
cagacagacg gataagtggc taaaactaag ttacacagtg tttcattcct aag             53

<210> SEQ ID NO 111
<211> LENGTH: 52
<212> TYPE: DNA
<213> ORGANISM: artificial sequence
<220> FEATURE:
<223> OTHER INFORMATION: nucleotide sequence in Figs 20-21

<400> SEQUENCE: 111
gtctgtctgc ctattcaccg attcaaacaa atgtgtcaca agtaaggat tc               52

<210> SEQ ID NO 112
<211> LENGTH: 52
<212> TYPE: DNA
<213> ORGANISM: artificial sequence
<220> FEATURE:
<223> OTHER INFORMATION: nucleotide sequence in Figs 20-21

<400> SEQUENCE: 112
cagacagacg gataagtggc taagtttgtt tacacagtgt ttcattccta ag              52

<210> SEQ ID NO 113
<211> LENGTH: 18
<212> TYPE: DNA
<213> ORGANISM: Mus musculus

<400> SEQUENCE: 113
tctgcctgtt caccgact                                                    18

<210> SEQ ID NO 114
<211> LENGTH: 20
<212> TYPE: DNA
<213> ORGANISM: Mus musculus

<400> SEQUENCE: 114
aatgtgccga aaaccatgga                                                  20
```

```
<210> SEQ ID NO 115
<211> LENGTH: 20
<212> TYPE: DNA
<213> ORGANISM: Mus musculus

<400> SEQUENCE: 115
tgactccacc caaggtctcc                                              20

<210> SEQ ID NO 116
<211> LENGTH: 20
<212> TYPE: DNA
<213> ORGANISM: Mus musculus

<400> SEQUENCE: 116
aaaagcagag attgcaaaca                                              20

<210> SEQ ID NO 117
<211> LENGTH: 20
<212> TYPE: DNA
<213> ORGANISM: Mus musculus

<400> SEQUENCE: 117
tgtgcttggc cagggcttc                                               20

<210> SEQ ID NO 118
<211> LENGTH: 20
<212> TYPE: DNA
<213> ORGANISM: Mus musculus

<400> SEQUENCE: 118
ggagctgagc tggtgggtga                                              20
```

TECHNIQUE FOR CREATING ANTIGEN-SPECIFIC REGULATORY T CELLS (TREG) IN WHICH EFFECTOR T CELL (TEFF) ANTIGEN RECEPTORS ARE USED

STATEMENT REGARDING SEQUENCE LISTING

The Sequence Listing associated with this application is provided in text format in lieu of a paper copy, and is hereby incorporated by reference into the specification. The name of the text file containing the Sequence Listing is 790132_406USPC_SEQUENCE_LISTING.txt. The text file is 233 KB, was created on Oct. 21, 2021, and is being submitted electronically via EFS-Web.

TECHNICAL FIELD

The present invention relates to a biotechnology engineering of T cells.

BACKGROUND ART

Regulatory T cells (Treg) are a cell population that is mainly responsible for immune response regulation in vivo. While development is ongoing for transplant therapy of Tregs amplified ex vivo for treatment of autoimmune diseases or induction of immune tolerance after allogenic transplantation, sufficient efficacy has not been attained. Since Tregs have antigen nonspecific immunosuppressive action, there is a risk of excessively suppressing normal immune responses to infections, malignant tumor, or the like.

The presence of antigen-specific Tregs exerting immunoregulatory action in response to a specific autoantigen or alloantigen has been elucidated in recent years. It is reported that antigen specific Tregs are more effective than conventional Tregs in an autoimmune disease model. However, a technology for manufacturing a Treg specific to any desired antigen has not been developed.

SUMMARY OF INVENTION

Solution to Problem

In one aspect, the present disclosure is characterized in that expression of a T cell receptor (TCR) of an effector T cell is effected in a T cell (e.g., regulatory T cell). In one embodiment, the present disclosure comprises introducing a full or partial TCR gene into a regulatory T cell so that TCRα and TCR are expressed as a pair. The present invention also provides a method of identifying and/or isolating a TCR with a high antigen binding capability in an effector T cell responsive to a desired antigen. In another aspect, the present inventions deletes an endogenous TCR in a regulatory T cell. In one embodiment of the invention, one feature of the method of the present disclosure is to readily isolate a TCR with high antigen binding capability from an effector T cell (Teff) responsive to a desired antigen and causing only a TCR isolated from Teff to be expressed in a regulatory T cell (Treg) with a deletion of an endogenous TCR.

In the present disclosure, a TCR with a high antigen binding capability can be identified based on a frequency of T cell receptor (TCR) clones that are present in an effector T cell population specific to an antigen. For identification of a TCR utilized in the present disclosure, a method of measuring a TCR repertoire comprising unbiasedly amplifying a nucleic acid sequence of the TCR can be used. In the present disclosure, a method of identifying and/or isolating a pair of TCRα and TCRβ with a high antigen binding capability can be used. For example, an effector T cell (Teff) group that is specifically responsive to a desired antigen can be separated using n HLA tetramer or the like to obtain a gene sequence comprising an antigen recognition region of a TCRα chain/TCRβ chain expressed thereby. Furthermore, the binding capability to a desired antigen of each obtained TCR clonotype can be evaluated.

In one aspect of the present disclosure, the method of the present disclosure can comprise removing an endogenous TCR gene in a regulatory T cells. For example, a TCR gene of a Treg separated from peripheral blood can be cleaved using a genome editing technology to suppress the expression of an endogenous TCR.

In one aspect of the invention, the method of the present disclosure can comprise introducing an identified highly functional TCR gene of a Teff into a Treg with an endogenous TCR gene removed. Therefore, a Treg expressing a TCR exhibiting a high binding ability specifically to a desired antigen can be made.

In the present disclosure, a T cell (e.g., regulatory T cell) manufactured using the method of the present disclosure is also provided. Such a regulatory T cell is useful in various situations where immune suppression is desirable. For example, the regulatory T cell of the present disclosure can be used in the treatment or prevention of an autoimmune disease, allergic disease, or graft-versus-host disease (GVHD), rejection, or graft failure in transplantation. The present disclosure also provides an article for use in the method of the invention.

For example, the present disclosure provides the following items.

(Item 1)

A method of producing a regulatory T cell specific to an antigen, comprising:

identifying a T cell receptor (TCR) clone that is present in an effector T cell population specific to the antigen in an effector T cell donor; and introducing a full or partial nucleic acid sequence of a gene of TCRα and a full or partial nucleic acid sequence of a gene of TCRβ, wherein the genes are contained in the clone, into a regulatory T cell so that the TCRα and the TCR are expressed as a pair.

(Item 2)

The method of the preceding item, wherein identifying the TCR clone comprises determining a TCR repertoire of the effector T cell population.

(Item 3) The method of any one of the preceding items, wherein the TCR clone is present at a frequency that is one standard deviation or greater from the mean of the frequency of presence of each clone in the effector T cell population.

(Item 4)

The method of any one of the preceding items, wherein the TCR clone is present at a frequency that is two standard deviation or greater from the mean of the frequency of presence of each clone in the effector T cell population.

(Item 5)

The method of any one of the preceding items, wherein the TCR clone is present at a frequency of about 10% or greater in the effector T cell population.

(Item 6)
The method of any one of the preceding items, wherein the full or partial nucleic acid sequence of the gene of the TCRα comprises a sequence corresponding to the CDR3 region of Vα-Jα.

(Item 7)
The method of any one of the preceding items, wherein the full or partial nucleic acid sequence of the gene of the TCRβ comprises a sequence corresponding to the CDR3 region of Vβ-D-Jβ.

(Item 8)
The method of any one of the preceding items, wherein the full or partial nucleic acid sequence of the gene of the TCRα comprises a cDNA sequence of Vα-Jα-Cα.

(Item 9)
The method of any one of the preceding items, wherein the full or partial nucleic acid sequence of the gene of the TCR comprises a cDNA sequence of Vβ-D-Jβ-Cβ.

(Item 10)
The method of any one of the preceding items, wherein the determining the TCR repertoire comprises:
(1) providing a nucleic acid sample comprising a nucleic acid sequence of a T cell receptor (TCR) unbiasedly amplified from the effector T cell population;
(2) determining the nucleic acid sequence contained in the nucleic acid sample; and
(3) calculating a frequency of appearance of each gene or a combination thereof based on the determined nucleic acid sequence to derive a TCR repertoire of the effector T cell population.

(Item 11)
The method of any one of the preceding items, wherein the determining of the TCR repertoire comprises:
(1) providing a nucleic acid sample comprising a nucleic acid sequence of TCR unbiasedly amplified from the effector T cell population, (1) comprising the following steps:
   (1-1) synthesizing a complementary DNA by using an RNA sample derived from a target cell as a template;
   (1-2) synthesizing a double stranded complementary DNA by using the complementary DNA as a template;
   (1-3) synthesizing an adaptor-added double stranded complementary DNA by adding a common adaptor primer sequence to the double stranded complementary DNA;
   (1-4) performing a first PCR amplification reaction by using the adaptor-added double stranded complementary DNA, a common adaptor primer consisting of the common adaptor primer sequence, and a first TCR C region specific primer, wherein the first TCR C region specific primer is designed to comprise a sequence that is sufficiently specific to a C region of interest of the TCR and not homologous with other genetic sequences, and comprise a mismatching base between subtypes downstream when amplified;
   (1-5) performing a second PCR amplification reaction by using a PCR amplicon of (1-4), the common adaptor primer, and a second TCR C region specific primer, wherein the second TCR C region specific primer is designed to have a sequence that is a complete match with the TCR C region in a sequence downstream the sequence of the first TCR C region specific primer, but comprise a sequence that is not homologous with other genetic sequences, and comprise a mismatching base between subtypes downstream when amplified; and
   (1-6) performing a third PCR amplification reaction by using a PCR amplicon of (1-5), an added common adaptor primer in which a nucleic acid sequence of the common adaptor primer comprises a first additional adaptor nucleic acid sequence, and an adaptor-added third TCR C region specific primer in which a second additional adaptor nucleic acid sequence is added to a third TCR C region specific sequence;
   wherein the third TCR C region specific primer is designed to have a sequence that is a complete match with the TCR C region in a sequence downstream to the sequence of the second TCR C region specific primer, but comprise a sequence that is not homologous with other genetic sequences, and comprise a mismatching base between subtypes downstream when amplified;
(2) determining the nucleic acid sequence comprised in the nucleic acid sample; and
(3) calculating a frequency of appearance of each gene or a combination thereof based on the determined nucleic acid sequence to derive a TCR repertoire of the effector T cell population.

(Item 12)
The method of any one of the preceding items, wherein the identifying the TCR clone comprises amplifying a gene of TCRα and a gene of TCRβ derived from the same cell and identifying a pair of TCRα and TCRβ in the effector T cell population.

(Item 13)
The method of any one of the preceding items, further comprising confirming whether the identified pair of TCRα and TCRβ has affinity to an antigen.

(Item 14)
The method of any one of the preceding items, further comprising cloning a full or partial nucleic acid sequence of TCRα and a full or partial nucleic acid sequence of TCR in the identified pair of TCRα and TCRβ.

(Item 15)
The method of any one of the preceding items, wherein the introducing comprises introducing the cloned full or partial nucleic acid sequence of TCRα and a full or partial nucleic acid sequence of TCRβ into the regulatory T cell.

(Item 16)
The method of any one of the preceding items, wherein the introducing comprises using a vector configured to express the TCRα and the TCR as a pair.

(Item 17)
The method of any one of the preceding items, wherein the vector comprises a nucleic acid sequence encoding Cys so that a disulfide bond is formed between the TCRα and the TCRβ to be expressed, has a coding sequence of the TCRα and the TCRβ codon optimized, is configured so that a leucine zipper is introduced into an intracellular region of the TCRα and the TCRβ, or is configured so that the TCRα and the TCRβ are expressed with a modification in a sugar chain.

(Item 18)
The method of any one of the preceding items, comprising using a vector encoding a Cα domain linked to a Vα chain and a Cβ domain linked to a Vβ chain, wherein the vector is configured so that the TCRα and the TCRβ are expressed as a pair.

(Item 19)
The method of any one of the preceding items, wherein the regulatory T cell is obtained from the effector T cell donor.

(Item 20)
The method of any one of the preceding items, further comprising removing an endogenous TCR gene of the regulator T cell.

(Item 21)

The method of any one of the preceding items, wherein the removal of the endogenous TCR gene is performed using a TCR specific TALEN.

(Item 22)

The method of any one of the preceding items, wherein the TALEN is provided as a polypeptide comprising a DNA binding domain and a functional domain or a nucleic acid encoding the polypeptide, wherein the DNA binding domain and the functional domain are connected by a polypeptide consisting of 35 to 55 amino acids, the DNA binding domain comprises a plurality of DNA binding modules consecutively from the N-terminal side, a combination of the xth amino acid and the yth amino acid in the 4n-3th DNA binding module from the N-terminus being identical for any n, a combination of the xth amino acid and the yth amino acid in the 4n-2th DNA binding module from the N-terminus being identical for any n, a combination of the xth amino acid and the yth amino acid in the 4n-1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n-3th DNA binding module from the N-terminus, the combination of the xth amino acid and the yth amino acid in the 4n-2th DNA binding module from the N-terminus, the combination of the xth amino acid and the yth amino acid in the 4n-1th DNA binding module from the N-terminus, and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers.

(Item 23)

The method of any one of the preceding items, comprising:

removing one of genes of endogenous TCRα and endogenous TCRβ in the regulatory T cell;

introducing a full or partial nucleic acid sequence of the TCRα gene or a full or partial nucleic acid sequence of the TCRβ gene into the regulatory T cell;

removing the other one of the genes of endogenous TCRα and endogenous TCR in the regulatory T cell; and reintroducing the full or partial nucleic acid sequence of the gene of TCRα or the full or partial nucleic acid sequence of the gene of TCRβ into the regulatory T cell.

(Item 24)

A method of producing a regulatory T cell specific to an antigen, comprising:

determining a TCR repertoire in an effector T cell population specific to the antigen in an effector T cell donor, comprising unbiasedly amplifying a TCR gene;

identifying a pair of TCRα and TCRβ in the effector T cell population;

checking whether the identified pair of TCRα and TCRβ has affinity to an antigen;

cloning a full or partial nucleic acid sequence of TCRα and a full or partial nucleic acid sequence of TCRβ in the identified pair of TCRα and TCRβ;

removing an endogenous TCR gene of a regulatory T cell; and introducing the cloned full or partial nucleic sequence of TCRα and full or partial nucleic acid sequence of TCR into the regulatory T cell so that the TCRα and the TCR are expressed as a pair.

(Item 24A)

The method of any one of the preceding items, having a feature of any one or more of the preceding items.

(Item 25)

A regulatory T cell manufactured by the method of any one of the preceding items.

(Item 26)

A regulatory T cell that is free of an endogenous TCR gene.

(Item 27)

A regulatory T cell, comprising a full or partial nucleic acid sequence of the gene of TCRα or a full or partial nucleic acid sequence of the gene of TCRβ, wherein the genes are included in a T cell receptor (TCR) clone that is present in an effector T cell population in an effector T cell donor.

(Item 28)

A regulatory T cell, which is free of an endogenous TCR gene and comprises a full or partial nucleic acid sequence of the gene of TCRα or a full or partial nucleic acid sequence of the gene of TCRβ, wherein the genes are included in a T cell receptor (TCR) clone that is present in an effector T cell population in an effector T cell donor.

(Item 29)

A composition comprising the regulatory T cell of any one of the preceding items for treating or preventing an autoimmune disease.

(Item 30)

A composition comprising the regulatory T cell of any one of the preceding items for treating or preventing an allergic disease.

(Item 31)

A composition comprising the regulatory T cell of any one of the preceding items for treating or preventing a graft-versus-host disease (GVHD), rejection, or graft failure in transplantation.

(Item 32)

A composition comprising a vector configured so that the TCRα and the TCRβ are expressed as a pair for use in the method of any one of the preceding items.

(Item 33)

A composition comprising an MHC tetramer for use in the method of any one of the preceding items.

(Item 34)

A composition comprising a polypeptide comprising a DNA binding domain and a functional domain or a nucleic acid encoding the polypeptide for use in the method of any one of the preceding items, wherein the DNA binding domain specifically binds to a TCR gene.

(Item 35)

A TCR repertoire of an effector T cell population or a portion thereof, or a nucleic acid encoding the same obtained by the method of any one of the preceding items.

(Item 36)

A composition for manufacturing a TCR modified T cell, comprising a TCR repertoire of an effector T cell population or a portion thereof, or a nucleic acid encoding the same obtained by the method of any one of the preceding items.

(Item 37)

The composition of any one of the preceding items, wherein the TCR modified T cell comprises a TCR modified regulatory T cell.

(Item 37A)

The composition of the preceding item, having the feature of one or more of the preceding items.

The present disclosure is intended so that one or more of the features can be provided not only as the explicitly disclosed combinations, but also as other combinations thereof. Additional embodiments and advantages of the present disclosure are recognized by those skilled in the art by reading and understanding the following detailed description, as needed.

Advantageous Effects of Invention

The present disclosure enables the production of a regulatory T cell that has antigen specificity and does not result in nonspecific immunosuppression, and can provide immunosuppression that can be regulated.

DESCRIPTION OF EMBODIMENTS

Figure 1:
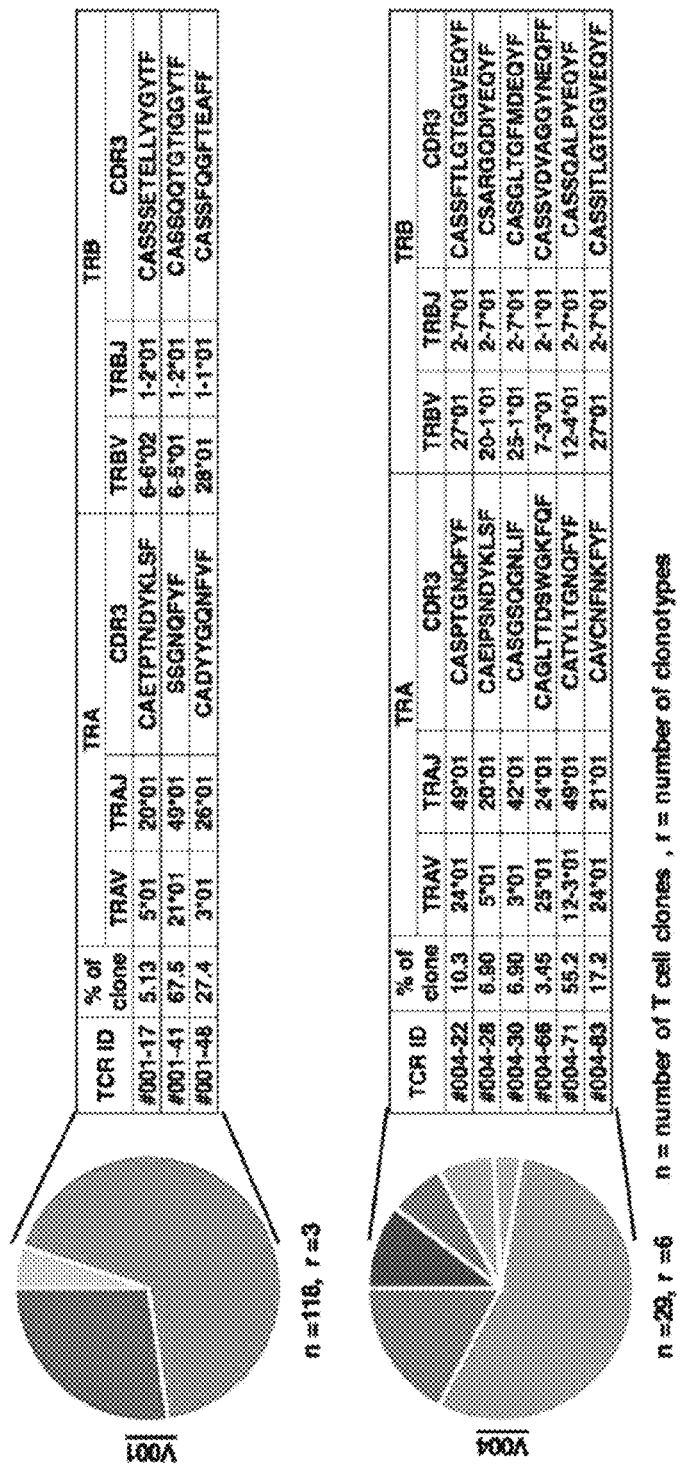
FIG. 1 is a diagram showing CMV NLV specific TCRα and TCRβ repertoires of a single cell. The figure shows a pair of CMV NLV specific TCRα and TCRβ of cells obtained from two HLA A2 antigen positive and CMV antibody positive healthy donors (V001 and V004). 118 and 29 T cells were analyzed from V001 and V004, respectively, and three types (TCR ID; 001-17, 48, and 41) and six types (TCR ID; 004-66, 22, 63, 30, 28, and 71) of respective CDR3α and CDR3β pairs were identified. CDR3 sequences corresponds to SEQ ID NO: 81 to 98, respectively.

The present disclosure is explained hereinafter while showing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

1. Definitions and Explanation of Basic Technologies

The definitions of the terms and/or details of the basic technologies that are especially used herein are explained hereinafter as appropriate.

As used herein, "effector T cell" refers to a differentiated and activated T cell that recognizes an antigen presented by an antigen presenting cell such as a B cell, macrophage, or dendritic cell via a T cell receptor. An effector T cell is also denoted herein as "Teff" or the like.

As used herein, "regulatory T cell" is a CD4 positive T cell exhibiting immunosuppressive action with positive Foxp3 expression. A regulatory T cell is also referred to as "Treg" herein. CD25 strong positive and CD127 expression weak positive can also be used as an indicator of a regulatory T cell. Treg is roughly classified into endogenous T cells (Naturally Occurring Regulatory T cell; nTreg) and inducible T cells with low self-recognition capability differentiated from naïve CD4 positive T cells (Inducible Regulatory T cell; iTreg).

As used herein, "flow cytometry" refers to a technology for measuring the number and individual physical/chemical/biological attributes of a cell, individual, and other biological particles suspended in a liquid. An apparatus using this technology is referred to as a "flow cytometer".

As used herein, "clonotype" refers to a recombinant sequence derived from a T cell or a B cell encoding a T cell receptor or an immunoglobulin molecule or a portion thereof. While, the genomic sequences of normal somatic cells are the same in an individual, the sequence is rearranged in each cell in a coding sequence of a T cell or B cell receptor, so that there are a plurality of clonotypes in T cells or B cells in an individual.

As used herein a "dominant" clone refers to a clone in a clone population with the greater frequency than a certain threshold value that can be appropriately determined by those skilled in the art.

As used herein, "T cell receptor (TCR)" refers to a receptor in a T cell. A TCR is a heterodimer receptor molecule consisting of two TCR polypeptide chains. There are αβ TCRs expressed in normal T cells and γδ TCRs with a special function. α and β chain TCR molecules form a complex with a plurality of CD3 molecules (CD3ζ chain, CD3ε chain, CD3γ chain, and CD3δ chain), transmit an intracellular signal after antigen recognition, and initiate various immune responses. Endogenous antigens such as a cancer antigen derived from a cancer cell or a viral antigen proliferated in a cell with a viral infection are presented as an antigen peptide on an MHC class I molecule. Further, an antigen derived from an exogenous microorganism is taken up by an antigen-presenting cell by endocytosis and processed, and then presented on an MHC class II molecule. Such antigens are recognized by TCRs expressed by each of CD8+ T cell and CD4+ T cell. It is also known that a costimulatory molecule such as a CD28, ICOS, or OX40 molecule is important for stimulation via a TCR molecule. For αβ TCRs, which are one of the primary objectives herein, a gene product of each of α and β is understood to express specificity by a unique combination.

The biological defense mechanism using the immune system is heavily dependent on the specific immunity provided mainly by T cells and B cells. In principle, T cells and B cells can specifically recognize and attack exogenous pathogens such as viruses or bacteria without reacting to autologous cells or molecules. For this reason, T cells and B cells have a mechanism that can recognize and distinguish various antigens from other organisms in addition to autoantigens by a receptor molecule expressed on the cell surface. In T cells, T cell receptors (TCR) function as an antigen receptor. An intracellular signal is transmitted by a stimulation from such antigen receptors, production of inflammatory cytokines, chemokines or the like are promoted, cell proliferation increases, and various immune responses are initiated.

TCR recognizes a peptide bound to a peptide binding cleft of a major histocompatibility complex (MHC) expressed on antigen presenting cells (peptide-MHC complex, pMHC) to distinguish autologous and heterologous and recognizes an antigen peptide (Cell 1994, 76, 287-299).

A TCR gene consists of numerous V regions (variable region, V), J regions (joining region, J), D regions (diversity region, D), and C regions (constant region, C) encoded by different regions in the genome. In a T cell differentiation process, such gene fragments are genetically rearranged in various combinations. α chain and γ chain TCRs express genes consisting of V-J-C, and β chain and δ chain TCRs express genes consisting of V-D-J-C. Diversity is created by rearrangement of such gene fragments. In addition, insertion or deletion of one or more bases between V and D or D and J gene fragments leads to the formation of a random amino acid sequence to create a more diverse TCR gene sequence.

A region where a TCR molecule directly binds to a pMHC complex surface (TCR footprint) is composed of diverse complementarity determining regions (CDR) within the V region, i.e., CDR1, CDR2, and CDR3 regions. The CDR3 region in particular comprises a part of a V region, a V-D region (α chain and γ chain) or a V-D-J region (βchain and δchain) formed by a random sequence, and a part of J region, forming the most diverse antigen recognition site. Meanwhile, the other regions are known as FRs (framework region) serving the role of forming a backbone structure of a TCR molecule. In a differentiation and maturation process of a T cell in the thymus gland, α chain TCR is genetically rearranged initially, and conjugates with a pTα molecule to form a pre-TCR complex molecule. An α chain TCR is then rearranged to form an αβ TCR molecule, and when a functional αβ TCR is not formed, rearrangement occurs in the other a chain TCR gene allele. It is known that after undergoing positive/negative selection in the thymus gland, a TCR with a suitable affinity is selected to acquire antigen specificity (Annual Review Immunology, 1993, 6, 309-326).

T cells produce one type of TCR with high specificity to a specific antigen. With numerous antigen specific T cells in the living body, a diverse TCR repertoire can be formed to effectively function as a defense mechanism against various pathogens.

As used herein, "highly functional TCR" refers to a TCR with a higher binding capability than other TCRs among TCRs with binding capability to a certain antigen. It can be determined whether a certain TCR is a highly functional TCR by, for example, incubating a cell expressing the TCR with an antigen tetramer-PE complex at a certain concentration (e.g., 10 μg/ml) and then measuring whether the TCR can bind to the antigen thereof with an affinity at which MFI (mean fluorescence intensity) in TCRαβ positive cells exceeds a certain value (e.g., 5000).

2. Preferred Embodiments

The preferred embodiments of the present disclosure are described hereinafter. It is understood that the embodiments provided hereinafter are provided to facilitate better understanding of the present disclosure, so that the scope of the present disclosure should not be limited by the following description. Thus, it is apparent that those skilled in the art can refer to the descriptions herein to make appropriate modifications within the scope of the present disclosure. It is also understood that the following embodiments of the present disclosure can be used alone or as a combination.

Each of the embodiments described below provides a comprehensive or specific example. The numerical values, shapes, materials, constituent elements, positions of arrangement and connection modes of the constituent elements, steps, order of steps, and the like in the following embodiments are one example, which is not intended to limit the Claims. Further, the constituent elements in the following embodiments that are not recited in the independent claims showing the most superordinate concept are described as an optional constituent element.

(2.1 Antigen Specific Regulatory T Cell)

In one aspect, the present disclosure provides a method of producing a regulatory T cell specific to an antigen, comprising: determining a TCR repertoire in an effector T cell population specific to the antigen in an effector T cell donor, comprising unbiasedly amplifying a TCR gene; identifying a pair of TCRα and TCRβ in the effector T cell population; checking whether the identified pair of TCRα and TCRβ has affinity to an antigen; cloning a full or partial nucleic acid sequence of TCRα and a full or partial nucleic acid sequence of TCRβ in the identified pair of TCRα and TCRβ; removing an endogenous TCR gene of a regulatory T cell; and introducing the cloned full or partial nucleic acid sequence of TCRα and full or partial nucleic acid sequence of TCR into the regulatory T cell so that the TCRα and the TCRβ are expressed as a pair.

Figure 18:
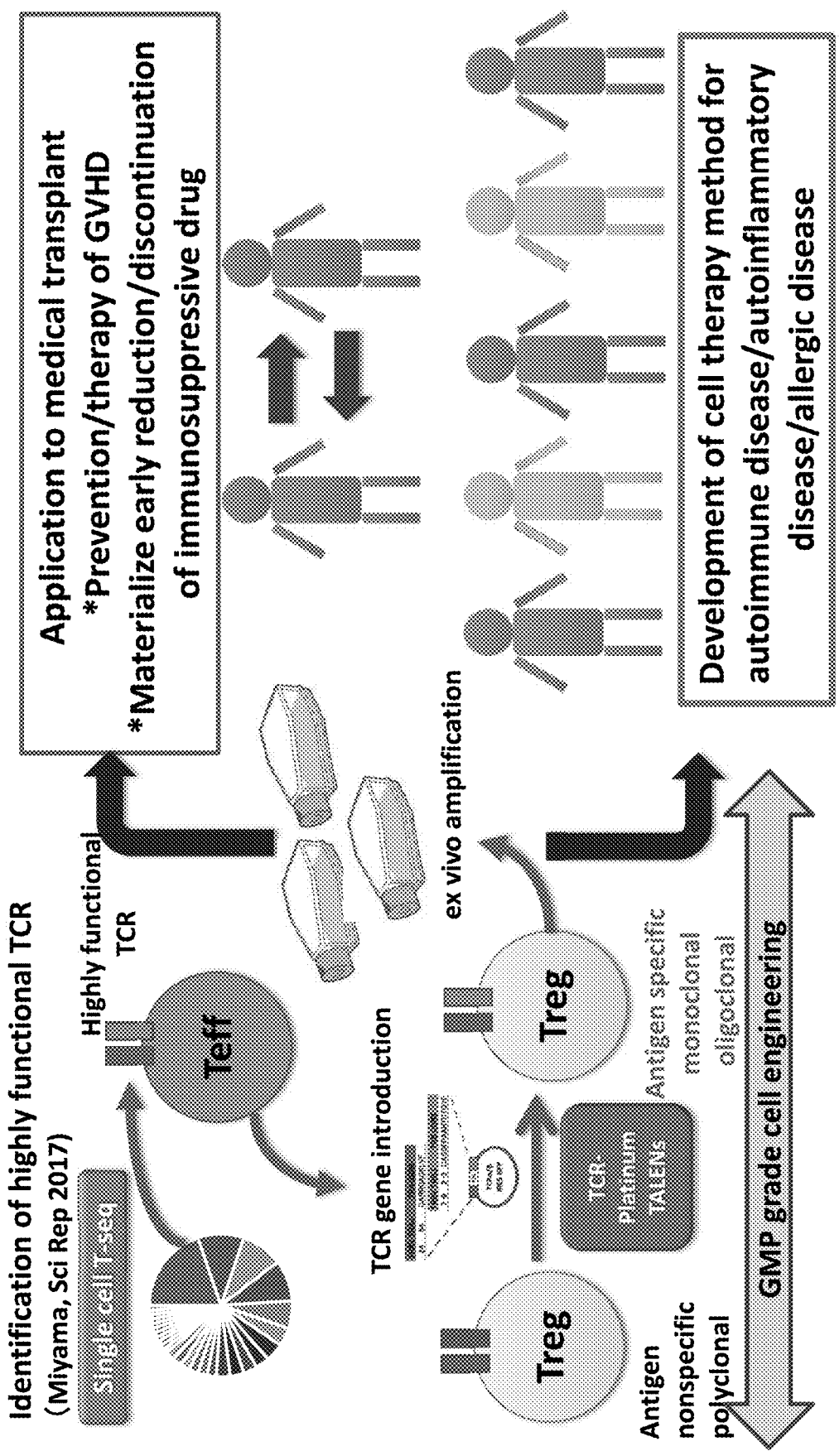
FIG. 18 is a diagram showing an example of a preferred embodiment of the invention. For example, the present disclosure can materialize an antigen specific Treg transfer therapy using a highly functional TCR.

A preferred embodiment is described in FIG. 18. A highly functional TCR is identified and introduced into an antigen nonspecific polyclonal regulatory T cell obtained from a donor, whereupon an endogenous TCR gene is preferably removed by editing or the like, and more preferably an endogenous TCR gene is edited using a Platinum TALEN. Preferably, the TCR described above is introduced so that the TCRs described above are expressed as a pair. The obtained antigen specific monoclonal or oligoclonal regulatory T cell is amplified ex vivo and transferred into a recipient. It is understood that antigen specific regulatory T cells obtained by the present disclosure are safe due to the lack of unknown antigen reactivity, and exhibits high antigen specific immunosuppression capability by using a highly functional TCR. A recipient can be the same or different individual as the donor of a regulator T cell.

The present disclosure can also provide any article for use in the method of the present disclosure. For example, the present disclosure can provide a composition comprising a vector configured to express the TCRα and the TCRβ as a pair for use in the method of the present disclosure. A composition comprising an MHC tetramer for use in the method of the present disclosure can also be provided.

The present disclosure can also provide a composition for use in the method of the present disclosure, comprising a polypeptide comprising a DNA binding domain and a functional domain or a nucleic acid encoding the polypeptide, wherein the DNA binding domain specifically binds to a TCR gene.

A TCR repertoire of an effector T cell population identified by the method of the present disclosure or a portion thereof, or a nucleic acid encoding the same is also within the scope of the present disclosure. A composition for manufacturing a TCR modified T cell comprising a TCR repertoire of an effector T cell population or a portion thereof, or a nucleic acid encoding the same is also provided. Preferably, a TCR modified T cell comprises a TCR modified regulatory T cell.

(2.2 T Cell Endogenous TCR Gene Modification)

One aspect of the present disclosure is a method of modifying an endogenous TCR gene in a T cell. This method can preferably comprise modifying a T cell so that an endogenous ICR is not expressed.

Another aspect of the present disclosure can comprise introducing an exogenous TCR into a T cell (e.g., by introducing a nucleic acid). Examples of T cells targeted by the present disclosure include, but are not limited to, regulatory T cells, effector T cells, helper T cells, natural killer T cells (NKT cells), γδ T cells, and the like. Modification/introduction of a ICR of a regulatory T cell is preferable as it leads to immune regulation including antigen specific immune tolerance. Since NKT cells or γδ T cells themselves have antigen nonspecific killer activity, there is a significance in introducing antigen specific TCRαβ by the method of the present disclosure. It is demonstrated that γδ T cells can generate antigen specific effector T cells by transduction of TCRαβ into a γδ T cell, as described in J Immunol. 2009 Jan. 1; 182(1): 164-70. (PMID: 19109147). It is effective to introduce a highly functional ICR identified by the present disclosure into a γδ T cell.

T cells or T cell population can be isolated by a conventional method from a sample obtained from a subject or the like, such as peripheral blood, bone marrow, tumor tissue, hematopoietic tissue, spleen, normal tissue, or lymph of the subject. Sample collection from peripheral blood can be advantageous for the noninvasiveness and simplicity thereof. For separation of T cell population, sorting by flow cytometry as well as cell separation using magnetism can also be used.

The present disclosure can utilize a first T cell for modifying an endogenous TCR gene and a second T cell having a TCR to be introduced. In this regard, the first T cell and the second T cell can be obtained from the same subject or different subjects (first donor and second donor). Furthermore, the modified first T cell can be used to treat the same subject, or a subject (recipient) who is different from either donor. In one preferred embodiment, the first T cell is a regulatory T cell, and the second T cell is an effector T cell.

Some embodiments of the present disclosure provides a modified T cell or a composition comprising the same. One embodiment provides an endogenous TCR gene-free regulatory T cell. Said T cell can impart desired antigen specificity safely without TCR gene mispairing.

Another embodiment provides a regulatory T cell comprising a full or partial nucleic acid sequence of a gene of TCRα and a full or partial nucleic acid sequence of a gene of TCRβ, wherein the genes are included in a T cell receptor (TCR) clone in an effector T cell population in an effector T cell donor. A T cell receptor (TCR) clone in a T cell population in a donor is considered highly functional. It is understood that a regulatory T cell having such a TCR exhibits antigen specific immunosuppression. The present disclosure also provides a regulatory T cell which is free of an endogenous TCR gene and comprises a full or partial nucleic acid sequence of a gene of TCRα and a full or partial nucleic acid sequence of a TCR gene contained in a T cell receptor (TCR) clone that is in an effector T cell population in an effector T cell donor.

(2.3 Analysis of Composition of T Cell Subpopulation)

The composition of a desired T cell subpopulation in a T cell population or a sample can be measured using a conventional method by those skilled in the art. Generally, the number of cells which are positive for a marker identifying a cell subpopulation of interest in a T cell population or a sample, or for a marker correlated with a desired feature (e.g., CD3) can be measured using flow cytometry or the like. A desired cell subpopulation can be separated simultaneously with flow cytometry technology. Examples of advantages of flow cytometry include ease of finding the ratio accounted for by cells introduced with a desired gene, high specificity and sensitivity, high reproducibility, ability to analyze a large number of cells, short time requirement, and the like.

A flow cytometer an instrument for measuring the optical property of a suspended matter (cell) from a homogeneous cell suspension. Cells pass through a focal point of a laser beam on a liquid flow. A flow cytometer can simultaneously measure, for individual cells, the optical properties of forward scatter, side scatter, and fluorescence of one or more different wavelengths from 500 to 4000 cells per second upon passage, and quickly and accurately measure biological properties such as the size and internal structure of the cells, and the amount of various antigens or nucleic acids within the cell membrane/cytoplasm/nucleus.

Scatter is light scattered to the surrounding from a collision with a cell. Forward scatter (FSC) is detected in front with respect to the laser beam axis, and scatter intensity is proportional to the surface area of a cell. Specifically, it is understood that cells are large for relatively larger FSC values, and cells are small for smaller FSC values. Side scatter (SSC) is detected at a position that is at 90 degrees (perpendicular) to the laser beam axis, and the scatter intensity is proportional to the state of cell granule or intracellular structure. Specifically, it is understood that the internal structure of a cell is more complex for a relatively large SSC value, and the internal structure of a cell is simpler for smaller SSC values.

Results of flow cytometry can be typically expressed as a dot plot, with FSC in the X axis and SSC in the Y axis. Each cell is indicated by a dot (point) in a diagram. The position thereof is determined by the relative values of FSC and SSC. Lymphocytes which have a relatively small size and simple internal structure are displayed on the bottom left section, granulocytes which have a large size and granules inside are displayed on the top right section, and monocytes which have a large size but a simple internal structure are displayed between lymphocytes and granulocytes, with each forming a population separated from one another.

Fluorescence refers to light generated when a fluorescent pigment labeling a cell is excited by an irradiated laser beam and releases energy. Flow cytometers (e.g., product name: Becton & Dickinson FACSCalibur) typically irradiate a 488 nm single wavelength laser beam and a 635 nm single wavelength laser beam. Although cells themselves have a property of emitting weak fluorescence (autofluorescence), actual specific detection of molecules of cells with fluorescence requires attachment of a fluorescent pigment to the cells or molecules thereof in advance in some form. For example, FITC (Fluorescein isothiocyanate) absorbs 488 nm excitation light and primarily emits 530 nm fluorescence (green). If antibodies are labeled with FITC in advance, this would result in a difference in the amount of bound antibodies in accordance with the amount of antigens on the cell surface and thus a difference in the fluorescence intensity of FITC, so that the amount of antigens on the cell surface can be estimated. FACSCalibur that can be used as an example is equipped with four fluorescence detectors, which can detect difference fluorescence wavelength regions. If a plurality of fluorescent pigments emitting lights of different wavelengths are prepared, up to four different antigens can be simultaneously detected. As fluorescent pigments other than FITC that are excited by a 488 nm single wavelength laser beam, PE (phycoerythrin) primarily emits 585 nm fluorescence, and PerCP (peridinin chlorophyll protein) and PE-Cy5 (carbocyanin-5) primarily emits 670 nm fluorescence. APC (allophycocyanin), which is a fluorescent pigment excited by a 635 nm single wavelength laser beam, primarily emits 670 nm fluorescence. These fluorescent pigments are combined with various antibodies and used in double or triple staining of cells. CD3, CD4, CD8, CD25, and TCR that are expressed on the surface of T lymphocytes, Foxp3 molecules expressed inside cells, and the like can be detected with a monoclonal antibody specifically reacting therewith.

Strictly speaking, there are two types of flow cytometers, i.e., instrument that only analyzes cells and instrument capable of separating (sorting) analyzed cells. The latter is known as "FACS". As used herein, "FACS" is an abbreviated of fluorescence-activated cell sorter, referring to an apparatus used in a method of analyzing surface antigens of free cells such as lymphocytes using a laser beam or sorting for a specific cell by the presence/absence of a surface antigen or the like.

Results of flow cytometry can be displayed as a histogram, dot plot, or the like. As used herein, "histogram" refers to a graph representing light signal intensity of each parameter on the X axis and cell count on the Y axis in measurement of fluorescence using a flow cytometer. With such a mode, a total of 10000 or more cells in total can be counted.

As used herein, "dot plot" refers to a plot of fluorescence intensity of two types of fluorescent pigments on the X and Y axes. With double- or triple-stained cells, the cells can be analyzed using a display method in which each fluorescence intensity is placed on the X or Y axis and individual cells correspond to each point on a two dimensional graph.

For example, peripheral blood or bone marrow liquid is collected, and then erythrocytes are removed by the hemolytic method or specific gravity centrifugation, then the residual is reacted with a fluorescently labeled antibody (antibody to antigen of interest and a control antibody thereof) and sufficiently washed for observation using flow cytometry. The detected scattered light or fluorescence is converted to an electric signal and analyzed by a computer. The result can distinguish lymphocytes, mononuclear cells, and granulocytes by representing the intensity of FSC as the cell size and the intensity of SSC as intracellular structure. The cell population of interest is gated thereafter as needed to examine the manner of antigen expression in the cells.

In practicing the method of the present disclosure, those skilled in the art can suitably identify a surface marker of the shown cells to fractionate or count the cells. CD antigens were agreed upon at an international workshop to be classified as clusters (clustering) mainly by the biochemical feature (especially molecular weight) of an antigen recognized thereby as the standard. This is known as CD classification. Many types of monoclonal antibodies that recognize a specific leukocyte differentiation antigen are named thereby under a unified convention, which is CD followed by a number, i.e., CD number (i.e., CD1, CD2, and the like).

Since CD3 molecules are present in the cell membrane and form a complex with a TCR, such molecules can be used as a marker for TCR expression.

It was found that CD4+ T cells highly expressing interleukine-2 receptor a chain, CD25 molecule, have a function of suppressing autoimmune diseases. CD4 and CD25 are used as regulatory T cell markers. Recently, it was found that a transcription factor Foxp3 is a master gene of Treg differentiation, so that Foxp3 is now widely used as a molecular marker identifying CD4+CD25+ Treg. CD127 is used as a cell surface marker for Treg other than Foxp3. It was found that Treg is abundant in the CD4+CD25 strong positive CD127 negative or weak positive T cell fraction.

(2.4. Analysis of TCR Repertoire)

One embodiment of the present disclosure provides a method comprising determining a TCR repertoire of a T cell population. For identification of a TCR clone that is in an effector T cell population which is specific to an antigen in a donor, it was found that a highly functional TCR clone can be identified by measuring the frequency of presence of each TCR clone (a chain or chain) that is in an effector T cell population.

An example of a method of determining a TCR repertoire is a method of analyzing the ratio of T cells expressing individual Vβ chains by flow cytometry using a specific Vβ chain specific antibody for how much of individual V chains is used by a T cell in a sample (FACS analysis).

TCR repertoire analysis through a molecular biological approach has been conceived based on information on a TCR gene obtained from a human genome sequence. This includes a method of extracting RNA from a cell sample and synthesizing a complementary DNA, and then subjecting a TCR gene to PCR amplification for quantification.

A nucleic acid can be extracted from a cell sample by using a tool that is known in the art such as RNeasy Plus Universal Mini Kit (QIAGEN). Total RNA can be extracted and purified from a cell dissolved in a TRIzol LS reagent by using an RNeasy Plus Universal Mini Kit (QIAGEN).

A complementary DNA can be synthesized from an extracted RNA by using any reverse transcriptase known in the art such as Superscript III™ (Invitrogen).

Those skilled in the art can appropriately perform PCR amplification of a TCR gene using any polymerase known in the art. However, an "unbiased" amplification of a gene with large variation such as a TCR gene can result in an advantageous effect for accurate measurement.

A method of designing numerous individual TCR V chain specific primers as primers used for PCR amplification and quantifying each by real-time PCR or the like, or a method of concurrently amplifying such specific primers (Multiple PCR) have been used. However, even for quantification of each V chain using an endogenous control, an accurate analysis cannot be conducted if many primers are used. Furthermore, Multiple PCR has a disadvantage in that a difference in amplification efficiencies among primers leads to a bias during PCR amplification. To overcome such a disadvantage of Multiple PCR, Tsuruta et al. reported Adaptor-ligation PCR for adding an adapter to the 5' terminus of a double stranded complementary DNA of a TCR gene, then amplifying all γδ TCR genes with a common adapter primer and a C region specific primer (Journal of Immunological Methods, 1994, 169, 17-23). This was also applied to amplification of an αβ TCR gene to develop Reverse dot blot (Journal of Immunological Methods, 1997, 201, 145-15) and Microplate hybridization assay (Human Immunology, 1997, 56, 57-69) for quantification with individual V chain specific oligoprobes.

A preferred embodiment of the present disclosure determined TCR diversity by amplifying, without changing the frequency of presence, TCR genes comprising all isotype and subtype genes with one set of primers consisting of one type of forward primer and one type of reverse primer as described in WO 2015/075939 (Repertoire Genesis Inc., the entire document is incorporated herein by reference). The following primer design is advantageous for unbiased amplification.

Focus was placed on the genetic structure of a TCR or BCR gene. An adaptor sequence is added, without setting a primer to highly diverse V regions, to the 5' terminal thereof to amplify all V region comprising genes. Such an adaptor can have any length or sequence in a base sequence. About 20 base pairs are optimal, but a sequence from 10 bases to 100 bases can be used. An adaptor added to the 3' terminal is removed with a restriction enzyme. In addition, all TCR genes are amplified by amplifying with a reverse primer specific to a C region which has a common sequence with an adaptor primer with the same sequence as a 20 base pair adaptor.

A complementary strand DNA is synthesized with a reverse transcriptase from a TCR or BCR gene messenger RNA and then a double stranded complementary DNA is synthesized. A double stranded complementary DNA comprising V regions with different lengths is synthesized by a reverse transcription reaction or a double strand synthesizing reaction. Adaptors consisting of 20 base pairs and 10 base pairs are added to the 5' terminal section of such genes by a DNA ligase reaction.

The genes can be amplified by setting a reverse primer to a C region of an α chain, β chain, γ chain or δ chain of TCRs. As reverse primers set in a C region, primers are set which match the sequences of each of Cβ, Cα, Cγ and Cδ of TCRs and have a mismatch to an extent that other C region sequences are not primed. A reverse primer of a C region is optimally produced while considering the base sequence, base composition, DNA melting temperature (Tm), or presence/absence of a self-complementary sequence, so that amplification with an adaptor primer is possible. A primer can be set in a region other than the base sequence that is different among allelic sequences in a C region sequence to uniformly amplify all alleles. A plurality of stages of nested PCR are performed in order to enhance the specificity of an amplification reaction.

The length (number of bases) of a primer candidate sequence is not particularly limited for a sequence not comprising a sequence that is different among allelic sequences for each primer. However, the number of bases is 10 to 100, preferably 15 to 50, and more preferably 20 to 30.

Use of such unbiased amplification is advantageous and preferred for identification of a low frequency (1/10,000 to 1/100,000 or less) gene. A TCR repertoire can be determined from read data that is obtained by sequencing a TCR gene amplified in this manner.

PCR amplification on a TCR gene from a human sample and utilization of next generation sequence analysis techniques can now materialize large-scale high efficiency TCR repertoire analysis, which obtains and analyzes more detailed gene information at a clone level from conventional small scale TCR repertoire analysis obtaining limited information such as V chain usage frequency or the like.

The sequencing approach is not limited as long as a sequence of a nucleic acid sample can be determined. While any approach known in the art can be utilized, it is preferable to use next generation sequencing (NGS). Examples of next generation sequencing include, but are not limited to, pyrosequencing, sequencing by synthesis, sequencing by ligation, ion semiconductor sequencing, and the like.

The obtained read data can be mapped to a reference sequence comprising V, D, and J genes to derive the unique number of reads and determine TCR diversity.

One embodiment prepares a reference database to be used for each of V, D, and J gene regions. Typically, a nucleic acid sequence data set for each allele or each region published by the IMGT is used, but is not limited thereto. Any data set with a unique ID assigned to each sequence can be used.

The obtained read data (including those subjected to appropriate processing such as trimming as needed) is used as the input sequence set to search for homology with a reference database for each gene region, and an alignment with the closest reference allele and the sequence thereof are recorded. In this regard, an algorithm with high tolerance for a mismatch except for C is used for homology search. When a common homology search program BLAST is used, shortening of the window size, reduction in mismatch penalty, and reduction in gap penalty are set for each region. The closest reference allele is selected by using a homology score, alignment length, kernel length (length of consecutively matching base sequence) and number of matching bases as indicators, which are applied in accordance with a defined order or priority. For an input sequence with determined V and J used in the present disclosure, a CDR3 sequence is extracted with the front of CDR3 on reference V and end of CDR3 on reference J as guides. This is translated into an amino acid sequence for use in classification of a D region. When a reference database of a D region is prepared, a combination of results of homology search and results of amino acid sequence translation is used as a classification result.

In view of the above, each allele of V, D and J is assigned for each sequence in an input set. The frequency of appearance by each of V, D and J or frequency of appearance of a combination thereof is subsequently calculated in the entire input set to derive a TCR repertoire. The frequency of appearance is calculated in a unit of allele or unit of gene name depending on the precision required in classification. The latter is made possible by translating each allele into a gene name.

After V region, J region, and C region are assigned to read data, matching reads can be added to calculate the number of reads detected in a sample and the ratio to the total number of reads (frequency) for each unique read (read without the same sequence). A diversity index or similarly index can be calculated with a statistical analysis software such as ESTIMATES or R (vegan) by using data such as number of samples, read type, or the number of reads. In a preferred embodiment, TCR repertoire analysis software (Repertoire Genesis Inc.) is used.

A preferred embodiment of the present disclosure measures TCR diversity using large-scale high efficiency TCR repertoire analysis. As used herein, "large-scale high efficiency repertoire analysis" is described in WO 2015/075939 (the entire disclosure thereof is incorporated herein by reference as needed) and is referred to as "large-scale high efficiency TCR repertoire analysis" when targeting TCR. This method comprises: (1) providing a nucleic acid sample comprising a nucleic acid sequence of a T cell receptor (TCR) which is amplified in an unbiased manner; (2) determining the nucleic acid sequence comprised in the nucleic acid sample; and (3) calculating a frequency of appearance of each gene or a combination thereof based on the determined nucleic acid sequence to derive a TCR repertoire of the effector T cell population.

In another embodiment, (1) providing a nucleic acid sample comprising a nucleic acid sequence of a TCR which is amplified in an unbiased manner can comprise:

(1-1) synthesizing a complementary DNA by using an RNA sample derived from a target cell as a template;

(1-2) synthesizing a double stranded complementary DNA by using the complementary DNA as a template;

(1-3) synthesizing an adaptor-added double stranded complementary DNA by adding a common adaptor primer sequence to the double stranded complementary DNA;

(1-4) performing a first PCR amplification reaction by using the adaptor-added double stranded complementary DNA, a common adaptor primer consisting of the common adaptor primer sequence, and a first TCR C region specific primer, wherein the first TCR C region specific primer is designed to comprise a sequence that is sufficiently specific to a C region of interest of the TCR and not homologous with other genetic sequences, and comprise a mismatching base between subtypes downstream when amplified;

(1-5) performing a second PCR amplification reaction by using a PCR amplicon of (1-4), the common adaptor primer, and a second TCR C region specific primer, wherein the second TCR C region specific primer is designed to have a sequence that is a complete match with the TCR C region in a sequence downstream the sequence of the first TCR C region specific primer, but comprise a sequence that is not homologous with other genetic sequences, and comprise a mismatching base between subtypes downstream when amplified; and (1-6) performing a third PCR amplification reaction by using a PCR amplicon of (1-5), an added common adaptor primer in which a nucleic acid sequence of the common adaptor primer comprises a first additional adaptor nucleic acid sequence, and an adaptor-added third TCR C region specific primer in which a second additional adaptor nucleic acid sequence is added to a third TCR C region specific sequence;

wherein the third TCR C region specific primer is designed to have a sequence that is a complete match with the TCR C region in a sequence downstream to the sequence of the second TCR C region specific primer, but comprise a sequence that is not homologous with other genetic sequences, and comprise a mismatching base between subtypes downstream when amplified. The specific detail of this method is described in WO 2015/075939. Those skilled in the art can perform analysis by appropriately referring to this document and the Examples of the present specification and the like.

(2.5. TCR Pair Identification)

In one embodiment of the present disclosure, a pair of a TCRα chain and a TCRβ chain is identified as a TCR clone that is in a T cell population. A TCR is understood to exert antigen specificity as a pair of α chain and β chain. The use of the identified pair can further ensure that antigen specificity is imparted to a T cell due to introduction of a pair of TCRs. Therefore, the step of identifying a TCR clone can comprise amplifying a gene of TCRα and a gene of TCRβ derived from the same cell and identifying a pair of TCRα and TCRβ in a T cell population. In another embodiment, the method can further comprise checking whether the identified pair of TCRα and TCRβ has affinity to an antigen. In still another embodiment, the method can further comprise cloning a full or partial nucleic acid sequence of TCRα and a full or partial nucleic acid sequence of TCRβ in the identified pair of TCRα and TCRβ.

For example, the technology described in Nature Medicine 19, 1542 to 1546 (2013) can be used as a technology for such pair identification. A human TCR cDNA is amplified from a single cell, cloned in an expression vector, and transduced into a TCR negative T cell (e.g., TG40 cell strain). TCR antigen specificity is evaluated by staining the T cell with an MHC tetramer or monitoring CD69 expression. Such a process can be performed in its entirety in 10 days or less.

Pair identification from a single cell is theoretically possible with a technology of simultaneously amplifying an α chain and a β chain by multiplex PCR such as those described in, for example, J Clin Invest. 2011 January; 121 (1): 288-95. doi: 10.1172/JCI44752. Epub 2010 Dec. 6. (PMID: 21135507), PloS one [23 May 2012, 7(5): e37338] (PMID: 22649519), and the like.

Some TCR pairing technologies have already been commercialized, which are described in the introduction of Trends Biotechnol. 2017 March; 35(3): 203-214. doi: 10.1016/j.tibtech.2016.09.010. Epub 2016 Oct. 26. (PMID: 28341036), and the like. Table 2 in said document describes a general single cell sequencing technology. For example, a technology using continuous-flow microfluidics (Fluidigm, Kolodziejczyk, A. A. et al. (2015) The technology and biology of single-cell RNA sequencing. Mol. Cell 58, 610-620), plate-based technology (Cellular Research/BD Biosciences, 65. Fan, H. C. et al. (2015) Expression profiling. Combinatorial labeling of single cells for gene expression cytometry. Science 347, 1258367), technology using droplet based microfluidics (10× Genomics, 76. Murphy, K. M. et al. (2016) Janeway's Immunobiology. (9th), Garland Science), and the like are described. In addition, a TCR high throughput pairing technology that does not require isolation of a single cell can also be used, such as the technology described in Sci Transl Med. 2015 Aug. 19; 7(301): 301ra131. doi: 10.1126/scitranslmed.aac5624. (PMID: 26290413). Those skilled in the art can identify a pair of TCRs using such an approach.

Examples of representative technologies for identifying a pair of TCRs include analysis of TCRs derived from a single cell, such as analysis after sorting with a flow cytometer, and single cell RNA-seq using a droplet generator. A single cell analysis kit using the SMART method is sold as a SMARTer® Human scTCR a/b Profiling Kit. An RNA with an unknown sequence on the 5' end side or an RNA without a common sequence can be amplified by a reverse transcription (RT) reaction, template switching (TS) reaction, and PCR reaction. An improved method of such methods can also be used.

If an antigen peptide of interest is known or expected in the analysis after sorting with a flow cytometer, it is possible to sort, by FACS, T cells with a TCR that reacts to the antigen peptide using a tetramer, determine an α chain and a β chain, and identify a pair of TCRs that react to the antigen peptide in a single cell analysis of about 100 to 300 cells. Even if the antigen peptide is unknown, the method can determine a primary pair when a combination can be considered from information for an α chain with high prevalence and β chain with high prevalence confirmed from analysis data for only α chain and only β chain.

Single cell RNA-seq used in a droplet creation apparatus can analyze up to 10000 single cells and analyze up to 10000 or more single cells at once without a two-stage analysis performed in a method using a flow cytometer when the antigen peptide described above is unknown.

Different approaches described above can be used for different purposes. While the objective of the step can be achieved by pair identification with a droplet based method capable of analyzing many cells, the objective of the step can also be achieved by analyzing about 100 to 300 single cells by creating a tetramer when an antigen peptide is known or expected. If the objective is to find a highly functional TCR, analysis of at most several hundred single cells is very cost-effective. If the objective is to comprehensively analyze low frequency TCRs (TCRs of naïve fraction, shared TCRs, or the like), it is understood that analysis using droplets is costly but advantageous.

Recently, single cell RNA-Seq methods have been developed and used in various studies (Hashimshony T et al: Cell Rep, 2(3): 666-673, 2012, Hashimshony T et al: Genome Biol, 17: 77, 2016). Various separation apparatuses such as FACS sorting, microwells, and microfluidic circuits are used for single cell analysis. A method using a droplet separation apparatus can create a single cell library in a highly efficient and simple manner.

TCRs can be analyzed at a single cell level by single cell RNA-Seq using a droplet creation apparatus. A droplet method can create a single cell library of 10000 cells in about 30 minutes by rapidly encapsulating a cell and a carrier of a solid phase oligoprobe in an approximately 100 μm water-in-oil droplet. In 2016's Cell journal, Mocosko et al. reported a Drop-Seq method using oligobeads (Macosko E Z et al: Cell, 161(5): 1202-1214, 2015), and Klein et al. reported an InDrop method using a hydrogel (Klein A M et al: Cell, 161(5): 1187-1201, 2015). Both methods attach a poly(T) probe to which a cell barcode (CBC) and a unique molecular index (UMI) are added to a carrier, and encapsulate a cell and an oligo-carrier in a droplet using a microchip. Subsequently, cDNA synthesis, PCR, and sequencing are performed to materialize scRNA-Seq.

Furthermore, Gene Capture Drop-Seq™ for highly efficiently determining a TCR pair gene has been developed by improving the Drop-Seq method. Gene Capture Drop-Seq™ is a technology for highly efficiently determining a TCR pair gene by attaching barcode labeled-α and β chain TCR oligomers to microbeads and selectively capturing TCR mRNA within a droplet. A method of determining a pair gene by simultaneously sequencing a cell barcode sequence and a CDR3 sequence using a gene-specific probe can efficiently identify a large number of pair genes without a high-spec sequencer. This technology is a useful single cell analysis method that can also be applied in subset analysis focused on expression of a specific gene or determination of a heavy chain and light chain pair of an antigen gene. Those skilled in the art can identify a pair of TCRα chain and TCR chain as a TCR clone that is present in a T cell population by using a technology such as those described above.

(2.6. Highly Functional TCR)

Figure 2:
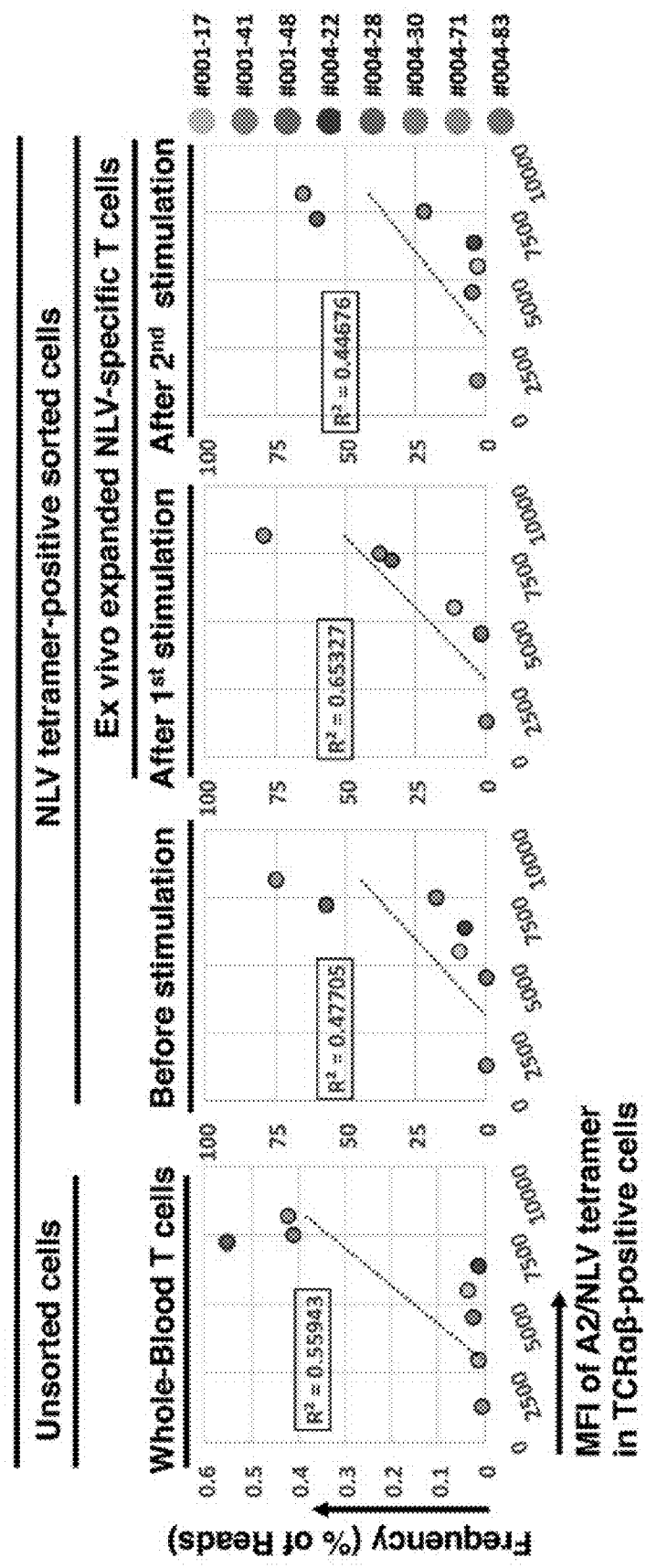
FIG. 2 is a scatter diagram showing the relationship between the frequency of each TCR pair in a TCR repertoire and affinity to an antigen. The vertical axis is the frequency in reads, and the horizontal axis indicates the binding affinity.

It was found that a TCR of a T cell clonotype shared frequently among different individuals is consistently detected in repertoires of all functional T cell subset (naïve, SCM, CM, EM, and EFF) and antigen specific T cell repertoires. It was found that a more dominant antigen specific TCR has higher epitope binding affinity and is derived from a clonotype that is more highly shared, as demonstrated in Example 1 herein (FIG. 2). Furthermore, such an antigen specific TCR is demonstrated to retain antigen affinity when introduced into other T cells in Example 1.

It is demonstrated that epitope binding affinity was higher for a dominant CMV NLV specific clonotype, and a dominant clonotype shares and comprises a TCR clonotype that is present at a relatively high frequency among different individuals (see, for example, Scientific Reports 7, Article number: 3663 (2017); the entire document is incorporated herein by reference for any purpose). It is shown that a more dominant CMV pp65 specific clonotype has a higher epitope binding affinity, and is derived from a clonotype that is more highly shared. This observation suggests that functional TCR clonotypes which are present in a given individual are relative small in numbers, but these clonotypes are shared at a high frequency among different individuals.

One embodiment of the present disclosure provides steps comprising introducing a TCR clone (full or partial nucleic acid sequence) that is present in a T cell population into a T cell. As described above, a clone that is predominantly present in an antigen specific T cell population of an individual has high antigen affinity. Use of such a clone is advantageous in imparting antigen specificity to a cell to be modified. However, a clone that is present in an antigen specific T cell population is comprised of a relatively small number of clonotypes. Any clone included therein can be utilized in impartation of antigen specificity even if the clone cannot be considered dominant. Preferably, a T cell population is an antigen specific effector T cell population.

A clone to be introduced can be a clone that is present at a greater frequency than the mean frequency of presence of each clone in an antigen specific T cell population. For example, a clone to be introduced can be present at a frequency that is 1 standard deviation or more, 2 standard deviation or more, or 3 standard deviation or more greater than the mean frequency of presence of each clone in an antigen specific T cell population.

A TCR clone to be introduced can be present at a frequency of about 1, about 2, about 5, about 8, about 10%, about 12%, or about 15% or greater in a T cell population.

(2.7. Removal of Endogenous TCR Gene)

It can be preferable to remove an endogenous TCR upon introduction of a TCR. It is reported in Proc Natl Acad Sci USA. 2010 Jun. 15; 107(24): 10972-7 (PMID: 20534461) that a mixed dimer can be formed by introducing a TCR in the presence of an endogenous TCR, resulting in the manifestation of new antigen reactivity.

When a TCR mixed dimer (pair of an endogenous TCR chain and exogenous TCR chain) is formed, it is not only possible that the expression of the introduced TCR chain and endogenous TCR chain decreases to impair specific reactivity, but also the mixed dimer has a potentially detrimental specificity. While the aforementioned reference reports that new reactivity was manifested by introduction of a TCR and most new reactivity was allo-HLA reactive, some with autoreactive activity was found. Mol Biol Rep. 2010 December; 37(8): 3951-6 (PMID: 20373027) describes the FRET method as a technology for quantitatively detecting a TCR generated by mispairing.

An endogenous TCR can be removed by modifying an endogenous TCR gene. An endogenous TCR can be removed, for example, by knocking down an endogenous TCR gene. Antisense method, RNAi, or the like can be utilized. An endogenous TCR can also be removed by knocking out an endogenous TCR gene. An endogenous TCR can be modified, for example, by deletion of all or part of the coding region, introduction of a mutation into a regulatory region, introduction of a nonsense or missense mutation, or the like.

Preferably, an endogenous TCR gene can be modified using a genome editing technology. Genome editing is a technology for modifying a target gene by utilizing a site specific nuclease. Examples of genome editing technology include ZFN, TALEN, CRISPR/Cas9, and the like, each having a binding domain for materializing DNA sequence specific linkage to a desired sequence and a cleavage domain for cleaving a DNA at a desired site of the sequence.

ZFN is an artificial restriction enzyme comprising a zinc finger domain and a DNA cleavage domain. A zinc finger domain can be modified to recognize any DNA base sequence, which enables a zinc finger nuclease to target a single sequence in a complex genome.

The CRISPR (Clustered Regularly Interspaced Short Palindromic Repeats)/Cas9 (Crispr ASsociated protein 9) system comprises two separate molecules, i.e., guide RNA and Cas9, whereas ZFN and TALEN are basically used as a single protein. A guide RNA can be specifically bound to a target site by including a complementary sequence of a DNA target site in the guide RNA. In view of the above, a Cas9 protein is bound so as to cover the guide RNA and DNA to cleave the DNA. Cas9 itself can be reused, so that it is sufficient to produce only guide RNA depending on the target site. Thus, multiplexing is considered simple.

TALEN (Transcription Activator-Like Effector Nuclease) is an artificial enzyme prepared by fusing a restriction enzyme FokI as a DNA cleavage domain to a DNA binding domain of a TALE protein secreted from a plant pathogenic bacteria *Xanthomonas*. A DNA binding domain of a TALE protein has a repeat structure of about 34 amino acids. Such a repeat unit is referred to as a module. The 12th and 13th amino acids therein are variable. The amino acids are portions that bind to a target sequence and are referred to as a "repeat variable diresidue" (RVD). TALEN uses molecules that bind to each of the opposite strands of a target DNA as a pair of L TALEN and R TALEN. For FokI to exhibit cleavage activity, TALEN needs to form a dimer while maintaining a suitable distance. Mismatch tolerance and off-target activity in TALEN are hardly reported. Thus, TALEN is characterized by high specificity. Since an unexpected adverse effect can be triggered if off-target modification is generated upon modification of T cells, use of TALEN with high specificity is preferable in the present disclosure.

In addition to conventional TALEN, various modified TALEN have been produced. Modification of an endogenous TCR gene with such a TALEN is preferable in view of high specificity and high modification efficiency. Examples herein demonstrate that complete elimination of endogenous TCRs of a T cell was made possible by using a modified TALEN.

Figure 17:
FIG. 17 is a diagram showing several examples of modified TALENs. The example of a DNA binding module of Voytas TALEN and the first sequence from the top in the example of a DNA binding module of Platinum TALEN correspond to SEQ ID NO: 1, and the rest corresponds to, from the top, SEQ ID NOs: 99 to 102 in order.
Figure 17:
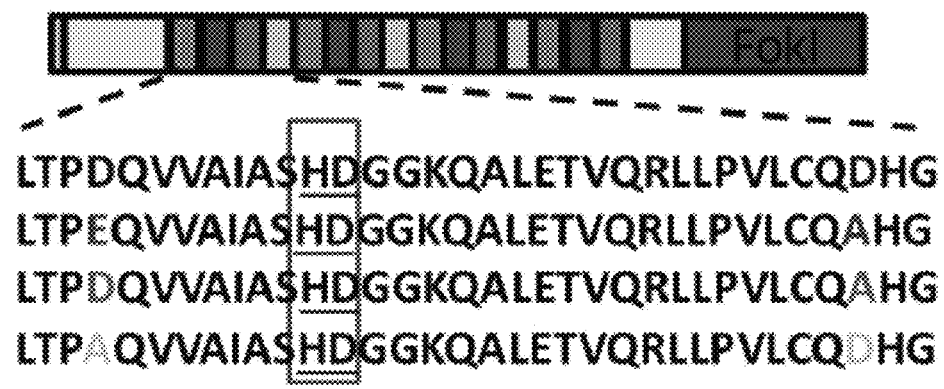
Figure 17:
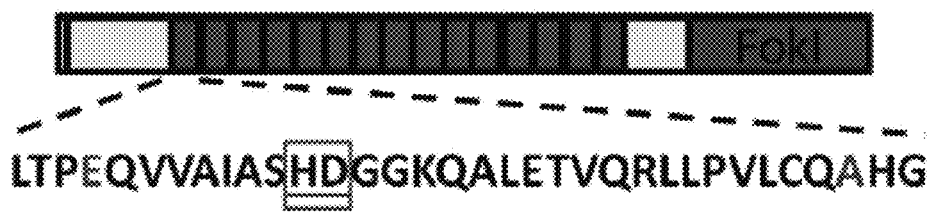
Figure 17:

Some examples of modified TALENs are shown in FIG. 17. For example, the 4th and 32nd amino acids of a module are modified in a SuperTALEN, and only specific modified repeats are assembled and used (PCT/JP2014/071116, entirety thereof is incorporated herein by reference). This SuperTALEN with two amino acids modified therein that are modified to E and A is a Zhang TALEN (type EA SuperTALEN). It is reported that activity increases for type EA shown in FIG. 17 as well as type QA.

The activity of Platinum TALEN is increased more than Voytas TALEN by a periodic arrangement with variation in the 4th and 32nd amino acids among the 34 amino acids contained in a DNA binding repeat of TALEN (Sakuma et al., Sci Rep, 2013). The method of the present disclosure preferably edits an endogenous TCR gene using Platinum TALEN. Platinum TALEN is described in Japanese Laid-Open Publication No. 2016-175922, whose entire content is incorporated herein by reference. More specifically, an endogenous TCR gene can be modified using the genome editing technology described below.

One embodiment of the present disclosure uses a polypeptide or a nucleic acid encoding the same that can have both high functionality by a functional domain and a high recognition specificity to a DNA sequence and is capable of safely exerting a desired function at a high probability, as well as can be manufactured by a simple operation, to modify an endogenous TCR gene.

A polypeptide, wherein a DNA binding domain and a functional domain are connected by a polypeptide consisting of 35 to 55 amino acids, and amino acids at two specific positions in a DNA binding module contained in the DNA binding domain exhibit different repeat forms for each of the four DNA binding modules, can have both high functionality by a functional domain and a high recognition specificity to a DNA sequence. A vector for expressing said polypeptide can be readily manufactured by using a vector set with a specific feature and a vector library with a specific feature.

In one embodiment of the present disclosure, the present disclosure can utilize a polypeptide comprising a DNA binding domain and a functional domain. The polypeptide wherein the DNA binding domain and the functional domain are connected by a polypeptide consisting of 35 to 55 amino acids, the DNA binding domain comprises a plurality of DNA binding modules consecutively from the N-terminal side, a combination of the xth amino acid and the yth amino acid in the 4n-3th DNA binding module from the N-terminus being identical for any n, a combination of the xth amino acid and the yth amino acid in the 4n-2th DNA binding module from the N-terminus being identical for any n, a combination of the xth amino acid and the yth amino acid in the 4n-1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n-3th DNA binding module from the N-terminus, the combination of the xth amino acid and the yth amino acid in the 4n-2th DNA binding module from the N-terminus, the combination of the xth amino acid and the yth amino acid in the 4n-1th DNA binding module from the N-terminus, and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers, or a nucleic acid encoding the same can be used. A functional domain can be a DNA cleavage domain. Polynucleotides encoding polypeptide are included thereby.

The present disclosure can also utilize a vector library for manufacturing a vector comprising a polynucleotide encoding the polypeptide described above, wherein the vector library is comprised of a plurality of vectors having, in order from the 5' end, a first restriction enzyme cleavage site, a polypeptide encoding four DNA binding modules, and a second restriction enzyme cleavage site, wherein the combination of the first restriction enzyme cleavage site and the second restriction enzyme cleavage site is a combination of a type A restriction enzyme cleavage site and a type B restriction enzyme cleavage site, a combination of a type A restriction enzyme cleavage site and a type C restriction enzyme cleavage site, a combination of a type A restriction enzyme cleavage site and a type D restriction enzyme cleavage site, a combination of a type A restriction enzyme cleavage site and a type E restriction enzyme cleavage site, a combination of a type B restriction enzyme cleavage site and a type C restriction enzyme cleavage site, a combination of a type C restriction enzyme cleavage site and a type D restriction enzyme cleavage site, or a combination of a type D restriction enzyme cleavage site and a type E restriction enzyme cleavage site, wherein the type A restriction enzyme cleavage site to type B restriction enzyme cleavage site each result in different cleavage ends from one another by cleavage with the same restriction enzyme, and in the four DNA binding modules, a combination of the xth amino acid and the yth amino acid in the 1st DNA binding module from the 5' end being identical for any vector, a combination of the xth amino acid and the yth amino acid in the 2nd DNA binding module from the 5' end being identical for any vector, a combination of the xth amino acid and the yth amino acid in the 3rd DNA binding module from the 5' end being identical for any vector, and a combination of the xth amino acid and the yth amino acid in the 4th DNA binding module from the 5' end being identical for any vector, the combination of the xth amino acid and the yth amino acid in the 1st DNA binding module from the 5' end, the combination of the xth amino acid and the yth amino acid in the 2nd DNA binding module from the 5' end, the combination of the xth amino acid and the yth amino acid in the 3rd DNA binding module from the 5' end, and the combination of the xth amino acid and the yth amino acid in the 4th DNA binding module from the 5' end are different from one another, and x is a natural number from 1 to 40, y is a natural number from 1 to 40, and x and y are different natural numbers.

The present invention can also utilize a vector set for manufacturing the vector library described above. In this regard, the vector set comprises a plurality of vectors comprising, in order from the 5' end, a first restriction enzyme cleavage site, a DNA binding module, and a second restriction enzyme cleavage site, the first restriction enzyme cleavage site and the second restriction enzyme cleavage site resulting in different cleavage ends from each other by cleaving with the same restriction enzyme, a combination of the xth amino acid and the yth amino acid in the DNA binding module being one of four different combinations, wherein x is a natural number from 1 to 40, y is a natural number from 1 to 40, and x and y are different natural numbers.

Since the polypeptide described above materializes high functionality by a functional domain and a high recognition specificity to a DNA sequence, an alteration of a desired TCR gene can be materialized safely and at a high probability by introducing a vector comprising a polynucleotide encoding the polypeptide described above into a cell. If the vector library described above is used, a vector for expressing a polypeptide having both high functionality by a functional domain and a high recognition specificity to a DNA sequence can be prepared readily and quickly.

Examples of origin of a DNA binding domain include the plant pathogen *Xanthomonas* TALE (Transcription Activator-Like Effector), Zinc finger, and the like.

Examples of functional domains include domains encoding enzymes, transcription regulatory factors, reporter proteins, and the like. Examples of enzymes include DNA modifying enzymes such as a recombinase, nuclease, ligase, kinase, and phosphatase, and other enzymes such as lactamase. As used herein, a domain encoding a nuclease is referred to as a DNA cleavage domain. Examples of transcription regulatory factors include activators, repressors, and the like. Examples of reporter proteins include fluorescent proteins such as a green fluorescent protein (GFP), humanized *Renilla reniformis* green fluorescent protein (hrGFP), enhanced green fluorescent protein (eGFP), enhanced blue fluorescent protein (eBFP), enhanced cyan fluorescent protein (eCFP), enhanced yellow fluorescent protein (eYFP), red fluorescent protein (RFP or DsRed), and mCherry; bioluminescent proteins such as firefly luciferase and *Renilla* luciferase; enzymes converting a chemiluminescent substrate such as alkaline phosphatase, peroxidase, chloramphenicol acetyltransferase, and β-galactosidase, and the like. A DNA cleavage domain preferably approaches another DNA cleavage domain to form a mulitmer, and attains improved nuclease activity. Examples of such a DNA cleavage domain include those derived from FokI.

A DNA binding domain and a functional domain are connected by a polypeptide consisting of 35 to 55, preferably 40 to 50, more preferably 45 to 49, and most preferably 47 amino acids.

A DNA binding domain can comprise a plurality of DNA binding modules consecutively from the N-terminal side. One DNA binding module specifically recognizes one base pair. The number of DNA binding modules contained in a DNA binding domain, from the viewpoint of attaining both high functionality of a functional domain and a high recognition specificity to a DNA sequence, is preferably 8 to 40, more preferably 12 to 25, and still more preferably 15 to 20. Examples of DNA binding modules include TAL effector repeat and the like. Examples of the length of a single DNA binding module include 20 to 45, 30 to 38, 32 to 36, 34, and the like. The length of a DNA binding module contained in a DNA binding domain is preferably the same for all DNA binding modules. Examples of a DNA binding module include the sequence of LTPDQVVA-IASHDGGKQALETVQRLLPVLCQDHG (SEQ ID NO: 1). For example, it is understood that if the 12th amino acid and the 13th amino acid of this sequence are H and D in this order, the DNA binding domain recognizes C as a base, and if the amino acids are N and G in this order, the DNA binding domain recognizes T as a base, and if the amino acids are N and I in this order, the DNA binding domain recognizes A as a base, and if the amino acids are N and N in this order, the DNA binding domain recognizes G as a base. Examples of DNA binding modules include a polypeptide with 85%, 90%, 95%, or 97% identity with the amino acid sequence of SEQ ID NO: 1 and substantially retains the function to recognize a base pair.

A combination of the xth amino acid and the yth amino acid in the 4n-3th DNA binding module from the N-terminus can be identical for any n. Further, a combination of the xth amino acid and the yth amino acid in the 4n-2th DNA binding module from the N-terminus can be identical for any n. Further, a combination of the xth amino acid and the yth amino acid in the 4n-1th DNA binding module from the N-terminus can be identical for any n. Further, a combination of the xth amino acid and the yth amino acid in the 4nth DNA binding module from the N-terminus can be identical for any n. In this regard, n is a natural number from 1 to 10, preferably a natural number from 1 to 7, and more preferably a natural number from 1 to 5. n is preferably a natural number that is sufficient to indicate all DNA binding modules contained in a DNA binding domain. x is a natural number from 1 to 40, preferably a natural number from 1 to 10, more preferably a natural number from 2 to 6, still more preferably a natural number from 3 to 5, and most preferably the natural number 4. y is a natural number from 1 to 40, preferably a natural number from 25 to 40, more preferably a natural number from 30 to 36, still more preferably a natural number from 31 to 33, and most preferably the natural number 32. x and y are different natural numbers. The values of x and y can be different depending on the length of the DNA binding modules used. x is preferably a numerical value indicating a position corresponding to the 2nd amino acid in a DNA binding module consisting of 34 amino acids. y is preferably a numerical value indicating a position corresponding to the 32nd amino acid in a DNA binding module consisting of 34 amino acids.

A combination of the xth amino acid and the yth amino acid in the 4n-3th DNA binding module from the N-terminus, a combination of the xth amino acid and the yth amino acid in the 4n-2th DNA binding module from the N-terminus, a combination of the xth amino acid and the yth amino acid in the 4n-1th DNA binding module from the N-terminus, and a combination of the xth amino acid and the yth amino acid in the 4nth DNA binding module from the N-terminus can be different from one another, wherein n is a natural number from 1 to 10, preferably a natural number from 1 to 7, more preferably a natural number from 1 to 5. n is preferably a natural number that is sufficient to indicate all DNA binding modules contained in a DNA binding domain. x is a natural number from 1 to 40, preferably a natural number from 1 to 10, more preferably a natural number from 2 to 6, still more preferably a natural number from 3 to 5, and most preferably the natural number 4. y is a natural number from 1 to 40, preferably a natural number from 25 to 40, more preferably a natural number from 30 to 36, still more preferably a natural number from 31 to 33, and most preferably the natural number 32. x and y are different natural numbers. Preferably, a combination of the xth amino acid and the yth amino acid in the 4n-3th DNA binding module from the N-terminus, a combination of the xth amino acid and the yth amino acid in the 4n-2th DNA binding module from the N-terminus, and a combination of the xth amino acid and the yth amino acid in the 4nth DNA binding module from the N-terminus can each be selected from the group consisting of a combination of, in order of x and y, a combination of D and D, a combination of E and A, a combination of D and A, and a combination of A and D.

Examples of vectors that can be used include plasmid vectors, cosmid vectors, viral vectors, artificial chromosome vectors, and the like. Examples of artificial chromosome vectors include yeast artificial chromosome vectors (YAC), bacterial artificial chromosome vectors (BAC), P1 artificial chromosome vectors (PAC), mouse artificial chromosome vectors (MAC), human artificial chromosome vectors (HAC), and the like. Examples of vector components include nucleic acids such as DNA and RNA, nucleic acid analogs such as GNA, LNA, BNA, PNA, and TNA, and the like. Vectors may be modified with a component other than a nucleic acid such as saccharides.

The polypeptide described above can be prepared by introducing a vector into a cell or the like to cause expression of the vector. A desired function corresponding to the functional domain e.g., DNA modification such as DNA recombination or DNA cleavage, expression of other enzymatic activity such as transcription regulation, or labeling of a DNA region with a reporter protein can be exerted in a cell by introducing a vector into a cell or the like to cause expression of the vector. if a functional domain is a DNA cleavage domain, a plurality of, preferably two vectors can be introduced into and expressed in a cell or the like to generate a base sequence specific double strand cleavage on a genomic DNA of the cell introduced with the vectors, and introduce a mutation in the genome of the cell. Examples of the origin of a cell introduced with a vector include animals such as fruit flies, zebra fish, and mammals such as mice, plants such as *Arabidopsis thaliana*, cultured cells such as ES cells and iPS cells, and the like.

(2.8. Introduction of Exogenous TCR)

One embodiment of the present disclosure provides a method comprising introducing a TCR into a T cell. A T cell is preferably a regulatory T cell. The introducing step can be a step of introducing a full or partial nucleic acid sequence of a gene of TCRα and a full or partial nucleic acid sequence of a gene of TCRβ. Preferably, a highly functional TCR described herein is introduced into a T cell. A highly functional TCR can be identified as a pair of TCRs. Preferably, a TCR is introduced so that such a TCRα chain and a TCRβ chain are expressed as a pair.

Introduction of TCRs so that they are expressed as a pair is described in Cancer Immunol Immunother. 2016 June; 65(6): 631-49 (PMID: 27138532) and the like. There are technologies for introducing TCRs so that they are expressed as a pair other than a method of forming a disulfide bond by Cys formation (introduction of a Cys residue) such as codon optimization/introduction of a leucine zipper into an intracellular region/sugar chain modification of TCR.

Examples of existing technologies for avoiding mispairing applied to TCR introducing vectors include:
1) introduction of Cys (Blood. 109: 2331, 2007);
2) Leucin zipper (Proc Natl Acad Sci. 91: 11408, 1994);
3) equal expression of α/β chains using a 2A sequence (optionally codon optimization) (J Mol Med 88: 1113, 2010);
4) removal of specific N-glycosylation site (J Exp Med. 206: 463, 2009);
5) use of intracellular domain of mice or the like (Cancer Res. 66: 8878, 2006; J Immunol. 184: 6223, 2010);
6) use of a single chain TCR (α-β-Constant) (Blood. 115: 5154, 2010);
and the like.

A TCR can bP introduced using a vector that enables such expression. For example, a vector can be configured to comprise a nucleic acid sequence encoding Cys so that a disulfide bond is formed between TCRα and TCR to be expressed, to codon optimize the coding sequence of TCRα and TCRβ, to introduce a leucine zipper into an intracellular region of TCRα and TCR, or to express TCRα and TCRβ with modification of a sugar chain.

In the present disclosure, full nucleic acids of a TCR clone that has been identified can be introduced, or only a part of the nucleic acids can be introduced as long as the binding affinity is maintained. In one embodiment, a part of a nucleic acid sequence of a gene of TCRα comprising a sequence corresponding to a CDR3 region of Vα-Jα can be introduced. A part of a nucleic acid sequence of a gene of TCR comprising a sequence corresponding to a CDR3 region of Vβ-D-Jβ can be introduced. A part of a nucleic acid sequence of a gene of TCRα comprising a cDNA sequence of Vα-Jα-Cα can be introduced. A part of a nucleic acid sequence of a gene of TCRβ comprising a cDNA sequence of Vβ-D-Jβ-Cβ can be introduced.

In one embodiment of the present disclosure, removal of an endogenous TCR gene and introduction of a TCR can be performed in two steps for complete substitution of an endogenous TCR. For example, a method is provided, comprising: removing one of genes of endogenous TCRα and endogenous TCRβ in a T cell, introducing a full or partial nucleic acid sequence of a gene of TCRα and a full or partial nucleic acid sequence of a gene of TCRβ into a T cell; and removing the other one of the genes of endogenous TCRα and endogenous TCRβ in the T cell, and reintroducing a full or partial nucleic acid sequence of a gene of TCRα and a full or partial nucleic acid sequence of a gene of TCRβ in the T cell.

An exogenous TCR can be knocked in and introduced into a genome without using a viral vector for complete substitution of an endogenous TCR. A knock-in technology using homologous recombination (HR) is known. A method mediated by microhomology-mediated end joining (MMEJ) can also be used instead of homologous recombination (HR). MMEJ is one of the DNA repairing mechanisms of eukaryotes. This is a mechanism of repairing by binding complementary sequences (5 to 25 base pairs) to each other between both cleaved ends generated upon double strand cleavage. When inserting an exogenous gene by utilizing the MMEJ repair mechanism, a recognition sequence of artificial nuclease is added to a donor vector, so that the sequence complementarily binds with a target site of a chromosome and a cleaved end of a vector upon double strand cleavage. A gene can be knocked into a target site by introducing the donor vector with an artificial nuclease (TALEN, CRISPR/Cas, and the like) (referred to as TAL-PITCh method and CRIS-PITCh method, respectively) (Nature Communications volume 5, Article number: 5560 (2014)). When an exogenous TCR is introduced using a viral vector, there is a theoretical risk of carcinogenicity while the probability may not be a practical issue. Thus, it can be advantageous to avoid using a viral vector in terms of avoiding such a risk.

3. Application

The regulatory T cell of the present disclosure can be used in treatment, therapy or prevention of autoimmune disease, allergic disease, or graft-versus-host disease (GVHD), rejection, or graft failure in transplantation because it is understood that antigen specific regulatory T cells are effective in suppressing immune responses to the antigen.

Examples of autoimmune diseases include, but are not limited to, rheumatoid arthritis (RA), Sjogren's syndrome, systemic lupus erythematosus (SLE), antiphospholipid syndrome, polymyositis/dermatomyositis, systemic sclerosis, mixed connective tissue disease, vasculitis syndrome, type I diabetes, Graves' disease, Hashimoto Disease, idiopathic Addison's disease, autoimmune hepatitis, Goodpasture syndrome, glomerulonephritis, autoimmune hemolytic anemia (AIHA), autoimmune thrombocytopenic purpura, autoimmune neutropenia, myasthenia gravis, pemphigus, vitiligo, idiopathic azoospermia, and the like. Examples of allergic diseases include, but are not limited to, hay fever, allergic rhinitis, bronchial asthma, atopic dermatitis, and the like. In addition, the antigen specific regulatory T cell of the present disclosure can be used for the treatment or prevention of diseases in which abnormal immune response to a specific antigen is involved in the onset or progression of the pathological condition.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. While the present invention is described hereinafter based on the Examples, the above descriptions and the following Examples are provided for the sole purpose of exemplification, not limitation of the present invention. Thus, the scope of the present invention is not limited to the embodiments and Examples that are specifically described herein and is limited only by the scope of claims.

EXAMPLES

The Examples are described hereinafter. The subjects used in the following Examples were handled, when needed, in compliance with the ethical guidelines for human genomic gene/analysis studies specified by the national government, ethical guidelines for medical studies involving humans, and the standards stipulated by the Hiroshima University. Even where it is not explicitly stated, animal experiments were conducted, when applicable, in accordance with the spirit of animal protection and relevant laws and regulations.

Example 1: Identification/Cloning of High Affinity Clone (Summary)

The objective of this Example is to demonstrate that an immunologically dominant clone is a high affinity clone, and demonstrate a method of identifying/cloning such a clone.

The distribution of the frequency of presence of TCR clones in an antigen specific T cell population after stimulating a T cell population with an antigen was measured, and each TCR clone was cloned. It was found from measuring the binding capability of each TCR clone to an antigen that a dominant clone in a T cell population had high antigen binding capability. Information related to this Example is also described in Scientific Reports 7, Article number: 3663 (2017). The entire document is incorporated herein by reference for any purpose.

(Materials and Methods)

[Donor Sample]

This Example was conducted in accordance with the principles of the Declaration of Helsinki. All experiments using human samples were conducted in accordance with the protocol approved by the ethics committee of the Hiroshima University. Peripheral blood mononuclear cells (PBMC) were obtained from five healthy donors who provided written consent. All donors were screened for the CMV serum conditions and subjected to genotyping for HLA-A, -B, -C, -DRB1, -DQB1, and -DPB1 alleles using a high resolution Luminex technology. The PBMCs were isolated using a standard Ficoll gradient separation protocol and then stored in liquid nitrogen.

[Flow Cytometry Analysis and Cell Sorting]

The expression of cell surface molecules was determined using the following fluorescently labeled monoclonal antibodies (mAb): allophycocyanin (APC) conjugated or fluorescein isothiocyanate (FITC) conjugated anti-CD8, allophycocyanin-hilite7 (APC-H7) conjugated anti-CD3, phycoerythrin-cyanine7 (PE-Cy7) conjugated anti-CD45RO mAb, brilliant violet 510 (BV510) conjugated anti-CD62L mAb, brilliant violet 421 (BV421) conjugated anti-CD197 mAb, APC conjugated anti-CD95, and APC conjugated anti-TCRar3. These antibodies were purchased from BD Bioscience (San Jose, Calif.). CMV pp65 specific T cells were reacted with phycoerythrin (PE) conjugated HLA-A*02-peptide tetramer as described in Kuzushima, K. et al. Tetramer-assisted identification and characterization of epitopes recognized by HLA A*2402-restricted Epstein-Barr virus-specific CD8+ T cells. Blood 101, 1460-1462 (2003). The CD8 binding site on MHC-I of the tetramer was intact. The inventors selected the NLVPMVATV (SEQ ID NO: 2) sequence of HLA-A*02 restricted CMV pp65 peptide (NLV peptide) as a model antigen. The MHC tetramer staining was performed for 15 minutes at room temperature, and then cell surface was stained for 30 minutes at 4° C. The concentration of tetramers used in all the experiments was 10 μg/ml, except for serial dilution experiments. Nonspecific tetrameter straining was checked using a negative control tetramer (HLA-A2-HIV (KLTPLCVTL (SEQ ID NO: 3)) tetramer-PE).

Flow cytometry analysis and cell sorting were performed using FACSCanto II (BD Biosciences, San Jose, Calif.) and FACSAria (BD Biosciences, San Jose, Calif.). All flow cytometry data was analyzed using the FlowJo software (Tree Star, Ashland, Oreg.). Dead cells and damaged cells were removed using 7-AAD, and doublet cells were removed using FSC-A/FSC-H and SSC-A/SSC-H. CD3+ CD8+ T cells were further fractionated into the following functional subsets: naïve, CD45RO-CD62L+CCR7+CD95-; SCM, CD45RO-CD62L+CCR7+CD95+; CM, CD45RO+ CD62L+CCR7+; EM, CD45RO+CD62L-CCR7-; and EFF, CD45RO-CD62L-CCR7-.

[Cell Culture]

PBMCs and sorted CD8+ T cells were cultured in X-VIVO (Lonza, Walkersville, N. Dak.) containing 10% AB serum, 2 mmol/l L-glutamine, and 1% penicillin/streptomycin. B-lymphoblastoid cell line (B-LCL) was cultured in RPMI 1640 (Sigma-Aldrich, St Louis, Mo.) containing 10% FBS, 2 mmol/l L-glutamine, and 1% penicillin/streptomycin. All cells were cultured in a humidifying incubator at 37° C. under a 5% $CO_2$ containing atmosphere.

Phytohemagglutinin (PHA) blasts were generated by culturing PBMCs in a CTL medium containing 5 µg/ml PHA-L (Sigma-Aldrich, St Louis, Mo.). On the next day, IL-2 (Peprotech, Rocky Hill, N.J.) was added to the final concentration of 50 U/ml. Half of the medium was then replaced twice with a fresh medium containing IL-2 (50 U/ml) and IL-7 (Peprotech, Rocky Hill, N.J.) (20 ng/ml) each week. PHA blasts were used after 14 days from starting the culture.

Jurkat cells engineered to lack TCR expression by CRISPR-Cas9 were established as follows. Briefly, after CRISPR-Cas9 mediated knockout of the endogenous TCRα chain, CD3 negative cells were enriched by flow sorting. The sorted cells were transduced with an episome vector comprising a TCRα chain, and then CD3 positive cells (Jurkat cells with a transduced α chain and an endogenous ẞ chain) were enriched by flow sorting. The endogenous TCRẞ of the sorted cells was knocked out with CRISPR-Cas9, and then CD3 negative cells (Jurkat cells without endogenous TCRα and TCRβ) were enriched. Single cell cloning of Jurkat cells was performed using a single cell sorting method by flow cytometry. Finally, a TCRβ chain was transduced into the cloned Jurkat cells, and Jurkat clones that were endogenous TCRα negative, endogenous TCRβ negative, and transduced TCRα negative were then selected. TCRα negative of a clone was confirmed by transducing TCRβ into the clone. TCRβ negative of a clone was confirmed by transducing TCRα into the clone. The clone was also transduced with a pMX-CD8α expression vector, and brightly stained with an anti-CD8 mAb.

[In Vitro Stimulation of CMV Pp65 Specific T Cell]

CD8+ T cells were isolated from PBMCs using CD8 microbeads. CD4+ T cells were removed from the rest of the cells using a CD4+ T-cell isolation kit (Miltenyi Biotec, Auburn, Calif.). The remaining CD4/CD8 double negative cells were used as antigen presenting cells (APC). After irradiation of radiation (35 Gy), the APCs were exposed to an NLV peptide for 2 hours at room temperature, and co-cultured with the same number of CD8+ T cells in a CTL medium containing IL-2 and IL-7. Synthetic NLV peptides were purchased from GenScript (Piscataway, N.J.). Half of the medium was exchanged twice each week.

[Semi-Quantitative Analysis of TCR Repertoire Using High Throughput NGS]

Comprehensive TC repertoire analysis using NGS and unbiased gene amplification method using adaptor ligation PCR was performed as summarized hereinafter. Total RNA was extracted from PBMC ($5 \times 10^6$) or sorted T cells, and converted into cDNA using a BSL-18E primer comprising poly$(T)_{18}$ and NotI sites. A double stranded (ds) DNA was then synthesized, and the end was blunted using a T4 DNA polymerase (Invitrogen). A P10EA/P20EA adaptor was ligated to the 5' terminus of the dsDNA, and then cleaved by NotI. After removing the adapter and primer, PCR was performed using a TRA constant region specific primer or a TRB constant region specific primer and P20EA. Second PCR was performed using a constant region specific P20EA primer with the same PCR conditions. The product of the second PCR was used for high throughput sequencing using an Illumina Miseq platform. After removing sequences with a low quality score, TCR repertoire analysis was performed using a bioinformatics software created by Repertoire Genesis Incorporation (Ibaraki, Japan). More details of individual procedures are described in the following sections.

[Unbiased Amplification of TCR Gene]

Total RNA was extracted from PBMCs or sorted T cells using an RNeasy Lipid Tissue Mini Kit (Qiagen, Hilden, Germany) in accordance with the manufacturer's instruction. The amount of RNA and purity were measured using Agilent 2200 TapeStation (Agilent Technologies, Palo Alto, Calif.). 1 µg of total RNA was converted into cDNA using Superscript III reverse transcriptase (Invitrogen, Carlsbad, Calif.). A BSL-18E primer comprising poly$(T)_{18}$ and NotI sites was used for cDNA synthesis. After the cDNA synthesis, a double stranded (ds) cDNA was synthesized using *Escherichia coli* DNA polymerase I (Invitrogen), *E. coli* DNA Ligase (Invitrogen), and RNase H (Invitrogen). The ends of the dscDNA were blunted using T4 DNA polymerase (Invitrogen). A P10EA/P20EA adaptor was ligated to the 5' end of the dscDNA, and then cleaved by NotI. After removing the adaptor and primer with a MinElute Reaction Cleanup kit (Qiagen), PCR was performed using a primer of P20EA and one of a TCRα chain constant region specific primer (CA1) or TCR chain constant region specific primer (CB1). The PCR conditions were 20 cycles of 95° C. (30 seconds), 55° C. (30 seconds), and 72° C. (1 minute). Second PCR was performed using a primer of P20EA and one of CA2 and CB2 under the same PCR conditions.

The primers used are shown in the following Table.

TABLE 1

Primer for next generation sequencing of rearranged T cell receptor gene segment

| Primer | Sequence | MID Tag |
|---|---|---|
| BSL-18E | AAAGCGGCCGCATGCTTTTTTTTTTTTTTTTTTVN | |
| P20EA | TAATACGACTCCGAATTCCC | |
| P10EA | GGGAATTCGG | |
| CA1 | TGTTGAAGGCGTTTGCACATGCA | |
| CA2 | GTGCATAGACCTCATGTCTAGCA | |
| CB1 | GAACTGGACTTGACAGCGGAACT | |

TABLE 1-continued

Primer for next generation sequencing
of rearranged T cell receptor gene segment

| Primer | Sequence | MID Tag |
|---|---|---|
| CB2 | AGGCAGTATCTGGAGTCATTGAG | |
| HuVaF-<br>01~10 | CCATCTCATCCCTGCGTGTCTCCGAC<u>TCAG</u>-{MID}-A<br>TAGGCAGACAGACTTGTCACTG | MID1~<br>ID11 |
| HuVbF-<br>01~10 | CCATCTCATCCCTGCGTGTCTCCGAC<u>TCAG</u>-{MID}-A<br>CACCAGTGTGGCCTTTTGGGTG | MID15~<br>MID24 |
| B-P20EA | *CCTATCCCCTGTGTGCCTTGGCAGTC*TAATACGACTCCGAATTCCC | |

Correspond to, from the top, SEQ ID NOs: 4 to 13. V: A/C/G, N: A/C/G/T, and sequence of adaptors A and B are respectively indicated by bold and bold italic.
The key sequence (TCAG) is indicated by underlines.
The MID tag sequences used for identification of a sample source are the following: MID1, ACGAGTGCGT; MID2, ACGCTCGACA; MID3, AGACGCACTC; MID4, AGCACTGTAG; MID5, ATCAGACACG; MID6, ATATCGCGAG; MID7, CGTGTCTCTA; MID8, CTCGCGTGTC; MID10, TCTCTATGCG; MID11, TGATACGTCT; MID15, TACGACGTA; MID16, TCACGTACTA; MID17, CGTCTAGTAC; MID18, TCTACGTAGC; MID19, TGTACTACTC; MID20, ACGACTACAG; MID21, CGTAGACTAG; MID22, TACGAGTATG; MID23, TACTCTCGTG; MID24, TAGAGACGAG (Each corresponding to SEQ ID NOs: 14 to 33 in the order of description)

[Amplicon Sequencing Using Roche 454 Sequencing System]

Amplicons for NGS were prepared from the product of second PCR using a P20EA primer and a fused tag primer (Table 1). The fused tag primer comprised an A adapter sequence (CCATCTCATCCCTGCGTGTCTCCGAC (SEQ ID NO: 34)), a 4 base sequence key (TCAG), and a molecule identification (MID) tag sequence (10 nucleotides). TCR constant region specific sequences were designed in accordance with the manufacturer's instruction. After PCR amplification, amplicons were evaluated using agarose gel electrophoresis. Incomplete fragments or primers were removed using Agencourt AMPure XP (Beckman Coulter, Brea, Calif.) in accordance with the manufacturer's instruction. The amount of purified amplicons was quantified using a Quant-iT PicoGreen dsDNA Assay Kit (Life Technologies, Carlsbad, Calif.). Each amplicon obtained from 10 samples by different fused tag primers was mixed at an equal molar concentration. Emulsion PCR (emPCR) was performed with a GS Junior Titanium emPCR Lib-L kit (Roche 454 Life Sciences, Branford, Conn.) in accordance with the manufacturer's instruction by using the amplicon mixture.

[Assignment of TRV and TRJ Segments]

All sequence reads were classified in accordance with the MID tag sequence thereof. Artificially added sequences (tags, adapters, and keys) and sequences with a low quality score were removed from both ends of sequence reads using the software provided with 454 Sequencing System. The remaining sequences were used in the assignment of TRAV and TRAJ of TCRα sequences and TRBV and TRBJ of TCRβ sequences. Sequences were assigned by determining the sequence with the highest percentage identity in a data set of reference sequences (54 TRAV, 61 TRAJ, 65 TRBV, and 14 TRBJ genes (including pseudogenes and open reading frame (ORF) reference sequences)) that are available from the ImMunoGeneTics Information System (IMGT) database (http://www.imgt.org). Data processing, assignment, and data aggregation were automatically performed using a repertoire analysis software (Repertoire Genesis, RG) independently developed by Repertoire Genesis Incorporation (Osaka, Japan). RG first assigns TRV and TRJ alleles to a query using BLASTN and IMGT data set. Identity between a query and reference sequence was calculated in this step. Parameters that increase the sensitivity and accuracy (E value threshold, minimum kernel, and high score segment pair (HSP) score) were optimized for each repertoire analysis. Next, RG estimates a CDR3 region of the query by examining a translated reading frame. RG then calculates the distribution of TRV-CDR3-TRJ patterns and generates graphs (e.g., TRV-TRJ use histogram or CDR3 length distribution chart). These steps were automatically performed after inputting the query.

[Data Analysis]

A translated nucleotide sequence of a CDR3 region spanned a range from conserved Cys104 to conserved Phe118 or Gly119 in accordance with the IMGT nomenclature. A unique sequence read (USR) was defined as 0% identity to the deduced amino acid sequence of a CDR3 domain of TRV, TRJ and other sequence reads. The RG software automatically counted the number of copies of the same NCR in each sample, and then ranked the NCRs in order of the number of copies. The percentage frequency of sequence reads of TRAV, TRAJ, TRBV, and TRBJ genes was calculated.

[Single Cell Sorting and RT-PCR]

To identify and characterize a CMV NLV specific TCRαβ pair expressed by a single cell, the inventors used a modified hTEC10 system (Kobayashi, E. et al. A new cloning and expression system yields and validates TCRs from blood lymphocytes of patients with cancer within 10 days. Nat. Med. 19, 1542-1546 (2013), Hamana, H., Shitaoka, K., Kishi, H., Ozawa, T. & Muraguchi, A. A novel, rapid and efficient method of cloning functional antigen specific T-cell receptors from single human and mouse T-cells. Biochem. Biophys. Res. Commun. 474, 709-714 (2016)) as follows. CD8/NLV tetramer double positive cells were sorted in each well of a 96-well PCR plate. cDNA was synthesized/amplified using multiplex RT-PCR. Gene specific primers used for amplifying a sequence encoding a TCRα chain and TCRβ chain were designed from a leader peptide sequence obtained from the IMGT database (http://www.imgt.org/). PCR reactions are described in detail in the following [RT-PCR analysis of TCRA and TCRB pairs]. TCR repertoire analysis was performed using the IMGT/V-Quest tool (http://www.imgt.org/).

[RT-PCR Analysis of TCRA and TCRB Pairs]

RT-PCR was performed in a reaction mixture comprising 0.1 µl of 40 U/µl RNase Inhibitor (NEB, Ipswich, Mass.), 0.1 µl of 200 U/µl PrimeScript II RTase (TaKaRa, Otsu, Japan), 0.4 µl of primer mixture, 0.025 µl of 2.5 U/µl PrimeStar HS DNA Polymerase (TaKaRa), 0.4 µl of 2.5 mM dNTP, and 2.5 µl of 5× PrimeStar GC buffer (TaKaRa). DEPC treated $H_2O$ was added, such that the final volume was 5 µl. The RT reaction was performed for 40 minutes at 45° C., and then the following PCR reaction was performed. 30 cycles of 1 minute at 98° C., then 10 seconds at 98° C., 5 seconds at 55° C., and 1 minute at 72° C. A PCR reactant was diluted 10-fold with water and then used as a template DNA for nested PCR. Nested PCR for amplifying TCRA and TCRB was performed with a different 96-well PCR plate. The reaction mixture included 2 µl of DNA template from the first PCR reaction, 0.4 µl of 10 µM of respective specific primer set (for TCRα, A-AD and A-RV2 primers, and for TCRβ, B-AD and B1-RV2 primers and B2-RV2 primer), 0.1 µl of 2.5 U/µl PrimeSTAR HS DNA Polymerase, 1.6 µl of 2.5 mM dNTP, 10 µl of 5× PrimeSTAR GC Buffer, 0.1 µl of 2.5 U/µl, and $H_2O$ (added until reaching a final volume of 20 µl). The PCR cycle was the following: 35 cycles of 1 minute at 98° C., then 10 seconds at 98° C., 5 seconds at 55° C., and 1 minute at 72° C. TCRA and TCRB PCR products were analyzed by Sanger sequencing.

[Studying the Binding Capability of Cloned TCR)

1) Each of the cloned TCRαβ pair genes (CMV pp65, NLVPMVATV: NLV specific) described above was transferred into a TCRαβ deficient Jurkat cell using a retroviral vector (pMXs-IRES GFP).
2) GFP positive cells were separated from the Jurkat cells introduced with each TCR gene using a cell sorter (Arian).
3) The Jurkat cells introduced with each TCR were stained with serially diluted NLV tetramers at concentrations of 2, 4, 6, 8, and 10 µg/ml.
4) The fluorescence intensity (MFI) of tetramer positive cells was measured using flow cytometry to analyze the binding capability of each TCR with a tetramer.

(Results)

The results are shown in FIGS. 1 and 2. For donors V001 and V004, T cell clones with the clonotypes shown in FIG. 1 were identified as antigen specific clonotypes. It was found that a population of antigen specific clones is comprised of a very small number of clones.

FIG. 2 shows the comparison of frequency of presence of each TCR clone measured by the method described above and bindability to antigens. A linear correlation is observed between the frequency and binding affinity from the results. It is understood that dominant clones within the antigen specific T cell population are high affinity clones.

Example 1-2

The step of [Semi-quantitative analysis of TCR repertoire using high throughput NGS] in Example 1 was performed by the following procedure using a different sequencer (Miseq, Illumina),

[Summary of Changes in the Experimental Protocol]

The same steps as Example 1 were performed from RNA-double stranded DNA synthesis. For PCR, the same steps were performed from 1st PCR to 2nd PCR, and the steps thereafter were performed as PCR for Miseq (Tag PCR and Index PCR). Changes in reagents included use of KAPA HiFi HotStart ReadyMix recommended as the PCR enzyme of next generation sequencing.

3-2-9: Sample Manipulation 7 (1st, 2nd PCR)

The flow for analyzing two genes of human TCRαβ is described.

<1st PCR>

The amount of reagent for 1 sample is shown.

Add 10 µL of 2×KAPA HiFi Hot Start Ready Mix to each of α and β tubes.

Add 7.6 µL of DW (for DNA, bottle) to each of α and β tubes. Add 0.2 µL of 10 µM P20EA primer to each of α and β tubes.

Add 0.2 µL of 10 µM CA1 primer to an α tube, and 0.2 µL of 10 µM CB1 primer to a β tube.

Add 2 µL of each dsDNA sample to a tube containing α or β solution.

Select the applicable setting (program name: KAPA20, conditions of 95° C. 3 min, 20 cycles (98° C. 20 sec, 65° C. 30 sec, 72° C. 1 min), 72° C. 2 min, lastly 12° C. forever) in a thermal cycler.

<2nd PCR>

The amount of reagent for 1 sample is shown.

Add 10 µL of 2×KAPA HiFi Hot Start Ready Mix to each of a and 8 tubes.

Add 6 µL of DW to each of α and β tubes.

Add 1 µL of 10 µM P20EA primer to each of α and β tubes.

Add 1 µL of 10 µM CA2 primer to an α tube, and 1 µL of 10 µM CB2 primer to a β tube.

Add 2 µL of a and β 1st PCR product to 2nd PCR tubes for a and 13 PCR, respectively.

Select the applicable setting (program name: KAPA20, conditions of 95° C. 3 min, 20 cycles (98° C. 20 sec, 65° C. 30 sec, 72° C. 1 min), 72° C. 2 min, lastly 12° C. forever) in a thermal cycler.

<DNA Purification 1>

3-2-10: Sample Manipulation 8 (AMpure Purification 1)

Use BECKMAN COULTER's Agencourt AMPure XP in this step.

Admix AMPure XP beads thoroughly until the mixture is homogenous, and dispense 8 µL into a tube.

Add 10 µL of 2nd PCR product to the tube into which AMPure XP beads have been dispensed, and place the tube on MM-Separater M96 to collect magnetic beads.

Remove the supernatant, rinse with 200 µL of 70% ethanol, place the supernatant on the MM-Separater M96 to collect magnetic beads.

Completely remove the supernatant, dispense 30 µL of DW (for DNA, bottle), vortex, and place on MM-Separator M96 to collect magnetic beads.

Collect 25 µL of supernatant.

<Tag PCR>

3-2-11: Sample Manipulation 9 (Tag PCR)

Add 10 µL of 2×KAPA HiFi Hot Start Ready Mix to each of α and β tubes.

Add 4.2 µL of DW (for DNA, bottle) to each of a and β tubes. Add 0.4 µL of 10 µM P22EA-ST1-R primer to each of a and β tubes.

Add 0.4 µL of 10 µM CA-ST1-R primer to an α tube, and 0.4 µL of 1.0 µM CB-ST1-R primer to a β tube.

Add 5 µL of each 2nd PCR purified sample to each tube containing α and β reagent mixture.

Select the applicable setting (program name: KAPA20, conditions of 95° C. 3 min, 20 cycles (98° C. 20 sec, 65° C. 30 sec, 72° C. 1 min), 72° C. 2 min, lastly 12° C. forever) in a thermal cycler.

<DNA Purification 2>
3-2-14: Sample Manipulation 11 (AMpure Purification 2)*
The manipulation in this section is the same as the protocol "3-2-10: Sample manipulation 8 (AMpure purification 1)"
<Design of Index PCR for Analyzing a Plurality of Specimens in One Sequencing>
3-2-15: Sample Manipulation 12 (Creation of Sheet Required for Index PCR)
3-2-15-1: The Main Point
Index PCR is performed to add an index sequence and P5/P7 sequence (portion binding to flowcell) to each sample.
Determine the order of arrangement of samples and primers in advance (matrix), and create a sample sheet with Illumina Experiment Manager.
An existing product of Illumina (Nextera XT Index Kit v2 Set A) is used as the index primer.
<Index PCR>
3-2-16: Sample Manipulation 13 (Index PCR)
The amount of reagent for 1 sample is indicated in this protocol.
Add 10 μL of 2×KAPA HiFi Hot Start Ready Mix to a tube.
Add 4 μL of DW (for DNA, bottle) to a tube.
Dispense 14 μL in an 8-strip PCR tube.
Dispense N primer 2 μL at a time.
Dispense S primer 2 μL at a time.
Dispense Tag PCR purified sample to a predetermined tube 2 μL at a time.
Select the applicable setting (program name: INDEX12, conditions of 95° C. 3 min, 12 cycles (95° C. 30 sec, 55° C. 30 sec, 72° C. 30 sec), 72° C. 5 min, lastly 4° C. forever) in a thermal cycler.
<Electrophoresis>
3-2-17: Sample Manipulation 14 (Electrophoresis and Evaluation 2)
About 650 bp for TCR genes
Prepare 1.5% agarose gel, and use Atlas ClearSight for staining.
Place gel in an electrophoresis vessel, and subject 4 μL of index PCR product to electrophoresis (30 minutes at 100 V) with a 100 bp DNA ladder and 10× Dye. Evaluate results of amplification using a UV transilluminator or digital camera.
if too thin, PCR conditions need to be changed (increased to 15 cycles) by returning to the protocol "3-2-16: Sample manipulation 13 (Index PCR)".
<Measurement of Concentration 1>
3-3-3: Sample Manipulation (DNA Concentration Measurement by Qubit)
Dilute DW (for DNA, bottle) 10-fold using an Index PCR product.
Dilute the dye included in a Qubit dsDNA HS Assay kit 200-fold with the included buffer.
Add 190 μL of diluted dye solution to two 500 μL dedicated tubes (for Standard) and 198 μL of diluted dye solution is added for specimens.
Add 10 each of Standard #1 and Standard #2 included in the Qubit dsDNA HS Assay kit to the 500 μL dedicated tubes (two tubes) to which 190 μL of diluted dye solution have been added.
Add 2 μL of Index PCR product to the 500 μL dedicated tubes (10 tubes) to which 198 μL of diluted dye solution have been added.
Activate Qubit. Select the measurement mode "dsDNA", and then select "High Sensitivity".

Move to the measurement screen and select "Read standards" at the bottom.
Measure Standard #1 and Standard #2 in order. Confirm that the value is several "10s" or "10s of thousands"
Set the amount of specimen input to 2 μL for measurement.
Since the range of measurement is 0.1 to 50 ng/μL, measurement is redone after dilution if the value is beyond the range.
Based on the measurement results, dispense specimens in separate tubes so that equal amount of DNA can be mixed from a plurality of specimens (generally, 50 to 60 specimens are simultaneously measured in Miseq sequencing) to prepare a pooled specimen.
<DNA Purification 3>
3-2-18: Sample Manipulation 15 (AMpure Purification 3)
The manipulation in this section is the same as the manipulation in the protocol "3-2-10: Sample manipulation 8 (AMpure purification 1)", but is adjusted in accordance with the amount of the pooled specimen.
<Concentration Measurement 2>
Same manipulation as 3-3-3: Sample manipulation (Dilution and DNA concentration measurement by Qubit).
Since the specimen concentration used in sequencing with Miseq is 4 nM (1.72 ng for 650 bp), the specimen is diluted to the designated concentration after measurement.
<Sequencing Run Using Miseq>
3-3: MiSeq Sequence Analysis
3-3-4: Sample Manipulation 2 (Denaturation of Phi-X and DNA Library)
Mix 5 of 0.2 N—NaOH with 5 μL of pooled specimen (DNA) prepared to be 4 nM.
Mix 5 μL of 0.2 N—NaOH with 5 μL of PhiX (sequence stabilization reagent; contains random bases) prepared to be 4 nM.
Dispense Hyb-Buffer in each mixture and mix so that the final concentration is 10 μM, DNA:PhiX=4:1 (PhiX is 20%) for final adjustments.
3-3-5: Sample Manipulation 3 (Miseq Run)
Illumina's Miseq is used for sequence analysis. MiSeq Reagent Kit v3 (600 cycles) MS-102-3003 is used as the primary sequencing reagent. The manipulation method includes dispensing a specimen that has undergone final adjustment into a designated well in a frozen reagent cassette and placing the cassette in the equipment.
Information such as primer sequences is described below.

TABLE 2

| Name | Sequence | Length |
|---|---|---|
| BSL-18E | AAAGCGGCCGCATGCTTTTTTTTTTTTTT TTTVN | 35 |
| P10A | GGGAATTOGG | 10 |
| P20EA | TAATACGACTCCGAATTCCC | 20 |
| P22EA-ST1-R | GTCTCGTGGGCTCGGAGATGTGTATAAGAG ACAGCTAATACGACTCCGAATTCCC | 55 |
| Tag-1 | GTCTCGTGGGCTCGGAGATGTGTATAAGAG ACA | 33 |
| Tag-2 | TCGTCGGCAGCGTCAGATGTGTATAAGAGA CAG | 33 |
| CA1 | TGTTGAAGGCGTTTGCACATGCA | 23 |
| CA2 | GTGCATAGACCTCATGTCTAGCA | 23 |

TABLE 2-continued

| Name | Sequence | Length |
|---|---|---|
| CAST 1-R | TCGTCGGCAGCGTCAGATGTGTATAAGAGA CAGGAGGGTCAGGGTTCTGGA | 51 |
| CB1 | GAACTGGACTTGACAGCGGAACT | 23 |
| CB2 | AGGCAGTATCTGGAGTCATTGAG | 23 |
| CB-ST1-R | TCGTCGGCAGCGTCAGATGTGTATAAGAGAC AGGCTCAAACACAGCGACCTC | 52 |

(Corresponding to, from the top, SEQ ID NOs: 4, 6, 5, 35 to 37, 7, 8, 38, 9, 10, and 39)

See https://support.illumina.com/content/dam/illumina-support/documents/documentation/chemistry documentation/experiment-design/illumina-adapter-sequences 1000000002694-01.pdf for more information on Index PCR primers.

Example 1-3

The portion of [Single cell sorting and RT-PCR] and [RT-PCR analysis of TCRA and TCRB pairs] in Example 1 can also be performed by the following procedures. This procedure was developed by improving Drop-Seq method as a Gene Capture Drop-Seq™ that highly efficiently determines TCR pair genes. A single cell TCR pair gene determination method using Gene Capture Drop-Seq™ and a manufacturing method of TCR specific oligobeads are described. More details of this procedure are described in Yodosha, "Jikken Igaku/Bessatsu" [Experimental Medicine/Extra Issue] Single Cell Analysis Protocol (issue published on Oct. 10, 2017). The entire document is incorporated herein by reference.

[Preparation]
(Equipment)
Dolomite Bio's single cell RNA-Seq system (FIG. 19A) (three P pumps, three sets of flow meters, cell agitator, digital microscope, single cell RNA-Seq chip)
MiSeq sequencer (Illumina)
Qubit 3.0 fluorometer (Thermo Fisher Scientific)
A single cell separation apparatus (Dolomite Bio) is comprised of three P pumps, three sets of flow meters, cell agitator, digital microscope, and single cell RNA-Seq chip. The apparatus is equipped with a monitor so that droplet formation can be viewed in real time, and is designed to be highly extensible thus enabling various assemblies.
(Reagents)
1. Beads Oligo Creation
TE 10 mM Tris-HCl, pH 8.0, 1 mM EDTA
TE/TW 10 mM Tris-HCl, pH 8.0, 1 mM EDTA, 0.1% Tween20
TE/SDS 10 mM Tris-HCl, pH 8.0, 1 mM EDTA, 0.5% SDS
Bst reaction stopper 100 mM KCl, 10 mM Tris-HCl (pH 8.0), 50 mM EDTA, 0.1% Tween20
NaOH detergent I 150 mM NaOH, 0.5% Brij35P
NaOH detergent II 100 mM NaGH, 0.5% Brij35P
Neutral buffer 100 mM NaCl, 100 mM Tris-HCl (pH 8.0), 10 mM EDTA, 0.1% Tween20
Oligo immobilized beads (custom synthesis, Chemgene)[1] (FIG. 19B)
Synthetic DNA
Bst 3.0 DNA Polymerase (NEB)
Exonuclease I (NEB)

[1]Synthesis of oligobeads was commissioned to ChemGene in the US. The oligobeads for RNA-Seq of Mocosko et al. consist of the SMART sequence (SEQ ID NO: 45) followed by 12 base mixed and pooled bases (cell barcode sequence, J), 8 base random sequence (unique molecular index, N), and 30 base Poly (T) sequence. An annealing sequence is added instead of a Poly (T) sequence to Gene Capture. Both a TCRα chain C region specific probe and a TCRβ chain C region specific probe are bound to a single bead by an extension reaction.

Probe oligos are bound to beads by an extension reaction. Oligobeads of a gene of interest can be created by synthesizing a gene-specific probe (GSP) with an annealing sequence and performing an extension reaction. Two genes forming a pair have the same cell barcode sequence, so that a pair gene can be determined from the sequence.

2. Cell Separation
Serum medium RPMI 1640 (Wako Pure Chemical), 10% FCS, penicillin/streptomycin (Wako Pure Chemical), 50 μM 2-mercaptoethanol
ACK lysis buffer 0.15 M $NH_4Cl$, 0.01 M $KHCO_3$, 0.1 mM $Na_2$ EDTA, pH 7.2 to 7.4
70 μm cell strainer (Corning)
MACS magnetic cell separator (Miltenyi Biotec)
$CD8a^+$ T Cell Biotin-Antibody Cocktail (Miltenyi Biotec)
Anti-Biotin MicroBeads (Miltenyi Biotec)
MACS LS column (Miltenyi Biotec)
MACS buffer PBS, 2 mM EDTA, 0.5% BSA 3. Single Cell Separation
100 μm filter
40 μm filter
Cell lysis solution 200 mM Tris-HCl (pH 7.5), 6% ficoll PM400 (GE Healthcare), 0.2% sarkosyl (20% N-Lauroylsarcosine sodium salt, Sigma-Aldrich), 20 mM EDTA, 1.5 M Betaine, 0.2×SSC, 5% DMSO
1 M DTT
Cell buffer PBS, 0.01% BSA
Droplet Generator Oil for EvaGreen (Bio-Rad)
Perfluorooctanol (PFO, Sigma-Aldrich)
6×SSC 4. Template Switching Reverse Transcription Reaction
Superscript IV (Thermo Fisher Scientific)
10 mM dNTPs (Promega)
RNasin® Plus RNase Inhibitor (Promega)
KAPA HiFi HotStart ReadyMix (KAPA Biosystems)
TSO oligo: GTCGCACGGTCCATCGCAGCAGT-CACAGG (1G), 1G: LNA oligo (SEQ ID NO: 40)
TSO PCR primer: GTCGCACGGTC-CATCGCAGCAGTC (SEQ ID NO: 41)
SMART PCT primer: AAGCAGTGGTAT-CAACGCAGAGT (SEQ ID NO: 42)
TSO_TAG primer: GTCTCGTGGGCTCG-GAGATGTGTATAAGA-GACAGCGTCGCACGGTCCATCGCAGCAGTC (SEQ ID NO: 43)
SMART_TAG primer: TCGTCGGCAGCGTCA-GATGTGTATAAGAGACAGAAGCAGTGGTAT-CAACGCAGAGT (SEQ ID NO: 44)
Nextera XT Index Kit v2 SetA (illumina)
Agencourt AMPure XP (Beckman Coulter)
EB buffer (5 mM Tris-HCl, pH 8.5)
Qubit dsDNA assay kit (Thermo Fisher Scientific)
(Cells)
T lymphoma cell line (EL-4)
Mouse splenocytes (C57BL/6)
[Protocol]
1. Creation of Oliqobeads
(1) Suspend custom oligobeads (10 μmole scale) obtained from ChemGene in 30 mL of TE/TW, centrifuge for 1 minute at 1000 g and wash (repeated twice). Beads can be readily washed and collected by suspending the beads in a buffer and centrifuging for 1 minute at 1000 g. Use a swing rotor to carefully remove the buffer so as not to suction the beads.

Figure 19:
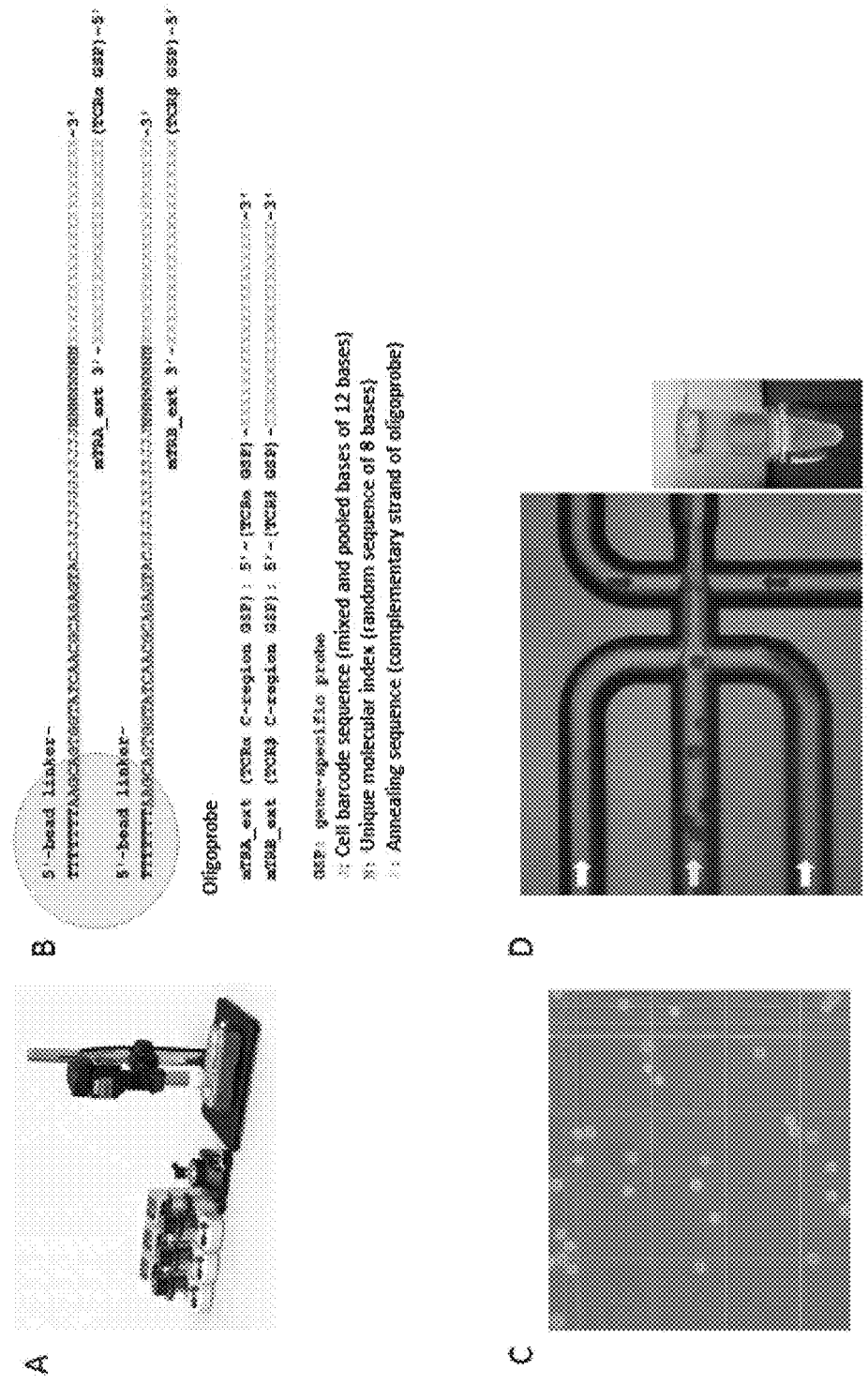
FIG. 19A shows a single cell RNA-Seq system from Dolomite Bio.
FIG. 19B shows an outline of Oligobeads. The SMART sequence in the Oligobeads corresponds to SEQ ID NO: 45.
FIG. 19C shows Oligobeads under a microscope.
FIG. 19D shows the bead flow and droplets in a microchip. The beads flow through the center line (yellow) and mix with two cell lines (white), and is injected into an oil line (red) to form a droplet (left diagram). The beads are randomly encapsulated by a droplet while passing through. The collected droplets (white) are separated from the oil layer (transparent) and can be readily retrieved.

(2) Count the beads using a hemocytometer (FIG. 19C). Suspend the beads in a TE/TW solution to attain 500,000 beads/mL, and refrigerate the beads. The beads can be refrigerated for a long period of time in TE/TW. The beads manufactured by ChemGene use TOYOPEARL HW. The beads have a diameter of about 30 µm.

(3) Dispense 1 mL of the bead suspension (500,000 beads) into an Eppendorf tube and centrifuge for 1 minute at 1000 g.

(4) Suspend the beads in 500 µL of 1× Isothermal buffer (NEB) and centrifuge for 1 minute at 1000 g (for prewashing with next extension reaction buffer).

(5) Prepare the next extension reaction solution and add the solution to the beads in (4).

TABLE 3

| Oligo extension reaction solution (µl) | |
| --- | --- |
| 10 × Isothermal buffer | 5 |
| 10 mM MgSO$_4$ | 1.5 |
| 10 mM dNTPs | 5 |
| 100 uM mTRA_ext | 5 |
| 100 uM mTRB_ext | 5 |
| DW | 26.5 |
| Total | 48 |

(6) After incubating for 2 minutes at 85° C., incubate the solution for 20 minutes at 60° C.

(7) Add 2 µL Est 3.0 polymerase (800 U/µL) and react with a heat rotator for 1 hour and 30 minutes at 60° C. Since beads precipitate during an enzymatic reaction, use of a heat rotator is desirable to maintain uniform reaction.

(8) Add 1 mL of Est reaction stopper, incubate for 30 minutes, and centrifuge for 1 minute at 1000 g (repeated twice).

(9) For exonuclease I treatment, add 1 mL of 1× exonuclease buffer and prewash, and centrifuge for 1 minute at 1000 g (single stranded DNA is degraded to remove unreacted bead bound oligos).

(10) Prepare the next exonuclease I reaction solution and suspend the beads.

TABLE 4

| 10 × exonuclease buffer | 5 |
| --- | --- |
| DW | 42.5 |
| Total | 47.5 |

(11) Add 2.5 µL exonuclease I (20 U/µL) so that the final concentration would be 1 U/L and react with a heat rotator for 45 minutes at 37° C.

(12) Suspend the beads in 1 mL of TE/SDS and centrifuge for 1 minute at 1000 g (repeated twice).

(13) Suspend the beads in 1 mL of NaOH detergent and centrifuge for 1 minute at 1000 g (double stranded DNA that binds to beads is denatured by alkaline washing to prepare a single stranded DNA probe).

(14) Suspend the beads in 1 mL of NaOH detergent II and centrifuge for 1 minute at 1000 g (repeated twice).

(15) Suspend the beads in 1 mL of TE/TW and centrifuge for 1 minute at 1000 g (repeated twice). Finally, suspend the beads in TE/TW so as to attain $5 \times 10^5$ beads/mL and refrigerate until use.

2. Preparation of Cells

<Mouse T Cell Line>

(1) Centrifuge a mouse T lymphoma cell line cultured in a serum medium for 5 minute at 800 g, and collect the cells.

(2) Wash the cells with 10 mL of serum medium.

(3) Suspend the cells in 10 mL of serum medium and filter the cells through a 75 µm cell strainer. Count the cells with a hemocytometer.

<Mouse Splenocytes>

(1) Dissect mice (C57BL/6, 6 week old) to extract the spleens. Prepare cells immediately before single cell separation as much as possible to reduce cell damage.

(2) Gently grind the spleens at the frosted section of a slide glass on a culture dish comprising 10 mL of serum medium.

(3) Transfer the serum medium to a 15 mL centrifuge tube and wait for debris to precipitate.

(4) Transfer the supernatant to another centrifuge tube and centrifuge for 5 minute at 800 g.

(5) After removing the supernatant, add 2 mL of ACK lysis buffer. Suspend the mixture and incubate for 2 minutes at room temperature to break the red blood cells.

(6) Add 10 mL of serum medium to stop hemolysis, and centrifuge for 5 minutes at 800 g.

(7) Suspend the cells in 10 mL of serum medium and filter the cells through a 75 µm cell strainer. Count the cells with a hemocytometer.

<Mouse Spleen CD8 Positive Cells>

(1) Fractionate $1 \times 10^8$ cell solution and centrifuge for 5 minutes at 800 g.

(2) Suspend the cells in 10 mL of ice-cooled MACS buffer and then centrifuge for 5 minutes at 800 g.

(3) Add 400 µL of CD8α$^+$ T Cell Biotin-Antibody Cocktail and incubate for 5 minutes on ice.

(4) Add 300 µL of MACS buffer, and then add 200 µL of Anti-Biotin Microbeads. Incubate the mixture for 10 minutes on ice.

(5) During this time, place an LS column in a magnetic separator and add 3 mL of MACS buffer to recycle the column.

(6) Load 1 mL of cell suspension into the LS column, and aggregate the flow-through.

(7) Further add 3 mL of MACS buffer and collect all flow-throughs.

(8) Add 6 mL of serum medium and centrifuge for 5 minutes at 800 g.

(9) Add 10 mL of serum medium and centrifuge for 5 minutes at 800 g.

(10) Add 4 mL of serum medium, and count the cells.

3. Separation of Single Cells 3-1. Set-up of Dolomite Bio's single cell separator (since microfiber contamination can cause line clogging, it is preferable to use a dust-free wiper for clean rooms to clean the lab bench so that dust or the like would not fall in.)

(1) Activate the compressor. Boot up a PC and dedicated controlling software (Mitos Flow Control Center).

(2) Check the connection of each line and install a microchip so that a flow channel can be viewed on a monitor under a microscope.

(3) Place filtered sterile water and control oil in a bottle in a P pump. Filter all reagents that are placed in a line in advance. Use Novec 7700 or FC40 (3M) for the run because EvaGreen Droplet Oil comprising a surfactant is expensive.

(4) Perform a test flow by setting the flow rate of cell lines and bead line to 40 μL/min and setting oil lines to 200 μL/min. The droplet size can be adjusted by changing the flow rate. While the size is about 85 μm under these conditions, the size can be adjusted to about 100 μm at 30 μL/min (cells), 30 μL/min (beads), and 166 μL/min (oil).
(5) Check that droplets are formed without any problems with a microscope.

3-2. Preparation of Beads (6) Fractionate $1.5 \times 10^5$ beads, centrifuge for 1 minute at 1000 g, and pellet down the beads.
(7) Add 500 μL of lysis buffer, prewash the beads, and centrifuge for 1 minute at 1000 g.
(8) Add 500 μL of lysis buffer and adjust the mixture to $3 \times 10^5$ beads/mL.
(9) Filter with a 70 um filter and then draw in with a 1 mL syringe.
(10) To inject beads in a 500 μL sample loop, switch the valve and slowly inject the beads while inverting the syringe. Perform the process while inverting the syringe so that the beads do not precipitate.
(11) Set the flow rate of the beads line to 40 μL/min and stand by with the valve closed.

3-3. Preparation of Cells

(12) Fractionate $1 \times 10^6$ cells suspended in a serum medium and centrifuge for 5 minutes at 800 g.
(13) Suspend the cells in 10 mL PBS/BSA and centrifuge for 5 minutes at 800 g.
(14) Suspend the cells in PBS/BSA so the concentration is $3 \times 10^5$ cells/mL and filter with a 70 μm filter and then set a bottle in a P pump. Cool the cells with ice to prevent degradation.
(15) RUN the separator at a flow rate of 40 μL/min while stirring with a stirrer bar.

3-4. Preparation of Oil

(16) Take out the bottle containing the control oil and place Droplet Generation Oil for EvaGreen for droplets in the P pump.
(17) Set the flow rate to 200 μL/min and confirm that oil is flowing and droplets are formed.

3-5. Preparation of Output Line

(18) Set an output line to a tube to collect droplets coming out from a microchip.
(19) Open the bead line to allow beads to flow in the microchip. Confirm that beads are flowing and droplets are formed while viewing the monitor screen (FIG. 19D). Droplets are formed at 4000/second under this condition. A bead is encapsulated into one of 20 droplets.
(20) Collect droplets for 15 to 20 minutes. Confirm that there are no more beads on the monitor screen. Two layers, i.e., top layer droplet and bottom layer oil, can be observed from the collected droplet solution.

4. Breakage of Droplets (1) Collect droplets into a tube and remove the the bottom layer of oil. Remove oil by aspiration with the tip end. Perform the following steps as quickly as possible.
(2) Dispense all droplets in the top layer (white) in 8-strip PCR tubes.
(3) Anneal droplets for 2 minutes at 75° C. and reduce the temperature by 1° C. at a 30 second interval from 65° C. to 50° C.
(4) Transfer all the droplets into a 50 mL conical tube and add 10 mL of cooled 6×SSC solution.
(5) Add 500 μL of perfluorooctanol (PFO) and vigorously vortex.
(6) Centrifuge for 1 minute at 1000 g and carefully remove the supernatant. Beads form a white layer. Note that beads may float up in 6×SSC. If beads do not precipitate, the beads can be recentrifuged or collected with a 25 μm filter. At the same time, remove the oil layer (clear) that has accumulated at the bottom.
(7) Add 10 mL of 6×SSC and vigorously vortex, and then centrifuge again for 1 minute at 1000 g. Carefully remove the supernatant and wash the beads (repeat twice).
(8) Transfer the white beads to an Eppendorf tube and centrifuge for 1 minute at 1000 g to remove the supernatant.

5. Template Switching Reverse Transcription Reaction (1) Add 100 μL of 5×RT buffer to bead pellets and centrifuge for 1 minute at 1000 g for prewashing.
(2) Prepare the following reverse transcription reaction solution and add beads.

TABLE 5

| Reverse transcription reaction solution | |
| --- | --- |
| 5 × 1st strand buffer | 10 μL |
| 0.1 M DTT | 2.5 μL |
| 10 mM dNTPs | 2.5 μL |
| 48 μM TSO[1] | 2.5 μL |
| RNasin Plus (40 U/μL) | 2.5 μL |
| DW | 28 μL |
| Total | 48 μL |

[1]To create a directional library, a template switching oligo (TSO) that is different from the head sequence is used. A SMART oligo added to heads can also be used.

(3) Add 2 μL of Superscript IV (200 U/μL) and incubate at 50° C. for 1 hour and 30 minutes with a heat rotator.
(4) Add 100 μL of TE/SDS solution and centrifuge for 1 minute at 1000 g to remove the supernatant.
(5) Add 100 μL of TE/TW solution and centrifuge for minute at 1000 g to remove the supernatant (repeat twice).
(6) Add 100 μL of 1× exonuclease buffer and centrifuge for 1 minute at 1000 g for prewashing.
(7) Add the following exonuclease reaction solution to the beads.

TABLE 6

| Exonuclease reaction solution | |
| --- | --- |
| 10 × exonuclease buffer | 2 μL |
| DW | 17 μL |
| Total | 19 μL |

(8) Add 1 μL of exonuclease (20 U/μL) and incubate with a heat rotator for 30 minutes at 37° C.
(9) Add 100 μL of TE/SDS solution and centrifuge for 1 minute at 1000 g to remove the supernatant (repeat twice).
(10) Add 100 of TE/TW solution and centrifuge for 1 minute at 1000 g to remove the supernatant (repeat twice).

6. PCR Reaction (1) Add 100 μL of DW and centrifuge for 1 minute at 1000 g to remove the supernatant.
(2) Prepare the following pre-PCR reaction solution and add beads.

TABLE 7

| pre-PCR reaction solution | |
| --- | --- |
| 2 × KAPA HiFi HotStart ReadyMix | 10 μL |
| 10 μM TSO PCR Primer[1] | 0.4 μL |

TABLE 7-continued

| pre-PCR reaction solution | |
| --- | --- |
| 10 μM SMART PCR primer | 0.4 μL |
| DW | 9.2 μL |
| Total | 20 μL |

Pre-PCR cycle
3 minutes at 98° C. (20 seconds st 98° C., 20 seconds at 65° C., and 3 minutes at 72° C.) 18 cycles, 5 minutes at 72° C.
[1]PCR can be performed with only a SMART PCR primer when using a SMART sequence as TSO.

(3) Add 12 μL of Ampure beads to 15 μL PCR product and incubate for 5 minutes at room temperature.

(4) Incubate for 2 minutes at room temperature on a magnet plate and remove the supernatant.

(5) Wash with 200 it of 70% ethanol (repeat twice).

(6) Completely remove the 70% ethanol and then dry up the beads for 1 minute.

(7) Add 15 of EB buffer (5 mM Tris-HCl, pH 8.5), vortex, and incubate for 1 minute.

(8) Incubate for 2 minutes at room temperature on a magnet plate and collect the supernatant in a new tube.

(9) Prepare the following PCR reaction solution, add 2 μL of purified pre-PCR reaction solution, and perform PCR in the next cycle.

TABLE 8

| PCR reaction solution | |
| --- | --- |
| 2 × KAPA HiFi HotStart ReadyMix | 10 μL |
| 10 μM TSO primer | 1 μL |
| 10 μM SMART primer | 1 μL |
| DW | 6 μL |
| Total | 18 μL |

PCR cycle
3 minutes at 98° C., (20 seconds at 9° C., 20 seconds at 65° C., and 3 minutes at 72° C.) 30 cycles, 5 minutes at 72° C.

(10) Check the PCR products by 2% agarose gel electrophoresis.

(11) Collect PCR products by purification with the same impure beads as (3) to (8).

(12) Prepare an INDEX tag added-PCR reaction solution, add 2 μL of purified PCR reaction solution, and perform PCR in the next cycle.

TABLE 9

| Tag PCR reaction solution | |
| --- | --- |
| 2 × KAPA HiFi HotStart ReadyMix | 10 μL |
| 10 μM TSO_TAG primer | 1 μL |
| 10 μM SMART_TAG primer | 1 μL |
| DW | 6 μL |
| Total | 18 μL |

TAG PCR cycle
3 minutes at 98° C., (20 seconds at 98° C., 20 seconds at 65° C., and 3 minutes at 72° C.) 18 cycles, 5 mintues at 72° C.

(13) Collect PCR products by purification with the same Ampure beads as (3) to (8).

(14) Prepare a PCR reaction solution for INDEX PCR, add 2 μL of purified PCR reaction solution, and perform PCR in the next cycle.

TABLE 10

| INDEX PCR reaction solution | |
| --- | --- |
| 2 × KAPA HiFi HotStart ReadyMix | 10 μL |
| N-primer | 2 μL |
| S-primer | 2 μL |
| DW | 4 μL |
| Total | 18 μL |

Tag PCR Cycle
3 minutes at 95° C., (30 seconds st 95° C., 20 seconds at 55° C., and 2 minutes at 72° C.) 14 cycles, 5 minutes at 72° C.

(15) Collect PCR products by purification with the same Ampure beads as (3) to (8).

(16) Measure the amount of DNA for the purified INDEX PCR product with Qubit 3.0 fluorometer using a Qubit dsDNA assay kit.

(17) Dilute the PCR product to attain 4 μM, and perform sequencing with MiSeq with a goal of 300000 to 1000000 reads.

7. TCR Repertoire

Analysis of the read total and assignment of V, D, and J region sequences with a mouse TCR reference sequence of sequence data was performed with a dedicated software for repertoire analysis developed by Repertoire Genesis. MiXCR, HighVQuest provided by IMGT, and the like are known as available TCR analysis software. Such software can also be used. Barcode matching between read sequences can be performed using Biostrings of R or a similar package.

[Discussion]

The analysis after sorting with a flow cytometer used in Example 1-1 and the droplet based approach described in Example 1-3 can be used for different objectives. If the objective is to find a highly functional TCR, analysis of at most several hundred single cells is very cost-effective. If the objective is to comprehensively analyze low frequency TCRs (TCRs of naïve fraction, shared TCRs, or the like), it is understood that analysis using droplets is costly but advantageous.

Example 2: Removal of Endogenous TCR (Summary)

This Example demonstrates complete removal of endogenous TCR genes by genome editing that targets a TCR gene.

(Materials and Method)

[mRNA Synthesis from Platinum TALEN]

(1) Plasmids of Left (L)-TALEN and Right (R)-TALEN for cleaving a TRA or IRE gene were treated with SmaI for 2 hours at 30° C.

(2) The plasmids were treated with Proteinase K for 20 minutes at 50° C. and purified with a QIAGEN PCR Purification Kit.

(3) mRNA was synthesized with an mMESSAGE MACHINE T7 Kit (Life technologies), followed by poly(A) Tailing Kit (Life technologies) and purified by LiCl precipitation method (in accordance with the Manufacturer's instruction).

In this Example, a pair of TALEN-TCR-alpha2 L19 and TALEN-TCR-alpha2 R19 was used for targeting a gene of TCRα. The full length sequences of these plasmids are represented by SEQ ID NO: 46 and SEQ ID NO: 47. The TALEN coding sequence of TALEN-TCR-alpha2 L19 is represented by SEQ ID NO: 52, and the amino acid sequence of said TALEN is represented by SEQ ID NO: 53. The TALEN coding sequence of TALEN-TCR-alpha2 R19 is represented by SEQ ID NO: 54, and the amino acid sequence of said TALEN is represented by SEQ ID NO: 55.

In this Example, a pair of TALEN-TCR-beta1_L19 and TALEN-TCR-beta1_R19, or TALEN-TCR-beta3 L19 and TALEN-TCR-beta3_R19 was used for targeting a gene of TCRβ. The full length sequences of these plasmids are represented by SEQ ID NO: 48, SEQ ID NO: 49, SEQ ID NO: 50, and SEQ ID NO: 51 in the order of description. The TALEN coding sequence of TALEN-TCR-beta1_L19 is represented by SEQ ID NO: 56, and the amino acid sequence of said TALEN is represented by SEQ ID NO: 57. The TALEN coding sequence of TALEN-TCR-beta1_R19 is represented by SEQ ID NO: 58, and the amino acid sequence of said TALEN is represented by SEQ ID NO: 59. The TALEN coding sequence of TALEN-TCR-beta3 L19 is represented by SEQ ID NO: 60, and the amino acid sequence of said TALEN is represented by SEQ ID NO: 61. The TALEN coding sequence of TALEN-TCR-beta3 R19 is represented by SEQ ID NO: 62, and the amino acid sequence of said TALEN is represented by SEQ ID NO: 63.

[Preparation of TCR Deficient T Cell Using Platinum TALEN mRNA]

(1) Jurkat cells were cultured for 3 days in RPMI 1640+10% FBS+2 mmol/l L-Glutamin+1% penicillin/streptomycin.

(2) By the following procedure, 10 μg each of TALEN-TCR-alpha2 L19 (TCRα-L-TALEN) mRNA and TALEN-TCR-alpha2 R19 (TCRα-R-TALEN) mRNA were introduced into cultured Jurkat cells when targeting a gene of TCRα, and a pair of TALEN-TCR-beta1_L19 (TCRβ1-L-TALEN) mRNA and TALEN-TCR-beta1_R19 (TCRβ1-R-TALEN) mRNA, or a pair of TALEN-TCR-beta3_L19 (TCRβ3-L-TALEN) mRNA and TALEN-TCR-beta3_R19 (TCRβ3-R-TALEN) mRNA was introduced into cultured Jurkat cells when targeting a gene of TCRβ (SE CellLine 4D-Nucleofector™ X Kit S).

(2-1) Cell pellets were prepared by centrifugation (400 G, 10 minutes, room temperature) of $5 \times 10^5$ to $1 \times 10^6$ Jurkat cells.

(2-2) The cell pellets were suspended in a total of 20 μl of Nucleofector solution prepared by adding 3.6 μl of Supplement to 16.4 μl of Nucleofector SE solution per reaction.

(2-3) A pair of TALEN mRNA for targeting a gene of TCRα or a TCRβ gene was added at 10 μg each.

(2-4) Nucleofection was performed using Amaxa 4D-Nucleofector (program: CL-120).

[Confirmation of Removal of Endogenous TCR]

It was confirmed that a CD3 negative fraction found by FACS after introduction of TALEN mRNA into Jurkat cells was manifested. Cells from sorting CD3 negative fractions were confirmed by FACS to be TCR (endogenous) negative. The expression intensity of CD3 obtained by FACS was analyzed with FACS analysis software (Flow Jo).

As to whether the manifested CD3/TCR negative fractions were obtained by introduction of TALEN, the presence of a cleavage fragment was checked by a T7 Endonuclease I (T7E1) assay.

[T7 Endonuclease I assay]

(1) PCR was performed using the extracted genomic DNA. PCR was performed for 10 minutes at 94° C., then 30 seconds at 94° C., 30 seconds at 55° C., and 1 minute at 72° C. for 30 cycles, and a reaction for 5 minutes at 72° C. in a reaction mixture of a final concentration 1× buffer, 200 μM dNTP, 0.4 μM primer, 2.5 to 5 ng DNA, and Excellent Taq HS (APRO Science).

(2) The primer sequences were the following.

[Chemical Formula 1]

| Primers | Sequences |
|---|---|
| TCR-alpha2-f | CTCTGCATGACTCACTAGCACTCTAT |
| TCR-alpha2-r | GACTGACTTAGTGAGCTGGGAAAGAT |
| TCR-beta1-c1-f | CTAATATGTGTCACTACCCCACGAG |
| TCR-beta1-c1-r | GAGAGTTACACAGGCCACATAGAAAG |
| TCR-beta1-c2-f | GAGGAGACATCACCTGGAATGTTAG |
| TCR-beta1-c2-r | GATATATTAGGCTGTGCTCTGGCTCT |

(Corresponding to, from the top, SEQ ID NO; 64 to 69)

(3) 1% agarose gel electrophoresis was performed to extract DNA using a Gel Extraction kit (QIAGEN).

(4) 200 to 250 ng of the extracted DNA was heated for 5 minutes at 95° C., then cooled to room temperature, and reannealed.

(5) T7 Endonuclease I was added for 30 minutes of treatment at 37° C. The DNA was then studied by electrophoresis with 2% gel.

Figure 3:
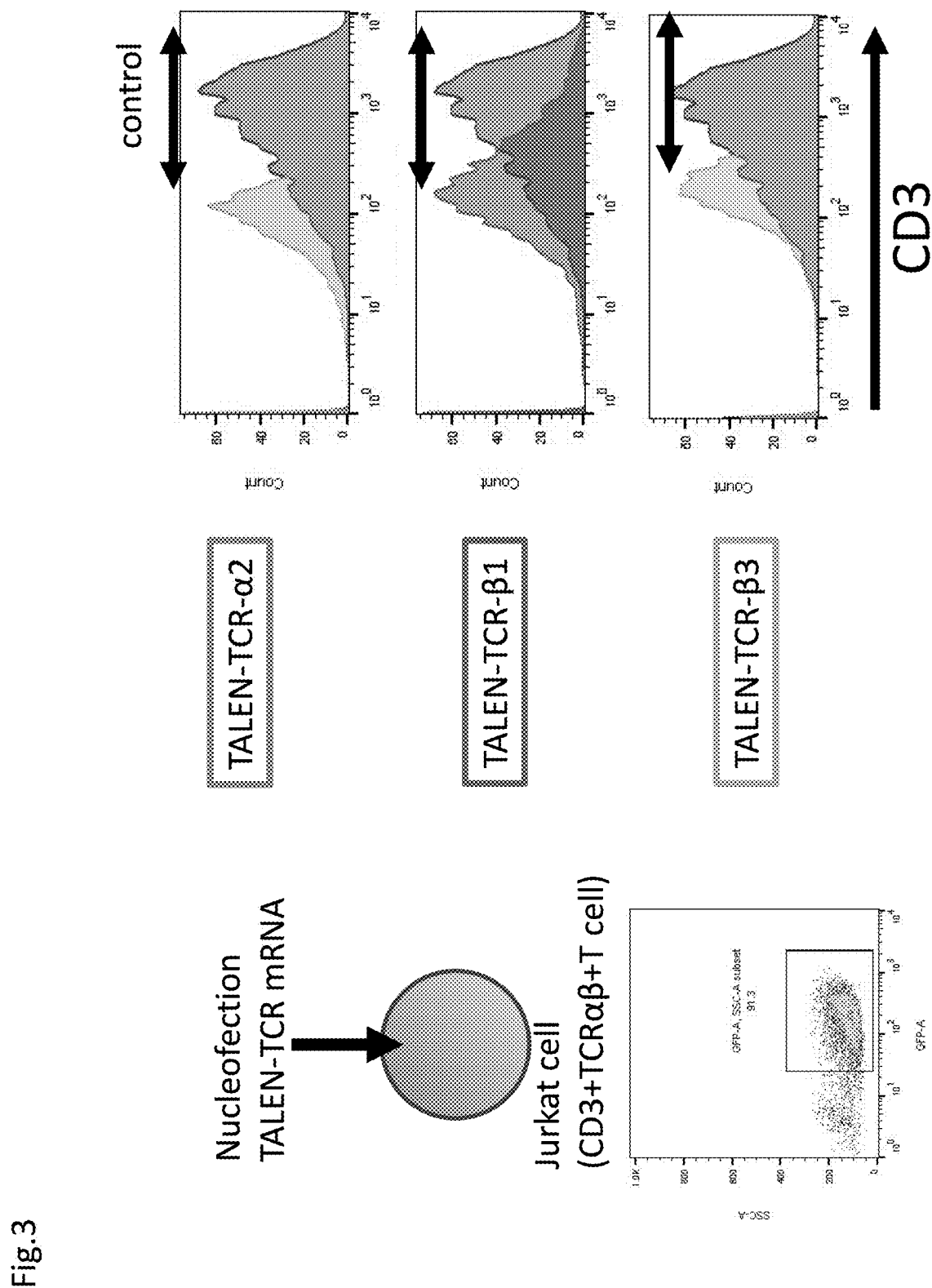
FIG. 3 is a histogram showing the change in CD3 expression compared to a control when an endogenous TCR gene is removed with TALEN (right panel). The left side of FIG. 3 shows the experimental scheme using TALEN-TCR mRNA and results of FACS analysis using GFP-A and SSC-A. CD3 expression can be utilized as a marker for TCR expression, and CD3 expression is shifted to negative compared to a control, thus indicating that an endogenous TCR gene was successfully removed.
Figure 4:
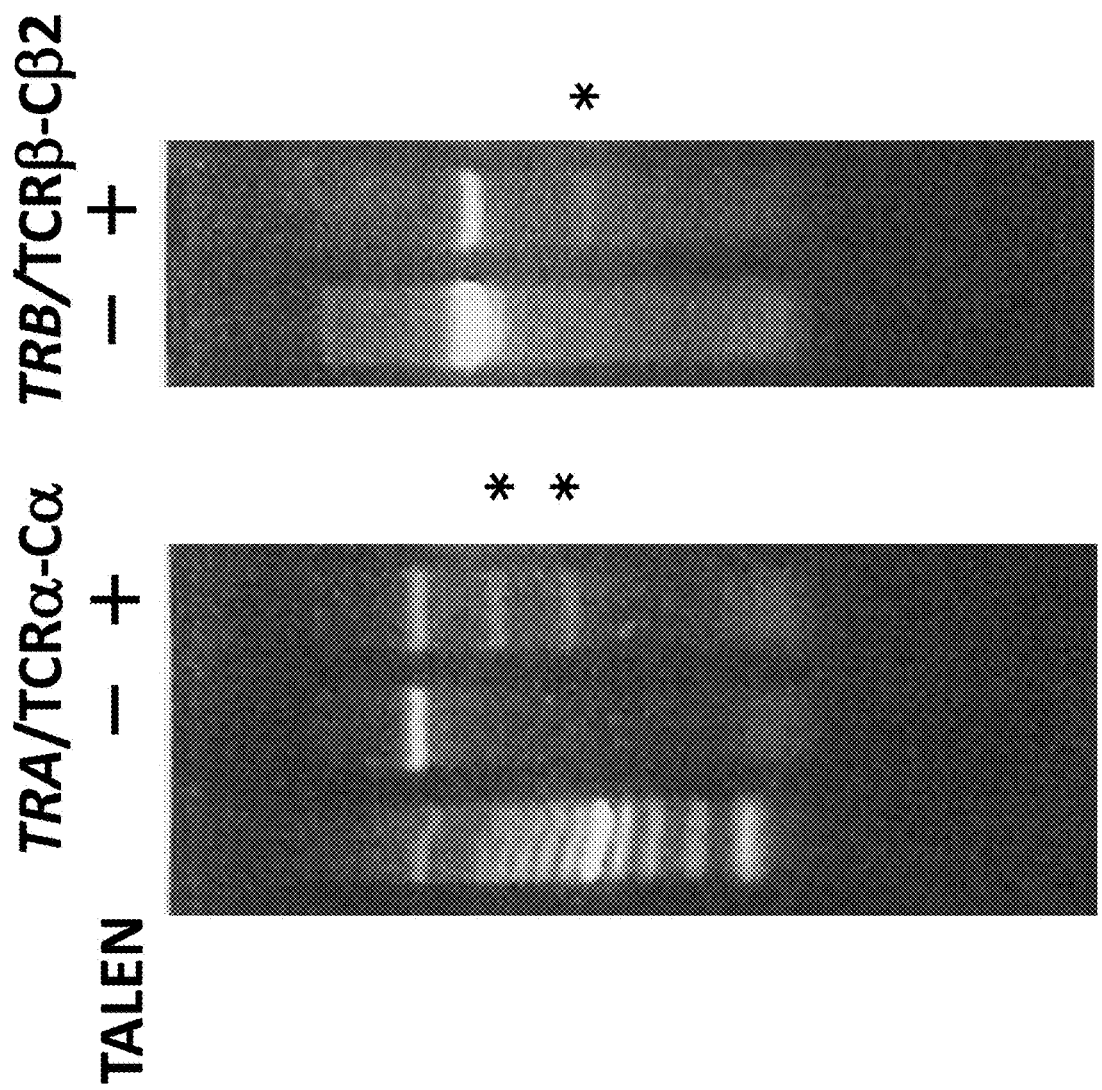
FIG. 4 is an electrophoretic diagram showing a T7E1 assay indicating successful cleavage of a TCR gene with TALEN. The figure shows that a TRA/TRB genes were cleaved in human T cell derived Jurkat cell strains (left and right panel, respectfully).

The results are shown in FIG. 3. It can be understood that each endogenous TCR gene was knocked out by genome editing targeting each TCR gene. FIG. 4 shows the results of a T7E1 assay. It is understood from FIG. 4 that the knockout of TCR genes is due to genome editing.

Example 3: Introduction of TCR (Summary)

This Example demonstrates that a TCR gene can be expressed in T cells without mispairing by using a cysteine mutated TCR introduction vector. A TCR gene was introduced with the removal of an endogenous TCR gene shown in Example to demonstrate that a T cell expressing only the introduced TCR can be created.

(Materials and Methods)

(1) T cells were stimulated with CD3/28 beads and cultured for 3 days with X-VIVO20+10% AB serum 2 mmol/l L-Glutamin 1% penicillin/streptomycin.

(2) TCRα-L-TALEN mRNA and TCRα-R-TALEN mRNA were introduced (P3 Primary Cell 4D-Nucleofector™ X Kit S) into the cultured T cells using an Amaxa 4D-Nucleofector by the following procedure.

(2-1) $5 \times 10^5$ to $1 \times 10^6$ T cells were centrifuged (400 g, 10 minutes, room temperature) to prepare cell pellets.

(2-2) The cell pellets were suspended in a total of 20 μl of Nucleofector solution prepared by adding 3.6 μl of Supplement to 16.4 μl of Nucleofector P3 solution per reaction.

(2-3) TCRα-L-TALEN mRNA and TCRα-R-TALEN mRNA were added at 10 μg each.

(2-4) Nuceofection (program: EO-115) was performed.

(2-5) The mixture was continuously cultured.

(2-6) After three days of Nucleofection, the efficiency of cleaving TCR genes was studied with respect to loss of expression of CD3 and TCRα and β by flow cytometry.

(3) CD3 negative fractions were collected by magnetic sorting or FACS (Aria II).

(4) The TCR gene of interest was introduced into the CD3 negative T cells obtained in (3) with a retroviral vector in accordance with the procedure described in detail below.

(5) On the next day, it was confirmed by FACS that a TCR positive CD3 positive fraction is manifested.

(6) The CD3 positive fraction was collected by magnetic sorting or FACS (Aria II).

(7) TCRβ3-L-TALEN mRNA and TCRβ3-R-TALEN mRNA were introduced into the CD3 positive T cells obtained in (6) by the same approach as (2).
(8) The CD3 negative fraction was collected by magnetic sorting or FACS (Aria II).
(9) The TCR gene of interest was introduced into the CD3 negative T cells obtained in (8) with a retroviral vector again by the same procedure.
(10) it was confirmed that a CD3 positive fraction is manifested. The fraction was collected by magnetic sorting or FACS (Aria II).

[Introduction of Desired TCR into TCR Deficient Cells]

The introduction of a TCR gene in the procedure described above was performed by the following procedure.
Day 1:
(1) PLAT-OP was seeded in a 10 cm dish and cultured to 70% confluence.
(2) 10 μg of vector and 5 μg of VSV-G were added to 1.4 ml of OPTI-MEM I and incubated for 5 minutes at room temperature.
(3) 50 μl of Lipofectamine 2000 was added to 1.4 ml of OPTI-MEM I and incubated for 5 minutes at room temperature.
(4) (2) and (3) were mixed and incubated for 20 minutes at room temperature.
(5) The mixture of (4) was added to a culture of PLAT-GP and cultured for 48 hours.
Day 4-1:
(1) Supernatant was collected from PLAT-GP and centrifuged (1500 rpm×5 min, 4° C.)
(2) The supernatant was passed through a 0.45 μM filter and further centrifuged (6000 G×16 hr, 4° C.)
Day 4-2:
TCR deficient T cells in the culture were dispensed in a 24 well plate at 5×10$^5$/well.
Day 5:
(1) The supernatant in the centrifuge tube of Day 4-1 (2) was removed and pellets were suspended in 500 μl of X-VIVO 20 to create a viral solution.
(2) After adding the viral solution to a medium of TCR deficient cells dispensed on the previous day and centrifuging (2000 rpm×30 min, 32° C.), culture was continued for 24 hours. The next day, the infection rate was checked by the ratio of GFP positive cells (flow cytometry) among viable cells.

[Cloning of TCR Gene to a pMXs-IRES-GFP Vector]
(1) A pMXs-IRES-GFP vector was cleaved with BamHI and NotI.
(2) A primer was designed so that an overlap sequence was formed at each binding section, specifically as follows:

[Chemical Formula 2]

Vα: 5'-TGGAGGAGAACCCTGGACCT-3'
    5'-GGTGAATAGGCAGACAGACTT-3'

Cα: 5'-GAGACTCTAAATCCAGTGAC-3'
    5'-GGGGGCGGAATTTACGTAGCGGCCGCTCAGCTGCT-3'

Vβ: 5'-TGCCGGATCTAGCTAGTTAATTAAGGATCCGAATTCCT GCAGG-3'
    5'-TTCACCCACCAGCTCAGCTC-3'

Cβ: 5'-TTCACCCACCAGCTCAGCTC-3'
    5'-AGGTCCAGGGTTCTCCTCCA-3'

(Corresponding to, from the top in order, SEQ ID NOs: 70 to 77}

(3) Each fragment was amplified by PCR using the primer in (2).
(4) The fragments obtained in (1) and (3) were purified.
The fragment of (1) (vector) was purified to attain 25 ng/μl.
The fragments of (2) (Vα, Cα, Vβ, Cβ) were each purified to attain 10 ng/μl.
(5) Gibson assembly reaction (NEB, Gibson Assembly Master Mix, in accordance with the Manufacture's Instruction) was performed. To 5 μl of Gibson Assembly Master Mix, 1 μl of vector, 0.75 μl of Vα, 0.75 μl of Vβ, 0.75 μl of Cα, and 0.75 μl of Cβ were added. 1 hour at 50° C.
(6) The reaction solution in (5) was diluted 4-fold, and the samples were transformed to competent cells (JM109).
(7) DNA was purified with Miniprep and studied by sequencing.

[Introduction Vector]

Figure 5:
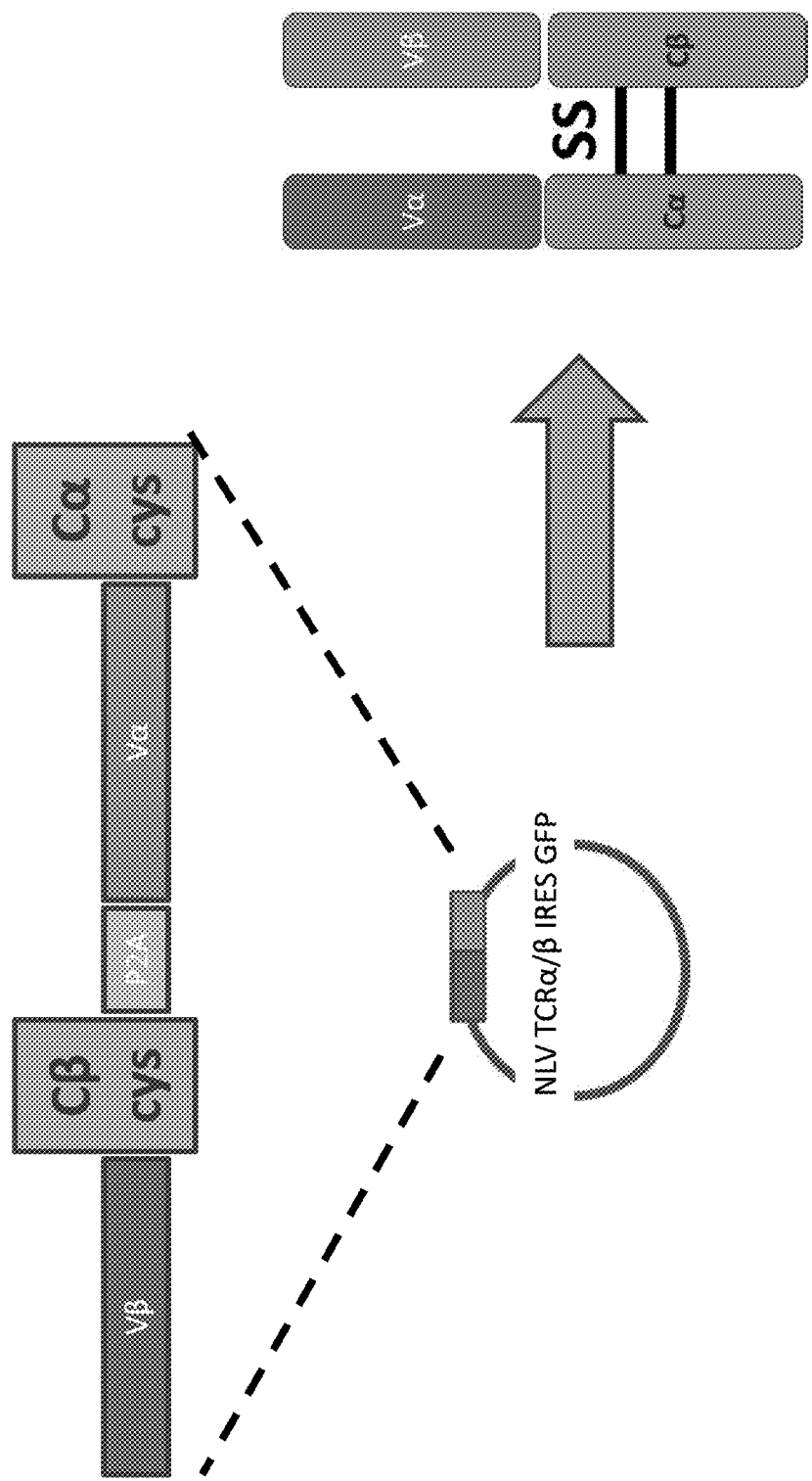
FIG. 5 is a schematic diagram of one example of an expression vector used in introduction of a TCR.

For the introduction vector, pMXs-IRES-GFP Retroviral Vector (Cell Biolabs, Inc.) was used as the backbone. A schematic diagram of a vector is shown in FIG. 5. The V region of TCRβ chain to be introduced, constant region of the TCR β chain (Cβ), P2A sequence, V region of a TCRα chain to be introduced, and constant region of the TCRα chain (Cα) were incorporated into and used at a introduced sequence portion of the pMXs-IRES-GFP Retroviral Vector in this order. Preparation of such a vector is described in Incorporation of Transmembrane Hydrophobic Mutations in the TCR Enhance Its Surface Expression and T Cell Functional Avidity Astar Haga-Friedman, Miryam Horovitz-Fried and Cyrille J. Cohen J Immunol 2012; 188: 5538-5546; Prepublished online 27 Apr. 2012.

By referring to Enhanced antitumor activity of T cells engineered to express T-cell receptors with a second disulfide bond. Cohen C J, Li Y F, El-Gamil M, Robbins P F, Rosenberg S A, Morgan R A. Cancer Res. 2007 Apr. 15; 67(8): 3898-903, an additional Cys was introduced to the C region to add one S—S bond. By referring to Incorporation of Transmembrane Hydrophobic Mutations in the TCR Enhance Its Surface Expression and T Cell Functional Avidity Astar Haga-Friedman, Miryam Horovitz-Fried and Cyrille J. Cohen J Immunol 2012; 188: 5538-5546; Prepublished online 27 Apr. 2012, a mutation to a hydrophobic amino acid was introduced into a transmembrane region.

A P2A sequence was used as a self-cleaving linker (J. H. Kim, S. R. Lee, L. H. Li, H. J. Park, J. H. Park, K. Y. Lee, et al., High cleavage efficiency of a 2A peptide derived from porcine teschovirus-1 in human cell lines, zebrafish and mice, PLoS One. (2011) 1-8. doi:10.1371/journal.pone.0018556.)

The amino acid sequences of the constant regions of the TCR α chain and TCR β chain that were used are the following.

[Chemical Formula 3]

(SEQ ID NO: 78)
>hTCR_alpha_const
XIQNPDPAVYQLRDSKSSDKSVCLFTDFDSQTNVSQSKDSDVYIT
DKTVLDMRSMDFKSNSAVAWSNKSDFACANAFNNSIIPEDTFFPS
PESSCDVKLVEKSFETDTNLNFQNLSVIGFRILLLKVAGFNLLMT
LRLWSS

[Chemical Formula 3]

(SEQ ID NO: 79)
>TCR_hum_Cbeta_1
EDLNKVFPPEVAVFEPSEAEISHTQKATLVCLATGFFPDHVELSW
WVNGKEVHSGVSTDPQPLKEQPALNDSRYCLSSRLRVSATFWQNP
RNHFRCQVQFYGLSENDEWTQDRAKPVTQIVSAEAWGRADCGFTS
VSYQQGVLSATILYEILLGKATLYAVLVSALVLMAMVKRKDF

[TCR Transgene]

A QYD specific TCRαβ gene was obtained from a CMV pp65 QYD antigen specific CD8+ T cells in the peripheral blood of a healthy individual by using hTEC10, and was used as the transgene.

[Antigen Specificity of Treg]

The binding affinity to a QYD antigen of a T cell to which TCR was introduced was measured to confirm introduction of the TCR. It was confirmed whether there is antigen specificity of Treg (QYD-Treg) by QYD tetramer staining.

(Results)

Figure 6:
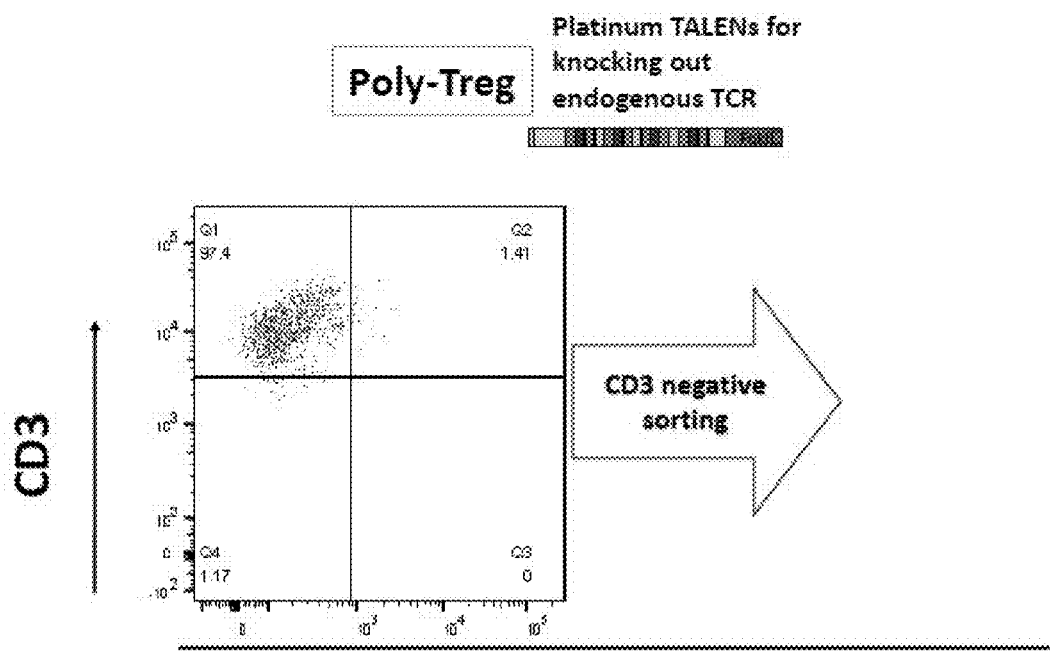
FIG. 6 is a diagram showing that polyclonal Treg TCR can be completely substituted with an antigen specific TCR by removing an endogenous TCR and introducing an exogenous antigen specific TCR.
Figure 7:
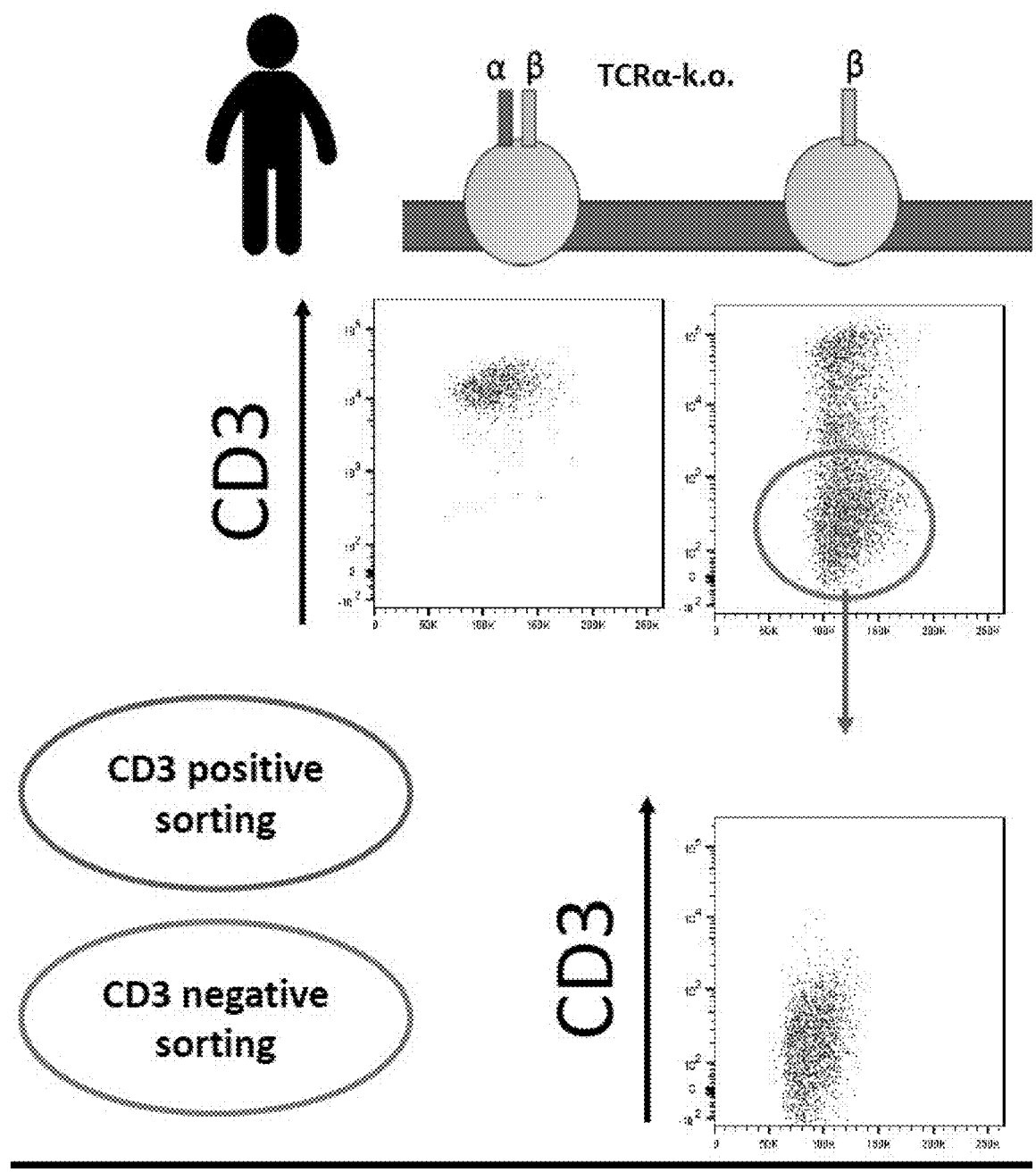
FIG. 7 is a schematic diagram showing the procedure for removing an endogenous TCR and introducing an exogenous antigen specific TCR by the method of the invention. The state of CD3 expression of cells in each step is shown. The middle row shows the distribution of CD3 expression of a cell population before sorting by CD3 expression. The bottom row shows the distribution of CD3 expression of a cell population after sorting by CD3 expression.

The results of introduction to regulatory T cells are shown in FIGS. 5 and 6. It is understood from the results of flow cytometry that only the introduced TCR is expressed in the T cells after modification.

Figure 8:
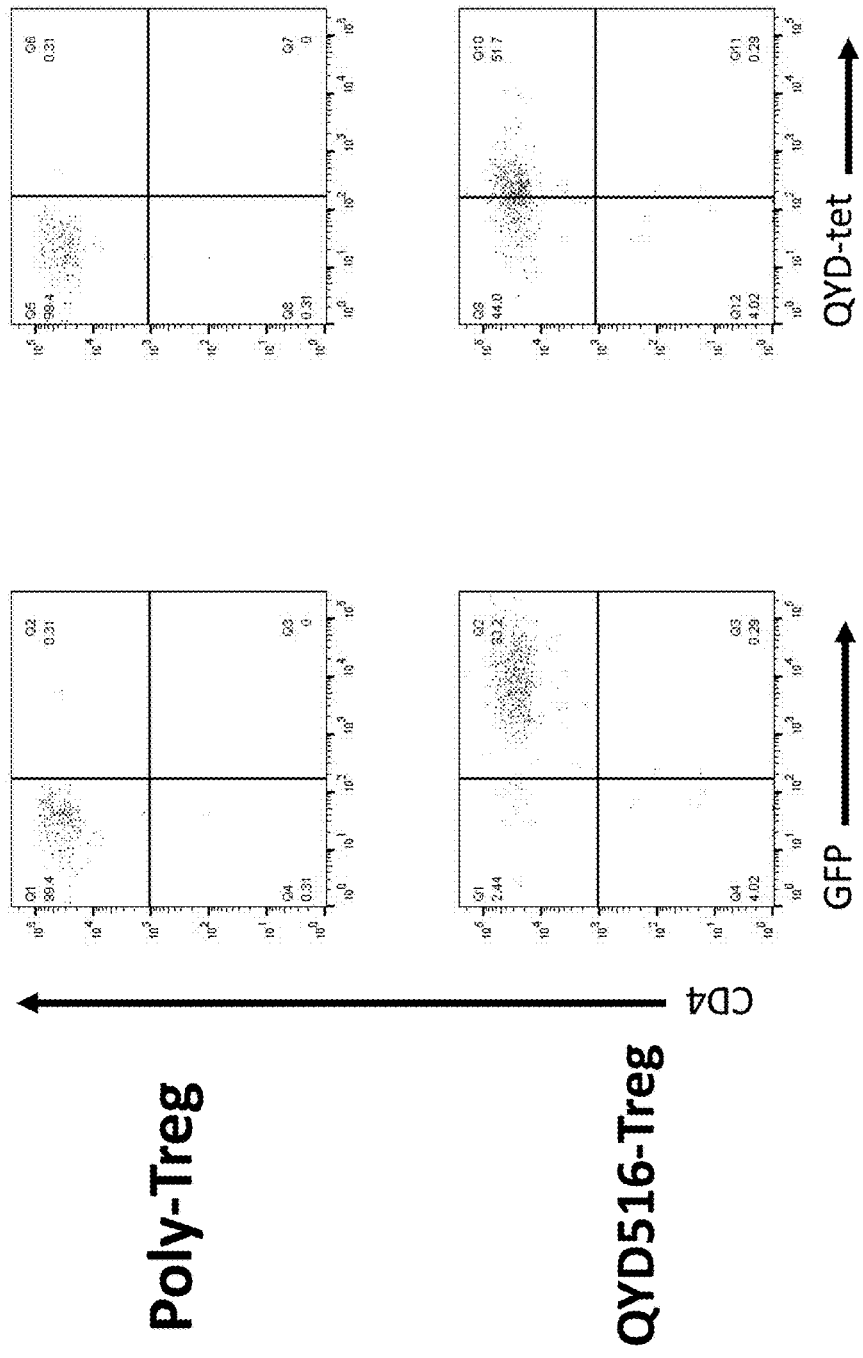
FIG. 8 is a diagram comparing the affinity of a polyclonal regulatory T cell (Poly-Treg) and regulatory T cell introduced with a TCR specific to a CMV antigen (QYD516) recognized by CD8+ T cells (QYD-Treg) to an antigen (QYD516). The left column shows GFP labels, and the right column shows QYD-tetramer labels. A functional subpopulation (CD4+) of each cell population was compared to polyclonal cells. It is understood that a group introduced with an antigen specific TCR has acquired affinity to an antigen.

The results of measuring the binding affinity to QYD are shown in FIG. 8. The binding affinity to QYD was increased in Treg introduced with a QYD specific TCR compared to polyclonal Treg.

Figure 9:
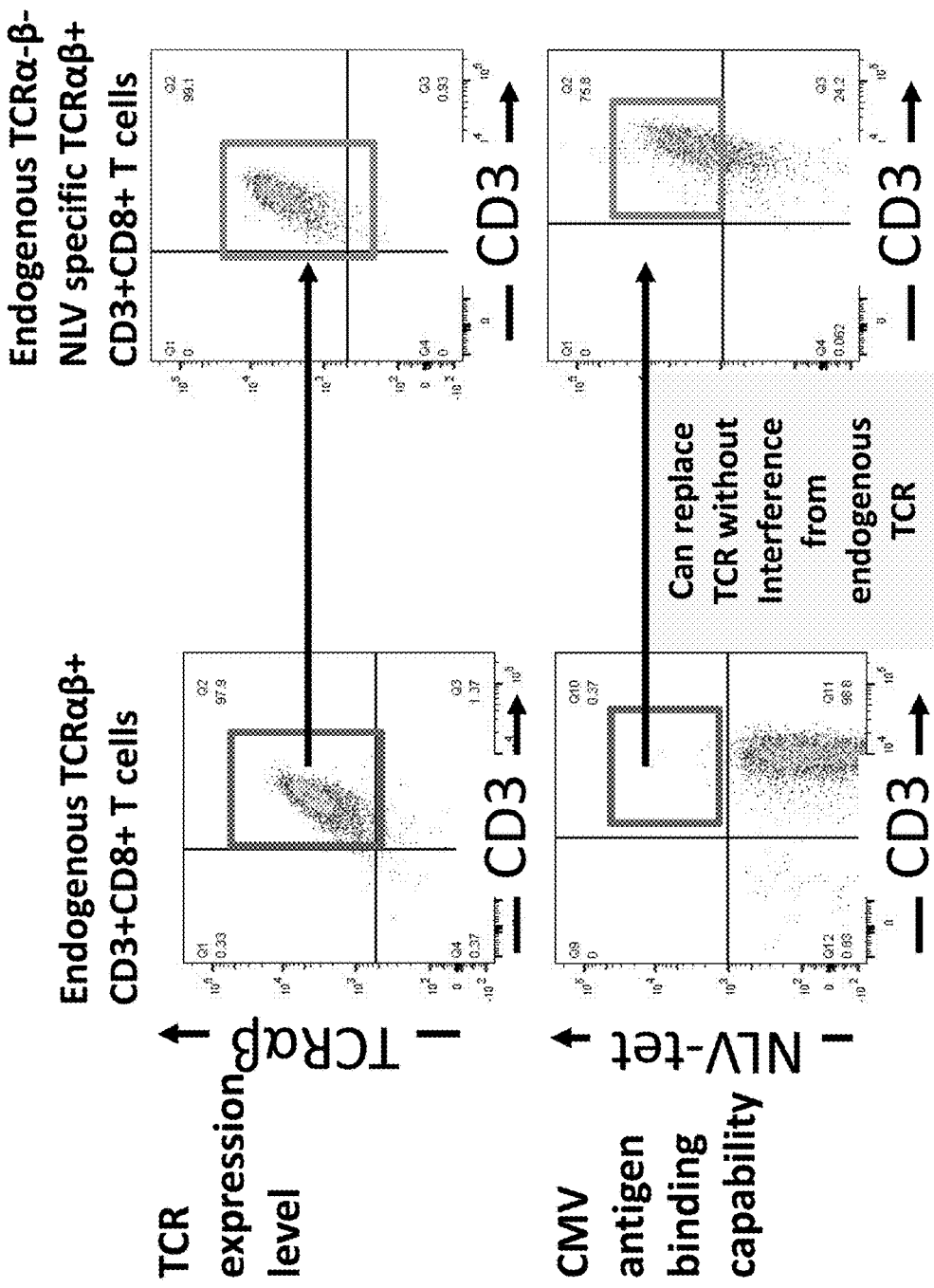
FIG. 9 shows the creation of cytomegalovirus specific cytotoxic T cells using the technology of the present disclosure (human peripheral blood T cells). The results of introducing a TCR into a cytotoxic T cell are shown. The top row shows results of analysis with the amount of expression of TCRαβ, and the bottom row shows results of analyzing the CMV antigen binding capability with an NLV-tetramer. The left column shows the analysis for a T cell having an endogenous TCR, and the right column shows analysis for a T cell with removal of an endogenous TCR and introduction of an NLV specific TCR. It is understood that a TCR was able to be replaced without interference from an endogenous TCR.

The results of similar TCR introduction to cytotoxic T cells are shown in FIG. 9. It is understood that TCR replacement was possible without interference from an endogenous TCR.

High affinity CMV pp65 NLV specific TCR expressing T cells were able to be established from knockdown of endogenous TCR by a TCR-specific TALEN and gene transfer by Cys-TCR.

Example 4: Properties of Manufactured Antigen Specific Regulatory T Cells (Summary)

The properties of antigen specific regulatory T cells manufactured in accordance with the approach in Example 3 were evaluated as follows.

[Confirmation of Retention of Treg Inherent Traits]

Antigen specific regulatory T cells manufactured in accordance with the approach in Example 3, polyclonal regulatory T cells, and TCR knockout regulatory T cells and control (CD25 negative CD4 positive T cell fraction) were stained with the following antibody, measured by FACS, and analyzed with respect to fluorescence intensity with FACS analysis software (flow jo) to investigate whether there is a difference in the properties of TCR replaced Treg and polyclonal Treg (before TCR replacement).

Figure 10:
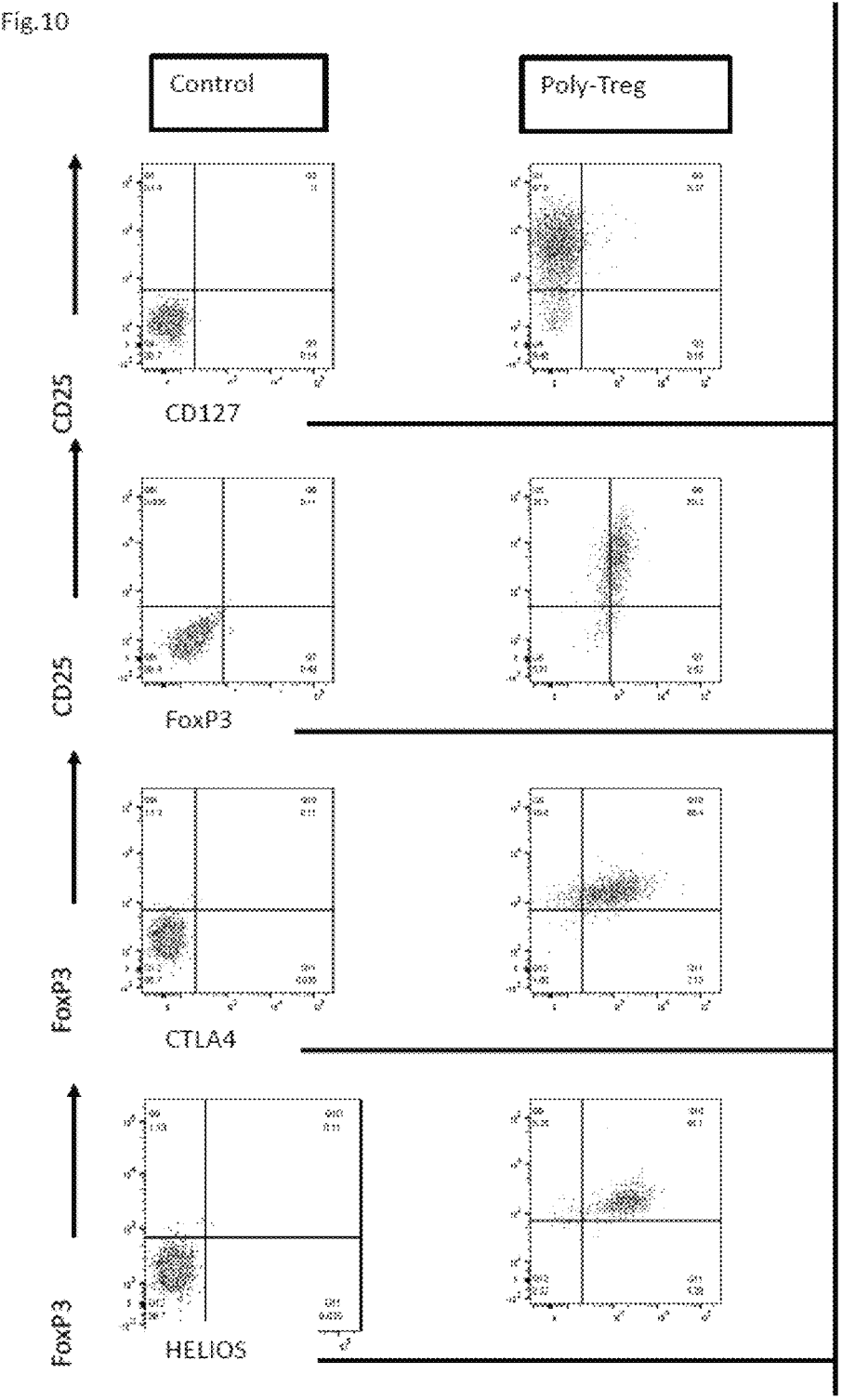
FIG. 10 is a dot plot showing the expression of a surface marker for an antigen specific regulatory T cell (rightmost column), polyclonal regulatory T cell (second column from left), TCR knockout regulatory T cell (second column from right), and control (CD25 negative CD4 positive T cell fraction; leftmost column). The top row shows analysis for CD127 and CD25, the second row from the top shows analysis for CD25 and FoxP3, the third row from the top shows analysis for FoxP3 and CTLA4, and the fourth row from the top shows analysis for FoxP3 and HELIOS.
Figure 11:
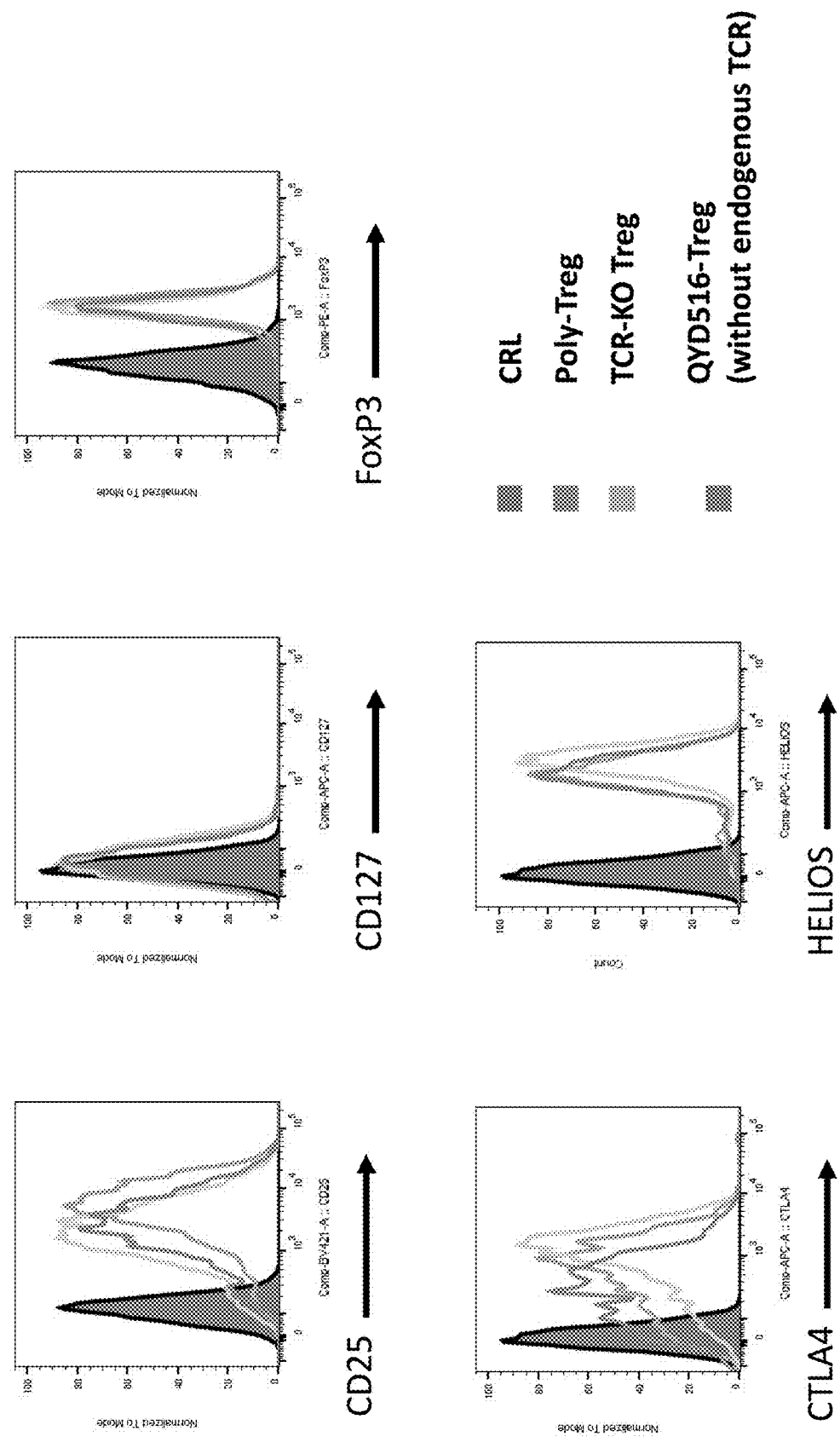
FIG. 11 is a histogram showing the expression of a surface marker for an antigen specific regulatory T cell, polyclonal regulatory T cell, TCR knockout regulatory T cell, and control (CD25 negative CD4 positive T cell fraction). The top row shows analysis for, from the left, CD25, CD127, and FoxP3, and the bottom row shows analysis for, from the left, CTLA4 and HELIOS.

Antibodies: Anti-human CD25 antibody, Anti-human CD127 antibody, Anti-human FoxP3 antibody, Anti-human CTLA-4 antibody, and Anti-human HELIOS antibody The results are shown in FIGS. 10 and 11. It was found that there is no significant difference in the surface marker expression of these cells, and traits inherent to regulatory T cells are retained after removal and introduction of TCR in the present invention.

[Growth in Response to Antigen Stimulation]

Tregs (QYD-Treg) obtained by TCR substitution in Example 3 were studied as to whether they recognizes QYD peptide antigens and grow, and more specifically as follows.
(1) QYD-Tregs were pelleted by centrifugation and were suspended with 1 ml of PBS.
(2) 1 μL of Cell trace violet was added (Invitrogen, Cell-Trace Violet Cell Proliferation Kit, cat #C34557), and the Treg was shielded from light and incubated for 20 minutes at 37° C.
(3) The Treg was washed twice with PBS (300 G, 10 min, room temperature).
(4) Peptide pulsed antigen presenting cells and cell trace violet labeled QYD-Treg were mixed in a T cell culture (X-VIVO20+10% AB serum 2 mmol/l L-Glutamin 1% penicillin/streptomycin) so that the cell counts would be 1:1, and cultured for 5 days in a 96 well plate.
(5) FACS confirmed that the fluorescence intensity of Cell trace violet was attenuated, and QYD-Treg was divided.

Figure 12:
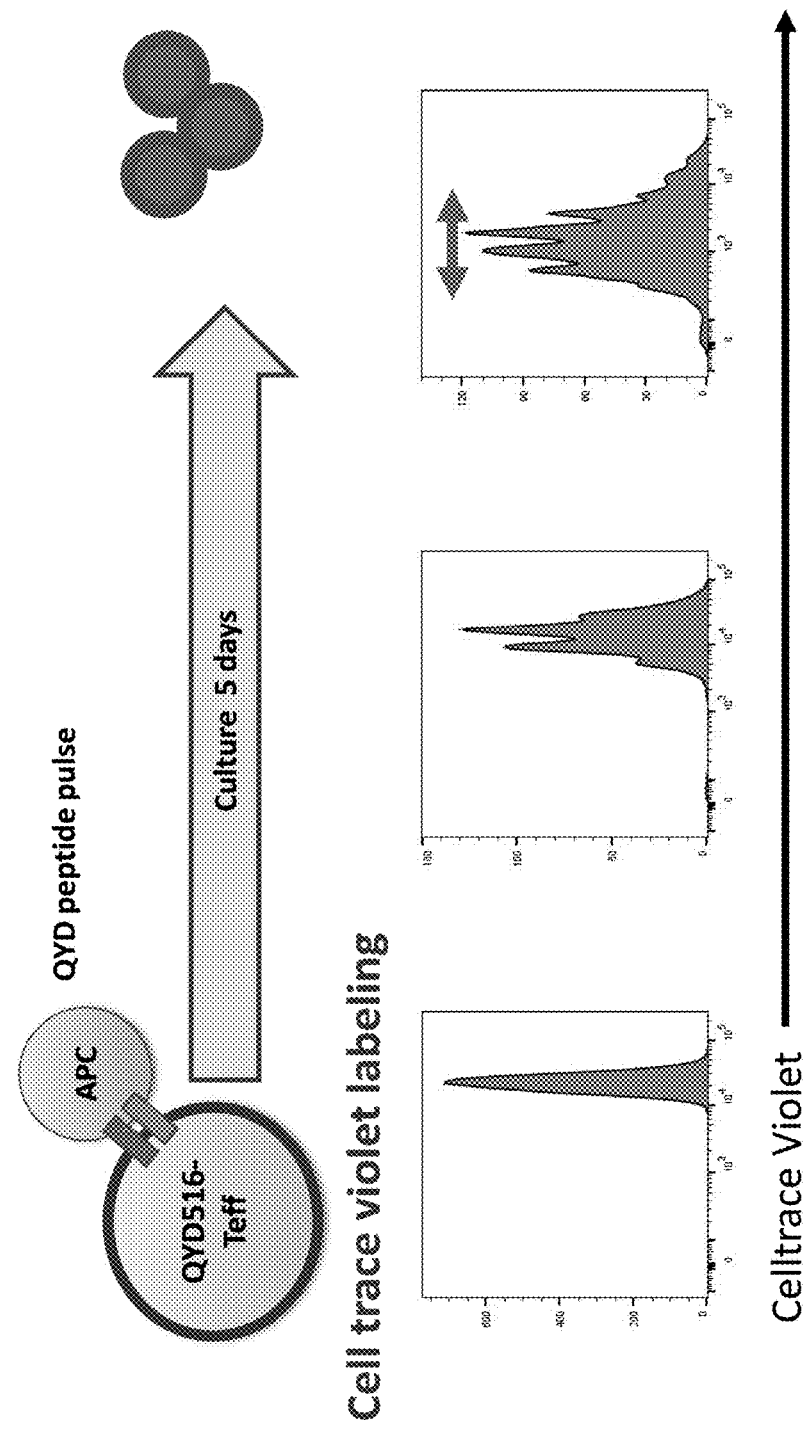
FIG. 12 is a diagram showing the growth of antigen specific effector T cells due to antigen stimulation. The growth is shown for, from the left, day 0, day 3, and day 5. It is understood that QYD-516 specific effector T cells grew in response to antigen stimulation.
Figure 13:
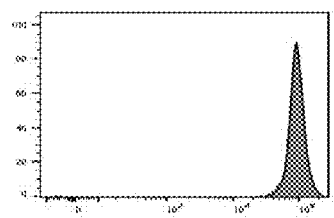
FIG. 13 shows growth of QYD-516 specific Treg that responded to antigen stimulation. The figure shows that the QYD-516 specific Treg grew in response to antigen stimulation by antigen presenting cells. While the growth of regulatory T cells was not observed for polyclonal regulatory T cells, growth was observed in an antigen specific regulatory T cell population.
Figure 13:
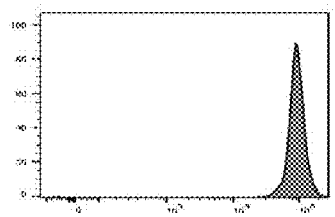
Figure 13:
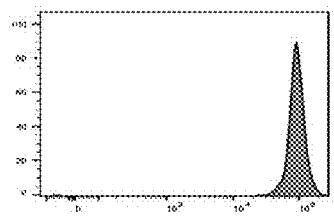
Figure 13:
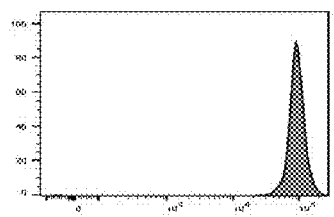

The results are shown in FIGS. 12 and 13. After 5 days of culture, the fluorescence intensity of Cell trace violet was attenuated. It is understood that QYD-Treg grew in response to antigen stimulation by antigen presenting cells. The growth was not observed in a group without QYD stimulation or the group of polyclonal regulatory T cells, demonstrating the highly specific response to antigen of the manufactured regulatory T cells by the method of the invention.

[Suppression of Antigen Specific Effector T Cell by Antigen Specific Regulatory T Cell]

It was studied whether Treg (QYD-Treg) obtained by TCR substitution suppresses antigen specific growth of QYD-Teff, more specifically in the following manner.

A. Separation of antigen presenting cells (separation of CD4 negative CD8 negative cells)

Miltenyi CD8 microbeads, human (130-045-201) were used, and a Miltenyi CD4+ T Cell isolation kit, human (130-096-533) was used:
(1) PBMCs were separated from 50 mL of peripheral blood with Ficoll-Paque PREMIUM, and cell pellets were created by centrifugation (400 G, 10 min, room temperature).
(2) The pellets were suspended in 80 μL of MACS Buffer, and of CD8 MicroBeads were added.
(3) The pellets were incubated for 15 minutes at 4° C.
(4) The pellets were washed with MACS Buffer (300 G, 10 min, room temperature).
(5) MACS Buffer was added so as to reach a total of 500 μL, and CD8− fractions were collected by magnetic separation and centrifuged (400 G, 10 min, room temperature) to create cell pellets.
(6) The pellets were suspended in 40 μL of MACS Buffer, and 10 μL of T Cell Biotin-Antibody Cocktail was added.
(7) The pellets were incubated for 5 minutes at 4° C.
(8) 30 μL of MACS Buffer and 20 μL of CD4+ T Cell MicroBead Cocktail were added.
(9) The pellets were incubated for 10 minutes at 4° C.
(10) MACS Buffer was added so as to reach a total of 500 μL, and CD4− fractions were collected by magnetic separation (CD4−8− T cells are formed).

B. Peptide Pulsing of Antigen Presenting Cells
(1) CD4−8− cells collected in A were suspended in 1 ml of X-VIVO 20
(2) A peptide (QYDPVAALF: QYD (SEQ ID NO: 80 endogenous)) was added so as to reach 1 μM.
(3) The cells were incubated for 2 hours at room temperature.
(4) 35 Gy of γ ray was irradiated.

C. Treg Suppression Assay (1) CD8+ T cells that have undergone gene transfer of QYD-TCR (QYD-T eff) were pelleted by centrifugation and were suspended with 1 ml of PBS.
(2) 1 µL of Cell trace violet was added (Invitrogen, Cell-Trace Violet Cell Proliferation Kit, cat #C34557), and the cells were shielded from light and incubated for 20 minutes at 37° C.
(3) The cells were washed twice with PBS (300 G, 10 min, room temperature).
(4) The antigen presenting cells that were peptide pulsed in a step of B and cell trace violet labeled QYD-Teff were mixed in a T cell culture (X-VIVO 20+10% AB serum+2 mmol/1 L-Glutamin+1% penicillin/streptomycin) so that the cell counts would be 2:1, and seeded in a 96 well plate.
(5) C. The Treg (Treg introduced with a desired TCR) cell count was adjusted and added to each well of (4) so that the ratio to cell counts with respect to CD8+ T cells would be 16:1, 8:1, 4:1, 2:1, or 1:1.
(6) Fluorescence intensity of cell trace violet under conditions of each cell ratio was measured by FACS on days 5 and 7 to confirm suppression of growth of QYD-Teff.

Figure 14:
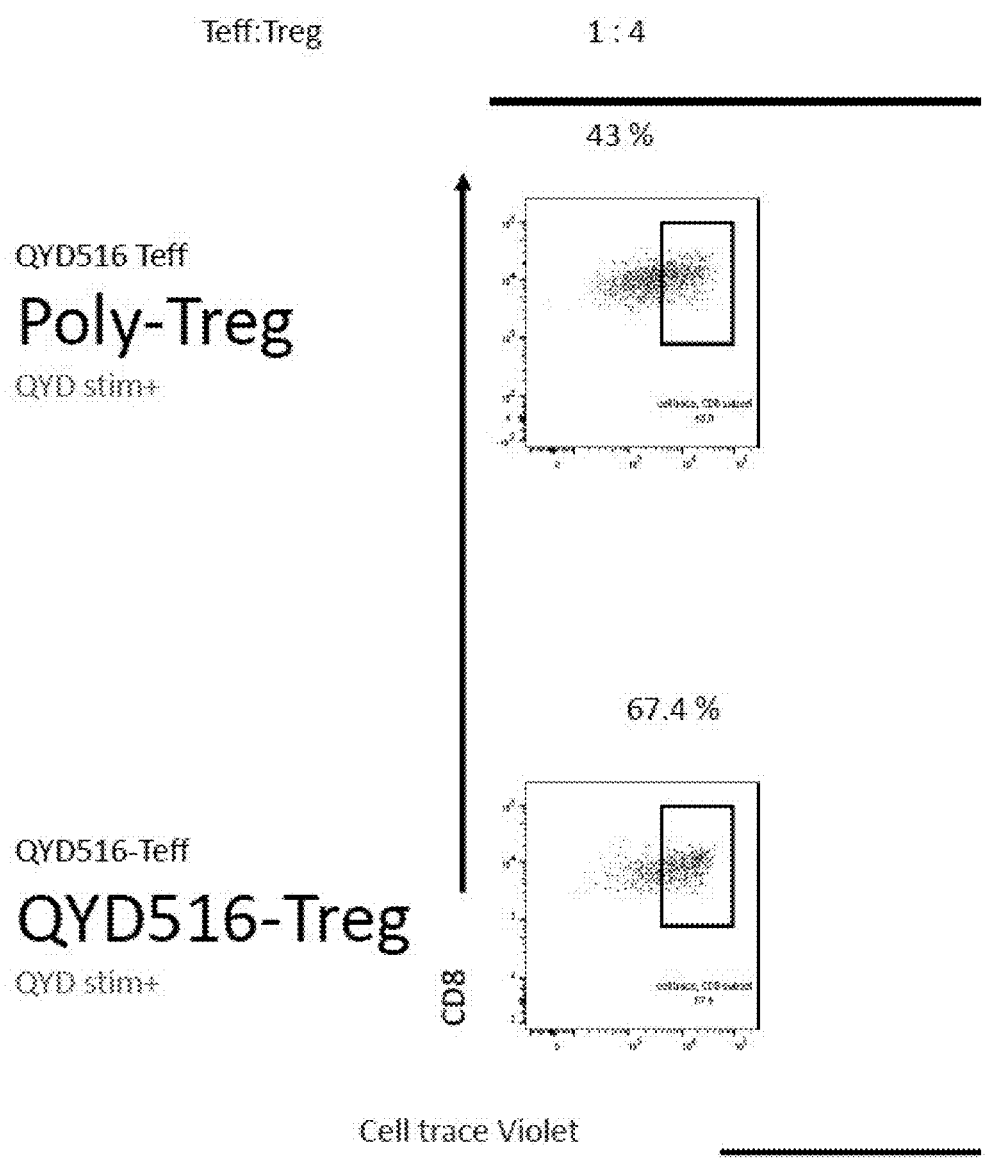
FIG. 14 is a diagram showing that the growth of antigen specific effector T cells due to antigen stimulation is suppressed by an antigen specific regulatory T cell. It is shown that QYD-Treg was better than Poly-Treg in suppression of QYD-Teff growth.
Figure 15:
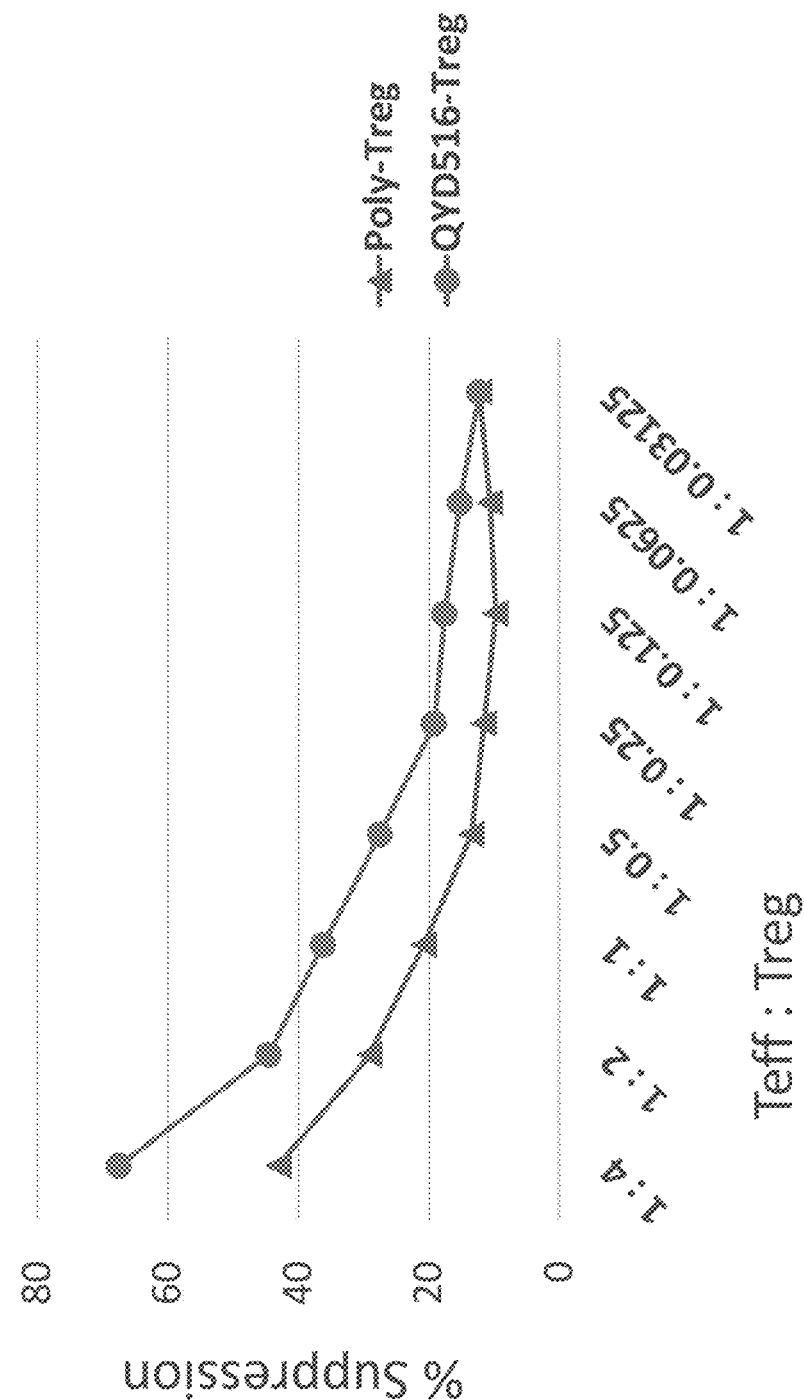
FIG. 15 is a diagram showing that the growth of antigen specific effector T cells due to antigen stimulation is suppressed by an antigen specific regulatory T cell. It is shown that QYD-Treg was better than Poly-Treg in suppression of QYD-Teff growth.

The results are shown in FIGS. 14 and 15. Antigen specific regulatory T cells exhibited significantly higher suppression of effector T cell growth compared to polyclonal regulatory T cells.

Example 5: In Vitro Immunosuppression by Antigen Specific Regulatory T Cells (Summary)

The objective of this Example is to demonstrate in vitro that antigen specific regulatory T cells manufactured in accordance with the method of the invention can be applied to autoimmune diseases.

MART-1 antigens, autoantigens of skin pigment cells, are target antigens that can be the cause of vitiligo, which is a refractory autoimmune disease in the field of dermatology. T cells that recognize this antigen are also present in the peripheral blood of healthy individuals.

(Materials and Methods)

(1) Clone a MART-1 specific TCRαβ pair gene using hTEC10 from a specimen of a healthy individual.
(2) Edit the TCR genome of regulatory T cells with Platinum TALEN to eliminate the expression of endogenous TCR.
(3) Grow regulatory T cells after genome editing.
(4) Introduce the cloned TCRαβ pair gene into the grown regulatory T cells.
(5) Evaluate the change in responsiveness to a MART-1 antigen of MART-1 antigen specific effector T cells or the like by co-culture with regulatory T cells introduced with a TCR gene.

(Results)

18 or more types of MART-1 specific TCRαβ pair genes can be cloned using hTEC10 from specimens of two healthy individuals. The binding affinity to MART-1 of these MART-1 specific TCRs can be evaluated to select the most highly functional TCR and create MART-1 antigen specific Treg introduced with a gene of said TCR. Immune responses to a MART-1 antigen as a model antigen of autoimmune disease is suppressed by the TCR substituted Treg described above.

Example 6: Analysis of Efficacy of Teff→Treg on Autoimmune Disease Mouse Model (Summary)

Figure 16:
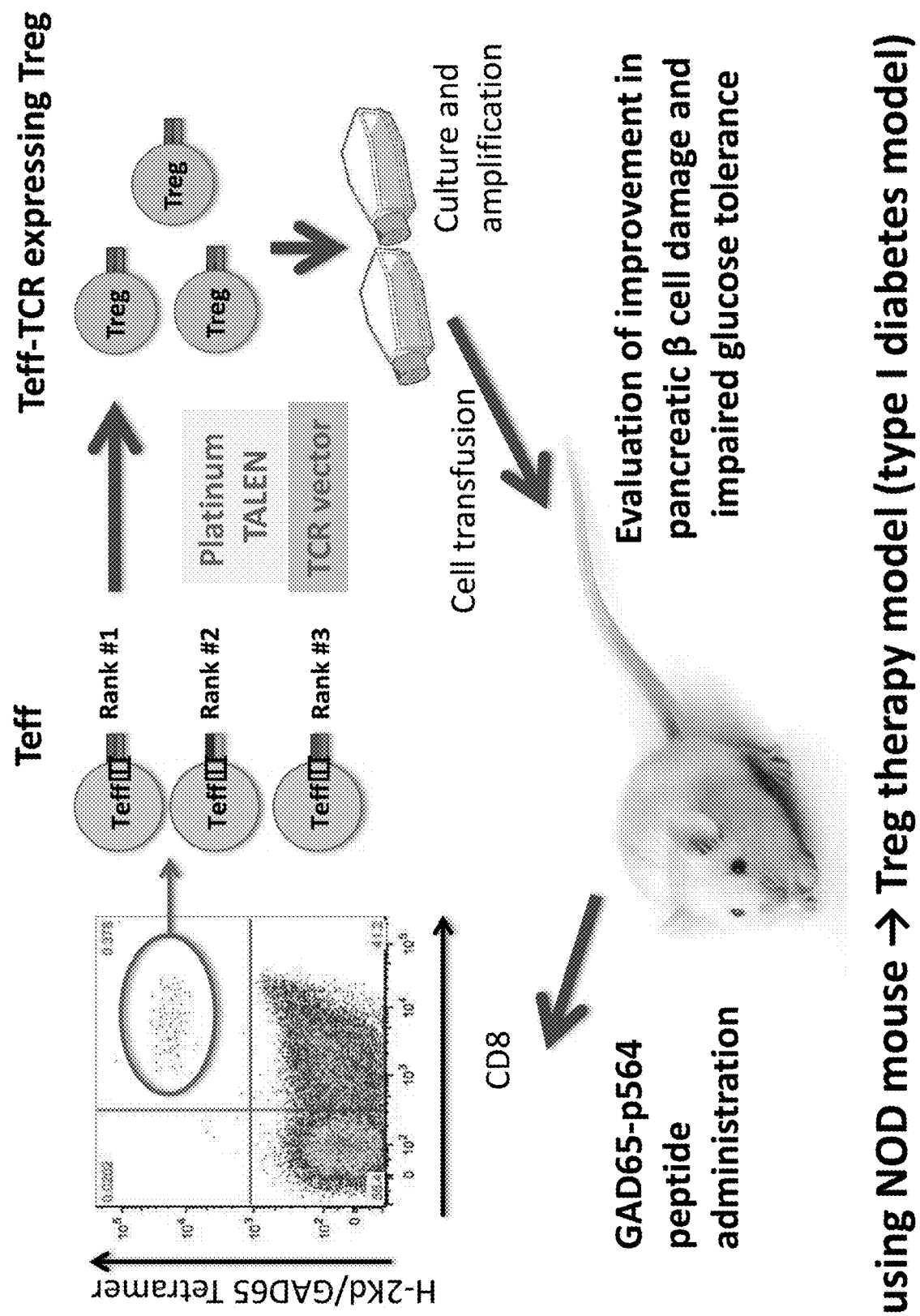
FIG. 16 is a diagram showing the summary of an experiment using an animal model in Example 6.

This Example shows immunosuppression by the manufactured antigen specific regulatory T cells in an animal model in order to demonstrate the in vivo applicability of antigen specific regulatory T cells to autoimmune diseases. The summary of this Example is shown in FIG. 16.

(Materials and Methods)

The following mouse and autoantigens are used to investigate the applicability to the following disease models.
Mouse model: NOD (non-obese diabetic) mouse
Autoantigen model: GAD65
Disease model: type I diabetes
Animal experiments are conducted as follows.
(1) Transnasally administer peptide antigen p546 (30 µg) from GAD65 to a 7-day old NOD mouse on days 7, 9, and 11 since birth.
(2) Separate p546 responsive effector CD8+ T cells (p546-Teff) from a 4-week old female mouse immunized by the method of (1) by flow cytometry by using an H-2Kd/p546 tetramer.
(3) Comprehensively identify TRAV and TRBV of p546-Teff with a next generation sequencer to confirm the presence of a high frequency clonotype, and then identify a pair by single cell cloning.
(4) Introduce p546 antigen responsive TCR (p546-TCReff) identified by the processes of (1) to (3) described above into a mouse T cell strain lacking the expression of an endogenous TCR using a retroviral vector, and determine the functional hierarchy thereof.
(5) Separate CD4+CD25+ regulatory T cells by the bead column method from the spleen/lymph node/peripheral blood of a 4-week old male NOD mouse and knock out TCR using Platinum TALEN.
(6) Introduce a candidate of highly functional p546-Teff-TCR obtained in the process of (4) into TCR knockout CD4+CD25+ regulatory T cells (p546-Teff-TCR expressing Treg).
(7) Amplify Treg introduced with a Mock vector and Treg introduced with p546-TCReff in the presence of anti-CD3/CD28 antibodies and IL-2, and transfuse the Treg into a NOD mouse that has developed type I diabetes, and compare whether improvement in pancreatic β cell damage and impaired glucose tolerance is achieved.

(Results)

Improvement in pancreatic β cell damage and impaired glucose tolerance is not observed in the NOD mouse transfused with Mock vector-introduced Treg, but improvement in pancreatic β cell damage and impaired glucose tolerance is observed in the NOD mouse transfused with p546-TCReff-introduced Treg.

Example 6-2: Cleavage of Mouse TCR (Summary)

Platinum TALEN was created for cleaving mouse TCR to evaluate the cleavage activity by an assay (SSA assay) using a reporter plasmid.

(Materials and Methods)

Three types of Platinum TALEN (TRA2-TALEN, TRB1-TALEN, and TRB2-TALEN) were created for cleavage of mouse TCR.

Mouse TRA2-TALEN, mouse TRB1-TALEN, and mouse TRB2-TALEN were designed to include a cleavage site within the TRA gene Cα2 region, TRB gene Cβ1 region, and TRB gene Cβ1 region of the mouse, respectively. The respective target sequences were:

mouse TRA2-TALEN: left side TCTGCCTGTT-CACCGACT (SEQ ID NO: 113) and right side AATGTGCCGAAAACCATGGA (SEQ ID NO: 114), mouse TRB1-TALEN: left side TGACTCCACC-CAAGGTCTCC (SEQ ID NO: 115) and right side AAAAGCAGAGATTGCAAACA (SEQ ID NO: 116), mouse TRB2-TALEN: left side TGTGCTTGGCCAGGGGCTTC (SEQ ID NO: 117) and right side GGAGCTGAGCTGGTGGGTGA (SEQ ID NO: 118). The preparation procedure for Platinum TALEN was in accordance with [Manufacture of Platinum TALEN] in (Example 2: Removal of endogenous TCR).

An SSA assay using human embryonic kidney derived cell strain HEK293T was conducted by the method described in the following URL (Sakuma T, et al. Genes to Cells 2013). http://www.mls.sci.hiroshima-u.ac.jp/smg/genome editing/documents/6-module.pdf (Results)

Figure 23:
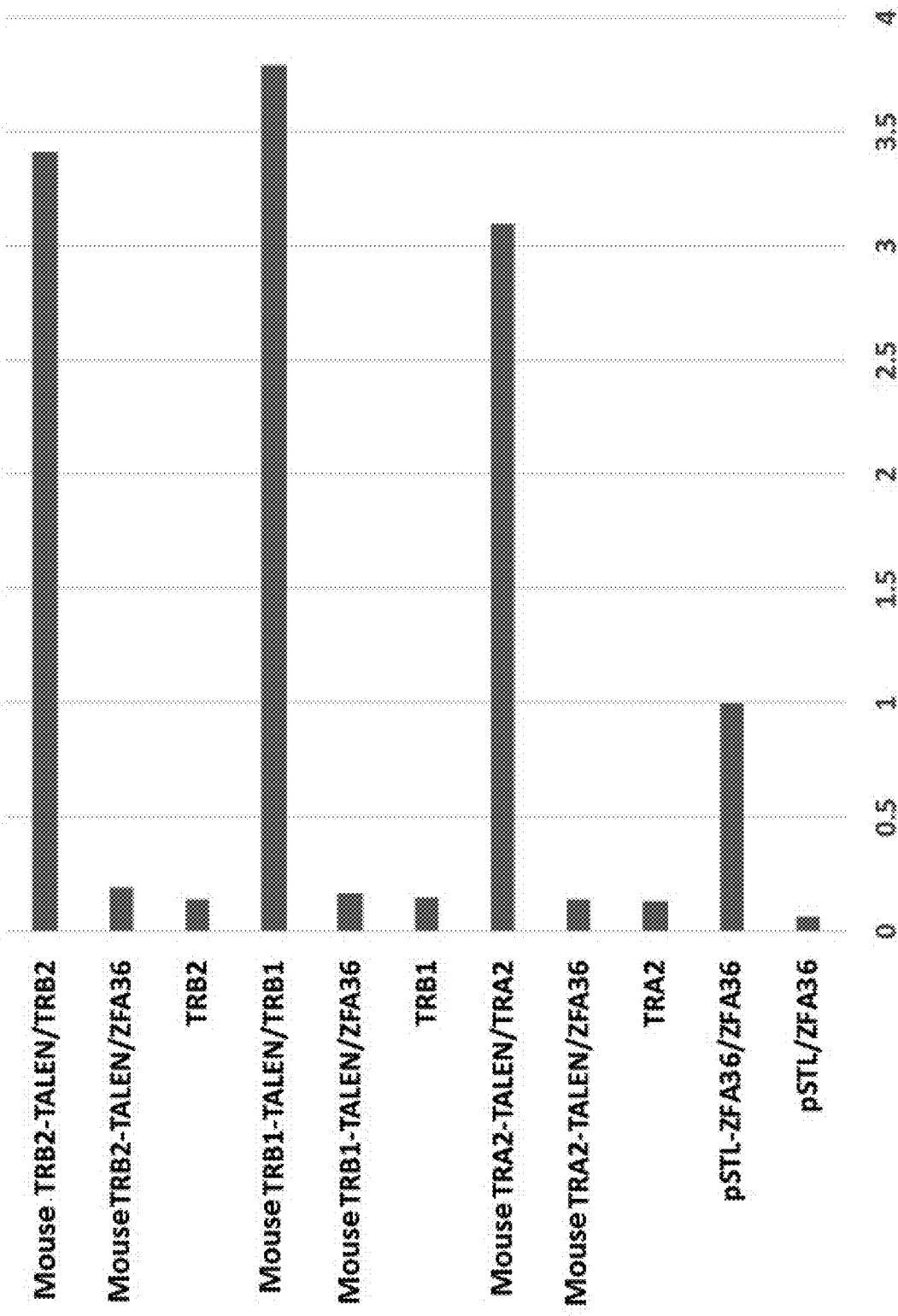
FIG. 23 is a diagram showing results of evaluating the cleavage activity of three types of platinum TALEN (TRA2-TALEN, TRB1-TALEN, and TRB2-TALEN) produced for cleaving a mouse TCR, by an assay method (SSA assay) using a reporter plasmid. It can be understood that if the cleavage activity of a zinc finger nuclease control (pSTL-ZFA36/ZFA36) is 1, the activities on a target cleavage site of mouse TRA2-TALEN, mouse TRB1-TALEN, and mouse TRB2-TALEN are 3.09-fold, 3.79-fold, and 3.41-fold, respectively. pSTL is a negative control for ZFA36. TRA2, TRB1, and TRB2 are each negative controls for only a reporter in the absence of TALEN, and TRA2-TALEN/ZFA36, TRB1-TALEN/ZFA36, and TRB2-TALEN/ZFA36 are each negative controls when a reporter gene is ZFA36.

The results are shown in FIG. 23. It can be understood that if the cleavage activity of a Zinc finger nuclease control (pSTL-ZFA36/ZFA36) is 1, the activity against the target cleavage site of mouse TRA2-TALEN, mouse TRB1-TALEN, and mouse TRB2-TALEN is 3.09-fold, 3.79-fold, and 3.41-fold, respectively. pSTL is a negative control of ZFA36. TRA2, TRB1, and TRB2 are negative controls of only a reporter in the absence of TALEN. TRA2-TALEN/ZFA36, TRB1-TALEN/ZFA36, and TRB2-TALEN/ZFA36 are each negative controls when the reporter gene is ZFA36.

Example 7: Example of Production

A product comprising one or more of the following components is provided for use in the method of the invention.

Means for editing a TCR gene: is provided in a form of a composition or the like for editing a TCR gene; and uses a genome editing enzyme (TALEN, CRISPR/Cas9, ZEN) that targets a TCR gene or the like. A targeting site and a functional domain are provided together, or they are provided separately. Alternatively, a genome editing enzyme is provided in a form of a polypeptide. A genome editing enzyme is provided in a form of an mRNA. A genome editing enzyme is provided with an introducing vector.

Means for checking for a mutation of an endogenous TCR gene: provides a PCR primer specific to an endogenous TCR gene. It is possible to check, before genome editing, that there is no mutation at a targeted site so that a specific editing can be performed.

Means for checking for the removal of an endogenous TCR gene: provides an antibody used in measurement of a change upon removal of endogenous TCR; provides an anti-CD3 antibody or anti-TCR antibody; and provides a labeled antibody.

Means for introducing an exogenous TCR: provides a vector or the like for introducing TCR; and uses a lentiviral vector incorporating a fluorescent pigment with low cytotoxicity such as Venus or a non-viral vector such as Sleeping Beauty utilizing transposon.

Means for detecting cells introduced with a gene: provides an antibody used in the measurement of a change upon introduction of an endogenous TCR; provides an anti-CD3 antibody or anti-TCR antibody; and provides a labeled antibody.

Example 8: TCR Substitution by TAL-PITCh Method (Summary)

The modified T cells of the invention can be created by the TAL-PITCh method without using a viral vector.

(Materials and Methods)

Creation of endogenous TCR deficient NY-ESO-1 specific T cells using TAL-PITCh method Endogenous TCR deficient NY-ESO-1 specific T cells were created in accordance with the procedure described below.

1. mRNA Synthesis from Platinum TALEN:

(1) Treat plasmids of Left (L)-TALEN and Right (R)-TALEN for cleaving a TRA or TRB gene for 2 hours at 30° C. with SmaI.

(2) Treat with Proteinase K for 20 minutes at 50° C. and then purify with a QIAGEN PCR Purification Kit.

(3) Synthesize mRNA with an mMESSAGE MACHINE T7 Kit (Life technologies), followed by poly(A) Tailing Kit (Life technologies) and purify the mRNA by LiCl precipitation method (in accordance with the Manufacturer's instruction).

Figure 20:
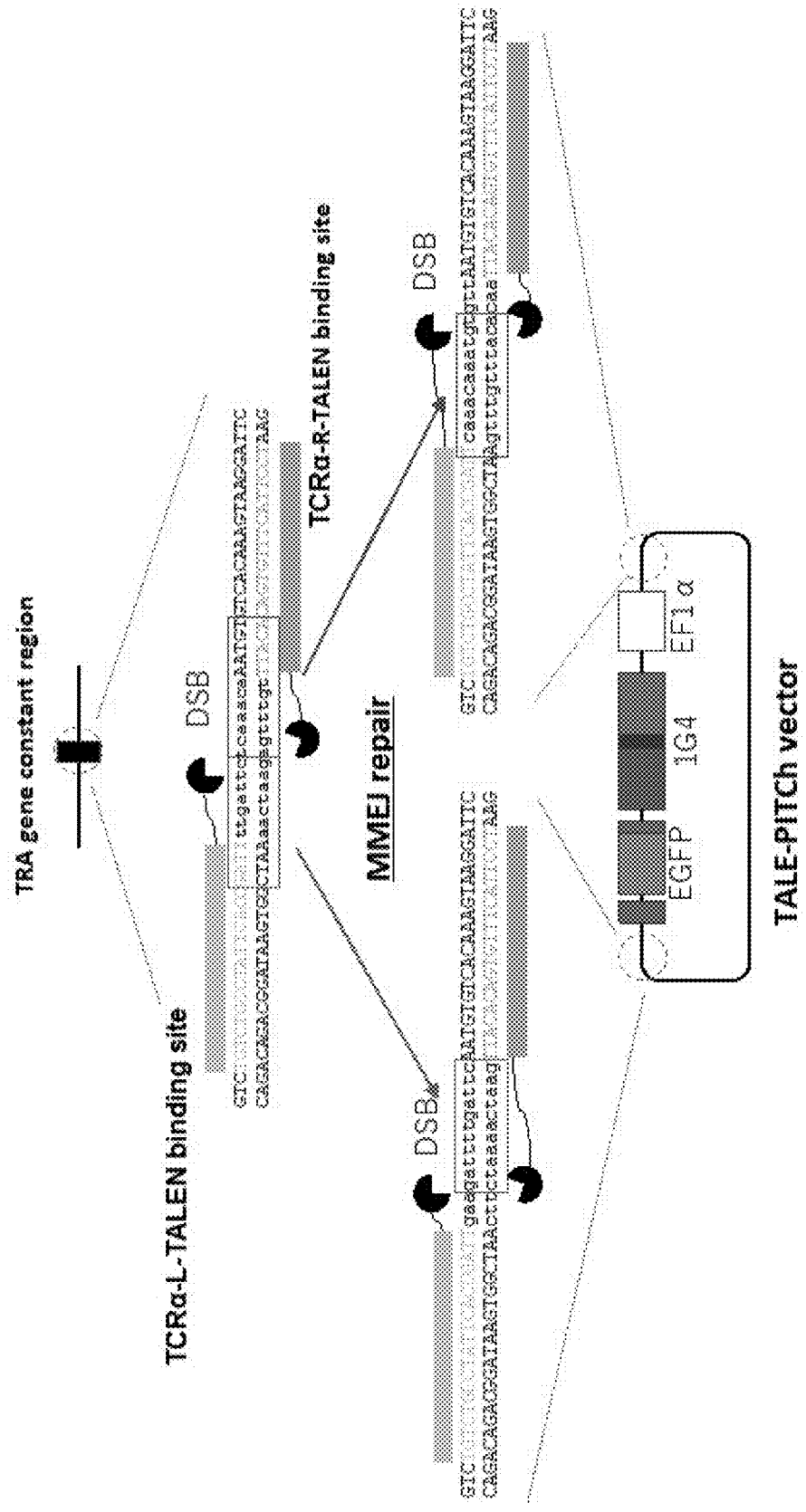
FIG. 20 is a schematic diagram showing the design of a TAL-PITCh vector. The sequences therein correspond to SEQ ID NOs: 120 and 121, respectively.
Figure 21:
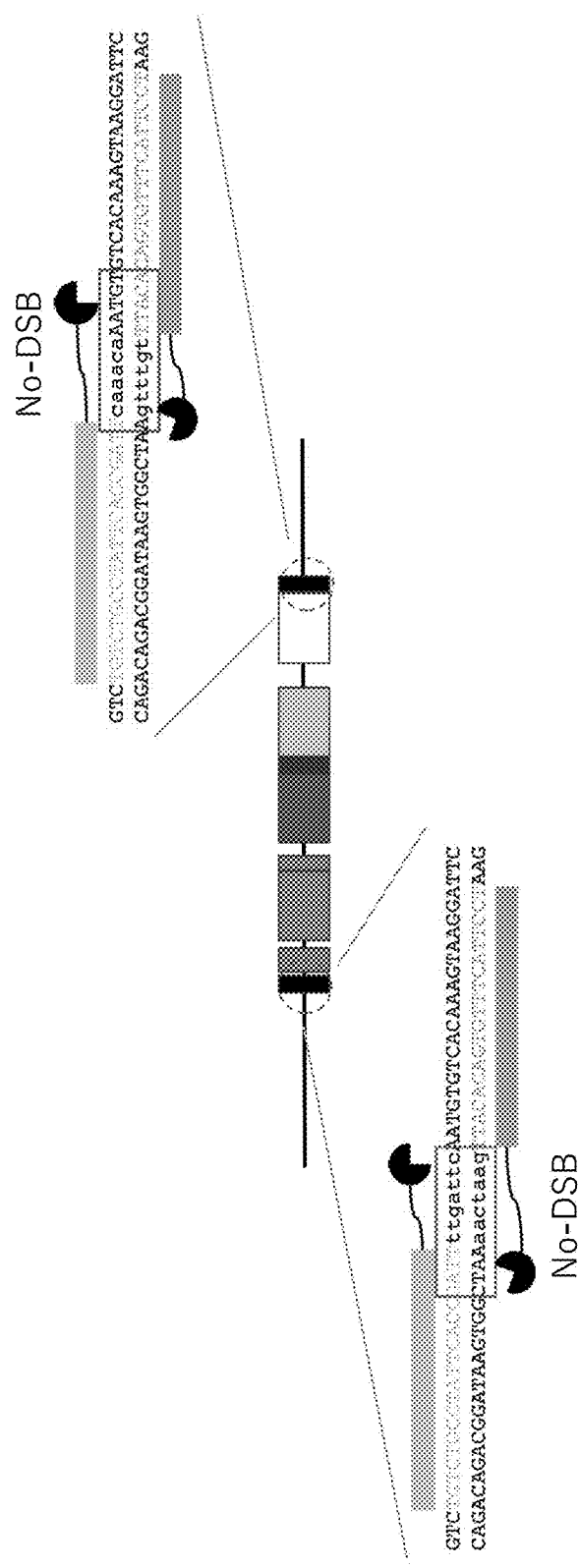
FIG. 21 is a schematic diagram showing the design of a TAL-PITCh vector. The sequences in the figure correspond to SEQ ID NOs: 120 and 121, respectively.

2. Design of TAL-PITCh Vector:

A TAL-PITCh vector is designed to be cleaved at both ends of a transgene with Left (L)-TALEN and Right (R)-TALEN for cleaving a TRA gene, such that a gene of interest is incorporated into the TRA gene cleavage site by microhomology mediated end joining (MMEJ) repair (FIG. 20; the portion surrounded by a square indicates a microhomology sequence). After the gene of interest is incorporated into the TRA gene cleavage site, there is a TALEN binding site at both ends, but not enough space to the cleavage site, so that a DNA double strand break (DSB) does not occur (FIG. 21). For a TAL-PITCh vector, a vector incorporating EGFP and a vector incorporating mKate2 are prepared to confirm by flow cytometry that both alleles of a TRA gene are cleaved (FIGS. 20 and 21 show a vector incorporating EGFP). For clinical applications, vectors with EGFP and mKate2 substituted with CD20 and CD34 as selection markers, respectively, are created.

3. Preparation of TRB Gene Cleaved T Cells Using Platinum TALEN mRNA:

(1) Stimulate peripheral blood T cells with CD3/28 beads, and culture the cells for 3 days with X-VIVO 20+10% AB serum+2 mmol/l L-Glutamin+1% penicillin/streptomycin.

(2) Introduce TCRβ-L-TALEN mRNA and TCRβ-R-TALEN mRNA into the cultured T cells using Amaxa 4D-Nucleofector (P3 Primary Cell 4D-Nucleofector™ X Kit S).

1) Prepare cell pellets from $5\times10^5$ to $1\times10^6$ T cells by centrifugation (400 G, 10 minutes, room temperature).

2) Suspend the cell pellets in a total of 20 μl of Nucleofector solution prepared by adding 3.6 μl of Supplement to 16.4 μl of Nucleofector P3 solution per reaction.

3) Add TCRβ-L-TALEN mRNA and TCRβ-R-TALEN mRNA at 10 μg each.

4) Perform Nucleofection (program: EO-115).

5) Continue culture.

6) Find the efficiency of cleavage of TCR gene after three days of Nucleofection by loss of expression of CD3 and TCRαβ by flow cytometry.

(3) Collect CD3 negative fractions by magnetic sorting or FACS (Aria II).

4. Introduction of NY-ESO-1 Specific TCR (1G4) into TRA Gene Cleavage Site Using TAL-PITCh Method:

(1) Stimulate TRB gene cleaved T cells obtained in 2 with CD3/28 beads and culture TRB gene cleaved T cells obtained in 2 for 3 days in X-VIVO 20+10% AB serum+2 mmol/l L-Glutamin+1% penicillin/streptomycin.

(2) Introduce TCRα-L-TALEN mRNA and TCRα-R-TALEN mRNA and 2 types of TAL-PITCh vectors (1G4-EGFP and 1G4-mKate2) into the cultured T cells using Amaxa 4D-Nucleofector (P3 Primary Cell 4D-Nucleofector™ X Kit S).

1) Prepare cell pellets from $5 \times 10^5$ to $1 \times 10^6$ T cells by centrifugation (400 G, 10 minutes, room temperature).

2) Suspend the cell pellets in a total of 20 µl of Nucleofector solution prepared by adding 3.6 µl of Supplement to 16.4 µl of Nucleofector P3 solution per reaction.

3) Add TCRα-L-TALEN mRNA, TCRα-R-TALEN mRNA, 1G4-EGFP TAL-PITCh vector, and 1G4-mKate2 TAL-PITCh vector at 10 µg each.

4) Perform Nucleofection (program: EO-115).

5) Continue culture.

6) Find the efficiency of introducing 1G4-EGFP and 1G4-mKate2 after three days of Nucleofection by expression of EGFP and mKate2 by flow cytometry.

(3) Collect fractions where EGFP and mKate2 are both positive by FACS (Aria II).

(Results)

Figure 22:
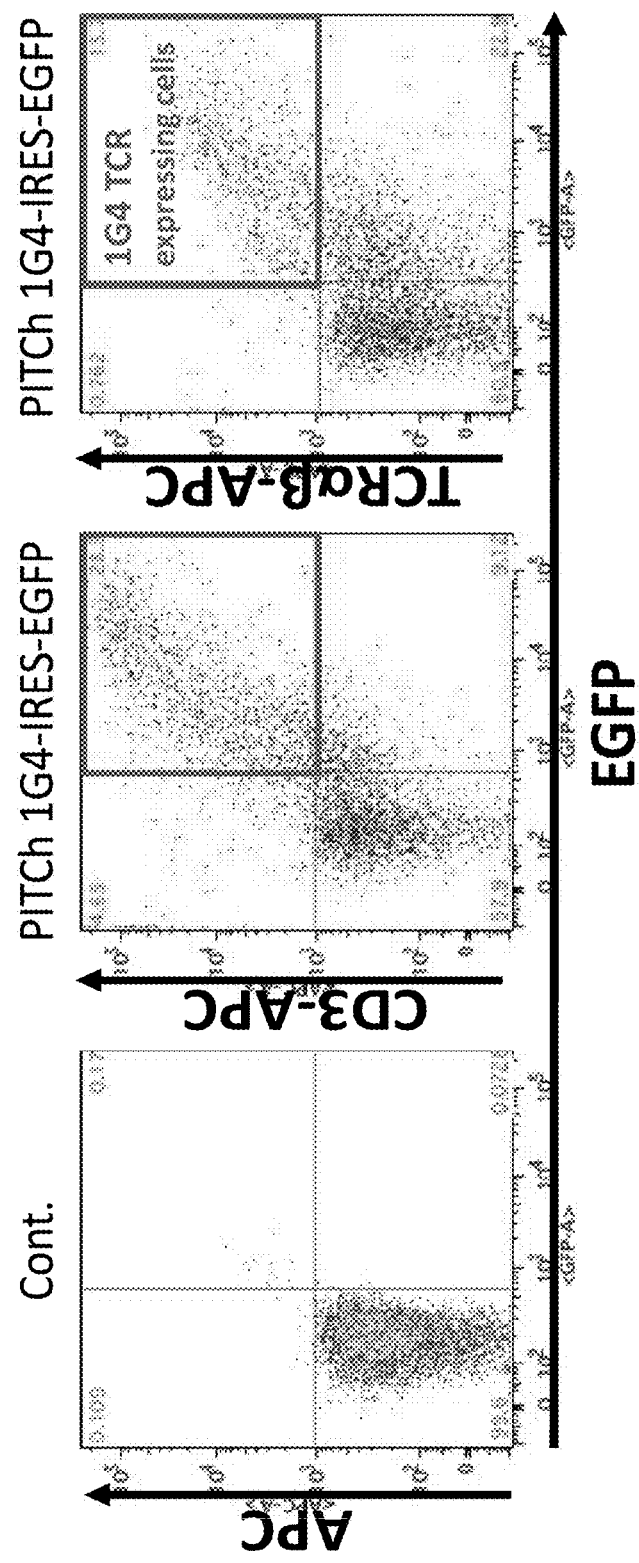
FIG. 22 is a diagram showing results of producing an endogenous TCR deficient NY-ESO-1 specific T cell using a TAL-PITCh vector.

As shown in FIG. 22, a cell population expressing 1G4 TCR was able to be obtained. It is understood that endogenous TCR deficient NY-ESO-1 specific T cells can be created by the TAL-PITCh method without using a viral vector. Endogenous TCR deficient T cells expressing TCR having a desired antigen specificity can be created without using a viral vector by introducing desired exogenous TCR in place of NY-ESO-1 specific TCR.

Example 9: Full Genome Sequencing of Created Cells

After cloning the created cells by limiting dilution method or the like, the full genome sequencing can be performed to evaluate the properties of cells by the following method.

[DNA Extraction Using QIAamp DNA Mini Kit] (in Accordance with the Manufacturer's Instruction)

1. Pipette 20 µl of QIAGEN Protease at the bottom of a 1.5 ml microtube.
2. Add $1 \times 10^5$ T cells suspended in 200 µl of PBS to the microtube.
3. Add 200 µl of Buffer AL to the sample.
4. Incubate for 10 minutes at 56° C.
5. Collect the solution adhering to the inside of a lid by spinning down the 1.5 ml microbe for several seconds.
6. After adding 200 µl of ethanol to the sample and vortexing the mixture for 15 seconds, collect the solution adhering to the inside of the lid by spinning down the 1.5 ml microbe for several seconds.
7. Apply the mixture from step 6 to a QIAamp Mini Spin Column. Close the lid and centrifuge for 1 minute at 6000×g. Transfer the QIAamp Mini Spin Column to a new 2 ml collection tube and discard collection tubes containing a filtrate.
8. Open the QIAamp Mini Spin Column and add 500 µl of Buffer AW1. Close the lid and centrifuge for 1 minute at 6000×g. Transfer the QIAamp Mini Spin Column to a new 2 ml collection tube and discard collection tubes containing a filtrate.
9. Open the QIAamp Mini Spin Column and add 500 µl of Buffer AW2. Close the lid and centrifuge for 3 minutes at 20000×g.
10. Transfer the QIAamp Mini Spin Column to a new 1.5 ml microtube and discard collection tubes containing a filtrate. Open the QIAamp Mini Spin Column and add 200 µl of purified water. After incubating for 1 minute at room temperature (20° C.), centrifuge for 1 minute at 6000×g to extract DNA.

[Creation of PCR Free Library and Full Genome Sequencing]

1. Fragment 1 µg a high molecular weight. DNA into an average of about 300 bp with Bioruptor Pico (Diagenode, Belgium) and analyze the post-treatment state with an Agilent Bioanalyzer (Agilent Technologies, USA).
2. Perform end repair, A-tailing, and index adaptor-ligation on the fragmented DNA and purify with Agentcourt AMPure XP beads (Beckman Coulter, USA).
3. Analyze the quality of the size and concentration of the prepared DNA library with Agilent Bioanalyzer (Agilent Technologies, USA) and Bio-Rad real time PCR system.
4. Sequence the DNA library with HiSeq Xten (Illumina, USA) in accordance with the manufacturer's instruction, and determine the full genome sequence based on the sequence of unique reads obtained at Q30% or greater and coverage of 30×.

[Note]

As disclosed above, the present invention is exemplified by the use of its preferred embodiments. However, it is understood that the scope of the present invention should be interpreted based solely on the Claims. It is also understood that any patent, any patent application, and any other references cited herein should be incorporated herein by reference in the same manner as the contents are specifically described herein. The present application claims priority to Japanese Patent Application No. 2017-197013 filed on Oct. 10, 2017 with the Japan Patent Office. The entire content thereof is incorporated herein by reference.

INDUSTRIAL APPLICABILITY

The present invention can be utilized in the treatment or prevention of a disease or condition on which immunosuppression is considered effective.

[Sequence Listing Free Text]

SEQ ID NO 1: example of the amino acid sequence of a TALE DNA binding module
SEQ ID NO 2: HLA-A*02 restricted CMV pp65 peptide
SEQ ID NO 3: HLA-A2-HIV
SEQ ID NO 4: BSL-18E primer
SEQ ID NO 5: P20EA primer
SEQ ID NO 6: P10EA primer
SEQ ID NO 7: CA1 primer
SEQ ID NO 8: CA2 primer
SEQ ID NO 9: CB1 primer
SEQ ID NO 10: CB2 primer
SEQ ID NO 11: HuVaF primer
SEQ ID NO 12: HuVbF primer
SEQ ID NO 13: B-P20EA primer
SEQ ID NO 14: MID1
SEQ ID NO 15: MID2
SEQ ID NO 16: MID3
SEQ ID NO 17: MID4
SEQ ID NO 18: MID5
SEQ ID NO 19: MID6
SEQ ID NO 20: MID7
SEQ ID NO 21: MID8

SEQ ID NO 22: MID10
SEQ ID NO 23: MID11
SEQ ID NO 24: MID15
SEQ ID NO 25: MID16
SEQ ID NO 26: MID17
SEQ ID NO 27: MID18
SEQ ID NO 28: MID19
SEQ ID NO 29: MID20
SEQ ID NO 30: MID21
SEQ ID NO 31: MID22
SEQ ID NO 32: MID23
SEQ ID NO 33: MID24
SEQ ID NO 34: A adapter sequence
SEQ ID NO 35: P22EA-ST1-R primer
SEQ ID NO 36: Tag-1 primer
SEQ ID NO 37: Tag-2 primer
SEQ ID NO 33: CA-ST1-R
SEQ ID NO 39: CB-ST1-R
SEQ ID NO 40: TSO oligo
SEQ ID NO 41: TSO PCR primer
SEQ ID NO 42: SMART PCR primer
SEQ ID NO 43: TSO_TAG primer
SEQ ID NO 44: SMART_TAG primer
SEQ ID NO 45: SMART sequence in oligobeads
SEQ ID NO 46: full length TALEN-TCR-alpha2_L19 plasmid
SEQ ID NO 47: full length TALEN-TCR-alpha2_R19 plasmid
SEQ ID NO 48: full length TALEN-TCR-beta1_L19 plasmid
SEQ ID NO 49: full length TALEN-TCR-beta1_R19 plasmid
SEQ ID NO 50: full length TALEN-TCR-beta3 L19 plasmid
SEQ ID NO 51: full length TALEN-TCR-beta3 R19 plasmid
SEQ ID NO 52: TALEN-TCR-alpha2 L19 TALEN coding sequence
SEQ ID NO 53: TALEN-TCR-alpha2 L19 TALEN amino acid sequence
SEQ ID NO 54: TALEN-TCR-alpha2 R19 TALEN coding sequence
SEQ ID NO 55: TALEN-TCR-alpha2 R19 TALEN amino acid sequence
SEQ ID NO 56: TALEN-TCR-beta1_L19 TALEN coding sequence
SEQ ID NO 57: TALEN-TCR-beta1_L19 TALEN amino acid sequence
SEQ ID NO 58: TALEN-TCR-beta1_R19 TALEN coding sequence
SEQ ID NO 59: TALEN-TCR-beta1_R19 TALEN amino acid sequence
SEQ ID NO 60: TALEN-TCR-beta3 L19 TALEN coding sequence
SEQ ID NO 61: TALEN-TCR-beta3 L19 TALEN amino acid sequence
SEQ ID NO 62: TALEN-TCR-beta3 R19 TALEN coding sequence
SEQ ID NO 63: TALEN-TCR-beta3 R19 TALEN amino acid sequence
SEQ ID NO 64: TCR-alpha2-f primer
SEQ ID NO 65: TCR-alpha2-r primer
SEQ ID NO 66: TCR-beta1-c1-f primer
SEQ ID NO 67: TCR-beta1-c1-r primer
SEQ ID NO 68: TCR-beta1-c2-f primer
SEQ ID NO 69: TCR-beta1-c2-r primer
SEQ ID NO 70: Vα cloning forward primer
SEQ ID NO 71: Vα cloning reverse primer
SEQ ID NO 72: Cα cloning forward primer
SEQ ID NO 73: Cα cloning reverse primer
SEQ ID NO 74: Vβ cloning forward primer
SEQ ID NO 75: Vβ cloning reverse primer
SEQ ID NO 76: Cβ cloning forward primer
SEQ ID NO 77: Cβ cloning reverse primer
SEQ ID NO 78: TCRα constant region for introduction
SEQ ID NO 79: TCR constant region for introduction
SEQ ID NO 80: QYD peptide
SEQ ID NO 81 to 98: example of CDR3 sequence of human TRA or IRE
SEQ ID NO 99 to 101: example of the amino acid sequence of DNA binding module of Platinum TALEN
SEQ ID NO 102: example of the amino acid sequence of DNA binding module of Zhang TALEN
SEQ ID NO 103 to 112: base sequences in FIGS. 20 and 21
SEQ ID NO 113: target sequence of mouse TRA2-TALEN on the left side
SEQ ID NO 114: target sequence of mouse TRA2-TALEN on the right side
SEQ ID NO 115: target sequence of mouse TRB1-TALEN on the left side
SEQ ID NO 116: target sequence of mouse TRB1-TALEN on the right side
SEQ ID NO 117: target sequence of mouse TRB2-TALEN on the left side
SEQ ID NO 118: target sequence of mouse TRB2-TALEN on the right side

The invention claimed is:

1. A method of producing a regulatory T cell specific to an antigen, comprising:
   identifying a T cell receptor (TCR) clone that is present in an effector T cell population specific to the antigen in an effector T cell donor;
   removing an endogenous TCR gene of a regulatory T cell; and introducing a full or partial nucleic acid sequence of a gene of TCRα and a full or partial nucleic acid sequence of a gene of TCRβ, wherein the genes are contained in the clone, into a regulatory T cell so that the TCRα and the TCRβ are expressed as a pair,
   wherein the removal of the endogenous TCR gene is performed using a pair of TCR specific TALENs,
   wherein each TALEN is provided as a polypeptide comprising a DNA binding domain and a functional domain or a nucleic acid encoding the polypeptide,
   wherein the DNA binding domain and the functional domain are connected by a polypeptide consisting of 35 to 55 amino acids,
   the DNA binding domain comprises a plurality of DNA binding modules consecutively from the N-terminal side,
   a combination of the xth amino add and the yth amino acid in the 4n-3th DNA binding module from the N-terminus being identical for any n,
   a combination of the xth amino acid and the yth amino acid in the 4n-2th DNA binding module from the N-terminus being identical for any n,
   a combination of the xth amino acid and the yth amino acid in the 4n-1th DNA binding module from the N-terminus being identical for any n, and
   a combination of the xth amino acid and the yth amino acid in the 4nth DNA binding module from the N-terminus being identical for any n,
   the combination of the xth amino acid and the yth amino acid in the 4n-3th DNA binding module from the N-terminus, the combination of the xth amino acid and the yth amino acid in the 4n-2th DNA binding module from the N-terminus, the combination of the xth amino acid and the yth amino acid in the 4n-1th DNA binding module from the N-terminus, and the combination of the xth amino acid and the yth amino acid in the 4nth DNA binding module from the N-terminus are different from one another, and
   n is a natural number from 1 to 10, x is a natural number from 1 to 40, y is a natural number from 1 to 40, and x and y are different natural numbers, and
   wherein the pair of TCR specific TALENs comprises (a) SEQ ID NOs 53 and 55, and (b-i) SEQ NOs: 57 and 59 or (b-ii) SEQ ID NOs: 61 and 63.

2. The method of claim 1, wherein identifying the TCR clone comprises determining a TCR repertoire of the effector T cell population.

3. The method of claim 2, wherein the determining the TCR repertoire comprises:
   (1) providing a nucleic acid sample comprising a nucleic acid sequence of a T cell receptor (TCR) unbiasedly amplified from the effector T cell population;
   (2) determining the nucleic acid sequence contained in the nucleic acid sample; and
   (3) calculating a frequency of appearance of each gene or a combination thereof based on the determined nucleic acid sequence to derive a TCR repertoire of the effector T cell population.

4. The method of claim 2, wherein the determining of the TCR repertoire comprises:
(1) providing a nucleic acid sample comprising a nucleic acid sequence of TCR unbiasedly amplified from the effector T cell population, (1) comprising the following steps:
  (1-1) synthesizing a complementary DNA by using an RNA sample derived from a target cell as a template;
  (1-2) synthesizing a double stranded complementary DNA by using the complementary DNA as a template;
  (1-3) synthesizing an adaptor-added double stranded complementary DNA by adding a common adaptor primer sequence to the double stranded complementary DNA;
  (1-4) performing a first PCR amplification reaction by using the adaptor-added double stranded complementary DNA, a common adaptor primer consisting of the common adaptor primer sequence, and a first TCR C region specific primer, wherein the first TCR C region specific primer is designed to comprise a sequence that is sufficiently specific to a C region of interest of the TCR and not homologous with other genetic sequences, and comprise a mismatching base between subtypes downstream when amplified;
  (1-5) performing a second PCR amplification reaction by using a PCR amplicon of (1-4), the common adaptor primer, and a second TCR C region specific primer, wherein the second TCR C region specific primer is designed to have a sequence that is a complete match with the TCR C region in a sequence downstream the sequence of the first TCR C region specific primer, but comprise a sequence that is not homologous with other genetic sequences, and comprise a mismatching base between subtypes downstream when amplified; and
  (1-6) performing a third PCR amplification reaction by using a PCR amplicon of (1-5), an added common adaptor primer in which a nucleic acid sequence of the common adaptor primer comprises a first additional adaptor nucleic acid sequence, and an adaptor-added third TCR C region specific primer in which a second additional adaptor nucleic acid sequence is added to a third TCR C region specific sequence;
  wherein the third TCR C region specific primer is designed to have a sequence that is a complete match with the TCR C region in a sequence downstream to the sequence of the second TCR C region specific primer, but comprises a sequence that is not homologous with other genetic sequences, and comprises a mismatching base between subtypes downstream when amplified;
(2) determining the nucleic acid sequence comprised in the nucleic acid sample; and
(3) calculating a frequency of appearance of each gene or a combination thereof based on the determined nucleic acid sequence to derive a TCR repertoire of the effector T cell population.

5. The method of claim 1, wherein the TCR clone is present at a frequency that is one standard deviation or greater from the mean of the frequency of presence of each clone in the effector T cell population.

6. The method of claim 1, wherein the TCR clone is present at a frequency that is two standard deviation or greater from the mean of the frequency of presence of each clone in the effector T cell population.

7. The method of claim 1, wherein the TCR clone is present at a frequency of about 10% or greater in the effector T cell population.

8. The method of claim 1, wherein the full or partial nucleic acid sequence of the gene of the TCRα comprises a sequence corresponding to the CDR3 region of Vα-Jα.

9. The method of claim 1, wherein the full or partial nucleic acid sequence of the gene of the TCRβ comprises a sequence corresponding to the CDR3 region of Vβ-D-Jβ.

10. The method of claim 1, wherein the full or partial nucleic acid sequence of the gene of the TCRα comprises a cDNA sequence of Vα-Jα-Cα.

11. The method of claim 1, wherein the full or partial nucleic acid sequence of the gene of the TCRβ comprises a cDNA sequence of Vβ-D-Jβ-Cβ.

12. The method of claim 1, wherein the identifying the TCR clone comprises amplifying a gene of TCRα and a gene of TCRβ derived from the same cell and identifying a pair of TCRα and TCRβ in the effector T cell population.

13. The method of claim 12, further comprising confirming whether the identified pair of TCRα and TCRβ has affinity to an antigen.

14. The method of claim 12, further comprising cloning a full or partial nucleic acid sequence of TCRα and a full or partial nucleic acid sequence of TCRβ in the identified pair of TCRα and TCRβ.

15. The method of claim 14, wherein the introducing comprises introducing the cloned full or partial nucleic acid sequence of TCRα and a full or partial nucleic acid sequence of TCRβ into the regulatory T cell.

16. The method of claim 1, wherein the introducing comprises using a vector configured to express the TCRα and the TCRfβ as a pair.

17. The method of claim 16, wherein the vector comprises a nucleic acid sequence encoding Cys so that a disulfide bond is formed between the TCRα and the TCRfβ to be expressed, has a coding sequence of the TCRα and the TCRfβ codon optimized, is configured so that a leucine zipper is introduced into an intracellular region of the TCRα and the TCRβ, or is configured so that the TCRα and the TCRfβ are expressed with a modification in a sugar chain.

18. The method of claim 1, comprising using a vector encoding a Cα domain linked to a Vα chain and a Cβ domain linked to a Vβ chain, wherein the vector is configured so that the TCRα and the TCRfβ are expressed as a pair.

19. The method of claim 1, wherein the regulatory T cell is obtained from the effector T cell donor.

20. The method of claim 1, comprising:
  removing one of genes of endogenous TCRα and endogenous TCRfβ in the regulatory T cell;
  introducing a full or partial nucleic acid sequence of the TCRα gene or a full or partial nucleic acid sequence of the TCRfβ gene into the regulatory T cell;
  removing the other one of the endogenous TCRα and endogenous TCRfβ genes in the regulatory T cell; and
  reintroducing the full or partial nucleic acid sequence of the gene of TCRα or the full or partial nucleic acid sequence of the gene of TCRfβ into the regulatory T cell.

21. A method of producing a regulatory T cell specific to an antigen, comprising:
  determining a TCR repertoire in an effector T cell population specific to the antigen in an effector T cell donor, comprising unbiasedly amplifying a TCR gene;
  identifying a pair of TCRα and TCRfβ in the effector T cell population;

checking whether the identified pair of TCRα and TCRfβ has affinity to an antigen;
cloning a full or partial nucleic acid sequence of TCRα and a full or partial nucleic acid sequence of TCRfβ in the identified pair of TCRα and TCRƒ3;
removing an endogenous TCR gene of a regulatory T cell; and
introducing the cloned full or partial nucleic sequence of TCRα and full or partial nucleic acid sequence of TCRfβ into the regulatory T cell so that the TCRα and the TCRβ are expressed as a pair, wherein the removal of the endogenous TCR gene is performed using a pair of TCR specific TALENs, wherein the pair of TCR specific TALENs comprises (i) SEQ ID NOs 53 and 55, (ii) SEQ ID NOs: 57 and 59, or (iii) SEQ ID NOs: 61 and 63, wherein each TALEN is provided as a polypeptide comprising a DNA binding domain and a functional domain or a nucleic acid encoding the polypeptide, wherein the DNA binding domain and the functional domain are connected by a polypeptide consisting of 35 to 55 amino acids, the DNA binding domain comprises a plurality of DNA binding modules consecutively from the N-terminal side, a combination of the xth amino acid and the yth amino acid in the 4n-3th DNA binding module from the N-terminus being identical for any n, a combination of the xth amino acid and the yth amino acid in the 4n-2th DNA binding module from the N-terminus being identical for any n, a combination of the xth amino acid and the yth amino acid in the 4n-1th DNA binding module from the N-terminus being identical for an n, and a combination of the xth amino acid and the yth amino acid in the 4nth DNA binding module from the N-terminus being identical for any n, the combination of the xth amino acid and the yth amino acid in the 4n-3th DNA binding module from the N-terminus, the combination of the xth amino acid and the yth amino acid in the 4n-2th DNA binding module from the N-terminus the combination of the xth amino acid and the yth amino acid in the 4n-1th DNA binding module from the N-terminus and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers.

* * * * *